(12) United States Patent
Dawson et al.

(10) Patent No.: US 9,841,427 B2
(45) Date of Patent: Dec. 12, 2017

(54) HCV ANTIGEN-ANTIBODY COMBINATION ASSAY AND METHODS AND COMPOSITIONS FOR USE THEREIN

(71) Applicant: Abbott Laboratories, Abbott Park, IL (US)

(72) Inventors: George J. Dawson, Libertyville, IL (US); Suresh M. Desai, Libertyville, IL (US); Robin A. Gutierrez, Gurnee, IL (US); A. Scott Muerhoff, Kenosha, WI (US); John Prostko, Kenosha, WI (US); M. Felicia Bogdan, Gurnee, IL (US); Christopher C. Marohnic, Kenosha, WI (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 14/851,471

(22) Filed: Sep. 11, 2015

(65) Prior Publication Data

US 2016/0123983 A1 May 5, 2016
US 2017/0003290 A9 Jan. 5, 2017

Related U.S. Application Data

(63) Continuation of application No. 14/139,108, filed on Dec. 23, 2013, now Pat. No. 9,194,873.

(60) Provisional application No. 61/788,136, filed on Mar. 15, 2013, provisional application No. 61/785,124, filed on Mar. 14, 2013.

(51) Int. Cl.
*G01N 33/53* (2006.01)
*G01N 33/576* (2006.01)
*G01N 33/543* (2006.01)
*G01N 33/569* (2006.01)

(52) U.S. Cl.
CPC ..... *G01N 33/5767* (2013.01); *G01N 33/5306* (2013.01); *G01N 33/54306* (2013.01); *G01N 33/56983* (2013.01); *G01N 2333/186* (2013.01); *G01N 2333/914* (2013.01); *G01N 2469/10* (2013.01); *G01N 2469/20* (2013.01)

(58) Field of Classification Search
CPC .. C12Q 1/707; C12Q 2563/131; C12Q 1/706; G01N 33/5767; G01N 2469/20; G01N 2469/10; G01N 2333/186; G01N 33/54306; G01N 33/581; C07K 16/109
See application file for complete search history.

(56) References Cited

U.S. PATENT DOCUMENTS

| | | |
|---|---|---|
| 4,338,397 A | 7/1982 | Gilbert et al. |
| 4,425,437 A | 1/1984 | Riggs |
| 4,431,739 A | 2/1984 | Riggs |
| 4,526,938 A | 7/1985 | Churchill |
| 4,554,101 A | 11/1985 | Hopp |
| 4,816,397 A | 3/1989 | Boss |
| 4,816,567 A | 3/1989 | Cabilly |
| 4,880,078 A | 11/1989 | Inoue et al. |
| 4,946,778 A | 8/1990 | Ladner |
| 5,006,309 A | 4/1991 | Khalil et al. |
| 5,063,081 A | 11/1991 | Cozette et al. |
| 5,089,424 A | 2/1992 | Khalil et al. |
| 5,128,326 A | 7/1992 | Balazs et al. |
| 5,135,875 A | 8/1992 | Meucci et al. |
| 5,223,409 A | 6/1993 | Ladner |
| 5,225,539 A | 7/1993 | Winter |
| 5,241,070 A | 8/1993 | Law |
| 5,242,828 A | 9/1993 | Bergstrom |
| 5,258,498 A | 11/1993 | Huston |
| 5,290,540 A | 3/1994 | Prince et al. |
| 5,294,404 A | 3/1994 | Grandone et al. |
| 5,350,671 A | 9/1994 | Houghton et al. |
| 5,352,803 A | 10/1994 | Mattingly |
| 5,359,093 A | 10/1994 | Adamczyk et al. |
| 5,399,346 A | 3/1995 | Anderson et al. |
| 5,403,484 A | 4/1995 | Ladner |
| 5,427,908 A | 6/1995 | Dower |
| 5,468,646 A | 11/1995 | Mattingly et al. |
| 5,496,925 A | 3/1996 | Mattingly |
| 5,516,637 A | 5/1996 | Huang |
| 5,530,101 A | 6/1996 | Queen |
| 5,543,524 A | 8/1996 | Mattingly et al. |
| 5,565,332 A | 10/1996 | Hoogenboom |
| 5,565,352 A | 10/1996 | Hochstrasser |
| 5,571,698 A | 11/1996 | Ladner |
| 5,573,904 A | 11/1996 | Mattingly |
| 5,580,717 A | 12/1996 | Dower |
| 5,585,089 A | 12/1996 | Queen |
| 5,593,896 A | 1/1997 | Adamczyk et al. |

(Continued)

FOREIGN PATENT DOCUMENTS

| | | |
|---|---|---|
| CA | 2450710 | 1/2003 |
| EP | 086631 | 8/1983 |

(Continued)

OTHER PUBLICATIONS

Wafaa M. El-Emshaty et al. Brazilian Journal of Microbiology (2011) 42: 303-309.*
Aach, R.D. et al., "Hepatitis C virus infection in post-transfusion hepatitis. An analysis with first- and second-generation assays," N. Engl. J. Med. (1991) 325(19):1325-1329.
Adamczyk et al., "Chemiluminescence quenching of pteroic acid-N-sulfonyl-acridinium-9-carboxamide conjugates by folate finding protein," Bioorg. Med. Chem. Lett. (2004) 14(9):2313-2317.

(Continued)

*Primary Examiner* — Bao Li
(74) *Attorney, Agent, or Firm* — Lisa V. Mueller; Michael Best & Friedrich LLP

(57) ABSTRACT

The present invention generally relates to combination immunoassays, reagents and kits for simultaneous detection of HCV antigens and anti-HCV antibodies in a test sample.

4 Claims, 1 Drawing Sheet

(56) References Cited

U.S. PATENT DOCUMENTS

| | | | |
|---|---|---|---|
| 5,624,821 A | 4/1997 | Winter | |
| 5,627,052 A | 5/1997 | Schrader | |
| 5,641,870 A | 6/1997 | Rinderknecht | |
| 5,648,260 A | 7/1997 | Winter | |
| 5,658,727 A | 8/1997 | Barbas | |
| 5,679,377 A | 10/1997 | Bernstein et al. | |
| 5,688,688 A | 11/1997 | Luciw et al. | |
| 5,693,762 A | 12/1997 | Queen | |
| 5,698,426 A | 12/1997 | Huse | |
| 5,705,330 A | 1/1998 | Shah et al. | |
| 5,714,350 A | 2/1998 | Co et al. | |
| 5,714,352 A | 2/1998 | Jakobovits | |
| 5,723,323 A | 3/1998 | Kauffman | |
| 5,733,743 A | 3/1998 | Johnson | |
| 5,750,753 A | 5/1998 | Kimae | |
| 5,753,430 A | 5/1998 | Mehta et al. | |
| 5,763,192 A | 6/1998 | Kauffman | |
| 5,766,886 A | 6/1998 | Studnicka | |
| 5,780,225 A | 7/1998 | Wigler | |
| 5,783,699 A | 7/1998 | Mattingly et al. | |
| 5,795,784 A | 8/1998 | Amquist et al. | |
| 5,807,715 A | 9/1998 | Morrison et al. | |
| 5,814,476 A | 9/1998 | Kauffman | |
| 5,817,483 A | 10/1998 | Kauffman | |
| 5,821,047 A | 10/1998 | Garrard | |
| 5,824,514 A | 10/1998 | Kauffman | |
| 5,855,913 A | 1/1999 | Hanes et al. | |
| 5,856,194 A | 1/1999 | Amquist et al. | |
| 5,874,064 A | 2/1999 | Edwards et al. | |
| 5,912,015 A | 6/1999 | Bernstein et al. | |
| 5,912,120 A | 6/1999 | Goldstein et al. | |
| 5,916,597 A | 6/1999 | Lee et al. | |
| 5,916,771 A | 6/1999 | Hori | |
| 5,934,272 A | 8/1999 | Lloyd et al. | |
| 5,939,598 A | 8/1999 | Kucherlapati | |
| 5,969,108 A | 10/1999 | McCafferty | |
| 5,976,862 A | 11/1999 | Kauffman | |
| 5,985,309 A | 11/1999 | Edwards et al. | |
| 5,985,320 A | 11/1999 | Edwards et al. | |
| 5,985,615 A | 11/1999 | Jakobovits | |
| 5,989,463 A | 11/1999 | Tracy et al. | |
| 5,989,905 A | 11/1999 | Houghton et al. | |
| 5,998,209 A | 12/1999 | Jokobovits | |
| 6,019,968 A | 2/2000 | Platz et al. | |
| 6,075,181 A | 6/2000 | Kucherlapati | |
| 6,091,001 A | 7/2000 | Jakobovits | |
| 6,096,319 A | 8/2000 | Seidel | |
| 6,114,598 A | 9/2000 | Kucherlapati | |
| 6,130,364 A | 10/2000 | Jakobovits | |
| 6,172,189 B1 | 1/2001 | Devare | |
| 6,180,370 B1 | 1/2001 | Queen | |
| 6,194,222 B1 | 2/2001 | Buechler et al. | |
| 6,204,023 B1 | 3/2001 | Robinson | |
| 6,225,047 B1 | 5/2001 | Hutchens et al. | |
| 6,306,579 B1 | 10/2001 | Seidel | |
| 6,329,209 B1 | 12/2001 | Wagner et al. | |
| 6,350,861 B1 | 2/2002 | Co et al. | |
| 6,555,114 B1 | 4/2003 | Leroux-Roels et al. | |
| 6,623,921 B2 | 9/2003 | Aoyagi | |
| 6,699,658 B1 | 3/2004 | Wittrup | |
| 6,727,092 B2 | 4/2004 | Shah | |
| 6,846,905 B2 | 1/2005 | Hackett et al. | |
| 6,914,128 B1 | 7/2005 | Salfeld | |
| 7,101,683 B2 * | 9/2006 | Shah | C07K 14/005 435/4 |
| 7,285,418 B2 | 10/2007 | Katrukha et al. | |
| 7,371,383 B2 | 5/2008 | Reed et al. | |
| 7,462,354 B2 | 12/2008 | Sette et al. | |
| 7,521,542 B2 | 4/2009 | Johnson et al. | |
| 7,612,181 B2 | 11/2009 | Wu | |
| 7,858,752 B2 | 12/2010 | Tu | |
| 7,871,625 B2 * | 1/2011 | Chien | C07K 14/005 424/189.1 |
| 7,888,004 B2 | 2/2011 | Coit et al. | |
| 8,030,026 B2 | 10/2011 | Brophy | |
| 8,193,318 B2 | 6/2012 | Koenig et al. | |
| 8,865,398 B2 * | 10/2014 | Rodgers | C07K 16/109 435/5 |
| 9,194,873 B2 * | 11/2015 | Dawson | G01N 33/54306 |
| 2002/0037868 A1 | 3/2002 | Budkowska | |
| 2002/0137134 A1 | 9/2002 | Gerngross | |
| 2003/0152948 A1 * | 8/2003 | Shah | C07K 14/005 435/6.12 |
| 2003/0170881 A1 | 9/2003 | Davis | |
| 2003/0186374 A1 | 10/2003 | Hufton | |
| 2004/0018577 A1 | 1/2004 | Campbell et al. | |
| 2004/0018590 A1 | 1/2004 | Gemgross et al. | |
| 2004/0072267 A1 | 4/2004 | Rieunier et al. | |
| 2005/0054078 A1 | 3/2005 | Miller et al. | |
| 2006/0018897 A1 | 1/2006 | Lee et al. | |
| 2006/0160164 A1 | 7/2006 | Miller et al. | |
| 2008/0020401 A1 | 1/2008 | Grenier et al. | |
| 2008/0113339 A1 * | 5/2008 | Rodgers | C07K 16/109 435/5 |
| 2008/0248493 A1 | 10/2008 | Mattingly et al. | |
| 2010/0297607 A1 | 11/2010 | Zheng | |
| 2012/0009196 A1 | 1/2012 | Muerhoff | |
| 2012/0046188 A1 | 2/2012 | Berland et al. | |
| 2014/0272931 A1 | 9/2014 | Ziemann | |
| 2014/0272932 A1 | 9/2014 | Muerhoff | |
| 2014/0272933 A1 | 9/2014 | Dawson et al. | |
| 2015/0024457 A1 | 1/2015 | Brophy | |

FOREIGN PATENT DOCUMENTS

| | | |
|---|---|---|
| EP | 0229246 | 7/1987 |
| EP | 0239400 | 9/1987 |
| EP | 0424634 | 5/1991 |
| EP | 0471293 | 2/1992 |
| EP | 0519596 | 12/1992 |
| EP | 0592106 | 4/1994 |
| EP | 0967485 | 12/1999 |
| EP | 1176195 | 1/2002 |
| EP | 1308507 | 5/2003 |
| EP | 1310796 | 5/2003 |
| EP | 2014302 | 1/2009 |
| FR | 2779526 | 12/1999 |
| WO | WO 90/01443 | 2/1990 |
| WO | WO 90/05144 | 5/1990 |
| WO | WO 90/05370 | 5/1990 |
| WO | WO 90/14424 | 11/1990 |
| WO | WO 90/14430 | 11/1990 |
| WO | WO 90/14443 | 11/1990 |
| WO | WO 91/05548 | 5/1991 |
| WO | WO 91/09630 | 7/1991 |
| WO | WO 91/09967 | 7/1991 |
| WO | WO 91/10741 | 7/1991 |
| WO | WO 91/17271 | 11/1991 |
| WO | WO 92/01047 | 1/1992 |
| WO | WO 92/02551 | 2/1992 |
| WO | WO 92/03461 | 3/1992 |
| WO | WO 92/09690 | 6/1992 |
| WO | WO 92/11272 | 7/1992 |
| WO | WO 92/15679 | 9/1992 |
| WO | WO 92/18619 | 10/1992 |
| WO | WO 92/19244 | 11/1992 |
| WO | WO 92/20791 | 11/1992 |
| WO | WO 92/22324 | 12/1992 |
| WO | WO 93/00365 | 1/1993 |
| WO | WO 93/01288 | 1/1993 |
| WO | WO 93/06213 | 4/1993 |
| WO | WO 93/11236 | 6/1993 |
| WO | WO 94/01778 | 1/1994 |
| WO | WO 94/02602 | 2/1994 |
| WO | WO 94/18219 | 8/1994 |
| WO | WO 95/15982 | 6/1995 |
| WO | WO 95/20401 | 8/1995 |
| WO | WO 96/20698 | 7/1996 |
| WO | WO 96/33735 | 10/1996 |
| WO | WO 96/34096 | 10/1996 |
| WO | WO 97/20032 | 6/1997 |
| WO | WO 97/29131 | 8/1997 |
| WO | WO 97/32572 | 9/1997 |
| WO | WO 97/44013 | 11/1997 |

(56) References Cited

FOREIGN PATENT DOCUMENTS

| WO | WO 98/16654 | 4/1998 |
|---|---|---|
| WO | WO 98/24893 | 6/1998 |
| WO | WO 98/31346 | 7/1998 |
| WO | WO 98/31700 | 7/1998 |
| WO | 98/37200 | 8/1998 |
| WO | WO 98/50433 | 11/1998 |
| WO | 99/09148 | 2/1999 |
| WO | WO 99/06834 | 2/1999 |
| WO | WO 99/15154 | 4/1999 |
| WO | WO 99/20253 | 4/1999 |
| WO | WO 99/45031 | 9/1999 |
| WO | WO 99/51773 | 10/1999 |
| WO | WO 99/53049 | 10/1999 |
| WO | WO 99/54342 | 10/1999 |
| WO | WO 99/66903 | 12/1999 |
| WO | WO 00/07023 | 2/2000 |
| WO | WO 00/09560 | 2/2000 |
| WO | WO 00/37504 | 6/2000 |
| WO | WO 00/56772 | 9/2000 |
| WO | WO 00/56934 | 9/2000 |
| WO | WO 00/56943 | 9/2000 |
| WO | 01/09609 | 2/2001 |
| WO | 01/21189 | 3/2001 |
| WO | WO 01/38360 | 5/2001 |
| WO | WO 01/83525 | 11/2001 |
| WO | 01/96875 | 12/2001 |
| WO | WO 02/072636 | 9/2002 |
| WO | 03/002749 | 1/2003 |
| WO | WO 03/016466 | 2/2003 |
| WO | WO 03/035835 | 5/2003 |
| WO | WO 03/086458 | 10/2003 |
| WO | 2004/070387 | 8/2004 |
| WO | WO 2005/000901 | 1/2005 |
| WO | WO 2005/010049 | 2/2005 |
| WO | WO 2005/035575 | 4/2005 |
| WO | WO 2005/068503 | 7/2005 |
| WO | WO 2005/100584 | 10/2005 |
| WO | WO 2008/028686 | 3/2008 |
| WO | 2008/051762 | 5/2008 |
| WO | WO 2008/070727 | 6/2008 |
| WO | WO 2008/120202 | 10/2008 |
| WO | WO 2010/060186 | 6/2010 |
| WO | 2011/163558 | 12/2011 |

OTHER PUBLICATIONS

Adamczyk et al., "Chemiluminescent acridinium-9-carboxamide boronic acid probes: application to a homogenous glycated hemoglobin assay," Bioorg. Med. Chem. Lett (2006) 16(5):1324-1328.

Adamczyk et al., "Homogenous chemiluminescent assays for free choline in human plasma and whole blood," Anal. Chim. Acta (2006) 579(1):61-67.

Adamczyk et al., "Intrinsic factor-mediated modulation of cyanocobalain-N-sulfonyl-acridinium-9-carboxamide chemiluminescence," Biorg. Med. Chem. Lett. (2004) 14(15):3917-3921.

Adamczyk et al., "Linker-mediated modulation of the chemiluminescent signal from N(10)-(3-sulfopropyl)-N-sulfonylacridinium-9-carboxamide tracers," Bioconjug. Chem. (2000) 11(5):714-724.

Adamczyk et al., "Modulation of the chemiluminescent signal from N10-(3-sulfopropyl)-N-sulfonylacridinium-9-carboximides," Tetrahedron (1999) 55:10899-10914.

Adamczyk et al., "Neopentyl 3-triflyloxypropanesulfonate. A reactive sulfopropylation reagent for the preparation of chemiluminescent labels," J. Org. Chem. (1998) 63:5636-5639.

Adamczyk et al., "Regiodependent luminescence quenching of biotinylated N-sulfonyl-acridinium-9-carboxamides by avidin," Org. Lett (2003) 5(21):3779-3782.

Adamczyk et al., "Synthesis of a chemiluminescent acridinium hydroxylamine (AHA) for the direct detection of abasic sites in DNA," Org. Lett. (1999) 1(5):779-781.

Alter et al., "The natural history of community-acquired heptatitis C in the United States. The Sentinel Counties Chronic non-A, non-B hepatitis study team," N. Eng. J. Med. (1992) 327(27):1899-1905.

Altschul, S.F. et al., "Gapped BLAST and PSI-BLAST: a new generation of protein database search programs," Nucleic Acids Res. (1997) 25:3389-3402.

Ames et al., "Conversion of murine Fabs isolated from a combinatorial phage display library to full length immunoglobulins," J. Immunol. Methods (1995) 184(2):177-186.

Anthony et al., "Racapitulation of IVIG anti-inflammatory activity with a recombinant IgG Fc," Science (2008) 320(5874):373-376.

Azzazy et al., "Phage display technology: clinical applications and recent innovations," Clin. Biochem. (2002) 35(6):425-445.

Babcook et al., "A novel strategy for generating monoclonal antibodies from single, isolated lymphocytes producing antibodies of defined specificities," Proc. Natl. Acad. Sci. USA (1996) 93(15):7843-7848.

Barbas et al., "Assembly of combinatorial antibody libraries on phage surfaces: the gene III site," Proc. Natl. Acad. Sci. USA (1991) 88(18):7978-7982.

Barbas et al., In vitro evolution of a neutralizing human antibody to human immunodeficiency virus type 1 to enhance affinity and broaden strain cross-reactivity, Proc. Natl. Acad. Sci. USA (1994) 91(9):3809-3813.

Beckett et al., "A minimal peptide substrate in biotin holoenzyme synthetase-catalyzed biotinylation," Protein Sci. (1999) 8(4):921-929.

Better et al., "*Escherichia coli* secretion of an active chimeric antibody fragment," Science (1988) 240(4855): 1041-1043.

Beidler et al., "Cloning and high level expression of a chimeric antibody with specificity for human carcinoembryonic antigen," J. Immunol. (1988) 141(11):4053-4060.

Biewenga et al., "IgA1 half olecules in human multiple myeloma and the in vitro production of similar fragments from intact IgA1 molecules," Clin. Exp. Immunol. (1983) 51(2):395-400.

Bird et al., "Single-chain antigen-binding proteins," Science (1988) 242(4877):423-426.

Bodor, G.S. et al., "Development of monoclonal antibodies for an assay of cardiac Troponin-I and preliminary results in suspected cases of myocardial infarction," Clinical Chem. (1992) 38:2203-2214.

Boder, E.T. et al., "Yeast surface display for screening combinatorial polypeptide libraries," Nature Biotech. (1997) 15:553-557.

Boulant et al., "Hepatitis C virus core protein is a dimeric alpha-helical protein exhibiting membrane protein features," J. Virol. (2005) 79(17):11353-11365.

Bresters et al., "Enhanced sensitivity of a second generation ELISA for antibody to hepatitis C virus," Vox Sang (1992) 62(4):213-217.

Brinkmann et al., "Phage display of disulfide-stabilized Fv fragments," J. Immunol. Methods (1995) 182(1):41-50.

Buchwald, H. et al., "Long-term, continuous intravenous heparin administration by an implantable infusion pump in ambulatory patients with recurrent venous thrombosis," Surgery (1980) 88:507-516.

Burton et al., "Human antibodies from combinatorial libraries," Adv. Immunol. (1994) 57:191-280.

Busch et al., "Committee report. Nucleic acid amplification testing of blood donors for transfusion-transmitted infectious diseases: Report of the Interorganizational Task Force on Nucleic Acid Amplification Testing of Blood Donors," Transfusion (2000) 40(2):143-159.

Carter et al., "Humanization of an anti-p185HER2 antibody for human cancer therapy," Proc. Natl. Acad. Sci. USA (1992) 89(10):4285-4289.

Choo et al., "Isolation of a cDNA clone derived from a blood-forne non-A, non-B viral hepatitus genome," Science (1989) 244(4902):359-362.

Chothia, C. et al., "Canonical structures for the hypervariable regions of immunoglobulins," J. Mol. Biol. (1987) 196(4):901-917.

Chothia, C. et al., "Conformations of immunoglobulin hypervariable regions," Nature (1989) 342(6252):877-883.

Chothia, C. et al., "Structural repertoire of the human VH segments," J. Mol. Biol. (1992) 227:799-817.

(56) References Cited

OTHER PUBLICATIONS

Clackson et al., "Making antibody fragments using phage display libraries," Nature (1991) 352(6336):624-628.
Cleek et al., "Biodegradable polymeric carriers for a bFGF antibody for cardiovascular application," Pro. Int. Symp. Control. Rel. Bioact. Mater. (1997) 24:853-854.
Co, M.S. et al., "Genetically engineered deglycosylation of the variable domain increases the affinity of an anti-CD33 monoclonal antibody," Mol. Immunol (1993) 30:1361-1367.
Colman, P.M., "Effects of amino acid sequence changes on antibody-antigen interactions," Research in Immunology (1994) 145:33-36.
Conrouce et al., "Anti-hepatitis C virus (anti-HCV) seroconversion in patients undergoing hemodialysis: comparison of second- and third-generation anti-HCV assays," Transfusion (1994) 34(9):790-795.
Conrouce et al., "Significance of NS3 and NS5 antigens in screening for HCV antibody," Lancet (1994) 343(8901);853-854.
Cummins, B. et al., "Cardiac-specific troponin radioimmunoassay in the diagnosis of acute myocardial infarction," Am. Heart Journal (1987) 113:1333-1344.
Dall'Acqua et al., "Contribution of domain interface residues to the stability of antibody CH3 domain homodimers," Biochem. (1988) 37(26):9266-9273.
Dijkema et al., "Cloning and expression of the chromosomal immune interferon gene of the rat," EMBO J. (1985) 4(3):761-767.
During et al., "Controlled release of dopamine from a polymeric brain implant: in vivo characterization," Ann. Neurol. (1989) 25:351-356.
Eng et al., "Internal initiation stimulates production of p8 minicore, a member of a newly discovered family of hepatitis C virus vore protein isoforms," J. Virol. (2009) 83(7):3104-3114.
Erikkson, S. et al., "Comparison of cardiac troponin. Immunoassays variably affected by circulating autoantibodies," Clin. Chem. (2005) 51(5):848-855.
Ferns et al., "Characterisation of a panel of monoclonal antibodies raised against recombinant 1, 6-9, and 19 HCV core protein," J. Med. Virol. (1996) 50(3):221-229.
Filatov, V.L. et al., "Epitope mapping of anti-troponin I monoclonal antibodies," Biochem. Mol. Biol. Int. (1998) 45(6):1179-1187.
Foote, J. et al., "Antibody frame work residues affecting the confirmation of the hypervariable loops," J. Mol. Biol. (1992) 224:487-499.
Fuchs et al., "Targeting recombinant antibodies to the surface of escherichia coli: fusion to a peptidoglycan associated lipoprotein," Biotechnology (1991) 9:1370-1372.
Garrard et al., "FAB assembly and enrichment in a monovalent phage display system," Biotechnology (1991) 9:1373-1377.
Gavilondo et al., "Antibody engineering at the millennium," Biotechniques (2000) 29(1):128-145.
Giege, R. et al., "An introduction to the crystalligenesis of biological macromolecules," Crystallization of Nucleic Acids and Proteins, a Practical Approach, 2nd Edition, Oxford University Press, New York (1999) 20 1-16.
Gillies et al., "High-level expression of chimeric antibodies using adapted cDNA variable region cassettes," J. Immunol. Methods (1989) 125:191-202.
Goodson, J.M. et al., Medical Applications of Controlled Release, Chapter 6, Dental Applications (1984) 2:115-138.
Gorman et al., "The Rous sarcoma virus long terminal repeat is a strong promoter when introduced into a variety of eukaryotic cells by DNA-mediated transfection," Proc. Natl. Acad. Sci. USA (1982) 79(22):6777-6781.
Gram, H. et al., "In vitro selection and affinity maturation of antibodies from a naïve combinatorial immunoglobulin library," Proc. Natl. Acad. Sci. (1992) 89(8):3576-3580.
Green et al, "Antigen-specific human monoclonal antibodies from mice engineered with human Ig heavy and light chain YACs," Nat. Genet. (1994) 7(1):13-21.

Green et al., "Regulation of B cell development by variable gene complexity in mice reconstituted with human immunoglobulin yeast artificial chromosomes," J. Exp. Med. (1998) 188(3):483-495.
Griffiths et al., "Human anti-self antibodies with high specificity from phage display libraries," EMBO J. (1993) 12(2):725-734.
Gu et al., "Three conformational snapshots of the hepatitis C virus NS3 helicase reveal a ratchet translocation mechanism," Proc. Natl. Acad. Sci. USA (2010) 107(2):521-528.
Hawkins et al., "Selection of phage antibodies by binding affinity. Mimicking affinity maturation," J. Mol. Biol. (1992) 226(3):889-896.
Hay, B.N. et al., "Bacteriophage cloning and escherichia coli expression of a human IgM fab," Hum. Antibodies Hybridomas (1992) 3(2):81-85.
Higgins et al., "Fast and sensitive multiple sequence alignments on a micro computer," CABIOS (1989) 5(2):151-153.
Hino, "Diagnosis of hepatitis C," Intervirology (1994) 37(2):77-86.
Holliger, P. et al., "Diabodies, small bivalent and bispecific antibody fragments," Proc. Natl. Acad. Sci. USA (1993) 90(14):6444-6448.
Hoogenboom et al., "Multi-subunit proteins on the surface of filamentous phage: methodologies for displaying antibody (Fab) heavy and light chains," Nucleic Acids Res. (1991) 19(15):4133-4137.
Hoogenboom et al., "natural and designer binding sites made by phage display technology," Immunol. Today (2000) 21(8):371-378.
Hoogenboom, "Designing and optimizing library selection strategies for generating high-affinity antibodies," Trends Biotechnol .(1997) 15(2):62-70.
Hope et al., "Sequence motifs required for lipid droplet association and protein stability are 1, 6-9, and 19 unique to the hepatitis C virus core protein," J. Gen. Virol. (2000) 81(Pt 8):1913-1925.
Howard, M.A. et al., "Intracerebral drug delivery in rats with lesion-induced memory deficits," J. Neurosurg. (1989) 71:105-112.
Huber et al., "Crystallographic structure studies of an IgG molecule and an Fc fragment," Nature (1976) 264(5585):415-420.
Huse et al., "Generation of a large combinatorial library of the immunoglobulin repertoire in phage lambda," Science (1989) 246(4935):1275-1281.
Huston et al., "Protein engineering of antibody binding sites: recovery of specific activity in an anti-digoxin single-chain Fv analogue produced in Escherichia coli," Proc. Natl. Acad. Sci. USA (1988) 85(16):5879-5883.
Huston et al., "Protein engineering of single-chain Fv analogs and fusion proteins," Methods Enzymol. (1991) 203:46-88.
Hytest 1999 Product Catalog, 3 pages.
Hytest 2000 General Product Catalog, 3 pages.
Hytest 2001-2002 General Product Catalog, 3 pages.
Hytest 2001 Cardiac Markers Panel, 4 pages.
Hytest 2003 General Product Catalog, 3 pages.
Hytest 2004-2005 General Product Catalog, 3 pages.
Hytest 2004 Cardiac Markers Panel, 4 pages.
Hytest 2005-2006 General Product Catalog, 3 pages.
Hytest 2005 Markers of Cardiovascular Diseases Catalog, 4 pages.
Hytest 2006-2007—General Product Catalog, 3 pages.
Hytest 2007-2008 General Product Catalog, 3 pages.
Hytest 2007 markers of Cardiovascular Diseases Catalog, 4 pages.
Hytest 2008-2009 General Product Catalog, 3 pages.
Hytest 2008 Markers of Cardiovascular Diseases and Metabolis Syndrome, 4 pages.
International Search Report and Written Opinion for Application No. PC/US2013/77499 dated May 20, 2014 (21 pages).
International Search Report and Written Opinion for Application No. PCT/US2013/077487 dated Apr. 22, 2014 (23 pages).
International Search Report and Written Opinion for Application No. PCT/US2010/024979 dated May 6, 2010 (16 pages).
International Search Report and Written Opinion for Application No. PCT/US2013/077504 dated Jul. 1, 2014 (14 pages).
Jackson et al., "In vitro antibody maturation. Improvement of a high affinity, neutralizing antibody against IL-1 beta," J. Immunol. (1995) 154(7:3310-3319.

(56) References Cited

OTHER PUBLICATIONS

Jay et al., "Chemical synthesis of a biologically active gene for human immune interferon-gamma. Prospect for site-specific mutagenesis and structure-function studies," J. Biol. Chem. (1984) 259(10):6311-6317.
Jayaraman et al., "Polymerase chain reaction-mediated gene synthesis: synthesis of a gene coding for isozyme C of horseradish peroxidase," Proc. Natl. Acad. Sci. USA (1991) 88(10):4084-4088.
Jefferis, R. et al., "Glycosylation of recombinant antibody therapeutics," Biotechnol. Prog. (2005) 21:11-16.
Johnsson et al., "Comparison of methods for immobilization to carboxymethyl dextran sensor surfaces by analysis of the specific activity of monoclonal antibodies," J. Mol. Recognit. (1995) 8(1-2):125-131.
Johnsson et al., "Immobilization of proteins to a carboxymethyldextran-modified gold surface for biospecific interaction analysis in surface plasmon resonance sensors," Anal. Biochem. (1991) 198(2):268-277.
Jones et al. "Replacing the complementarity-determining regions in a human antibody with those from a mouse," Nature (1986) 321(6069):522-525.
Jonsson et al., "Introducing a biosensor based techology for real-time biospecific interaction analysis," Ann. Biol. Clin. (Paris) (1993) 51(1):19-26.
Jonsson et al., "Real-time biospecific interaction analysis using surface plasmon resonance and a sensor chip technology," Biotechniques (1991) 11(5):620-627.
Kabat et al, Sequences of Proteins of Immunological Interest, National Institutes of Health, Bethesda, Maryland (1987) and (1991), 4th Edition, 4 pages.
Kabat et al., "Attempts to locate complementarity-determining residues in the variable positions of light and heavy chains," Ann. NY Acad. Sci. (1971) 190:382-393.
Kabat et al., Sequences of Proteins of Immunological Interest, 5th Edition, Department of Health and Human Services, NIH Publication No. 91-3242 (1991), 11 pages.
Katrukha et al., "Degradation of cardiac troponin: implication for reliable immunodetection," Clin. Chem. (1998) 44(12):2433-2440.
Katrukha, "Troponin. Measurement: the concept of a precise immunoassay," Clin. Lab. Internat. (2006) 30(5): 14-16.
Katrukha, "New approach to standardization of human cardiac Troponin I (cTnI)," Scand. J. Clin. Lab. Invest. (1999) 59(Suppl 230):124-127.
Katrukha, "Biochemical factors influencing measurement of cardiac troponin I in serum," Clin. Chem. Lab Med. (1999) 37(11/12):1091-1095.
Katrukha, "Antibody selection strategies in cardiac troponin assays," Cardiac Markers, Second Edition 173-185.
Kaufman, R.J. et al., "Amplification and expression of sequences cotransfected with a modular dihydrofolate reductase complementary DNA gene," Mol. Biol. (1982) 159:601-621.
Kellermann et al., "Antibody discovery: the use of transgenic mice to generate human monoclonal antibodies for therapeutics," Curr. Opin. Biotechnol. (2002) 13(6):593-597.
Kettleborough et al., "Isolation of tumor cell-specific single-chain Fv from immunized mice using phage-antibody libraries and the re-construction of whole antibodies from these antibody fragments," Eur. J. Immunol. (1994) 24(4):952-958.
Kim et al., "Identifying amino acid residues that influence plasma clearance of murine IgG1 fragments by site-directed mutagenesis," Eur. J. Immunol. (1994) 24(3):542-548.
Kim et al., "Mutational analysis of the hepatitis C virus RNA helicase," J. Virology (1997) 71(12):9400-9409.
Kim et al., "Template requirements for De Novo RNA synthesis by hepatitis C virus nonstructural protein 5B polymerase on the viral X RNA," J. Virology (2002) 76(14):6944-6956.
Kim, D. et al., "Mutational analysis of the hepatitis C virus RNA helicase," J. Virology (1997) 71(12):9400-9409.
Kim, M. et al., "Template requirements for De Novo RNA synthesis by Hepatitus C virus nonstructural protein 5B polymerase on the viral X RNA," J. Virol. (2002) 76(14):6944-6945.
Kipriyanov, S.M. et al., "Single-chain antibody streptavidin fusions: tetrameric bifunctional ScFv-complexes with biotin binding activity and enhanced affinity to antigen," Human Antibodies and Hybridomas (1995) 6:93-101.
Kipriyanov, S.M. et al., "Recombinant single-chain Fv fragments carrying c-terminal cysteine residues: production of bivalent and biotinylated miniantibodies," Mol. Immunol. (1994) 31:1047-1058.
Kleinman et al., "Increased detection of hepatitis C virus (HCV)-infected blood donors by a multiple-antigen HCV enzyme immunoassay," Transfusion (1992) 32(9):805-813.
Kohler et al., "Continuous cultures of fused cells secreting antibody of predefined specificity," Nature (1975) 256(5517):495-497.
Koniermann, Antibody Engineering, p. 790, Springer-Verlag, New York (2001).
Kuo et al., "An assay for circulating antibodies to a major etiologic virus of human non-A, non-B hepatitis," Science (1989) 244(4902):362-364.
Kyte et al., "A simple method for displaying the hydropathic character of a protein," J. Mol. Biol. (1982) 157(1):105-132.
Lam et al., "Microencapsulation of recombinant humanized monoclonal antibody for local delivery," Proc. Int'l Symp. Control Rel. Bioact. Mater. (1997) 24:759-760.
Langer et al., "Chemical physical structure of polymers as carriers for controlled release of bioactive agents: a review," J. Macromol. Sci. Rev. Macromol. Chem. (1983) 23:61-126.
Langer et al., "New methods of drug delivery," Science (1990) 249:1527-1533.
Laperche et al., "Simultaneous detection of hepatitis C virus (HCV) core antigen and anti- 1, 6-9, and 19 HCV antibodies improves the early detection of HCV infection," J. Clin. Microbiol. (2005) 43(8):3877-3883.
Lee et al., "Increased detection of hepatitis C virus infection in commercial plasma donors by a third-generation screening assay," Transfusion (1995) 35(10):845-849.
Levy, R.J. et al "Inhibition of calcification of bioprosthetic heart valves by local controlled-release diphosphonate," Science (1985) 228:190-192.
Little et al., "Of mice and men: hybridoma and recombinant antibodies," Immunol. Today (2000) 21(8):364-370.
MacCallum et al., "Antibody-antigen interactions: contact analysis and binding site topography," J. Mol. Biol. (1996) 262(5):732-745.
Marchalonis et al., "Evolutionary factors in the emergence of the combinatorial germline antibody repertoire," Adv. Exp. Med. Biol. (2001) 484:13-30.
Marks et al., "By-passing immunization. building high affinity human antibodies by chain shuffling," Biotechnology (NY) (1992) 10(7):779-783.
Mattingly, "Chemiluminescent 10-methyl-acridinium-9-(N-sulphonylcarboxamide) salts> Synthesis and kinetics of light emission," J. Biolumin. Chemilumin (1991) 6(2):107-114.
McCafferty et al., "Phage antibodies: filamentous phage displaying antibody variable domains," Nature (1990) 348(6301):552-554.
McCapra et al., "Chemiluminescence involving peroxide decompositions," Photochemistry and Photobiology 1965) 4:1111-1121.
Medical Applicants of Controlled Release, Langer and Wise (eds), CRC Press, Boca Raton, Florida (1974).
Mendez et al., "Functional transplant of megabase human immunoglobulin loci recapitulates human antibody response in mice," Nat. Genet. (1997) 15(2):146-156.
Mimms et al., "Specificity of anti-HCV ELISA assessed by reactivity to three immunodominant HCV regions," Lancet (1990) 336(8730):1590-1591.
Mizushima et al., "pEF-BOS, a powerful mammalian expression vector," Nucleic Acids Research (1990) 18:5322-5323.
Morota et al., "A new sensitive and automated chemiluminescent microparticle immunoassay for quantitative determination of hepatitis C virus core antigen," J. Virol. Methods (2009) 157(1):8-14.
Morrison et al., "Numeric human antibody molecules: mouse antigen-binding domains with human constant region domains," Proc. Natl. Acad. Sci. (1984) 81:6851-6855.

(56) References Cited

OTHER PUBLICATIONS

Morrison, "Transfectomas provide novel chimeric antibodies," Science (1985) 229(4719):1202-1207.
Mullinax et al., "Expression of a heterodimeric Fab antibody protein in one cloning step," Biotequnicues (1992) 12(6):864-869.
Needleman et al., J. Mol. Biol. (1970) 48:443.
Neuberger et al., "Recombinant antibodies possessing novel effector functions," Nature (1984) 312:604-608.
Ning et al., "Intratumoral radioimmunotherapy of a human colon cancer xenograft using a sustained-released gel," Radiotherapy and Oncology (1996) 39:179-189.
Oellerich, "Enzyme-immunoassay: a review," J. Clin. Chem. Clin. Biochem. (1984) 22(12):895-904.
Ogata et al., "Nucleide sequence and mutation rate of the H strain of hepatitis C virus," Proc. Natl. Acad. Sci. USA (1991) 88(8):3392-3396.
Oi et al., "Chimeric antibodies," BioTechniques (1986) 4(3):214-311.
Padlan et al., "A possible procedure for reducing the immunogenicity of antibody variable domains while preserving their ligand-binding properties," Mol. Immunol. (1991) 28(4-5):489-498.
Padlan et al., "Identification of specificity-determining residues in antibodies," FASEB J. (1995) 9(1):133-139.
Panina-Bordignon et al., "Universally immunogenic T cell epitopes: promiscuous binding to human MHC class II and promiscuous recognition by T cells," Eur. J. Immunol. (1989) 19(12):2237-2242.
Paul, Fundamental Immunology, 3rd Edition (1993) pp. 292-295, under the heading "FV Structure and Diversity in Three Dimensions".
Pearson et al., "Improved tools for biological sequence comparison," Proc. Natl. Acad. Sci. (1988) 85:2444-2448.
Peronnet et al., "Isoelectric point determination of cardiac troponin I forms present 1n plasma from patients with myocardial infarction," (2007) 377(1-2):243-247.
Persic et al., "An integrated vector system for the eukaryotic expression of antibodies or their fragments after selection from phage display libraries," Gene (1997) 187(1):9-18.
Poljak, "Production and structure of diabodies," Structure (1994) 2(12):1121-1123.
Presta et al., "Humanization of an antibody directed against IgE," J. Immunol. (1993) 151(5):2623-2632.
Queen et al., "A humanized antibody that binds to the interleukin 2 receptor," Proc. Natl. Acad. Sci. USA (1989) 86(24):10029-10033.
Quinn, F. et al., "36 Bulk Reagent Random-access analyzer: Architect; 2000," The Immunoassay Handbook, 2nd Edition (2001) 363-367.
Rama, D. et al., "Epitope localization of monoclonal antibodies used in human troponin I immunoenzymometric assay," Hybridoma (1997) 16(2):153-157.
Razavi et al., "Stable and versatile active acridinium esters I," Luminescence (2000) 15(4):239-244.
Razavi et al., "Stable and versatile active acridinium esters II," Luminescence (2000) 15(4):245-249.
Reverse Translate a Protein (1998) (www.vivo.colostae.edu/molkit/translate/index.html), 1 page.
Riechmann et al., "Reshaping human antibodies for therapy," Nature (1988) 332(6162):323-327.
Roberts et al., "RNA-peptide fusions for the in vitro selection of peptides and proteins," Proc. Natl. Acad. Sci. USA (1997) 94(23):12297-12302.
Roguska et al., "Human ization of murine monoclonal antibodies through variable domain resurfacing," Proc. Natl. Acad. Sci. USA (1994) 91(3):969-973.
Rudikoff et al., "Single amino acid substitution altering antigen-binding specificity," Proc. Natl. Acad. Sci USA (1982) 79(6):1979-1983.
Sallberg et al., "Immunogenicity and antigenicity of the ATPase/helicase domain of the hepatitis C virus non-structural 3 protein," J. Gen. Virol. (1996) 77(Pt 11):2721-2728.
Sambrook et al., A Laboratory Manual, Molecular Cloning, 2nd Edition, Cold Spring Harbor Laboratory Press, Cold Spring Harbor, New York (1989) 30 pages.
Saudek et al., "A preliminary trial of the programmable implantable medication system for insulin delivery," N. Engl. J. Med. (1989) 321:574-579.
Sawai et al., "Direct production of the Fab fragment derived from the sperm immobilizing antibody using polymerase chain reaction and cDNA expression vectors," Am. J. Reprod. Immunol. (1995) 34(1):26-34.
Schier et al., "Identification of functional and structural amino-acid residues by parsimonious mutagenesis," Gene (1996) 169(2):147-155.
Schiestl et al., "High efficiency transformation of intact yeast cells using single stranded nucleic acids as a carrier," Current Genetics (1989) 16(5-6):339-346.
Seligmann et al., "Immunochemical study of a human myeloma IgG1 half molecule," Ann. Immunol. (1978) 129:855-870.
Shah et al., "Combination HCV core antigen and antibody assay on a fully automated chemiluminescence analyzer," Transfusion (2003) 43:1067-1074.
Shapiro et al., "DNA target motifs of somatic mutagenesis in antibody genes," Crit. rEv. Immunol. (2002) 22(3): 183 -200.
Shavinskaya, A. et al., "The lipid droplet binding domain of hepatitis C virus core protein is a major determinant for efficient virus assembly," J. Biol. Chem. (2007) 282(51):37158-37169.
Shields, R.L. et al., "Lack of fucose on human IgG1 N-linked oligosaccharide improves binding to human FcγRIII and antibody dependent cellular toxicity," J. Biol. Chem. (2002) 277:26733-26740.
Shu et al., "Secretion of a single-gene-encoded immunoglobulin from myeloma cells," Proc. Natl. Acad. Sci. USA (1993) 90(17):7995-7999.
Sims et al., "A humanized CD18 antibody can block function without cell destruction," J. Immunol. (1993) 151(4):2296-2308.
Skerra et al., "Assembly of a functional immunoglobulin Fv fragment in *Escherichia coli*," Science (1988) 240(4855): 1038-1041.
Smith et al., "Comparison of biosequences," Appl. Math. (1981) 2:482-489.
Song et al., "Antibody mediated lung targeting of long-circulating emulsions," PDA Journal of Pharmaceutical Science and Technology (1995) 50:372-377.
Studnicka et al, "Human-engineered monoclonal antibodies retain full specific binding activity by preserving non-CDR complementarity-odulating residues," Protein Eng. (1994) 7(6):805-814.
Table Showing Codon-amino acid Abbreviations (www.hgmd.cf.ac.uk/docs/cd_amino.html), printed Jan. 23, 2013, 3 pages.
Tai et al., "Structural-based mutational analysis of the hepatitis C Virus NS3 helicase," J. Virology (2001) 74(17):8289-8207.
Takeda et al., "Constsruction of chimaeric processed immunoglobulin genes containing mouse variable and human constant region sequences," Nature (1985) 314:452-454.
Tamura et al., "MEGA5: molecular evolutionary genetics analysis using maximum likelihood, evolutionary distance, and maximum parsimony methods," Mol. Biol. Evol. (2011) 28(10):2731-2739.
Taylor et al., "A transgenic mouse that expresses a diversity of human sequence heavy and light chain immunoglobulins," Nucl. Acids Res. (1992) 20(23):6287-6295.
Thies et al., "Folding and association of the antibody domain CH3: prolyl isomerization preceeds dimerization," J. Mol. Biol. (1999) 293(1):67-79.
Thompson et al., "CLUSTAL W: improving the sensitivity of progressive multiple sequence alignment through sequence weighting, position-specific gap penalties and weight matrix choice," Nucl. Acids. Res. (1994) 22(22):4673-4680.
Umana et al., "Engineered glycoforms of an antineuro-blastoma. IgG1 with optimized antibody-dependent cellular cytotoxic activity," Nat. Biotech. (1999) 17:176-181.
Urlaub et al., "Isolation of Chinese hamster cell mutants deficient in dehydrofolate reductase activity," Proc. Natl. Acad. Sci. (1980) 77:4216-4220.
Verhoeyen et al., "Reshaping human antibodies: grafting an antilysozyme activity," Science (1988) 239(4847): 1534-1536.

(56) References Cited

OTHER PUBLICATIONS

Wallemacq et al., "Evaluation of the new AxSYM cyclosporine assay: comparison with TDx monoclonal whole blood and EMIT cyclosporine assays," Clin. Chem. (1999) 45(3):432-435.
Wallick, S.C. et al., "Glycosylation of a VH residue of a monoclonal antibody against alpha(1-6) dextran increases its affinity for antigens," Exp. Med. (1988) 168:1099-1109.
Ward et al., "Binding activities of a repertoire of single immunoglobulin variable domains secreted from *Escherichia coli*," Nature (1989) 341(6242):544-546.
West et al., "Crystal structure and immunologbulin G binding properties of the human major histocompatibility complex-related Fc receptor," Biochem. (2000) 39(32):9698-9708.
Winnaker et al., From Genes to Cones, Verlagsgesellschaft, Weinheim, Germany (1987).
Wright, A. et al., "Antibody variable region glycosylation: position effects on antigen binding and carbohydrate structure," EMBO J. (1991) 10:2717-2723.
Wu et al, "Receptor-mediated in vitro gene transformation by a soluble DNA carrier system," J. Biol. Chem. (1987) 262:4429-4432.
Yatscoff et al., "Abbott TDx monoclonal antibody assay evaluated for measuring cyclosporine in whole blood," Clin. Chem. (1990) 36(11):1969-1973.
Yelton et al., "Affinity maturation of the BR96 anti-carcinoma antibody by codon-based mutagenesis," J. Immunol. (1995) 155(4):1994-2004.
Ylikotila et al., "Utilization of recombinant fab fragments in a cTnI immunoassay conducted in spot wells," Clinc. Biochem. (2006) 39:843-850.
Zapata et al., "Engineering linear F(ab)2 fragments for efficient production in escherichia coli and enhanced antiproliferative activity," Protein Eng. (1995) 8(10):1057-1062.
U.S. Office Action for U.S. Appl. No. 14/139,053 dated Oct. 6, 2015 (15 pages).
U.S. Office Action for U.S. Appl. No. 14/138,991 dated Sep. 21, 2015 (9 pages).
U.S. Office Action for U.S. Appl. No. 14/139,108 dated Jan. 21, 2015 (11 pages).
U.S. Notice of Allowance for U.S. Appl. No. 14/139,108 dated Jul. 17, 2015 (5 pages).
U.S. Office Action for U.S. Appl. No. 12/391,937 dated Feb. 24, 2011 (15 pages).
U.S. Notice of Allowance for U.S. Appl. No. 12/391,937 dated Aug. 5, 2011 (13 pages).
U.S. Notice of Allowance for U.S. Appl. No. 14/035,420 dated Feb. 27, 2015 (8 pages).
U.S. Office Action for U.S. Appl. No. 14/035,420 dated Mar. 18, 2014 (9 pages).
U.S. Office Action for U.S. Appl. No. 90/012,377 dated Feb. 6, 2013 (15 pages).
European Extended Search Report for Application No. 13878042.4 dated Sep. 29, 2016 (8 pages).
European Extended Search Report for Application No. 13880371.3 dated Oct. 10, 2016 (13 pages).
U.S. Office Action for U.S. Appl. No. 14/139,053 dated May 4, 2016 (8 pages).
U.S. Office Advisory Action for U.S. Appl. No. 14/139,053 dated Jul. 20, 2016 (5 pages).
Co-pending U.S. Appl. No. 15/079,013, filed Mar. 23, 2016, Robert Ziemann.
U.S. Notice of Allowance for U.S. Appl. No. 14/138,991 dated Feb. 23, 2016 (7 pages).
U.S. Office Action for U.S. Appl. No. 14/461,082 dated Apr. 15, 2016 (7 pages).
U.S. Office Action for U.S. Appl. No. 14/139,053 dated Oct. 21, 2016 (6 pages).
U.S. Notice of Allowance for U.S. Appl. No. 14/139,053 dated May 8, 2017 (10 pages).
European Patent Office for Application No. 13878437.6 dated Sep. 1, 2017 (6 pages).
United States Patent Office Action for U.S. Appl. No. 14/461,082 dated Aug. 9, 2017 (5 pages).

\* cited by examiner

Position of HCV NS3 Recombinant Proteins

| Label | Region |
|---|---|
| NS3 | (HCV 1027-1206, NS3 1-180) |
| 9NB49 | (HCV 1192-1457, NS3 166-431) |
| 9NB49-1 | (HCV 1192-1453, NS3 166-427) |
| d1 | (HCV 1192-1356, NS3 166-330) |
| d2* | (HCV 1357-1457, NS3 331-431) |
| d3* | (HCV 1512-1658, NS3 486-632) |
| d1d2ext | (HCV 1192-1510, NS3 166-484) |
| d2d3* | (HCV 1357-1658, NS3 331-632) |
| d2ext* | (HCV 1357-1510, NS3 331-484) |
| d1d2d3 (NS3h) | (HCV 1192-1658, NS3 166-632) |
| extd3* | (HCV 1458-1658, NS3 432-632) |

*(HCV 1192-1215, NS3 166-189)

Numbered according to: Kuiken et al. (Hepatology, 2006, 44(5):1355-1361)

Regions: Protease (HCV 1027-1206), Chimeric Mab epitope, Helicase
HCV Polyprotein positions: 1027, 1127, 1227, 1327, 1427, 1527, 1627, 1657
NS3 Protein positions: 0, 100, 200, 300, 400, 500, 600, 631

SEQUENCE LISTING

<160> NUMBER OF SEQ ID NOS: 125

<210> SEQ ID NO 1
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
```

```
gaaatcccgt tctacggtaa agctatcccg ctcgaggtta tcaaggtgg tcgtcacctg    600 attttctgcc actctaaaaa aaaatgcgac gaactggctg ctaagcttgt tgctctgggt    660
atcaacgctg ttgcttacta ccgtggtctg gacgtttctg ttatcccgac ttctggtgac    720
gttgttgttg tggccactga cgctctgatg actggttaca ctggtgactt cgactctgtt    780
atcgattgca cacttgc                                                   798
```

<210> SEQ ID NO 2
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys
            260                 265

<210> SEQ ID NO 3
<211> LENGTH: 798
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 3

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga cccgtctgt tgctgctact ctgggtttcg gcgcctacat gtctaaagct      240
cacggtatcg acccgaacat tcgtactggt gtacgtacta tcactactgg ttctccgatc     300
acttactcta cttacggtaa attcctggct gacggtggta gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca acacttgc                                                   798
```

<210> SEQ ID NO 4
<211> LENGTH: 266
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Ala Val Asp Phe Ile Pro Val Glu Asn Leu Glu Thr Thr Met Arg Ser
  1               5                  10                  15

Pro Val Phe Thr Asp Asn Ser Ser Pro Val Val Pro Gln Ser Phe
             20                  25                  30

Gln Val Ala His Leu His Ala Pro Thr Gly Ser Gly Lys Ser Thr Lys
         35                  40                  45

Val Pro Ala Ala Tyr Ala Ala Gln Gly Tyr Lys Val Leu Val Leu Asn
     50                  55                  60

Pro Ser Val Ala Ala Thr Leu Gly Phe Gly Ala Tyr Met Ser Lys Ala
 65                  70                  75                  80

His Gly Ile Asp Pro Asn Ile Arg Thr Gly Val Arg Thr Ile Thr Thr
                 85                  90                  95

Gly Ser Pro Ile Thr Tyr Ser Thr Tyr Gly Lys Phe Leu Ala Asp Gly
            100                 105                 110

Gly Ser Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190
```

Val Ile Lys Gly Gly Arg His Leu Ile Phe Cys His Ser Lys Lys Lys
            195                 200                 205

Cys Asp Glu Leu Ala Ala Lys Leu Val Ala Leu Gly Ile Asn Ala Val
        210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys
            260                 265

<210> SEQ ID NO 5
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gctgttgact ttatcccggt tgaaaatctc gagactacta tgcgttctcc ggttttcact    60
gacaactctt ctccgccggt tgttccgcag tctttccagg ttgctcacct gcatgctccg   120
actggttctg gtaaatctac taaagttcca gctgcttacg ctgctcaggg ttacaaagtt   180
ctggttctga acccgtctgt tgctgctact ctgggtttcg gcgcctacat gtctaaagct   240
cacggtatcg acccgaacat tcgtactggt gtacgtacta tcactactgg ttctccgatc   300
acttactcta cttacggtaa attcctggct gacggtggtt gctctggtgg tgcttacgat   360
atcatcatca gcgacgaatg ccactctact gacgctactt ctatcctggg tatcggtacc   420
gttctggacc aggctgaaac tgcaggtgct cgtctggttg ttctggctac tgctactccg   480
ccgggttctg ttactgttcc gcacccgaac atcgaagaag ttgctctgtc gactactggt   540
gaaatcccgt tctacggtaa agctatcccg ctcgaggtta tcaaaggtgg tcgtcacctg   600
atttttctgcc actctaaaaa aaaatgcgac gaactggctg ctaagcttgt tgctctgggt   660
atcaacgctg ttgcttacta ccgtggtctg gacgtttctg ttatcccgac ttctggtgac   720
gttgttgttg tggccactga cgctctgatg actggttaca ctggtgactt cgactctgtt   780
atcgattgca acacttgc                                                 798

<210> SEQ ID NO 6
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Ser Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys
                260                 265

<210> SEQ ID NO 7
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct cgacgaaag ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca acacttgc                                                   798

<210> SEQ ID NO 8
<211> LENGTH: 266

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Ala Val Asp Phe Ile Pro Val Glu Asn Leu Glu Thr Thr Met Arg Ser
1               5                   10                  15
Pro Val Phe Thr Asp Asn Ser Ser Pro Val Pro Gln Ser Phe
            20                  25                  30
Gln Val Ala His Leu His Ala Pro Thr Gly Ser Gly Lys Ser Thr Lys
        35                  40                  45
Val Pro Ala Ala Tyr Ala Ala Gln Gly Tyr Lys Val Leu Val Leu Asn
50                  55                  60
Pro Ser Val Ala Ala Thr Leu Gly Phe Gly Ala Tyr Met Ser Lys Ala
65                  70                  75                  80
His Gly Ile Asp Pro Asn Ile Arg Thr Gly Val Arg Thr Ile Thr Thr
                85                  90                  95
Gly Ser Pro Ile Thr Tyr Ser Thr Tyr Gly Lys Phe Leu Ala Asp Gly
            100                 105                 110
Gly Cys Ser Gly Gly Ala Tyr Asp Ile Ile Ile Cys Asp Glu Ser His
        115                 120                 125
Ser Thr Asp Ala Thr Ser Ile Leu Gly Ile Gly Thr Val Leu Asp Gln
130                 135                 140
Ala Glu Thr Ala Gly Ala Arg Leu Val Val Leu Ala Thr Ala Thr Pro
145                 150                 155                 160
Pro Gly Ser Val Thr Val Pro His Pro Asn Ile Glu Glu Val Ala Leu
                165                 170                 175
Ser Thr Thr Gly Glu Ile Pro Phe Tyr Gly Lys Ala Ile Pro Leu Glu
            180                 185                 190
Val Ile Lys Gly Gly Arg His Leu Ile Phe Cys His Ser Lys Lys Lys
        195                 200                 205
Cys Asp Glu Leu Ala Ala Lys Leu Val Ala Leu Gly Ile Asn Ala Val
210                 215                 220
Ala Tyr Tyr Arg Gly Leu Asp Val Ser Val Ile Pro Thr Ser Gly Asp
225                 230                 235                 240
Val Val Val Val Ala Thr Asp Ala Leu Met Thr Gly Tyr Thr Gly Asp
                245                 250                 255
Phe Asp Ser Val Ile Asp Cys Asn Thr Cys
            260                 265
```

<210> SEQ ID NO 9
<211> LENGTH: 798
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga accgtctgt tgctgctact ctgggtttcg gcgcctacat gtctaaagct      240
cacggtatcg acccgaacat tcgtactggt gtacgtacta tcactactgg ttctccgatc     300
```

```
acttactcta cttacggtaa attcctggct gacggtggtt gctctggtgg tgcttacgat    360
atcatcatct gcgacgaatg ccactctact gacgctactt ctatcctggg tatcggtacc    420
gttctggacc aggctgaaac tgcaggtgct cgtctggttg ttctggctac tgctactccg    480
ccgggttctg ttactgttcc gcacccgaac atcgaagaag ttgctctgtc gactactggt    540
gaaatcccgt tctacggtaa agctatcccg ctcgaggtta tcaaaggtgg tcgtcacctg    600
attttcagcc actctaaaaa aaaatgcgac gaactggctg ctaagcttgt tgctctgggt    660
atcaacgctg ttgcttacta ccgtggtctg gacgtttctg ttatcccgac ttctggtgac    720
gttgttgttg tggccactga cgctctgatg actggttaca ctggtgactt cgactctgtt    780
atcgattgca acacttgc                                                  798
```

<210> SEQ ID NO 10
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Ala Val Asp Phe Ile Pro Val Glu Asn Leu Glu Thr Thr Met Arg Ser
1               5                   10                  15

Pro Val Phe Thr Asp Asn Ser Ser Pro Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Ser His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys
```

<210> SEQ ID NO 11
<211> LENGTH: 798
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
gctgttgact ttatcccggt tgaaaatctc gagactacta tgcgttctcc ggttttcact    60
gacaactctt ctccgccggt tgttccgcag tctttccagg ttgctcacct gcatgctccg   120
actggttctg gtaaatctac taagttcca gctgcttacg ctgctcaggg ttacaaagtt   180
ctggttctga acccgtctgt tgctgctact ctgggtttcg gcgcctacat gtctaaagct   240
cacggtatcg acccgaacat tcgtactggt gtacgtacta tcactactgg ttctccgatc   300
acttactcta cttacggtaa attcctggct gacggtggtt gctctggtgg tgcttacgat   360
atcatcatct gcgacgaatg ccactctact gacgctactt ctatcctggg tatcggtacc   420
gttctggacc aggctgaaac tgcaggtgct cgtctggttg ttctggctac tgctactccg   480
ccgggttctg ttactgttcc gcacccgaac atcgaagaag ttgctctgtc gactactggt   540
gaaatcccgt ctacggtaa agctatcccg ctcgaggtta tcaaaggtgg tcgtcacctg   600
attttctgcc actctaaaaa aaaaagcgac gaactggctg ctaagcttgt tgctctgggt   660
atcaacgctg ttgcttacta ccgtggtctg gacgtttctg ttatcccgac ttctggtgac   720
gttgttgttg tggccactga cgctctgatg actggttaca ctggtgactt cgactctgtt   780
atcgattgca acacttgc                                                 798
```

<210> SEQ ID NO 12
<211> LENGTH: 266
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Ala Val Asp Phe Ile Pro Val Glu Asn Leu Glu Thr Thr Met Arg Ser
1               5                   10                  15
Pro Val Phe Thr Asp Asn Ser Ser Pro Val Val Pro Gln Ser Phe
            20                  25                  30
Gln Val Ala His Leu His Ala Pro Thr Gly Ser Gly Lys Ser Thr Lys
        35                  40                  45
Val Pro Ala Ala Tyr Ala Ala Gln Gly Tyr Lys Val Leu Val Leu Asn
    50                  55                  60
Pro Ser Val Ala Ala Thr Leu Gly Phe Gly Ala Tyr Met Ser Lys Ala
65                  70                  75                  80
His Gly Ile Asp Pro Asn Ile Arg Thr Gly Val Arg Thr Ile Thr Thr
                85                  90                  95
Gly Ser Pro Ile Thr Tyr Ser Thr Tyr Gly Lys Phe Leu Ala Asp Gly
            100                 105                 110
Gly Cys Ser Gly Gly Ala Tyr Asp Ile Ile Ile Cys Asp Glu Cys His
        115                 120                 125
Ser Thr Asp Ala Thr Ser Ile Leu Gly Ile Gly Thr Val Leu Asp Gln
    130                 135                 140
```

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
            165                 170                 175

Ser Thr Thr Gly Glu Ile Pro Phe Tyr Gly Lys Ala Ile Pro Leu Glu
        180                 185                 190

Val Ile Lys Gly Gly Arg His Leu Ile Phe Cys His Ser Lys Lys Lys
    195                 200                 205

Ser Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys
            260                 265

<210> SEQ ID NO 13
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gctgttgact ttatcccggt tgaaaatctc gagactacta tgcgttctcc ggttttcact        60
gacaactctt ctccgccggt tgttccgcag tctttccagg ttgctcacct gcatgctccg       120
actggttctg gtaaatctac taaagttcca gctgcttacg ctgctcaggg ttacaaagtt       180
ctggttctga acccgtctgt tgctgctact ctgggtttcg gcgcctacat gtctaaagct       240
cacggtatcg acccgaacat tcgtactggt gtacgtacta tcactactgg ttctccgatc       300
acttactcta cttacggtaa attcctggct gacggtggta gctctggtgg tgcttacgat       360
atcatcatca gcgacgaaag ccactctact gacgctactt ctatcctggg tatcggtacc       420
gttctggacc aggctgaaac tgcaggtgct cgtctggttg ttctggctac tgctactccg       480
ccgggttctg ttactgttcc gcacccgaac atcgaagaag ttgctctgtc gactactggt       540
gaaatcccgt tctacggtaa agctatcccg ctcgaggtta tcaaaggtgg tcgtcacctg       600
attttctgcc actctaaaaa aaaatgcgac gaactggctg ctaagcttgt tgctctgggt       660
atcaacgctg ttgcttacta ccgtggtctg gacgtttctg ttatcccgac ttctggtgac       720
gttgttgttg tggccactga cgctctgatg actggttaca ctggtgactt cgactctgtt       780
atcgattgca acacttgc                                                    798

<210> SEQ ID NO 14
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
    35                  40                  45

Val Pro Ala Ala Tyr Ala Ala Gln Gly Tyr Lys Val Leu Val Leu Asn
 50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Ser Ser Gly Gly Ala Tyr Asp Ile Ile Ile Ser Asp Glu Ser His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys
                260                 265

<210> SEQ ID NO 15
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gctgttgact ttatcccggt tgaaaatctc gagactacta tgcgttctcc ggttttcact     60
gacaactctt ctccgccggt tgttccgcag tctttccagg ttgctcacct gcatgctccg    120
actggttctg gtaaatctac taaagttcca gctgcttacg ctgctcaggg ttacaaagtt    180
ctggttctga acccgtctgt tgctgctact ctgggtttcg gcgcctacat gtctaaagct    240
cacggtatcg acccgaacat tcgtactggt gtacgtacta tcactactgg ttctccgatc    300
acttactcta cttacggtaa attcctggct gacggtggtt gctctggtgg tgcttacgat    360
atcatcatct cgacgaatg ccactctact gacgctactt ctatcctggg tatcggtacc    420
gttctggacc aggctgaaac tgcaggtgct cgtctggttg ttctggctac tgctactccg    480
ccgggttctg ttactgttcc gcacccgaac atcgaagaag ttgctctgtc gactactggt    540
gaaatcccgt tctacggtaa agctatcccg ctcgaggtta tcaaaggtgg tcgtcacctg    600
attttcagcc actctaaaaa aaaaagcgac gaactggctg ctaagcttgt tgctctgggt    660

```
atcaacgctg ttgcttacta ccgtggtctg gacgtttctg ttatcccgac ttctggtgac      720
gttgttgttg tggccactga cgctctgatg actggttaca ctggtgactt cgactctgtt      780
atcgattgca acacttgc                                                    798
```

<210> SEQ ID NO 16
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Ser His Ser Lys Lys Lys
        195                 200                 205

Ser Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys
            260                 265
```

<210> SEQ ID NO 17
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
gctgttgact ttatcccggt tgaaaatctc gagactacta tgcgttctcc ggttttcact       60
gacaactctt ctccgccggt tgttccgcag tctttccagg ttgctcacct gcatgctccg      120
actggttctg gtaaatctac taaagttcca gctgcttacg ctgctcaggg ttacaaagtt      180
ctggttctga acccgtctgt tgctgctact ctgggtttcg gcgcctacat gtctaaagct      240
cacggtatcg acccgaacat tcgtactggt gtacgtacta tcactactgg ttctccgatc      300
acttactcta cttacggtaa attcctggct gacggtggta gctctggtgg tgcttacgat      360
atcatcatca gcgacgaaag ccactctact gacgctactt ctatcctggg tatcggtacc      420
gttctggacc aggctgaaac tgcaggtgct cgtctggttg ttctggctac tgctactccg      480
ccgggttctg ttactgttcc gcacccgaac atcgaagaag ttgctctgtc gactactggt      540
gaaatcccgt tctacggtaa agctatcccg ctcgaggtta tcaaaggtgg tcgtcacctg      600
attttcagcc actctaaaaa aaaagcgac gaactggctg ctaagcttgt tgctctgggt      660
atcaacgctg ttgcttacta ccgtggtctg gacgtttctg ttatcccgac ttctggtgac      720
gttgttgttg tggccactga cgctctgatg actggttaca ctggtgactt cgactctgtt      780
atcgattgca acacttgc                                                    798
```

<210> SEQ ID NO 18
<211> LENGTH: 266
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Ser Ser Gly Gly Ala Tyr Asp Ile Ile Ile Ser Asp Glu Ser His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Ser His Ser Lys Lys Lys
        195                 200                 205

Ser Asp Glu Leu Ala Ala Lys Leu Val Ala Leu Gly Ile Asn Ala Val
```

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys
            260                 265

<210> SEQ ID NO 19
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

| | | | | | |
|---|---|---|---|---|---|
| gctgttgact | ttatcccggt | tgaaaatctc | gagactacta | tgcgttctcc | ggttttcact | 60 |
| gacaactctt | ctccgccggt | tgttccgcag | tctttccagg | ttgctcacct | gcatgctccg | 120 |
| actggttctg | gtaaatctac | taaagttcca | gctgcttacg | ctgctcaggg | ttacaaagtt | 180 |
| ctggttctga | acccgtctgt | tgctgctact | ctgggtttcg | cgcctacat | gtctaaagct | 240 |
| cacggtatcg | acccgaacat | tcgtactggt | gtacgtacta | tcactactgg | ttctccgatc | 300 |
| acttactcta | cttacggtaa | attcctggct | gacggtggtt | gctctggtgg | tgcttacgat | 360 |
| atcatcatct | gcgacgaatg | ccactctact | gacgctactt | ctatcctggg | tatcggtacc | 420 |
| gttctggacc | aggctgaaac | tgcaggtgct | cgtctggttg | ttctggctac | tgctactccg | 480 |
| ccgggttctg | ttactgttcc | gcacccgaac | atcgaagaag | ttgctctgtc | gactactggt | 540 |
| gaaatcccgt | tctacggtaa | agctatcccg | ctcgaggtta | tcaaaggtgg | tcgtcacctg | 600 |
| attttctgcc | actctaaaaa | aaaatgcgac | gaactggctg | ctaagcttgt | tgctctgggt | 660 |
| atcaacgctg | ttgcttacta | ccgtggtctg | gacgtttctg | ttatcccgac | ttctggtgac | 720 |
| gttgttgttg | tggccactga | cgctctgatg | actggttaca | ctggtgactt | cgactctgtt | 780 |
| atcgattgca | acacttgcgt | tactcagacc | gtagatttta | gcctggaccc | gactttcact | 840 |
| atcgaaacga | tcaccctgcc | gcaggatgca | gtttcccgta | cccagcgtcg | tggccgtacc | 900 |
| ggtcgcggca | aaccgggtat | ttaccgtttc | gtggcgccgg | cgagcgtcc | atccggtatg | 960 |
| ttcgatagct | ctgttctgtg | tgagtgttat | gacgcgggtt | gcgcgtggta | cgaactgact | 1020 |
| ccggctgaaa | ctactgtacg | cctgcgtgca | tacatgaata | cgcccgggtct | gccggtgtgt | 1080 |
| caagaccacc | tggaattttg | ggaaggtgtc | tttactggcc | tgacccatat | cgacgcacac | 1140 |
| tttctgtccc | agactaaaca | gtctggtgaa | aacctgccgt | acctggtggc | gtatcaagcc | 1200 |
| actgtgtgcg | cccgtgcgca | ggcgccgcca | ccgagctggg | accaaatgtg | gaagtgcctg | 1260 |
| atccgtctga | aaccgaccct | gcacggtccg | acgccactgc | tgtaccgcct | gggtgcagtg | 1320 |
| cagaacgaaa | tcacgctgac | gcaccgggtc | actaaataca | ttatgacttg | catgagcgca | 1380 |
| gacctggaag | tggtgacttc | c | | | | 1401 |

<210> SEQ ID NO 20
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 20

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
            35                  40                  45

Val Pro Ala Ala Tyr Ala Ala Gln Gly Tyr Lys Val Leu Val Leu Asn
50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415
```

```
Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
    450                 455                 460

Val Thr Ser
465

<210> SEQ ID NO 21
<211> LENGTH: 495
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taagttccca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
ccgggttctg ttact                                                      495

<210> SEQ ID NO 22
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
    130                 135                 140
```

Ala Glu Thr Ala Gly Ala Arg Leu Val Val Leu Ala Thr Ala Thr Pro
145                 150                 155                 160

Pro Gly Ser Val Thr
            165

<210> SEQ ID NO 23
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
gctgttgact ttatcccggt tgaaaatctc gagactacta tgcgttctcc ggttttcact      60
gacaactctt ctgttccgca cccgaacatc gaagaagttg ctctgtcgac tactggtgaa    120
atcccgttct acggtaaagc tatcccgctc gaggttatca aggtggtcg tcacctgatt     180 ttctgccact ctaaaaaaaa atgcgacgaa ctggctgcta agcttgttgc tctgggtatc    240
aacgctgttg cttactaccg tggtctggac gtttctgtta cccgacttc tggtgacgtt    300 gttgttgtgg ccactgacgc tctgatgact ggttacactg gtgacttcga ctctgttatc    360
gattgcaaca cttgc                                                    375

<210> SEQ ID NO 24
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ala Val Asp Phe Ile Pro Val Glu Asn Leu Glu Thr Thr Met Arg Ser
1               5                   10                  15

Pro Val Phe Thr Asp Asn Ser Ser Val Pro His Pro Asn Ile Glu Glu
            20                  25                  30

Val Ala Leu Ser Thr Thr Gly Glu Ile Pro Phe Tyr Gly Lys Ala Ile
        35                  40                  45

Pro Leu Glu Val Ile Lys Gly Gly Arg His Leu Ile Phe Cys His Ser
    50                  55                  60

Lys Lys Lys Cys Asp Glu Leu Ala Ala Lys Leu Val Ala Leu Gly Ile
65                  70                  75                  80

Asn Ala Val Ala Tyr Tyr Arg Gly Leu Asp Val Ser Val Ile Pro Thr
                85                  90                  95

Ser Gly Asp Val Val Val Ala Thr Asp Ala Leu Met Thr Gly Tyr
            100                 105                 110

Thr Gly Asp Phe Asp Ser Val Ile Asp Cys Asn Thr Cys
        115                 120                 125

<210> SEQ ID NO 25
<211> LENGTH: 513
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
gctgttgact ttatcccggt tgaaaatctc gagactacta tgcgttctcc ggttttcact      60

```
gacaactctt ctttcgatag ctctgttctg tgtgagtgtt atgacgcggg ttgcgcgtgg      120
tacgaactga ctccggctga aactactgta cgcctgcgtg catacatgaa tacgccgggt      180
ctgccggtgt gtcaagacca cctggaattt tgggaaggtg tctttactgg cctgacccat      240
atcgacgcac actttctgtc ccagactaaa cagtctggtg aaaacctgcc gtacctggtg      300
gcgtatcaag ccactgtgtg cgcccgtgcg caggcgccgc caccgagctg ggaccaaatg      360
tggaagtgcc tgatccgtct gaaaccgacc ctgcacggtc cgacgccact gctgtaccgc      420
ctgggtgcag tgcagaacga aatcacgctg acgcacccgg tcactaaata cattatgact      480
tgcatgagcg cagacctgga agtggtgact tcc                                   513
```

<210> SEQ ID NO 26
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Ala Val Asp Phe Ile Pro Val Glu Asn Leu Glu Thr Thr Met Arg Ser
1               5                   10                  15

Pro Val Phe Thr Asp Asn Ser Ser Phe Asp Ser Ser Val Leu Cys Glu
            20                  25                  30

Cys Tyr Asp Ala Gly Cys Ala Trp Tyr Glu Leu Thr Pro Ala Glu Thr
        35                  40                  45

Thr Val Arg Leu Arg Ala Tyr Met Asn Thr Pro Gly Leu Pro Val Cys
    50                  55                  60

Gln Asp His Leu Glu Phe Trp Glu Gly Val Phe Thr Gly Leu Thr His
65                  70                  75                  80

Ile Asp Ala His Phe Leu Ser Gln Thr Lys Gln Ser Gly Glu Asn Leu
                85                  90                  95

Pro Tyr Leu Val Ala Tyr Gln Ala Thr Val Cys Ala Arg Ala Gln Ala
            100                 105                 110

Pro Pro Pro Ser Trp Asp Gln Met Trp Lys Cys Leu Ile Arg Leu Lys
        115                 120                 125

Pro Thr Leu His Gly Pro Thr Pro Leu Leu Tyr Arg Leu Gly Ala Val
    130                 135                 140

Gln Asn Glu Ile Thr Leu Thr His Pro Val Thr Lys Tyr Ile Met Thr
145                 150                 155                 160

Cys Met Ser Ala Asp Leu Glu Val Val Thr Ser
                165                 170
```

<210> SEQ ID NO 27
<211> LENGTH: 978
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
gctgttgact ttatcccggt tgaaaatctc gagactacta tgcgttctcc ggttttcact      60
gacaactctt ctgttccgca cccgaacatc gaagaagttg ctctgtcgac tactggtgaa     120
atcccgttct acggtaaagc tatcccgctc gaggttatca aggtggtcg tcacctgatt      180 ttctgccact ctaaaaaaaa atgcgacgaa ctggctgcta agcttgttgc tctgggtatc     240
```

-continued

```
aacgctgttg cttactaccg tggtctggac gtttctgtta tcccgacttc tggtgacgtt      300
gttgttgtgg ccactgacgc tctgatgact ggttacactg gtgacttcga ctctgttatc      360
gattgcaaca cttgcgttac tcagaccgta gattttagcc tggacccgac tttcactatc      420
gaaacgatca ccctgccgca ggatgcagtt tcccgtaccc agcgtcgtgg ccgtaccggt      480
cgcggcaaac cgggtattta ccgtttcgtg gcgccgggcg agcgtccatc cggtatgttc      540
gatagctctg ttctgtgtga gtgttatgac gcgggttgcg cgtggtacga actgactccg      600
gctgaaacta ctgtacgcct gcgtgcatac atgaatacgc cgggtctgcc ggtgtgtcaa      660
gaccacctgg aattttggga aggtgtcttt actggcctga cccatatcga cgcacacttt      720
ctgtcccaga ctaaacagtc tggtgaaaac ctgccgtacc tggtggcgta tcaagccact      780
gtgtgcgccc gtgcgcaggc gccgccaccg agctgggacc aaatgtggaa gtgcctgatc      840
cgtctgaaac cgaccctgca cggtccgacg ccactgctgt accgcctggg tgcagtgcag      900
aacgaaatca cgctgacgca cccggtcact aaatacatta tgacttgcat gagcgcagac      960
ctggaagtgg tgacttcc                                                    978
```

<210> SEQ ID NO 28
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Ala Val Asp Phe Ile Pro Val Glu Asn Leu Glu Thr Thr Met Arg Ser
1               5                   10                  15

Pro Val Phe Thr Asp Asn Ser Ser Val Pro His Pro Asn Ile Glu Glu
            20                  25                  30

Val Ala Leu Ser Thr Thr Gly Glu Ile Pro Phe Tyr Gly Lys Ala Ile
        35                  40                  45

Pro Leu Glu Val Ile Lys Gly Gly Arg His Leu Ile Phe Cys His Ser
    50                  55                  60

Lys Lys Lys Cys Asp Glu Leu Ala Ala Lys Leu Val Ala Leu Gly Ile
65                  70                  75                  80

Asn Ala Val Ala Tyr Tyr Arg Gly Leu Asp Val Ser Val Ile Pro Thr
                85                  90                  95

Ser Gly Asp Val Val Val Ala Thr Asp Ala Leu Met Thr Gly Tyr
            100                 105                 110

Thr Gly Asp Phe Asp Ser Val Ile Asp Cys Asn Thr Cys Val Thr Gln
        115                 120                 125

Thr Val Asp Phe Ser Leu Asp Pro Thr Phe Thr Ile Glu Thr Ile Thr
    130                 135                 140

Leu Pro Gln Asp Ala Val Ser Arg Thr Gln Arg Arg Gly Arg Thr Gly
145                 150                 155                 160

Arg Gly Lys Pro Gly Ile Tyr Arg Phe Val Ala Pro Gly Glu Arg Pro
                165                 170                 175

Ser Gly Met Phe Asp Ser Ser Val Leu Cys Glu Cys Tyr Asp Ala Gly
            180                 185                 190

Cys Ala Trp Tyr Glu Leu Thr Pro Ala Glu Thr Thr Val Arg Leu Arg
        195                 200                 205

Ala Tyr Met Asn Thr Pro Gly Leu Pro Val Cys Gln Asp His Leu Glu
    210                 215                 220
```

```
Phe Trp Glu Gly Val Phe Thr Gly Leu Thr His Ile Asp Ala His Phe
225                 230                 235                 240

Leu Ser Gln Thr Lys Gln Ser Gly Glu Asn Leu Pro Tyr Leu Val Ala
            245                 250                 255

Tyr Gln Ala Thr Val Cys Ala Arg Ala Gln Ala Pro Pro Ser Trp
        260                 265                 270

Asp Gln Met Trp Lys Cys Leu Ile Arg Leu Lys Pro Thr Leu His Gly
            275                 280                 285

Pro Thr Pro Leu Leu Tyr Arg Leu Gly Ala Val Gln Asn Glu Ile Thr
        290                 295                 300

Leu Thr His Pro Val Thr Lys Tyr Ile Met Thr Cys Met Ser Ala Asp
305                 310                 315                 320

Leu Glu Val Val Thr Ser
                325

<210> SEQ ID NO 29
<211> LENGTH: 534
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gctgttgact ttatcccggt tgaaaatctc gagactacta tgcgttctcc ggttttcact    60
gacaactctt ctgttccgca cccgaacatc gaagaagttg ctctgtcgac tactggtgaa   120
atcccgttct acggtaaagc tatcccgctc gaggttatca aggtggtcg tcacctgatt   180 ttctgccact ctaaaaaaaa atgcgacgaa ctggctgcta agcttgttgc tctgggtatc   240
aacgctgttg cttactaccg tggtctggac gtttctgtta tcccgacttc tggtgacgtt   300
gttgttgtgg ccactgacgc tctgatgact ggttacactg gtgacttcga ctctgttatc   360
gattgcaaca cttgcgttac tcagaccgta gattttagcc tggaccccgac tttcactatc   420 gaaacgatca ccctgccgca ggatgcagtt tcccgtaccc agcgtcgtgg ccgtaccggt   480
cgcggcaaac cgggtatttta ccgtttcgtg gcgccgggcg agcgtccatc cggt         534

<210> SEQ ID NO 30
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ala Val Asp Phe Ile Pro Val Glu Asn Leu Glu Thr Thr Met Arg Ser
1               5                  10                  15

Pro Val Phe Thr Asp Asn Ser Ser Val Pro His Pro Asn Ile Glu Glu
            20                  25                  30

Val Ala Leu Ser Thr Thr Gly Glu Ile Pro Phe Tyr Gly Lys Ala Ile
        35                  40                  45

Pro Leu Glu Val Ile Lys Gly Gly Arg His Leu Ile Phe Cys His Ser
    50                  55                  60

Lys Lys Lys Cys Asp Glu Leu Ala Ala Lys Leu Val Ala Leu Gly Ile
65                  70                  75                  80

Asn Ala Val Ala Tyr Tyr Arg Gly Leu Asp Val Ser Val Ile Pro Thr
                85                  90                  95
```

Ser Gly Asp Val Val Val Ala Thr Asp Ala Leu Met Thr Gly Tyr
                100                 105                 110

Thr Gly Asp Phe Asp Ser Val Ile Asp Cys Asn Thr Cys Val Thr Gln
            115                 120                 125

Thr Val Asp Phe Ser Leu Asp Pro Thr Phe Thr Ile Glu Thr Ile Thr
        130                 135                 140

Leu Pro Gln Asp Ala Val Ser Arg Thr Gln Arg Gly Arg Thr Gly
145                 150                 155                 160

Arg Gly Lys Pro Gly Ile Tyr Arg Phe Val Ala Pro Gly Glu Arg Pro
                165                 170                 175

Ser Gly

<210> SEQ ID NO 31
<211> LENGTH: 957
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca cacttgcgt tactcagacc gtagatttta gcctggaccc gactttcact     840
atcgaaacga tcaccctgcc gcaggatgca gtttcccgta cccagcgtcg tggccgtacc     900
ggtcgcggca aaccgggtat ttaccgtttc gtggcgccgg gcgagcgtcc atccggt      957

<210> SEQ ID NO 32
<211> LENGTH: 319
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys

|  | | | | 35 | | | | 40 | | | | 45 | | | |
|---|---|---|---|---|---|---|---|---|---|---|---|---|---|---|---|

Val Pro Ala Ala Tyr Ala Ala Gln Gly Tyr Lys Val Leu Val Leu Asn
 50                  55                  60

Pro Ser Val Ala Ala Thr Leu Gly Phe Gly Ala Tyr Met Ser Lys Ala
 65                  70                  75                  80

His Gly Ile Asp Pro Asn Ile Arg Thr Gly Val Arg Thr Ile Thr Thr
                 85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Cys Asp Glu Cys His
        115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly
305                 310                 315

<210> SEQ ID NO 33
<211> LENGTH: 675
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

| gctgttgact | ttatcccggt | tgaaaatctc | gagactacta | tgcgttctcc | ggttttcact | 60 |
|---|---|---|---|---|---|---|
| gacaactctt | ctgttactca | gaccgtagat | tttagcctgg | acccgacttt | cactatcgaa | 120 |
| acgatcaccc | tgccgcagga | tgcagtttcc | cgtacccagc | gtcgtggccg | taccggtcgc | 180 |
| ggcaaaccgg | gtatttaccg | tttcgtggcg | ccgggcgagc | gtccatccgg | tatgttcgat | 240 |
| agctctgttc | tgtgtgagtg | ttatgacgcg | ggttgcgcgt | ggtacgaact | gactccggct | 300 |
| gaaactactg | tacgcctgcg | tgcatacatg | aatacgccgg | tctgccggt | gtgtcaagac | 360 |
| cacctggaat | tttgggaagg | tgtctttact | ggcctgaccc | atatcgacgc | acactttctg | 420 |
| tcccagacta | acagtctggt | gaaaacctg | ccgtacctgg | tggcgtatca | agccactgtg | 480 |

```
tgcgcccgtg cgcaggcgcc gccaccgagc tgggaccaaa tgtggaagtg cctgatccgt    540
ctgaaaccga ccctgcacgg tccgacgcca ctgctgtacc gcctgggtgc agtgcagaac    600
gaaatcacgc tgacgcaccc ggtcactaaa tacattatga cttgcatgag cgcagacctg    660
gaagtggtga cttcc                                                     675
```

<210> SEQ ID NO 34
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Ala Val Asp Phe Ile Pro Val Glu Asn Leu Glu Thr Thr Met Arg Ser
1               5                   10                  15

Pro Val Phe Thr Asp Asn Ser Ser Val Thr Gln Thr Val Asp Phe Ser
            20                  25                  30

Leu Asp Pro Thr Phe Thr Ile Glu Thr Ile Thr Leu Pro Gln Asp Ala
        35                  40                  45

Val Ser Arg Thr Gln Arg Arg Gly Arg Thr Gly Arg Gly Lys Pro Gly
    50                  55                  60

Ile Tyr Arg Phe Val Ala Pro Gly Glu Arg Pro Ser Gly Met Phe Asp
65                  70                  75                  80

Ser Ser Val Leu Cys Glu Cys Tyr Asp Ala Gly Cys Ala Trp Tyr Glu
                85                  90                  95

Leu Thr Pro Ala Glu Thr Thr Val Arg Leu Arg Ala Tyr Met Asn Thr
            100                 105                 110

Pro Gly Leu Pro Val Cys Gln Asp His Leu Glu Phe Trp Glu Gly Val
        115                 120                 125

Phe Thr Gly Leu Thr His Ile Asp Ala His Phe Leu Ser Gln Thr Lys
    130                 135                 140

Gln Ser Gly Glu Asn Leu Pro Tyr Leu Val Ala Tyr Gln Ala Thr Val
145                 150                 155                 160

Cys Ala Arg Ala Gln Ala Pro Pro Pro Ser Trp Asp Gln Met Trp Lys
                165                 170                 175

Cys Leu Ile Arg Leu Lys Pro Thr Leu His Gly Pro Thr Pro Leu Leu
            180                 185                 190

Tyr Arg Leu Gly Ala Val Gln Asn Glu Ile Thr Leu Thr His Pro Val
        195                 200                 205

Thr Lys Tyr Ile Met Thr Cys Met Ser Ala Asp Leu Glu Val Val Thr
    210                 215                 220

Ser
225
```

<210> SEQ ID NO 35
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
gctgttgact ttatcccggt tgaaaatctc gagactacta tgcgttctcc ggttttcact     60
gacaactctt ctccgccggt tgttccgcag tctttccagg ttgctcacct gcatgctccg    120
```

```
actggttctg gtaactctac taaagttcca gctgcttacg ctgctcaggg ttacaaagtt      180
ctggttctga acccgtctgt tgctgctact ctgggtttcg gcgcctacat gtctaaagct      240
cacggtatcg acccgaacat tcgtactggt gtacgtacta tcactactgg ttctccgatc      300
acttactcta cttacggtaa attcctggct gacggtggtt gctctggtgg tgcttacgat      360
atcatcatct gcgacgaatg ccactctact gacgctactt ctatcctggg tatcggtacc      420
gttctggacc aggctgaaac tgcaggtgct cgtctggttg ttctggctac tgctactccg      480
ccgggttctg ttactgttcc gcacccgaac atcgaagaag ttgctctgtc gactactggt      540
gaaatcccgt ctactggtaa agctatcccg ctcgaggtta tcaaaggtgg tcgtcacctg      600
attttctgcc actctaaaaa aaaatgcgac gaactggctg ctaagcttgt tgctctgggt      660
atcaacgctg ttgcttacta ccgtggtctg gacgtttctg ttatcccgac ttctggtgac      720
gttgttgttg tggccactga cgctctgatg actggttaca ctggtgactt cgactctgtt      780
atcgattgca acacttgcgt tactcagacc gtagatttta gcctggaccc gactttcact      840
atcgaaacga tcaccctgcc gcaggatgca gtttcccgta cccagcgtcg tggccgtacc      900
ggtcgcggca aaccgggtat ttaccgtttc gtggcgccgg cgagcgtcc atccggtatg       960 ttcgatagct ctgttctgtg tgagtgttat gacgcgggtt gcgcgtggta cgaactgact     1020
ccggctgaaa ctactgtacg cctgcgtgca tacatgaata cgccgggtct gccggtgtgt     1080
caagaccacc tggaattttg ggaaggtgtc tttactggcc tgacccatat cgacgcacac     1140
tttctgtccc agactaaaca gtctggtgaa aacctgccgt acctggtggc gtatcaagcc     1200
actgtgtgcg cccgtgcgca ggcgccgcca ccgagctggg accaaatgtg gaagtgcctg     1260
atccgtctga aaccgaccct gcacggtccg acgccactgc tgtaccgcct gggtgcagtg     1320
cagaacgaaa tcacgctgac gcacccggtc actaaataca ttatgacttg catgagcgca     1380
gacctggaag tggtgacttc c                                              1401
```

<210> SEQ ID NO 36
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Asn Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
                180                 185                 190

Val Ile Lys Gly Gly Arg His Leu Ile Phe Cys His Ser Lys Lys Lys
            195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
                260                 265                 270

Phe Ser Leu Asp Pro Thr Phe Thr Ile Glu Thr Ile Thr Leu Pro Gln
            275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
                340                 345                 350

Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
            450                 455                 460

Val Thr Ser
465

<210> SEQ ID NO 37
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
gctgttgact ttatcccggt tgaaaatctc gagactacta tgcgttctcc ggttttcact    60

```
gacaactctt ctccgccggt tgttccgcag tctttccagg ttgctcacct gcatgctccg      120
actggttctg gtaaagcgac taaagttcca gctgcttacg ctgctcaggg ttacaaagtt      180
ctggttctga acccgtctgt tgctgctact ctgggtttcg gcgcctacat gtctaaagct      240
cacggtatcg acccgaacat tcgtactggt gtacgtacta tcactactgg ttctccgatc      300
acttactcta cttacggtaa attcctggct gacggtggtt gctctggtgg tgcttacgat      360
atcatcatct gcgacgaatg ccactctact gacgctactt ctatcctggg tatcggtacc      420
gttctggacc aggctgaaac tgcaggtgct cgtctggttg ttctggctac tgctactccg      480
ccgggttctg ttactgttcc gcacccgaac atcgaagaag ttgctctgtc gactactggt      540
gaaatcccgt tctacggtaa agctatcccg ctcgaggtta tcaaaggtgg tcgtcacctg      600
attttctgcc actctaaaaa aaaatgcgac gaactggctg ctaagcttgt tgctctgggt      660
atcaacgctg ttgcttacta ccgtggtctg gacgtttctg ttatcccgac ttctggtgac      720
gttgttgttg tggccactga cgctctgatg actggttaca ctggtgactt cgactctgtt      780
atcgattgca acacttgcgt tactcagacc gtagatttta gcctggaccc gactttcact      840
atcgaaacga tcaccctgcc gcaggatgca gtttcccgta cccagcgtcg tggccgtacc      900
ggtcgcggca accgggtat ttaccgtttc gtggcgccgg gcgagcgtcc atccggtatg      960
ttcgatagct ctgttctgtg tgagtgttat gacgcgggtt gcgcgtggta cgaactgact     1020
ccggctgaaa ctactgtacg cctgcgtgca tacatgaata cgccgggtct gccggtgtgt     1080
caagaccacc tggaattttg ggaaggtgtc tttactggcc tgacccatat cgacgcacac     1140
tttctgtccc agactaaaca gtctggtgaa aacctgccgt acctggtggc gtatcaagcc     1200
actgtgtgcg cccgtgcgca ggcgccgcca ccgagctggg accaaatgtg gaagtgcctg     1260
atccgtctga aaccgaccct gcacggtccg acgccactgc tgtaccgcct gggtgcagtg     1320
cagaacgaaa tcacgctgac gcaccccggtc actaaataca ttatgacttg catgagcgca     1380
gacctggaag tggtgacttc c                                                1401
```

<210> SEQ ID NO 38
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ala Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110
```

Gly Cys Ser Gly Gly Ala Tyr Asp Ile Ile Ile Cys Asp Glu Cys His
            115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
                180                 185                 190

Val Ile Lys Gly Gly Arg His Leu Ile Phe Cys His Ser Lys Lys Lys
                195                 200                 205

Cys Asp Glu Leu Ala Ala Lys Leu Val Ala Leu Gly Ile Asn Ala Val
                210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
                260                 265                 270

Phe Ser Leu Asp Pro Thr Phe Thr Ile Glu Thr Ile Thr Leu Pro Gln
                275                 280                 285

Asp Ala Val Ser Arg Thr Gln Arg Arg Gly Arg Thr Gly Arg Gly Lys
                290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
                340                 345                 350

Asn Thr Pro Gly Leu Pro Val Cys Gln Asp His Leu Glu Phe Trp Glu
                355                 360                 365

Gly Val Phe Thr Gly Leu Thr His Ile Asp Ala His Phe Leu Ser Gln
                370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                    405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
                435                 440                 445

Pro Val Thr Lys Tyr Ile Met Thr Cys Met Ser Ala Asp Leu Glu Val
450                 455                 460

Val Thr Ser
465

<210> SEQ ID NO 39
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctga gaaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca acacttgcgt tactcagacc gtagatttta gcctggaccc gactttcact     840
atcgaaacga tcaccctgcc gcaggatgca gtttcccgta cccagcgtcg tggccgtacc     900
ggtcgcggca aaccgggtat ttaccgtttc gtggcgccgg cgagcgtcc atccggtatg     960
ttcgatagct ctgttctgtg tgagtgttat gacgcgggtt gcgcgtggta cgaactgact    1020
ccggctgaaa ctactgtacg cctgcgtgca tacatgaata cgccgggtct gccggtgtgt    1080
caagaccacc tggaattttg ggaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg gaagtgcctg    1260
atccgtctga aaccgaccct gcacggtccg acgccactgc tgtaccgcct gggtgcagtg    1320
cagaacgaaa tcacgctgac gcacccggtc actaaataca ttatgacttg catgagcgca    1380
gacctggaag tggtgacttc c                                              1401
```

<210> SEQ ID NO 40
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Glu Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
```

```
                100             105             110
Gly Cys Ser Gly Gly Ala Tyr Asp Ile Ile Cys Asp Glu Cys His
            115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
                260                 265                 270

Phe Ser Leu Asp Pro Thr Phe Thr Ile Glu Thr Ile Thr Leu Pro Gln
            275                 280                 285

Asp Ala Val Ser Arg Thr Gln Arg Arg Gly Arg Thr Gly Arg Gly Lys
        290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
    370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
        450                 455                 460

Val Thr Ser
465

<210> SEQ ID NO 41
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
```

-continued

<400> SEQUENCE: 41

```
gctgttgact ttatcccggt tgaaaatctc gagactacta tgcgttctcc ggttttcact    60
gacaactctt ctccgccggt tgttccgcag tctttccagg ttgctcacct gcatgctccg   120
actggttctg gtaaatctac taaagttcca gctgcttacg ctgctcaggg ttacaaagtt   180
ctggttctga acccgtctgt tgctgctact ctgggtttcg gcgccagcat gtctaaagct   240
cacggtatcg acccgaacat tcgtactggt gtacgtacta tcactactgg ttctccgatc   300
acttactcta cttacggtaa attcctggct gacggtggtt gctctggtgg tgcttacgat   360
atcatcatct gcgacgaatg ccactctact gacgctactt ctatcctggg tatcggtacc   420
gttctggacc aggctgaaac tgcaggtgct cgtctggttg ttctggctac tgctactccg   480
ccgggttctg ttactgttcc gcacccgaac atcgaagaag ttgctctgtc gactactggt   540
gaaatcccgt tctacggtaa agctatcccg ctcgaggtta tcaaggtgg tcgtcacctg   600
attttctgcc actctaaaaa aaaatgcgac gaactggctg ctaagcttgt tgctctgggt   660
atcaacgctg ttgcttacta ccgtggtctg gacgtttctg ttatcccgac ttctggtgac   720
gttgttgttg tggccactga cgctctgatg actggttaca ctggtgactt cgactctgtt   780
atcgattgca acacttgcgt tactcagacc gtagatttta gcctggaccc gactttcact   840
atcgaaacga tcaccctgcc gcaggatgca gtttcccgta cccagcgtcg tggccgtacc   900
ggtcgcggca aaccgggtat ttaccgtttc gtggcgccgg gcgagcgtcc atccggtatg   960
ttcgatagct ctgttctgtg tgagtgttat gacgcgggtt gcgcgtggta cgaactgact  1020
ccggctgaaa ctactgtacg cctgcgtgca tacatgaata cgccgggtct gccggtgtgt  1080
caagaccacc tggaattttg ggaaggtgtc tttactggcc tgacccatat cgacgcacac  1140
tttctgtccc agactaaaca gtctggtgaa aacctgccgt acctggtggc gtatcaagcc  1200
actgtgtgcg cccgtgcgca ggcgccgcca ccgagctggg accaaatgtg gaagtgcctg  1260
atccgtctga aaccgaccct gcacggtccg acgccactgc tgtaccgcct gggtgcagtg  1320
cagaacgaaa tcacgctgac gcacccggtc actaaataca ttatgacttg catgagcgca  1380
gacctggaag tggtgacttc c                                            1401
```

<210> SEQ ID NO 42
<211> LENGTH: 467
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 42

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Ser Met Ser Lys Ala
65                  70                  75                  80

His Gly Ile Asp Pro Asn Ile Arg Thr Gly Val Arg Thr Ile Thr Thr
                85                  90                  95
```

```
Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
    370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
    450                 455                 460

Val Thr Ser
465

<210> SEQ ID NO 43
<211> LENGTH: 1401
<212> TYPE: DNA
<213> ORGANISM: Artificial Sequence
<220> FEATURE:
```

-continued

<223> OTHER INFORMATION: Description of Artificial Sequence: Synthetic
      polynucleotide

<400> SEQUENCE: 43

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcaacgaatg ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca acacttgcgt tactcagacc gtagatttta gcctggaccc gactttcact     840
atcgaaacga tcaccctgcc gcaggatgca gtttcccgta cccagcgtcg tggccgtacc     900
ggtcgcggca aaccgggtat ttaccgtttc gtggcgccgg cgagcgtcc atccggtatg     960
ttcgatagct ctgttctgtg tgagtgttat gacgcgggtt gcgcgtggta cgaactgact    1020
ccggctgaaa ctactgtacg cctgcgtgca tacatgaata cgccgggtct gccggtgtgt    1080
caagaccacc tggaattttg ggaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg gaagtgcctg    1260
atccgtctga aaccgaccct gcacggtccg acgccactgc tgtaccgcct gggtgcagtg    1320
cagaacgaaa tcacgctgac gcacccggtc actaaataca ttatgacttg catgagcgca    1380
gacctggaag tggtgacttc c                                              1401
```

<210> SEQ ID NO 44
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80
```

-continued

```
His Gly Ile Asp Pro Asn Ile Arg Thr Gly Val Arg Thr Ile Thr Thr
             85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Cys Asn Glu Cys His
            115                 120                 125

Ser Thr Asp Ala Thr Ser Ile Leu Gly Ile Gly Thr Val Leu Asp Gln
            130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
                180                 185                 190

Val Ile Lys Gly Gly Arg His Leu Ile Phe Cys His Ser Lys Lys Lys
            195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
                260                 265                 270

Phe Ser Leu Asp Pro Thr Phe Thr Ile Glu Thr Ile Thr Leu Pro Gln
            275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
            370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
            450                 455                 460

Val Thr Ser
465

<210> SEQ ID NO 45
<211> LENGTH: 1401
<212> TYPE: DNA
```

<210> SEQ ID NO 45
<211> LENGTH: 1401
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga accgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgaccagtg ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca acacttgcgt tactcagacc gtagatttta gcctggaccc gactttcact     840
atcgaaacga tcaccctgcc gcaggatgca gtttcccgta cccagcgtcg tggccgtacc     900
ggtcgcggca aaccgggtat ttaccgtttc gtggcgccgg cgagcgtcc atccggtatg     960
ttcgatagct ctgttctgtg tgagtgttat gacgcgggtt gcgcgtggta cgaactgact    1020
ccggctgaaa ctactgtacg cctgcgtgca tacatgaata cgccgggtct gccggtgtgt    1080
caagaccacc tggaattttg ggaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg gaagtgcctg    1260
atccgtctga aaccgaccct gcacggtccg acgccactgc tgtaccgcct gggtgcagtg    1320
cagaacgaaa tcacgctgac gcaccgggtc actaaataca ttatgacttg catgagcgca    1380
gacctggaag tggtgacttc c                                              1401
```

<210> SEQ ID NO 46
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
```

```
                65                  70                  75                  80
            His Gly Ile Asp Pro Asn Ile Arg Thr Gly Val Arg Thr Ile Thr Thr
                                85                  90                  95
            Gly Ser Pro Ile Thr Tyr Ser Thr Tyr Gly Lys Phe Leu Ala Asp Gly
                               100                 105                 110
            Gly Cys Ser Gly Gly Ala Tyr Asp Ile Ile Cys Asp Gln Cys His
                               115                 120                 125
            Ser Thr Asp Ala Thr Ser Ile Leu Gly Ile Gly Thr Val Leu Asp Gln
                130                 135                 140
            Ala Glu Thr Ala Gly Ala Arg Leu Val Val Leu Ala Thr Ala Thr Pro
            145                 150                 155                 160
            Pro Gly Ser Val Thr Val Pro His Pro Asn Ile Glu Glu Val Ala Leu
                                165                 170                 175
            Ser Thr Thr Gly Glu Ile Pro Phe Tyr Gly Lys Ala Ile Pro Leu Glu
                               180                 185                 190
            Val Ile Lys Gly Gly Arg His Leu Ile Phe Cys His Ser Lys Lys Lys
                            195                 200                 205
            Cys Asp Glu Leu Ala Ala Lys Leu Val Ala Leu Gly Ile Asn Ala Val
                210                 215                 220
            Ala Tyr Tyr Arg Gly Leu Asp Val Ser Val Ile Pro Thr Ser Gly Asp
            225                 230                 235                 240
            Val Val Val Ala Thr Asp Ala Leu Met Thr Gly Tyr Thr Gly Asp
                                245                 250                 255
            Phe Asp Ser Val Ile Asp Cys Asn Thr Cys Val Thr Gln Thr Val Asp
                            260                 265                 270
            Phe Ser Leu Asp Pro Thr Phe Thr Ile Glu Thr Ile Thr Leu Pro Gln
                275                 280                 285
            Asp Ala Val Ser Arg Thr Gln Arg Arg Gly Arg Thr Gly Arg Gly Lys
                290                 295                 300
            Pro Gly Ile Tyr Arg Phe Val Ala Pro Gly Glu Arg Pro Ser Gly Met
            305                 310                 315                 320
            Phe Asp Ser Ser Val Leu Cys Glu Cys Tyr Asp Ala Gly Cys Ala Trp
                                325                 330                 335
            Tyr Glu Leu Thr Pro Ala Glu Thr Thr Val Arg Leu Arg Ala Tyr Met
                            340                 345                 350
            Asn Thr Pro Gly Leu Pro Val Cys Gln Asp His Leu Glu Phe Trp Glu
                355                 360                 365
            Gly Val Phe Thr Gly Leu Thr His Ile Asp Ala His Phe Leu Ser Gln
                370                 375                 380
            Thr Lys Gln Ser Gly Glu Asn Leu Pro Tyr Leu Val Ala Tyr Gln Ala
            385                 390                 395                 400
            Thr Val Cys Ala Arg Ala Gln Ala Pro Pro Ser Trp Asp Gln Met
                                405                 410                 415
            Trp Lys Cys Leu Ile Arg Leu Lys Pro Thr Leu His Gly Pro Thr Pro
                            420                 425                 430
            Leu Leu Tyr Arg Leu Gly Ala Val Gln Asn Glu Ile Thr Leu Thr His
                435                 440                 445
            Pro Val Thr Lys Tyr Ile Met Thr Cys Met Ser Ala Asp Leu Glu Val
                450                 455                 460
            Val Thr Ser
            465

<210> SEQ ID NO 47
```

<211> LENGTH: 1401
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaaag ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca acacttgcgt tactcagacc gtagatttta gcctggaccc gactttcact     840
atcgaaacga tcaccctgcc gcaggatgca gtttcccgta cccagcgtcg tggccgtacc     900
ggtcgcggca accgggtat ttaccgtttc gtggcgccgg cgagcgtcc atccggtatg     960
ttcgatagct ctgttctgtg tgagtgttat gacgcgggtt gcgcgtggta cgaactgact    1020
ccggctgaaa ctactgtacg cctgcgtgca tacatgaata cgcccgggtct gccggtgtgt    1080
caagaccacc tggaattttg ggaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg gaagtgcctg    1260
atccgtctga aaccgaccct gcacggtccg acgccactgc tgtaccgcct gggtgcagtg    1320
cagaacgaaa tcacgctgac gcaccggtc actaaataca ttatgacttg catgagcgca    1380
gacctggaag tggtgacttc c                                              1401
```

<210> SEQ ID NO 48
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

```
Ala Val Asp Phe Ile Pro Val Glu Asn Leu Glu Thr Thr Met Arg Ser
1               5                  10                  15

Pro Val Phe Thr Asp Asn Ser Ser Pro Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60
```

```
Pro Ser Val Ala Ala Thr Leu Gly Phe Gly Ala Tyr Met Ser Lys Ala
 65                  70                  75                  80

His Gly Ile Asp Pro Asn Ile Arg Thr Gly Val Arg Thr Ile Thr Thr
             85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Cys Asp Glu Ser His
            115                 120                 125

Ser Thr Asp Ala Thr Ser Ile Leu Gly Ile Gly Thr Val Leu Asp Gln
            130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
                180                 185                 190

Val Ile Lys Gly Gly Arg His Leu Ile Phe Cys His Ser Lys Lys Lys
            195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
                260                 265                 270

Phe Ser Leu Asp Pro Thr Phe Thr Ile Glu Thr Ile Thr Leu Pro Gln
            275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
            370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
            450                 455                 460

Val Thr Ser
465
```

<210> SEQ ID NO 49
<211> LENGTH: 1401
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 49

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taagttcca gctgcttacg ctgctcaggg ttacaaagtt     180
ctggttctga accgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg cgcctctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca acacttgcgt tactcagacc gtagatttta gcctggaccc gactttcact     840
atcgaaacga tcaccctgcc gcaggatgca gtttcccgta cccagcgtcg tggccgtacc     900
ggtcgcggca accgggtat ttaccgtttc gtggcgccgg cgagcgtcc atccggtatg     960
ttcgatagct ctgttctgtg tgagtgttat gacgcgggtt gcgcgtggta cgaactgact    1020
ccggctgaaa ctactgtacg cctgcgtgca tacatgaata cgccgggtct gccggtgtgt    1080
caagaccacc tggaattttg ggaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg aagtgcctg    1260
atccgtctga aaccgaccct gcacggtccg acgccactgc tgtaccgcct gggtgcagtg    1320
cagaacgaaa tcacgctgac gcacccggtc actaaataca ttatgacttg catgagcgca    1380
gacctggaag tggtgacttc c                                              1401
```

<210> SEQ ID NO 50
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45
```

```
Val Pro Ala Ala Tyr Ala Ala Gln Gly Tyr Lys Val Leu Val Leu Asn
    50                  55                  60
Pro Ser Val Ala Ala Thr Leu Gly Phe Gly Ala Tyr Met Ser Lys Ala
65                  70                  75                  80
His Gly Ile Asp Pro Asn Ile Arg Thr Gly Val Arg Thr Ile Thr Thr
                85                  90                  95
Gly Ser Pro Ile Thr Tyr Ser Thr Tyr Gly Lys Phe Leu Ala Asp Gly
                100                 105                 110
Gly Cys Ser Gly Gly Ala Tyr Asp Ile Ile Cys Asp Glu Cys Ala
            115                 120                 125
Ser Thr Asp Ala Thr Ser Ile Leu Gly Ile Gly Thr Val Leu Asp Gln
    130                 135                 140
Ala Glu Thr Ala Gly Ala Arg Leu Val Val Leu Ala Thr Ala Thr Pro
145                 150                 155                 160
Pro Gly Ser Val Thr Val Pro His Pro Asn Ile Glu Glu Val Ala Leu
                165                 170                 175
Ser Thr Thr Gly Glu Ile Pro Phe Tyr Gly Lys Ala Ile Pro Leu Glu
                180                 185                 190
Val Ile Lys Gly Gly Arg His Leu Ile Phe Cys His Ser Lys Lys Lys
    195                 200                 205
Cys Asp Glu Leu Ala Ala Lys Leu Val Ala Leu Gly Ile Asn Ala Val
    210                 215                 220
Ala Tyr Tyr Arg Gly Leu Asp Val Ser Val Ile Pro Thr Ser Gly Asp
225                 230                 235                 240
Val Val Val Val Ala Thr Asp Ala Leu Met Thr Gly Tyr Thr Gly Asp
                245                 250                 255
Phe Asp Ser Val Ile Asp Cys Asn Thr Cys Val Thr Gln Thr Val Asp
                260                 265                 270
Phe Ser Leu Asp Pro Thr Phe Thr Ile Glu Thr Ile Thr Leu Pro Gln
    275                 280                 285
Asp Ala Val Ser Arg Thr Gln Arg Arg Gly Arg Thr Gly Arg Gly Lys
    290                 295                 300
Pro Gly Ile Tyr Arg Phe Val Ala Pro Gly Glu Arg Pro Ser Gly Met
305                 310                 315                 320
Phe Asp Ser Ser Val Leu Cys Glu Cys Tyr Asp Ala Gly Cys Ala Trp
                325                 330                 335
Tyr Glu Leu Thr Pro Ala Glu Thr Thr Val Arg Leu Arg Ala Tyr Met
                340                 345                 350
Asn Thr Pro Gly Leu Pro Val Cys Gln Asp His Leu Glu Phe Trp Glu
                355                 360                 365
Gly Val Phe Thr Gly Leu Thr His Ile Asp Ala His Phe Leu Ser Gln
    370                 375                 380
Thr Lys Gln Ser Gly Glu Asn Leu Pro Tyr Leu Val Ala Tyr Gln Ala
385                 390                 395                 400
Thr Val Cys Ala Arg Ala Gln Ala Pro Pro Ser Trp Asp Gln Met
                405                 410                 415
Trp Lys Cys Leu Ile Arg Leu Lys Pro Thr Leu His Gly Pro Thr Pro
                420                 425                 430
Leu Leu Tyr Arg Leu Gly Ala Val Gln Asn Glu Ile Thr Leu Thr His
    435                 440                 445
Pro Val Thr Lys Tyr Ile Met Thr Cys Met Ser Ala Asp Leu Glu Val
450                 455                 460

Val Thr Ser
```

<210> SEQ ID NO 51
<211> LENGTH: 1401
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg cgcctacat gtctaaagct      240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaaagcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca acacttgcgt tactcagacc gtagatttta gcctggaccc gactttcact     840
atcgaaacga tcaccctgcc gcaggatgca gtttcccgta cccagcgtcg tggccgtacc     900
ggtcgcggca aaccgggtat ttaccgtttc gtggcgccgg cgagcgtcc atccggtatg      960
ttcgatagct ctgttctgtg tgagtgttat gacgcgggtt gcgcgtggta cgaactgact    1020
ccggctgaaa ctactgtacg cctgcgtgca tacatgaata cgcccgggtct gccggtgtgt    1080
caagaccacc tggaattttg ggaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg gaagtgcctg    1260
atccgtctga aaccgaccct gcacggtccg acgccactgc tgtaccgcct gggtgcagtg    1320
cagaacgaaa tcacgctgac gcacccggtc actaaatca ttatgacttg catgagcgca     1380
gacctggaag tggtgacttc c                                              1401
```

<210> SEQ ID NO 52
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

```
Ala Val Asp Phe Ile Pro Val Glu Asn Leu Glu Thr Thr Met Arg Ser
1               5                  10                  15

Pro Val Phe Thr Asp Asn Ser Ser Pro Val Pro Gln Ser Phe
            20                  25                  30

Gln Val Ala His Leu His Ala Pro Thr Gly Ser Gly Lys Ser Thr Lys
```

-continued

```
              35                  40                  45
Val Pro Ala Ala Tyr Ala Ala Gln Gly Tyr Lys Val Leu Val Leu Asn
 50                  55                  60
Pro Ser Val Ala Ala Thr Leu Gly Phe Gly Ala Tyr Met Ser Lys Ala
 65                  70                  75                  80
His Gly Ile Asp Pro Asn Ile Arg Thr Gly Val Arg Thr Ile Thr Thr
                 85                  90                  95
Gly Ser Pro Ile Thr Tyr Ser Thr Tyr Gly Lys Phe Leu Ala Asp Gly
                100                 105                 110
Gly Cys Ser Gly Gly Ala Tyr Asp Ile Ile Cys Asp Glu Cys His
            115                 120                 125
Ser Thr Asp Ala Thr Ser Ile Leu Gly Ile Gly Thr Val Leu Asp Gln
    130                 135                 140
Ala Glu Thr Ala Gly Ala Arg Leu Val Val Leu Ala Thr Ala Thr Pro
145                 150                 155                 160
Pro Gly Ser Val Thr Val Pro His Pro Asn Ile Glu Glu Val Ala Leu
                165                 170                 175
Ser Thr Thr Gly Glu Ile Pro Phe Tyr Gly Lys Ala Ile Pro Leu Glu
                180                 185                 190
Val Ile Lys Gly Gly Arg His Leu Ile Phe Cys His Ser Lys Lys Lys
            195                 200                 205
Ser Asp Glu Leu Ala Ala Lys Leu Val Ala Leu Gly Ile Asn Ala Val
    210                 215                 220
Ala Tyr Tyr Arg Gly Leu Asp Val Ser Val Ile Pro Thr Ser Gly Asp
225                 230                 235                 240
Val Val Val Val Ala Thr Asp Ala Leu Met Thr Gly Tyr Thr Gly Asp
                245                 250                 255
Phe Asp Ser Val Ile Asp Cys Asn Thr Cys Val Thr Gln Thr Val Asp
                260                 265                 270
Phe Ser Leu Asp Pro Thr Phe Thr Ile Glu Thr Ile Thr Leu Pro Gln
            275                 280                 285
Asp Ala Val Ser Arg Thr Gln Arg Arg Gly Arg Thr Gly Arg Gly Lys
    290                 295                 300
Pro Gly Ile Tyr Arg Phe Val Ala Pro Gly Glu Arg Pro Ser Gly Met
305                 310                 315                 320
Phe Asp Ser Ser Val Leu Cys Glu Cys Tyr Asp Ala Gly Cys Ala Trp
                325                 330                 335
Tyr Glu Leu Thr Pro Ala Glu Thr Thr Val Arg Leu Arg Ala Tyr Met
                340                 345                 350
Asn Thr Pro Gly Leu Pro Val Cys Gln Asp His Leu Glu Phe Trp Glu
            355                 360                 365
Gly Val Phe Thr Gly Leu Thr His Ile Asp Ala His Phe Leu Ser Gln
    370                 375                 380
Thr Lys Gln Ser Gly Glu Asn Leu Pro Tyr Leu Val Ala Tyr Gln Ala
385                 390                 395                 400
Thr Val Cys Ala Arg Ala Gln Ala Pro Pro Ser Trp Asp Gln Met
                405                 410                 415
Trp Lys Cys Leu Ile Arg Leu Lys Pro Thr Leu His Gly Pro Thr Pro
            420                 425                 430
Leu Leu Tyr Arg Leu Gly Ala Val Gln Asn Glu Ile Thr Leu Thr His
    435                 440                 445
Pro Val Thr Lys Tyr Ile Met Thr Cys Met Ser Ala Asp Leu Glu Val
450                 455                 460
```

Val Thr Ser
465

<210> SEQ ID NO 53
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttacg gtgactt cgactctgtt     780
atcgattgca acacttgcgt tactcagacc gtagatttta gcctggaccc gactttcact     840
atcgaaacga tcaccctgcc gcaggatgca gtttcccgta cccagcgtcg tggccgtacc     900
ggtcgcggca accgggtat ttaccgtttc gtggcgccgg gcgagcgtcc atccggtatg     960
ttcgatagct ctgttctgtg tgagtgttat gacgcgggt gcgcgtggta cgaactgact    1020
ccggctgaaa ctactgtacg cctgcgtgca tacatgaata cgccgggtct gccggtgtgt    1080
caagaccacc tggaattttg ggaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg aagtgcctg    1260
atccgtctga aaccgaccct gcacggtccg acgccactgc tgtaccgcct gggtgcagtg    1320
cagaacgaaa tcacgctgac gcacccggtc actaaataca ttatgacttg catgagcgca    1380
gacctggaag tggtgacttc c                                              1401
```

<210> SEQ ID NO 54
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Ala Val Asp Phe Ile Pro Val Glu Asn Leu Glu Thr Thr Met Arg Ser
1               5                   10                  15

Pro Val Phe Thr Asp Asn Ser Ser Pro Pro Val Val Pro Gln Ser Phe
            20                  25                  30

-continued

```
Gln Val Ala His Leu His Ala Pro Thr Gly Ser Gly Lys Ser Thr Lys
         35                  40                  45

Val Pro Ala Ala Tyr Ala Ala Gln Gly Tyr Lys Val Leu Val Leu Asn
 50                  55                  60

Pro Ser Val Ala Ala Thr Leu Gly Phe Gly Ala Tyr Met Ser Lys Ala
 65                  70                  75                  80

His Gly Ile Asp Pro Asn Ile Arg Thr Gly Val Arg Thr Ile Thr Thr
                     85                  90                  95

Gly Ser Pro Ile Thr Tyr Ser Thr Tyr Gly Lys Phe Leu Ala Asp Gly
                 100                 105                 110

Gly Cys Ser Gly Gly Ala Tyr Asp Ile Ile Cys Asp Glu Cys His
             115                 120                 125

Ser Thr Asp Ala Thr Ser Ile Leu Gly Ile Gly Thr Val Leu Asp Gln
         130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                 165                 170                 175

Ser Thr Thr Gly Glu Ile Pro Phe Tyr Gly Lys Ala Ile Pro Leu Glu
                 180                 185                 190

Val Ile Lys Gly Gly Arg His Leu Ile Phe Cys His Ser Lys Lys Lys
             195                 200                 205

Cys Asp Glu Leu Ala Ala Lys Leu Val Ala Leu Gly Ile Asn Ala Val
             210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Gly Gly Asp
                 245                 250                 255

Phe Asp Ser Val Ile Asp Cys Asn Thr Cys Val Thr Gln Thr Val Asp
                 260                 265                 270

Phe Ser Leu Asp Pro Thr Phe Thr Ile Glu Thr Ile Thr Leu Pro Gln
             275                 280                 285

Asp Ala Val Ser Arg Thr Gln Arg Arg Gly Arg Thr Gly Arg Gly Lys
             290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                 325                 330                 335

Tyr Glu Leu Thr Pro Ala Glu Thr Thr Val Arg Leu Arg Ala Tyr Met
             340                 345                 350

Asn Thr Pro Gly Leu Pro Val Cys Gln Asp His Leu Glu Phe Trp Glu
             355                 360                 365

Gly Val Phe Thr Gly Leu Thr His Ile Asp Ala His Phe Leu Ser Gln
370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                 405                 410                 415

Trp Lys Cys Leu Ile Arg Leu Lys Pro Thr Leu His Gly Pro Thr Pro
             420                 425                 430

Leu Leu Tyr Arg Leu Gly Ala Val Gln Asn Glu Ile Thr Leu Thr His
             435                 440                 445
```

Pro Val Thr Lys Tyr Ile Met Thr Cys Met Ser Ala Asp Leu Glu Val
            450                 455                 460

Val Thr Ser
465

<210> SEQ ID NO 55
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca acacttgcgt tactcagacc gtagatttta gcctggaccc gacttttcact     840 atcgaaacga tcaccctgcc gcaggatgca gtttcccgta cccatcgtcg tggccgtacc     900
ggtcgcggca aacccgggtat ttaccgtttc gtggcgccgg cgagcgtcc atccggtatg     960 ttcgatagct ctgttctgtg tgagtgttat gacgcgggtt gcgcgtggta cgaactgact    1020
ccggctgaaa ctactgtacg cctgcgtgca tacatgaata cgccgggtct gccggtgtgt    1080
caagaccacc tggaattttg ggaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg gaagtgcctg    1260
atccgtctga aaccgaccct gcacggtccg acgccactgc tgtaccgcct gggtgcagtg    1320
cagaacgaaa tcacgctgac gcacccggtc actaaataca ttatgacttg catgagcgca    1380
gacctggaag tggtgacttc c                                              1401
```

<210> SEQ ID NO 56
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Ala Val Asp Phe Ile Pro Val Glu Asn Leu Glu Thr Thr Met Arg Ser
1               5                   10                  15

```
Pro Val Phe Thr Asp Asn Ser Ser Pro Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
 50                  55                  60

Pro Ser Val Ala Ala Thr Leu Gly Phe Gly Ala Tyr Met Ser Lys Ala
 65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Cys Asp Glu Cys His
        115                 120                 125

Ser Thr Asp Ala Thr Ser Ile Leu Gly Ile Gly Thr Val Leu Asp Gln
        130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr His Arg Arg Gly Arg Thr Gly Arg Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
```

```
                435                 440                 445
Pro Val Thr Lys Tyr Ile Met Thr Cys Met Ser Ala Asp Leu Glu Val
        450                 455                 460

Val Thr Ser
465

<210> SEQ ID NO 57
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca acacttgcgt tactcagacc gtagatttta gcctggaccc gactttcact     840
atcgaaacga tcaccctgcc gcaggatgca gtttcccgta cccagcgtcg tggcgcgacc     900
ggtcgcggca aacggggtat ttaccgtttc gtggcgccgg cgagcgtcc atccggtatg     960 ttcgatagct ctgttctgtg tgagtgttat gacgcgggtt gcgcgtggta cgaactgact    1020
ccggctgaaa ctactgtacg cctgcgtgca tacatgaata cgcccgggtct gccggtgtgt    1080 caagaccacc tggaattttg ggaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg gaagtgcctg    1260
atccgtctga aaccgaccct gcacggtccg acgccactgc tgtaccgcct gggtgcagtg    1320
cagaacgaaa tcacgctgac gcacccggtc actaaataca ttatgacttg catgagcgca    1380
gacctggaag tggtgacttc c                                               1401

<210> SEQ ID NO 58
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Ala Val Asp Phe Ile Pro Val Glu Asn Leu Glu Thr Thr Met Arg Ser
```

```
1               5                   10                  15
Pro Val Phe Thr Asp Asn Ser Ser Pro Val Val Pro Gln Ser Phe
                20                  25                  30
Gln Val Ala His Leu His Ala Pro Thr Gly Ser Gly Lys Ser Thr Lys
                35                  40                  45
Val Pro Ala Ala Tyr Ala Ala Gln Gly Tyr Lys Val Leu Val Leu Asn
    50                  55                  60
Pro Ser Val Ala Ala Thr Leu Gly Phe Gly Ala Tyr Met Ser Lys Ala
65                  70                  75                  80
His Gly Ile Asp Pro Asn Ile Arg Thr Gly Val Arg Thr Ile Thr Thr
                85                  90                  95
Gly Ser Pro Ile Thr Tyr Ser Thr Tyr Gly Lys Phe Leu Ala Asp Gly
                100                 105                 110
Gly Cys Ser Gly Gly Ala Tyr Asp Ile Ile Ile Cys Asp Glu Cys His
                115                 120                 125
Ser Thr Asp Ala Thr Ser Ile Leu Gly Ile Gly Thr Val Leu Asp Gln
    130                 135                 140
Ala Glu Thr Ala Gly Ala Arg Leu Val Val Leu Ala Thr Ala Thr Pro
145                 150                 155                 160
Pro Gly Ser Val Thr Val Pro His Pro Asn Ile Glu Glu Val Ala Leu
                165                 170                 175
Ser Thr Thr Gly Glu Ile Pro Phe Tyr Gly Lys Ala Ile Pro Leu Glu
                180                 185                 190
Val Ile Lys Gly Gly Arg His Leu Ile Phe Cys His Ser Lys Lys Lys
                195                 200                 205
Cys Asp Glu Leu Ala Ala Lys Leu Val Ala Leu Gly Ile Asn Ala Val
    210                 215                 220
Ala Tyr Tyr Arg Gly Leu Asp Val Ser Val Ile Pro Thr Ser Gly Asp
225                 230                 235                 240
Val Val Val Val Ala Thr Asp Ala Leu Met Thr Gly Tyr Thr Gly Asp
                245                 250                 255
Phe Asp Ser Val Ile Asp Cys Asn Thr Cys Val Thr Gln Thr Val Asp
                260                 265                 270
Phe Ser Leu Asp Pro Thr Phe Thr Ile Glu Thr Ile Thr Leu Pro Gln
                275                 280                 285
Asp Ala Val Ser Arg Thr Gln Arg Arg Gly Ala Thr Gly Arg Gly Lys
    290                 295                 300
Pro Gly Ile Tyr Arg Phe Val Ala Pro Gly Glu Arg Pro Ser Gly Met
305                 310                 315                 320
Phe Asp Ser Ser Val Leu Cys Glu Cys Tyr Asp Ala Gly Cys Ala Trp
                325                 330                 335
Tyr Glu Leu Thr Pro Ala Glu Thr Thr Val Arg Leu Arg Ala Tyr Met
                340                 345                 350
Asn Thr Pro Gly Leu Pro Val Cys Gln Asp His Leu Glu Phe Trp Glu
                355                 360                 365
Gly Val Phe Thr Gly Leu Thr His Ile Asp Ala His Phe Leu Ser Gln
                370                 375                 380
Thr Lys Gln Ser Gly Glu Asn Leu Pro Tyr Leu Val Ala Tyr Gln Ala
385                 390                 395                 400
Thr Val Cys Ala Arg Ala Gln Ala Pro Pro Ser Trp Asp Gln Met
                405                 410                 415
Trp Lys Cys Leu Ile Arg Leu Lys Pro Thr Leu His Gly Pro Thr Pro
                420                 425                 430
```

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
    450                 455                 460

Val Thr Ser
465

<210> SEQ ID NO 59
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

| gctgttgact ttatcccggt tgaaaatctc gagactacta tgcgttctcc ggttttcact | 60 |
| gacaactctt ctccgccggt tgttccgcag tctttccagg ttgctcacct gcatgctccg | 120 |
| actggttctg gtaaatctac taaagttcca gctgcttacg ctgctcaggg ttacaaagtt | 180 |
| ctggttctga acccgtctgt tgctgctact ctgggtttcg cgcctacat gtctaaagct | 240 |
| cacggtatcg acccgaacat cgtactggt gtacgtacta tcactactgg ttctccgatc | 300 |
| acttactcta cttacggtaa attcctggct gacggtggtt gctctggtgg tgcttacgat | 360 |
| atcatcatct gcgacgaatg ccactctact gacgctactt ctatcctggg tatcggtacc | 420 |
| gttctggacc aggctgaaac tgcaggtgct cgtctggttg ttctggctac tgctactccg | 480 |
| ccgggttctg ttactgttcc gcacccgaac atcgaagaag ttgctctgtc gactactggt | 540 |
| gaaatcccgt tctacggtaa agctatcccg ctcgaggtta tcaaaggtgg tcgtcacctg | 600 |
| atttctgcc actctaaaaa aaaatgcgac gaactggctg ctaagcttgt tgctctgggt | 660 |
| atcaacgctg ttgcttacta ccgtggtctg gacgtttctg ttatcccgac ttctggtgac | 720 |
| gttgttgttg tggccactga cgctctgatg actggttaca ctggtgactt cgactctgtt | 780 |
| atcgattgca acacttgcgt tactcagacc gtagatttta gcctggaccc gactttcact | 840 |
| atcgaaacga tcaccctgcc gcaggatgca gtttcccgta cccagcgtcg tggccgtacc | 900 |
| ggtaaaggca aacgggtat ttaccgtttc gtggcgccgg cgagcgtcc atccggtatg | 960 |
| ttcgatagct ctgttctgtg tgagtgttat gacgcgggtt gcgcgtggta cgaactgact | 1020 |
| ccggctgaaa ctactgtacg cctgcgtgca tacatgaata cgcccgggtct gccggtgtgt | 1080 |
| caagaccacc tggaattttg ggaaggtgtc tttactggcc tgacccatat cgacgcacac | 1140 |
| tttctgtccc agactaaaca gtctggtgaa aacctgccgt acctggtggc gtatcaagcc | 1200 |
| actgtgtgcg cccgtgcgca ggcgccgcca ccgagctggg accaaatgtg gaagtgcctg | 1260 |
| atccgtctga aaccgaccct gcacggtccg acgccactgc tgtaccgcct gggtgcagtg | 1320 |
| cagaacgaaa tcacgctgac gcaccccggtc actaaataca ttatgacttg catgagcgca | 1380 |
| gacctggaag tggtgacttc c | 1401 |

<210> SEQ ID NO 60
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

-continued

```
Ala Val Asp Phe Ile Pro Val Glu Asn Leu Glu Thr Met Arg Ser
1               5                   10                  15

Pro Val Phe Thr Asp Asn Ser Ser Pro Val Pro Gln Ser Phe
            20                  25              30

Gln Val Ala His Leu His Ala Pro Thr Gly Ser Gly Lys Ser Thr Lys
        35              40                  45

Val Pro Ala Ala Tyr Ala Ala Gln Gly Tyr Lys Val Leu Val Leu Asn
50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
                100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
        130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
                180                 185                 190

Val Ile Lys Gly Gly Arg His Leu Ile Phe Cys His Ser Lys Lys Lys
                195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
                260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Lys Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
                340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
        370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415
```

Trp Lys Cys Leu Ile Arg Leu Lys Pro Thr Leu His Gly Pro Thr Pro
             420                 425                 430

Leu Leu Tyr Arg Leu Gly Ala Val Gln Asn Glu Ile Thr Leu Thr His
         435                 440                 445

Pro Val Thr Lys Tyr Ile Met Thr Cys Met Ser Ala Asp Leu Glu Val
     450                 455                 460

Val Thr Ser
465

<210> SEQ ID NO 61
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca acacttgcgt tactcagacc gtagatttta gcctggaccc gactttcact     840
atcgaaacga tcaccctgcc gcaggatgca gtttcccgta cccagcgtcg tggccgtacc     900
ggtcgcggca aaccgggtat ttaccgtttc gtggcgccgg cgagcgtcc atccggtatg     960
ttcgatagct ctgttctgtg tgagtgttat gacgcgggta gcgcgtggta cgaactgact    1020
ccggctgaaa ctactgtacg cctgcgtgca tacatgaata cgcccgggtct gccggtgtgt    1080
caagaccacc tggaattttg ggaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg gaagtgcctg    1260
atccgtctga aaccgaccct gcacggtccg acgccactgc tgtaccgcct gggtgcagtg    1320
cagaacgaaa tcacgctgac gcacccggtc actaaataca ttatgacttg catgagcgca    1380
gacctggaag tggtgacttc c                                             1401
```

<210> SEQ ID NO 62
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

| Ala | Val | Asp | Phe | Ile | Pro | Val | Glu | Asn | Leu | Glu | Thr | Thr | Met | Arg | Ser |
|-----|-----|-----|-----|-----|-----|-----|-----|-----|-----|-----|-----|-----|-----|-----|-----|
| 1 | | | | 5 | | | | | 10 | | | | | 15 | |

Pro Val Phe Thr Asp Asn Ser Ser Pro Val Val Pro Gln Ser Phe
            20              25              30

Gln Val Ala His Leu His Ala Pro Thr Gly Ser Gly Lys Ser Thr Lys
          35              40              45

Val Pro Ala Ala Tyr Ala Ala Gln Gly Tyr Lys Val Leu Val Leu Asn
    50              55              60

Pro Ser Val Ala Ala Thr Leu Gly Phe Gly Ala Tyr Met Ser Lys Ala
65              70              75              80

His Gly Ile Asp Pro Asn Ile Arg Thr Gly Val Arg Thr Ile Thr Thr
              85              90              95

Gly Ser Pro Ile Thr Tyr Ser Thr Tyr Gly Lys Phe Leu Ala Asp Gly
          100            105           110

Gly Cys Ser Gly Gly Ala Tyr Asp Ile Ile Cys Asp Glu Cys His
         115           120          125

Ser Thr Asp Ala Thr Ser Ile Leu Gly Ile Gly Thr Val Leu Asp Gln
   130               135              140

Ala Glu Thr Ala Gly Ala Arg Leu Val Val Leu Ala Thr Ala Thr Pro
145              150             155           160

Pro Gly Ser Val Thr Val Pro His Pro Asn Ile Glu Glu Val Ala Leu
              165            170          175

Ser Thr Thr Gly Glu Ile Pro Phe Tyr Gly Lys Ala Ile Pro Leu Glu
         180           185          190

Val Ile Lys Gly Gly Arg His Leu Ile Phe Cys His Ser Lys Lys Lys
         195           200          205

Cys Asp Glu Leu Ala Ala Lys Leu Val Ala Leu Gly Ile Asn Ala Val
   210               215              220

Ala Tyr Tyr Arg Gly Leu Asp Val Ser Val Ile Pro Thr Ser Gly Asp
225              230             235           240

Val Val Val Val Ala Thr Asp Ala Leu Met Thr Gly Tyr Thr Gly Asp
              245            250          255

Phe Asp Ser Val Ile Asp Cys Asn Thr Cys Val Thr Gln Thr Val Asp
         260           265          270

Phe Ser Leu Asp Pro Thr Phe Thr Ile Glu Thr Ile Thr Leu Pro Gln
     275              280            285

Asp Ala Val Ser Arg Thr Gln Arg Arg Gly Arg Thr Gly Arg Gly Lys
   290               295             300

Pro Gly Ile Tyr Arg Phe Val Ala Pro Gly Glu Arg Pro Ser Gly Met
305              310             315           320

Phe Asp Ser Ser Val Leu Cys Glu Cys Tyr Asp Ala Gly Ser Ala Trp
              325            330          335

Tyr Glu Leu Thr Pro Ala Glu Thr Thr Val Arg Leu Arg Ala Tyr Met
         340           345          350

Asn Thr Pro Gly Leu Pro Val Cys Gln Asp His Leu Glu Phe Trp Glu
         355           360          365

Gly Val Phe Thr Gly Leu Thr His Ile Asp Ala His Phe Leu Ser Gln
         370           375          380

Thr Lys Gln Ser Gly Glu Asn Leu Pro Tyr Leu Val Ala Tyr Gln Ala
385              390             395           400

Thr Val Cys Ala Arg Ala Gln Ala Pro Pro Pro Ser Trp Asp Gln Met

```
                    405                 410                 415
Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
            450                 455                 460

Val Thr Ser
465

<210> SEQ ID NO 63
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
gctgttgact ttatcccggt tgaaaatctc gagactacta tgcgttctcc ggttttcact    60
gacaactctt ctccgccggt tgttccgcag tctttccagg ttgctcacct gcatgctccg   120
actggttctg gtaaatctac taaagttcca gctgcttacg ctgctcaggg ttacaaagtt   180
ctggttctga accgtctgt tgctgctact ctgggtttcg cgcctacat gtctaaagct    240 cacggtatcg acccgaacat tcgtactggt gtacgtacta tcactactgg ttctccgatc   300
acttactcta cttacggtaa attcctggct gacggtggtt gctctggtgg tgcttacgat   360
atcatcatct gcgacgaatg ccactctact gacgctactt ctatcctggg tatcggtacc   420
gttctggacc aggctgaaac tgcaggtgct cgtctggttg ttctggctac tgctactccg   480
ccgggttctg ttactgttcc gcaccgaac atcgaagaag ttgctctgtc gactactggt    540
gaaatcccgt tctacggtaa agctatcccg ctcgaggtta tcaaaggtgg tcgtcacctg   600
attttctgcc actctaaaaa aaatgcgac gaactggctg ctaagcttgt tgctctgggt   660
atcaacgctg ttgcttacta ccgtggtctg gacgtttctg ttatcccgac ttctggtgac   720
gttgttgttg tggccactga cgctctgatg actggtaca ctggtgactt cgactctgtt    780
atcgattgca acacttgcgt tactcagacc gtagatttta gcctggaccc gactttcact   840
atcgaaacga tcaccctgcc gcaggatgca gtttcccgta cccagcgtcg tggccgtacc   900
ggtcgcggca aaccgggtat ttaccgtttc gtggcgccgg cgagcgtcc atccggtatg    960 ttcgatagct ctgttctgtg tgagtgttat gacgcgggtt gcgcggcgta cgaactgact  1020
ccggctgaaa ctactgtacg cctgcgtgca tacatgaata cgccgggtct gccggtgtgt  1080
caagaccacc tggaattttg ggaaggtgtc tttactggcc tgacccatat cgacgcacac  1140
tttctgtccc agactaaaca gtctggtgaa aacctgccgt acctggtggc gtatcaagcc  1200
actgtgtgcg cccgtgcgca ggcgccgcca ccgagctggg accaaatgtg gaagtgcctg  1260
atccgtctga aaccgaccct gcacggtccg acgccactgc tgtaccgcct gggtgcagtg  1320
cagaacgaaa tcacgctgac gcaccggtc actaaataca ttatgacttg catgagcgca   1380
gacctggaag tggtgacttc c                                            1401

<210> SEQ ID NO 64
<211> LENGTH: 467
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 64

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Ala
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
370                 375                 380

Thr Lys Gln Ser Gly Glu Asn Leu Pro Tyr Leu Val Ala Tyr Gln Ala
385                 390                 395                 400
```

Thr Val Cys Ala Arg Ala Gln Ala Pro Pro Ser Trp Asp Gln Met
            405                 410                 415

Trp Lys Cys Leu Ile Arg Leu Lys Pro Thr Leu His Gly Pro Thr Pro
        420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
    450                 455                 460

Val Thr Ser
465

<210> SEQ ID NO 65
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
gctgttgact ttatcccggt tgaaaatctc gagactacta tgcgttctcc ggttttcact        60
gacaactctt ctccgccggt tgttccgcag tctttccagg ttgctcacct gcatgctccg       120
actggttctg gtaaatctac taaagttcca gctgcttacg ctgctcaggg ttacaaagtt       180
ctggttctga acccgtctgt tgctgctact ctgggtttcg gcgcctacat gtctaaagct       240
cacggtatcg acccgaacat tcgtactggt gtacgtacta tcactactgg ttctccgatc       300
acttactcta cttacggtaa attcctggct gacggtggtt gctctggtgg tgcttacgat       360
atcatcatct gcgacgaatg ccactctact gacgctactt ctatcctggg tatcggtacc       420
gttctggacc aggctgaaac tgcaggtgct cgtctggttg ttctggctac tgctactccg       480
ccgggttctg ttactgttcc gcacccgaac atcgaagaag ttgctctgtc gactactggt       540
gaaatcccgt tctacggtaa agctatcccg ctcgaggtta tcaaaggtgg tcgtcacctg       600
attttctgcc actctaaaaa aaaatgcgac gaactggctg ctaagcttgt tgctctgggt       660
atcaacgctg ttgcttacta ccgtggtctg acgtttctg ttatcccgac ttctggtgac       720
gttgttgttg tggccactga cgctctgatg actggttaca ctggtgactt cgactctgtt       780
atcgattgca acacttgcgt tactcagacc gtagattta gcctggaccc gactttcact       840
atcgaaacga tcaccctgcc gcaggatgca gtttcccgta cccagcgtcg tggccgtacc       900
ggtcgcggca aaccgggtat ttaccgtttc gtggcgccgg cgagcgtcc atccggtatg       960 ttcgatagct ctgttctgtg tgagtgttat gacgcgggtt gcgcgtggta cgaactgact      1020
ccggctgaaa ctactgtacg cctgcgtgca tacatgaata cgccgggtct gccggtgtct      1080
caagaccacc tggaattttg gaaggtgtc tttactggcc tgacccatat cgacgcacac      1140
tttctgtccc agactaaaca gtctggtgaa aacctgccgt acctggtggc gtatcaagcc      1200
actgtgtgcg cccgtgcgca ggcgccgcca ccgagctggg accaaatgtg gaagtgcctg      1260
atccgtctga aaccgaccct gcacggtccg acgccactgc tgtaccgcct gggtgcagtg      1320
cagaacgaaa tcacgctgac gcaccccggtc actaaataca ttatgacttg catgagcgca      1380
gacctggaag tggtgacttc c                                                 1401

<210> SEQ ID NO 66
<211> LENGTH: 467
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 66

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
            35                  40                  45

Val Pro Ala Ala Tyr Ala Ala Gln Gly Tyr Lys Val Leu Val Leu Asn
50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
                100                 105                 110

Gly Cys Ser Gly Gly Ala Tyr Asp Ile Ile Ile Cys Asp Glu Cys His
            115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
            195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
            275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Ser Gln Asp His Leu Glu Phe Trp Glu
            355                 360                 365

Gly Val Phe Thr Gly Leu Thr His Ile Asp Ala His Phe Leu Ser Gln
370                 375                 380
```

```
Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
            405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
    450                 455                 460

Val Thr Ser
465

<210> SEQ ID NO 67
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
gctgttgact ttatcccggt tgaaaatctc gagactacta tgcgttctcc ggttttcact      60
gacaactctt ctccgccggt tgttccgcag tctttccagg ttgctcacct gcatgctccg    120
actggttctg gtaaatctac taaagttcca gctgcttacg ctgctcaggg ttacaaagtt    180
ctggttctga acccgtctgt tgctgctact ctgggtttcg gcgcctacat gtctaaagct    240
cacggtatcg acccgaacat tcgtactggt gtacgtacta tcactactgg ttctccgatc    300
acttactcta cttacggtaa attcctggct gacggtggtt gctctggtgg tgcttacgat    360
atcatcatct gcgacgaatg ccactctact gacgctactt ctatcctggg tatcggtacc    420
gttctggacc aggctgaaac tgcaggtgct cgtctggttg ttctggctac tgctactccg    480
ccgggttctg ttactgttcc gcacccgaac atcgaagaag ttgctctgtc gactactggt    540
gaaatcccgt ctacggtaa agctatcccg ctcgaggtta tcaaaggtgg tcgtcacctg    600
attttctgcc actctaaaaa aaaatgcgac gaactggctg ctaagcttgt tgctctgggt    660
atcaacgctg ttgcttacta ccgtggtctg gacgtttctg ttatccccgac ttctggtgac    720 gttgttgttg tggccactga cgctctgatg actggttaca ctggtgactt cgactctgtt    780
atcgattgca cacttgcgt tactcagacc gtagatttta gcctggaccc gactttcact    840
atcgaaacga tcaccctgcc gcaggatgca gtttcccgta cccagcgtcg tggccgtacc    900
ggtcgcggca aaccgggtat ttaccgtttc gtggcgccgg gcgagcgtcc atccggtatg    960
ttcgatagct ctgttctgtg tgagtgttat gacgcgggtt gcgcgtggta cgaactgact   1020
ccggctgaaa ctactgtacg cctgcgtgca tacatgaata cgccgggtct gccggtgtgt   1080
caagaccacc tggaattttg gaaggtgtc tttactggcc tgacccatat cgacgcacac   1140
tttctgtccc agactaaaca gtctggtgaa aacctgccgt acctggtggc gtatcaagcc   1200
actgtgtgcg cccgtgcgca ggcgccgcca ccgagctggg accaaatgtg gaagtgcctg   1260
atccgtctga aaccgaccct gcacggtccg acgccactgc tgtaccgcct gggtgcagtg   1320
cagaacgaaa tcacgctgac gcacccggtc actaaataca ttatgactag catgagcgca   1380
gacctggaag tggtgacttc c                                             1401

<210> SEQ ID NO 68
```

<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
```

```
                 370               375                380
Thr Lys Gln Ser Gly Glu Asn Leu Pro Tyr Leu Val Ala Tyr Gln Ala
385                 390                395                400

Thr Val Cys Ala Arg Ala Gln Ala Pro Pro Pro Ser Trp Asp Gln Met
                405                410                415

Trp Lys Cys Leu Ile Arg Leu Lys Pro Thr Leu His Gly Pro Thr Pro
                420                425                430

Leu Leu Tyr Arg Leu Gly Ala Val Gln Asn Glu Ile Thr Leu Thr His
            435                440                445

Pro Val Thr Lys Tyr Ile Met Thr Ser Met Ser Ala Asp Leu Glu Val
        450                455                460

Val Thr Ser
465

<210> SEQ ID NO 69
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg cgcctctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaatgcgac gaactggctg ctaagcttgt tgctctgggt     660
atcaacgctg ttgcttacta ccgtggtctg acgtttctg ttatcccgac ttctggtgac     720
gttgttgttg tggccactga cgctctgatg actggttaca ctggtgactt cgactctgtt     780
atcgattgca acacttgcgt tactcagacc gtagattta gcctggaccc gactttcact     840
atcgaaacga tcaccctgcc gcaggatgca gtttccgta cccagcgtcg tggcgcgacc     900
ggtcgcggca aaccgggtat ttaccgtttc gtggcgccgg cgagcgtcc atccggtatg     960
ttcgatagct ctgttctgtg tgagtgttat gacgcgggtt gcgcgtggta cgaactgact    1020
ccggctgaaa ctactgtacg cctgcgtgca tacatgaata cgcccgggtct gccggtgtgt    1080
caagaccacc tggaattttg ggaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg gaagtgcctg    1260
atccgtctga aaccgaccct gcacggtccg acgccactgc tgtaccgcct gggtgcagtg    1320
cagaacgaaa tcacgctgac gcaccccggtc actaaatca ttatgacttg catgagcgca    1380
gacctggaag tggtgacttc c                                               1401
```

<210> SEQ ID NO 70
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

```
Ala Val Asp Phe Ile Pro Val Glu Asn Leu Glu Thr Thr Met Arg Ser
1               5                   10                  15

Pro Val Phe Thr Asp Asn Ser Ser Pro Val Pro Gln Ser Phe
            20                  25                  30          Phe

Gln Val Ala His Leu His Ala Pro Thr Gly Ser Gly Lys Ser Thr Lys
            35                  40                  45

Val Pro Ala Ala Tyr Ala Ala Gln Gly Tyr Lys Val Leu Val Leu Asn
50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
                100                 105                 110

Gly Cys Ser Gly Gly Ala Tyr Asp Ile Ile Cys Asp Glu Cys Ala
            115                 120                 125

Ser Thr Asp Ala Thr Ser Ile Leu Gly Ile Gly Thr Val Leu Asp Gln
        130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Ala Thr Gly Arg Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365
```

```
Gly Val Phe Thr Gly Leu Thr His Ile Asp Ala His Phe Leu Ser Gln
        370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
    450                 455                 460

Val Thr Ser
465

<210> SEQ ID NO 71
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
```

| | | | | | |
|---|---|---|---|---|---|
| gctgttgact | ttatcccggt | tgaaaatctc | gagactacta | tgcgttctcc | ggttttcact | 60 |
| gacaactctt | ctccgccggt | tgttccgcag | tctttccagg | ttgctcacct | gcatgctccg | 120 |
| actggttctg | gtaaatctac | taaagttcca | gctgcttacg | ctgctcaggg | ttacaaagtt | 180 |
| ctggttctga | cccgtctgt | tgctgctact | ctgggtttcg | gcgcctacat | gtctaaagct | 240 |
| cacggtatcg | acccgaacat | tcgtactggt | gtacgtacta | tcactactgg | ttctccgatc | 300 |
| acttactcta | cttacggtaa | attcctggct | gacggtggtt | gctctggtgg | tgcttacgat | 360 |
| atcatcatct | gcgacgaaag | ccactctact | gacgctactt | ctatcctggg | tatcggtacc | 420 |
| gttctggacc | aggctgaaac | tgcaggtgct | cgtctggttg | ttctggctac | tgctactccg | 480 |
| ccgggttctg | ttactgttcc | gcacccgaac | atcgaagaag | ttgctctgtc | gactactggt | 540 |
| gaaatcccgt | tctacggtaa | agctatcccg | ctcgaggtta | tcaaaggtgg | tcgtcacctg | 600 |
| atttctgcc | actctaaaaa | aaaaagcgac | gaactggctg | ctaagcttgt | tgctctgggt | 660 |
| atcaacgctg | ttgcttacta | ccgtggtctg | gacgtttctg | ttatcccgac | ttctggtgac | 720 |
| gttgttgttg | tggccactga | cgctctgatg | actggttaca | ctggtgactt | cgactctgtt | 780 |
| atcgattgca | acacttgcgt | tactcagacc | gtagatttta | gcctggaccc | gactttcact | 840 |
| atcgaaacga | tcaccctgcc | gcaggatgca | gtttcccgta | cccagcgtcg | tggccgtacc | 900 |
| ggtcgcggca | aacgggtat | ttaccgtttc | gtggcgccgg | gcgagcgtcc | atccggtatg | 960 |
| ttcgatagct | ctgttctgtg | tgagtgttat | gacgcgggtt | gcgcgtggta | cgaactgact | 1020 |
| ccggctgaaa | ctactgtacg | cctgcgtgca | tacatgaata | cgccgggtct | gccggtgtgt | 1080 |
| caagaccacc | tggaattttg | ggaaggtgtc | tttactggcc | tgacccatat | cgacgcacac | 1140 |
| tttctgtccc | agactaaaca | gtctggtgaa | aacctgccgt | acctggtggc | gtatcaagcc | 1200 |
| actgtgtgcg | cccgtgcgca | ggcgccgcca | ccgagctggg | accaaatgtg | gaagtgcctg | 1260 |
| atccgtctga | aaccgaccct | gcacggtccg | acgccactgc | tgtaccgcct | gggtgcagtg | 1320 |
| cagaacgaaa | tcacgctgac | gcacccggtc | actaaataca | ttatgacttg | catgagcgca | 1380 | gacctggaag tggtgacttc c                                                                1401

<210> SEQ ID NO 72
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

```
Ala Val Asp Phe Ile Pro Val Glu Asn Leu Glu Thr Thr Met Arg Ser
1               5                   10                  15

Pro Val Phe Thr Asp Asn Ser Ser Pro Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Ser His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Ser Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350
```

```
Asn Thr Pro Gly Leu Pro Val Cys Gln Asp His Leu Glu Phe Trp Glu
            355                 360                 365
Gly Val Phe Thr Gly Leu Thr His Ile Asp Ala His Phe Leu Ser Gln
    370                 375                 380
Thr Lys Gln Ser Gly Glu Asn Leu Pro Tyr Leu Val Ala Tyr Gln Ala
385                 390                 395                 400
Thr Val Cys Ala Arg Ala Gln Ala Pro Pro Pro Ser Trp Asp Gln Met
                405                 410                 415
Trp Lys Cys Leu Ile Arg Leu Lys Pro Thr Leu His Gly Pro Thr Pro
                420                 425                 430
Leu Leu Tyr Arg Leu Gly Ala Val Gln Asn Glu Ile Thr Leu Thr His
            435                 440                 445
Pro Val Thr Lys Tyr Ile Met Thr Cys Met Ser Ala Asp Leu Glu Val
            450                 455                 460
Val Thr Ser
465

<210> SEQ ID NO 73
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga accgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaaag ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca acacttgcgt tactcagacc gtagattta gcctggaccc gactttcact     840
atcgaaacga tcaccctgcc gcaggatgca gtttcccgta cccagcgtcg tggccgtacc     900
ggtcgcggca aaccgggtat ttaccgtttc gtggcgccgg cgagcgtcc atccggtatg     960 ttcgatagct ctgttctgtg tgagtgttat gacgcgggta gcgcgtggta cgaactgact    1020
ccggctgaaa ctactgtacg cctgcgtgca tacatgaata cgccgggtct gccggtgtgt    1080
caagaccacc tggaatttg gaaggtgtc tttactggcc tgacccatat cgacgcacac    1140
tttctgtccc agactaaaca gtctggtgaa aacctgccgt acctggtggc gtatcaagcc    1200
actgtgtgcg cccgtgcgca ggcgccgcca ccgagctggg accaaatgtg gaagtgcctg    1260
atccgtctga aaccgaccct gcacggtccg acgccactgc tgtaccgcct gggtgcagtg    1320
```

```
cagaacgaaa tcacgctgac gcacccggtc actaaataca ttatgacttg catgagcgca      1380
gacctggaag tggtgacttc c                                                1401
```

<210> SEQ ID NO 74
<211> LENGTH: 467
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 74

```
Ala Val Asp Phe Ile Pro Val Glu Asn Leu Glu Thr Thr Met Arg Ser
1               5                   10                  15

Pro Val Phe Thr Asp Asn Ser Ser Pro Val Pro Gln Ser Phe
            20                  25                  30      Phe

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Ser His
        115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Ser Ala Trp
                325                 330                 335

Tyr Glu Leu Thr Pro Ala Glu Thr Thr Val Arg Leu Arg Ala Tyr Met
```

```
                    340             345             350
Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
        370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
    450                 455                 460

Val Thr Ser
465

<210> SEQ ID NO 75
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
gctgttgact ttatcccggt tgaaaatctc gagactacta tgcgttctcc ggttttcact       60
gacaactctt ctccgccggt tgttccgcag tctttccagg ttgctcacct gcatgctccg      120
actggttctg gtaaatctac taaagttcca gctgcttacg ctgctcaggg ttacaaagtt      180
ctggttctga acccgtctgt tgctgctact ctgggtttcg cgcctacat gtctaaagct       240 cacggtatcg acccgaacat tcgtactggt gtacgtacta tcactactgg ttctccgatc      300
acttactcta cttacggtaa attcctggct gacggtggtt gctctggtgg tgcttacgat      360
atcatcatct gcgacgaaag ccactctact gacgctactt ctatcctggg tatcggtacc      420
gttctggacc aggctgaaac tgcaggtgct cgtctggttg ttctggctac tgctactccg      480
ccgggttctg ttactgttcc gcacccgaac atcgaagaag ttgctctgtc gactactggt      540
gaaatcccgt tctacggtaa agctatcccg ctcgaggtta tcaaaggtgg tcgtcacctg      600
attttctgcc actctaaaaa aaaatgcgac gaactggctg ctaagcttgt tgctctgggt      660
atcaacgctg ttgcttacta ccgtggtctg gacgtttctg ttatcccgac ttctggtgac      720
gttgttgttg tggccactga cgctctgatg actggttaca ctggtgactt cgactctgtt      780
atcgattgca cacttgcgt tactcagacc gtagatttta gcctggaccc gactttcact      840
atcgaaacga tcaccctgcc gcaggatgca gtttcccgta cccagcgtcg tggccgtacc      900
ggtcgcggca aaccgggtat ttaccgtttc gtggcgccgg cgagcgtcc atccggtatg      960 ttcgatagct ctgttctgtg tgagtgttat gacgcgggtt gcgcgtggta cgaactgact     1020
ccggctgaaa ctactgtacg cctgcgtgca tacatgaata cgccgggtct gccggtgagt     1080
caagaccacc tggaattttg gaaggtgtc tttactggcc tgacccatat cgacgcacac      1140
tttctgtccc agactaaaca gtctggtgaa aacctgccgt acctggtggc gtatcaagcc     1200
actgtgtgcg cccgtgcgca ggcgccgcca ccgagctggg accaaatgtg gaagtgcctg     1260
```

-continued

```
atccgtctga aaccgaccct gcacggtccg acgccactgc tgtaccgcct gggtgcagtg   1320
cagaacgaaa tcacgctgac gcacccggtc actaaataca ttatgacttg catgagcgca   1380
gacctggaag tggtgacttc c                                             1401
```

<210> SEQ ID NO 76
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

```
Ala Val Asp Phe Ile Pro Val Glu Asn Leu Glu Thr Thr Met Arg Ser
1               5                   10                  15

Pro Val Phe Thr Asp Asn Ser Ser Pro Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Ser His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335
```

```
Tyr Glu Leu Thr Pro Ala Glu Thr Thr Val Arg Leu Arg Ala Tyr Met
                340                 345                 350

Asn Thr Pro Gly Leu Pro Val Ser Gln Asp His Leu Glu Phe Trp Glu
            355                 360                 365

Gly Val Phe Thr Gly Leu Thr His Ile Asp Ala His Phe Leu Ser Gln
370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
                435                 440                 445

Pro Val Thr Lys Tyr Ile Met Thr Cys Met Ser Ala Asp Leu Glu Val
            450                 455                 460

Val Thr Ser
465

<210> SEQ ID NO 77
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaaag ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt ctactggtaa agctatcccg ctcgaggtta tcaaaggtgg tcgtcacctg     600
attttctgcc actctaaaaa aaaatgcgac gaactggctg ctaagcttgt tgctctgggt     660
atcaacgctg ttgcttacta ccgtggtctg gacgtttctg ttatcccgac ttctggtgac     720
gttgttgttg tggccactga cgctctgatg actggttaca ctggtgactt cgactctgtt     780
atcgattgca cacttgcgt tactcagacc gtagatttta gcctggaccc gactttcact     840
atcgaaacga tcaccctgcc gcaggatgca gtttcccgta cccagcgtcg tggccgtacc     900
ggtcgcggca aaccgggtat ttaccgtttc gtggcgccgg cgagcgtcc atccggtatg     960
ttcgatagct ctgttctgtg tgagtgttat gacgcgggtt gcgcgtggta cgaactgact    1020
ccggctgaaa ctactgtacg cctgcgtgca tacatgaata cgccgggtct gccggtgtgt    1080
caagaccacc tggaattttg gaaggtgtc tttactggcc tgacccatat cgacgcacac    1140
tttctgtccc agactaaaca gtctggtgaa aacctgccgt acctggtggc gtatcaagcc    1200
```

```
actgtgtgcg cccgtgcgca ggcgccgcca ccgagctggg accaaatgtg gaagtgcctg   1260
atccgtctga aaccgaccct gcacggtccg acgccactgc tgtaccgcct gggtgcagtg   1320
cagaacgaaa tcacgctgac gcacccggtc actaaataca ttatgactag catgagcgca   1380
gacctggaag tggtgacttc c                                             1401
```

<210> SEQ ID NO 78
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Ala Val Asp Phe Ile Pro Val Glu Asn Leu Glu Thr Thr Met Arg Ser
1               5                   10                  15

Pro Val Phe Thr Asp Asn Ser Ser Pro Val Pro Gln Ser Phe
            20                  25                  30        Phe

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Ser His
        115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320
```

```
Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
    370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
                435                 440                 445

Pro Val Thr Lys Tyr Ile Met Thr Ser Met Ser Ala Asp Leu Glu Val
        450                 455                 460

Val Thr Ser
465
```

<210> SEQ ID NO 79
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

```
gctgttgact ttatcccggt tgaaaatctc gagactacta tgcgttctcc ggttttcact     60
gacaactctt ctccgccggt tgttccgcag tctttccagg ttgctcacct gcatgctccg    120
actggttctg gtaaatctac taaagttcca gctgcttacg ctgctcaggg ttacaaagtt    180
ctggttctga accagtctgt tgctgctact ctgggtttcg gcgcctacat gtctaaagct    240
cacggtatcg acccgaacat tcgtactggt gtacgtacta tcactactgg ttctccgatc    300
acttactcta cttacggtaa attcctggct gacggtggtt gctctggtgg tgcttacgat    360
atcatcatct gcgacgaaag ccactctact gacgctactt ctatcctggg tatcggtacc    420
gttctggacc aggctgaaac tgcaggtgct cgtctggttg ttctggctac tgctactccg    480
ccgggttctg ttactgttcc gcacccgaac atcgaagaag ttgctctgtc gactactggt    540
gaaatcccgt tctacggtaa agctatcccg ctcgaggtta tcaaaggtgg tcgtcacctg    600
attttctgcc actctaaaaa aaaaagcgac gaactggctg ctaagcttgt tgctctgggt    660
atcaacgctg ttgcttacta ccgtggtctg gacgtttctg ttatcccgac ttctggtgac    720
gttgttgttg tggccactga cgctctgatg actggttaca ctggtgactt cgactctgtt    780
atcgattgca acacttgcgt tactcagacc gtagattta gcctggaccc gactttcact    840
atcgaaacga tcaccctgcc gcaggatgca gtttcccgta cccagcgtcg tggccgtacc    900
ggtcgcggca aaccgggtat ttaccgtttc gtggcgccgg cgagcgtcc atccggtatg    960 ttcgatagct ctgttctgtg tgagtgttat gacgcgggtt gcgcgtggta cgaactgact   1020
ccggctgaaa ctactgtacg cctgcgtgca tacatgaata cgccgggtct gccggtgtgt   1080
caagaccacc tggaattttg ggaaggtgtc tttactggcc tgacccatat cgacgcacac   1140
```

-continued

```
tttctgtccc agactaaaca gtctggtgaa aacctgccgt acctggtggc gtatcaagcc   1200
actgtgtgcg cccgtgcgca ggcgccgcca ccgagctggg accaaatgtg aagtgcctg    1260 atccgtctga aaccgaccct gcacggtccg acgccactgc tgtaccgcct gggtgcagtg   1320
cagaacgaaa tcacgctgac gcacccggtc actaaataca ttatgacttg catgagcgca   1380
gacctggaag tggtgacttc c                                              1401
```

<210> SEQ ID NO 80
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
Ala Val Asp Phe Ile Pro Val Glu Asn Leu Glu Thr Thr Met Arg Ser
1               5                  10                  15

Pro Val Phe Thr Asp Asn Ser Ser Pro Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Gln Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Ser His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Ser Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
    290                 295                 300

Pro Gly Ile Tyr Arg Phe Val Ala Pro Gly Glu Arg Pro Ser Gly Met
```

```
            305                 310                 315                 320
        Phe Asp Ser Val Leu Cys Glu Cys Tyr Asp Ala Gly Cys Ala Trp
                        325                 330                 335

Tyr Glu Leu Thr Pro Ala Glu Thr Thr Val Arg Leu Arg Ala Tyr Met
                    340                 345                 350

Asn Thr Pro Gly Leu Pro Val Cys Gln Asp His Leu Glu Phe Trp Glu
                355                 360                 365

Gly Val Phe Thr Gly Leu Thr His Ile Asp Ala His Phe Leu Ser Gln
            370                 375                 380

Thr Lys Gln Ser Gly Glu Asn Leu Pro Tyr Leu Val Ala Tyr Gln Ala
        385                 390                 395                 400

Thr Val Cys Ala Arg Ala Gln Ala Pro Pro Pro Ser Trp Asp Gln Met
                        405                 410                 415

Trp Lys Cys Leu Ile Arg Leu Lys Pro Thr Leu His Gly Pro Thr Pro
                    420                 425                 430

Leu Leu Tyr Arg Leu Gly Ala Val Gln Asn Glu Ile Thr Leu Thr His
                435                 440                 445

Pro Val Thr Lys Tyr Ile Met Thr Cys Met Ser Ala Asp Leu Glu Val
            450                 455                 460

Val Thr Ser
        465

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ggcggctgca gcggtggcgc g                                                  21

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Gly Cys Ser Gly Gly Ala
1               5

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gatgaatgtc atagcaccga t                                                  21

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 84

Asp Glu Cys His Ser Thr Asp
1               5

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
agcaaaaaga aatgcgatga a                                             21

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Lys Lys Lys Cys Asp Glu
1               5

<210> SEQ ID NO 87
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Ala Val Asp Phe Ile Pro Val Glu Asn Leu Thr Thr Met Arg Ser
1               5                   10                  15

Pro Val Phe Thr Asp Asn Ser Ser Pro Pro Val Val Pro Gln Ser Phe
                20                  25                  30

Gln Val Ala His Leu His Ala Pro Thr Gly Ser Gly Lys Ser Thr Lys
            35                  40                  45

Val Pro Ala Ala Tyr Ala Ala Gln Gly Tyr Lys Val Leu Val Leu Asn
        50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
                100                 105                 110

Gly Cys Ser Gly Gly Ala Tyr Asp Ile Ile Ile Cys Asp Glu Cys His
            115                 120                 125

Ser Thr Asp Ala Thr Ser Ile Leu Gly Ile Gly Thr Val Leu Asp Gln
        130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu

```
                180             185              190
Val Ile Lys Gly Gly Arg His Leu Ile Phe Cys His Ser Lys Lys Lys
                195             200              205
Cys Asp Glu Leu Ala Ala Lys Leu Val Ala Leu Gly Ile Asn Ala Val
            210             215             220
Ala Tyr Tyr Arg Gly Leu Asp Val Ser Val Ile Pro Thr Ser Gly Asp
225             230             235             240
Val Val Val Val Ala Thr Asp Ala Leu Met Thr Gly Tyr Thr Gly Asp
                245             250             255
Phe Asp Ser Val Ile Asp Cys Asn Thr Cys Val Thr Gln Thr Val Asp
                260             265             270
Phe Ser Leu Asp Pro Thr Phe Thr Ile Glu Thr Ile Thr Leu Pro Gln
                275             280             285
Asp Ala Val Ser Arg Thr Gln Arg Arg Gly Arg Thr Gly Arg Gly Lys
                290             295             300
Pro Gly Ile Tyr Arg Phe Val Ala Pro Gly Glu Arg Pro Ser Gly Met
305             310             315             320
Phe Asp Ser Ser Val Leu Cys Glu Cys Tyr Asp Ala Gly Cys Ala Trp
                325             330             335
Tyr Glu Leu Thr Pro Ala Glu Thr Thr Val Arg Leu Arg Ala Tyr Met
                340             345             350
Asn Thr Pro Gly Leu Pro Val Cys Gln Asp His Leu Glu Phe Trp Glu
                355             360             365
Gly Val Phe Thr Gly Leu Thr His Ile Asp Ala His Phe Leu Ser Gln
                370             375             380
Thr Lys Gln Ser Gly Glu Asn Leu Pro Tyr Leu Val Ala Tyr Gln Ala
385             390             395             400
Thr Val Cys Ala Arg Ala Gln Ala Pro Pro Ser Trp Asp Gln Met
                405             410             415
Trp Lys Cys Leu Ile Arg Leu Lys Pro Thr Leu His Gly Pro Thr Pro
                420             425             430
Leu Leu Tyr Arg Leu Gly Ala Val Gln Asn Glu Ile Thr Leu Thr His
                435             440             445
Pro Val Thr Lys Tyr Ile Met Thr Cys Met Ser Ala Asp Leu Glu Val
                450             455             460
Val Thr
465

<210> SEQ ID NO 88
<211> LENGTH: 3011
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Ser Thr Asn Pro Lys Pro Gln Lys Lys Asn Lys Arg Asn Thr Asn
1               5                   10                  15
Arg Arg Pro Gln Asp Val Lys Phe Pro Gly Gly Gly Gln Ile Val Gly
                20                  25                  30
Gly Val Tyr Leu Leu Pro Arg Arg Gly Pro Arg Leu Gly Val Arg Ala
                35                  40                  45
Thr Arg Lys Thr Ser Glu Arg Ser Gln Pro Arg Gly Arg Arg Gln Pro
50                  55                  60
```

-continued

```
Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Thr Gly Leu Tyr His Val Thr Asn Asp Cys Pro
        195                 200                 205

Asn Ser Ser Ile Val Tyr Glu Ala Ala Asp Ala Ile Leu His Thr Pro
210                 215                 220

Gly Cys Val Pro Cys Val Arg Glu Gly Asn Ala Ser Arg Cys Trp Val
225                 230                 235                 240

Ala Met Thr Pro Thr Val Ala Thr Arg Asp Gly Lys Leu Pro Ala Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Gly Cys
290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Met Ala Gln
                325                 330                 335

Leu Leu Arg Ile Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Phe Ala Gly Val Asp Ala Glu Thr
370                 375                 380

Thr His Val Thr Gly Gly Ser Ala Gly His Thr Val Ser Gly Phe Val
385                 390                 395                 400

Ser Leu Leu Ala Pro Gly Ala Lys Gln Asn Val Gln Leu Ile Asn Thr
                405                 410                 415

Asn Gly Ser Trp His Leu Asn Ser Thr Ala Leu Asn Cys Asn Asp Ser
            420                 425                 430

Leu Asn Thr Gly Trp Leu Ala Gly Leu Phe Tyr His His Lys Phe Asn
        435                 440                 445

Ser Ser Gly Cys Pro Glu Arg Leu Ala Ser Cys Arg Pro Leu Thr Asp
450                 455                 460

Phe Asp Gln Gly Trp Gly Pro Ile Ser Tyr Ala Asn Gly Ser Gly Pro
465                 470                 475                 480

Asp Gln Arg Pro Tyr Cys Trp His Tyr Pro Pro Lys Pro Cys Gly Ile
```

```
                485                 490                 495
Val Pro Ala Lys Ser Val Cys Gly Pro Val Tyr Cys Phe Thr Pro Ser
            500                 505                 510
Pro Val Val Gly Thr Thr Asp Arg Ser Gly Ala Pro Thr Tyr Ser
            515                 520                 525
Trp Gly Glu Asn Asp Thr Asp Val Phe Val Leu Asn Asn Thr Arg Pro
            530                 535                 540
Pro Leu Gly Asn Trp Phe Gly Cys Thr Trp Met Asn Ser Thr Gly Phe
545                 550                 555                 560
Thr Lys Val Cys Gly Ala Pro Pro Cys Val Ile Gly Gly Ala Gly Asn
                565                 570                 575
Asn Thr Leu His Cys Pro Thr Asp Cys Phe Arg Lys His Pro Asp Ala
            580                 585                 590
Thr Tyr Ser Arg Cys Gly Ser Gly Pro Trp Ile Thr Pro Arg Cys Leu
            595                 600                 605
Val Asp Tyr Pro Tyr Arg Leu Trp His Tyr Pro Cys Thr Ile Asn Tyr
            610                 615                 620
Thr Ile Phe Lys Ile Arg Met Tyr Val Gly Gly Val Glu His Arg Leu
625                 630                 635                 640
Glu Ala Ala Cys Asn Trp Thr Arg Gly Glu Arg Cys Asp Leu Glu Asp
                645                 650                 655
Arg Asp Arg Ser Glu Leu Ser Pro Leu Leu Leu Thr Thr Thr Gln Trp
            660                 665                 670
Gln Val Leu Pro Cys Ser Phe Thr Thr Leu Pro Ala Leu Ser Thr Gly
            675                 680                 685
Leu Ile His Leu His Gln Asn Ile Val Asp Val Gln Tyr Leu Tyr Gly
            690                 695                 700
Val Gly Ser Ser Ile Ala Ser Trp Ala Ile Lys Trp Glu Tyr Val Val
705                 710                 715                 720
Leu Leu Phe Leu Leu Leu Ala Asp Ala Arg Val Cys Ser Cys Leu Trp
                725                 730                 735
Met Met Leu Leu Ile Ser Gln Ala Glu Ala Ala Leu Glu Asn Leu Val
            740                 745                 750
Ile Leu Asn Ala Ala Ser Leu Ala Gly Thr His Gly Leu Val Ser Phe
            755                 760                 765
Leu Val Phe Phe Cys Phe Ala Trp Tyr Leu Lys Gly Lys Trp Val Pro
            770                 775                 780
Gly Ala Val Tyr Thr Phe Tyr Gly Met Trp Pro Leu Leu Leu Leu Leu
785                 790                 795                 800
Leu Ala Leu Pro Gln Arg Ala Tyr Ala Leu Asp Thr Glu Val Ala Ala
                805                 810                 815
Ser Cys Gly Gly Val Val Leu Val Gly Leu Met Ala Leu Thr Leu Ser
            820                 825                 830
Pro Tyr Tyr Lys Arg Tyr Ile Ser Trp Cys Leu Trp Trp Leu Gln Tyr
            835                 840                 845
Phe Leu Thr Arg Val Glu Ala Gln Leu His Val Trp Ile Pro Pro Leu
850                 855                 860
Asn Val Arg Gly Gly Arg Asp Ala Val Ile Leu Leu Met Cys Ala Val
865                 870                 875                 880
His Pro Thr Leu Val Phe Asp Ile Thr Lys Leu Leu Leu Ala Val Phe
            885                 890                 895
Gly Pro Leu Trp Ile Leu Gln Ala Ser Leu Leu Lys Val Pro Tyr Phe
            900                 905                 910
```

```
Val Arg Val Gln Gly Leu Leu Arg Phe Cys Ala Leu Ala Arg Lys Met
        915                 920                 925
Ile Gly Gly His Tyr Val Gln Met Val Ile Ile Lys Leu Gly Ala Leu
        930                 935                 940
Thr Gly Thr Tyr Val Tyr Asn His Leu Thr Pro Leu Arg Asp Trp Ala
945                 950                 955                 960
His Asn Gly Leu Arg Asp Leu Ala Val Ala Val Glu Pro Val Phe
                    965                 970                 975
Ser Gln Met Glu Thr Lys Leu Ile Thr Trp Gly Ala Asp Thr Ala Ala
                    980                 985                 990
Cys Gly Asp Ile Ile Asn Gly Leu  Pro Val Ser Ala Arg  Arg Gly Arg
                995                 1000                1005
Glu Ile Leu Leu Gly Pro Ala  Asp Gly Met Val Ser  Lys Gly Trp
    1010                1015                1020
Arg Leu Leu Ala Pro Ile Thr  Ala Tyr Ala Gln Gln  Thr Arg Gly
    1025                1030                1035
Leu Leu Gly Cys Ile Ile Thr  Ser Leu Thr Gly Arg  Asp Lys Asn
    1040                1045                1050
Gln Val Glu Gly Glu Val Gln  Ile Val Ser Thr Ala  Ala Gln Thr
    1055                1060                1065
Phe Leu Ala Thr Cys Ile Asn  Gly Val Cys Trp Thr  Val Tyr His
    1070                1075                1080
Gly Ala Gly Thr Arg Thr Ile  Ala Ser Pro Lys Gly  Pro Val Ile
    1085                1090                1095
Gln Met Tyr Thr Asn Val Asp  Gln Asp Leu Val Gly  Trp Pro Ala
    1100                1105                1110
Pro Gln Gly Ser Arg Ser Leu  Thr Pro Cys Thr Cys  Gly Ser Ser
    1115                1120                1125
Asp Leu Tyr Leu Val Thr Arg  His Ala Asp Val Ile  Pro Val Arg
    1130                1135                1140
Arg Arg Gly Asp Ser Arg Gly  Ser Leu Leu Ser Pro  Arg Pro Ile
    1145                1150                1155
Ser Tyr Leu Lys Gly Ser Ser  Gly Gly Pro Leu Leu  Cys Pro Ala
    1160                1165                1170
Gly His Ala Val Gly Ile Phe  Arg Ala Ala Val Cys  Thr Arg Gly
    1175                1180                1185
Val Ala Lys Ala Val Asp Phe  Ile Pro Val Glu Asn  Leu Glu Thr
    1190                1195                1200
Thr Met Arg Ser Pro Val Phe  Thr Asp Asn Ser Ser  Pro Pro Val
    1205                1210                1215
Val Pro Gln Ser Phe Gln Val  Ala His Leu His Ala  Pro Thr Gly
    1220                1225                1230
Ser Gly Lys Ser Thr Lys Val  Pro Ala Ala Tyr Ala  Ala Gln Gly
    1235                1240                1245
Tyr Lys Val Leu Val Leu Asn  Pro Ser Val Ala Ala  Thr Leu Gly
    1250                1255                1260
Phe Gly Ala Tyr Met Ser Lys  Ala His Gly Ile Asp  Pro Asn Ile
    1265                1270                1275
Arg Thr Gly Val Arg Thr Ile  Thr Thr Gly Ser Pro  Ile Thr Tyr
    1280                1285                1290
Ser Thr Tyr Gly Lys Phe Leu  Ala Asp Gly Gly Cys  Ser Gly Gly
    1295                1300                1305
```

```
Ala Tyr Asp Ile Ile Ile Cys Asp Glu Cys His Ser Thr Asp Ala
        1310            1315                1320
Thr Ser Ile Leu Gly Ile Gly Thr Val Leu Asp Gln Ala Glu Thr
        1325            1330                1335
Ala Gly Ala Arg Leu Val Val Leu Ala Thr Ala Thr Pro Pro Gly
        1340            1345                1350
Ser Val Thr Val Pro His Pro Asn Ile Glu Glu Val Ala Leu Ser
        1355            1360                1365
Thr Thr Gly Glu Ile Pro Phe Tyr Gly Lys Ala Ile Pro Leu Glu
        1370            1375                1380
Val Ile Lys Gly Gly Arg His Leu Ile Phe Cys His Ser Lys Lys
        1385            1390                1395
Lys Cys Asp Glu Leu Ala Ala Lys Leu Val Ala Leu Gly Ile Asn
        1400            1405                1410
Ala Val Ala Tyr Tyr Arg Gly Leu Asp Val Ser Val Ile Pro Thr
        1415            1420                1425
Ser Gly Asp Val Val Val Ala Thr Asp Ala Leu Met Thr Gly
        1430            1435                1440
Tyr Thr Gly Asp Phe Asp Ser Val Ile Asp Cys Asn Thr Cys Val
        1445            1450                1455
Thr Gln Thr Val Asp Phe Ser Leu Asp Pro Thr Phe Thr Ile Glu
        1460            1465                1470
Thr Ile Thr Leu Pro Gln Asp Ala Val Ser Arg Thr Gln Arg Arg
        1475            1480                1485
Gly Arg Thr Gly Arg Gly Lys Pro Gly Ile Tyr Arg Phe Val Ala
        1490            1495                1500
Pro Gly Glu Arg Pro Ser Gly Met Phe Asp Ser Ser Val Leu Cys
        1505            1510                1515
Glu Cys Tyr Asp Ala Gly Cys Ala Trp Tyr Glu Leu Thr Pro Ala
        1520            1525                1530
Glu Thr Thr Val Arg Leu Arg Ala Tyr Met Asn Thr Pro Gly Leu
        1535            1540                1545
Pro Val Cys Gln Asp His Leu Glu Phe Trp Glu Gly Val Phe Thr
        1550            1555                1560
Gly Leu Thr His Ile Asp Ala His Phe Leu Ser Gln Thr Lys Gln
        1565            1570                1575
Ser Gly Glu Asn Leu Pro Tyr Leu Val Ala Tyr Gln Ala Thr Val
        1580            1585                1590
Cys Ala Arg Ala Gln Ala Pro Pro Pro Ser Trp Asp Gln Met Trp
        1595            1600                1605
Lys Cys Leu Ile Arg Leu Lys Pro Thr Leu His Gly Pro Thr Pro
        1610            1615                1620
Leu Leu Tyr Arg Leu Gly Ala Val Gln Asn Glu Ile Thr Leu Thr
        1625            1630                1635
His Pro Val Thr Lys Tyr Ile Met Thr Cys Met Ser Ala Asp Leu
        1640            1645                1650
Glu Val Val Thr Ser Thr Trp Val Leu Val Gly Gly Val Leu Ala
        1655            1660                1665
Ala Leu Ala Ala Tyr Cys Leu Ser Thr Gly Cys Val Val Ile Val
        1670            1675                1680
Gly Arg Val Val Leu Ser Gly Lys Pro Ala Ile Ile Pro Asp Arg
        1685            1690                1695
Glu Val Leu Tyr Arg Glu Phe Asp Glu Met Glu Glu Cys Ser Gln
```

-continued

```
            1700                1705                1710
His Leu Pro Tyr Ile Glu Gln Gly Met Met Leu Ala Glu Gln Phe
    1715                1720                1725

Lys Gln Lys Ala Leu Gly Leu Leu Gln Thr Ala Ser Arg Gln Ala
    1730                1735                1740

Glu Val Ile Ala Pro Ala Val Gln Thr Asn Trp Gln Lys Leu Glu
    1745                1750                1755

Thr Phe Trp Ala Lys His Met Trp Asn Phe Ile Ser Gly Ile Gln
    1760                1765                1770

Tyr Leu Ala Gly Leu Ser Thr Leu Pro Gly Asn Pro Ala Ile Ala
    1775                1780                1785

Ser Leu Met Ala Phe Thr Ala Ala Val Thr Ser Pro Leu Thr Thr
    1790                1795                1800

Ser Gln Thr Leu Leu Phe Asn Ile Leu Gly Gly Trp Val Ala Ala
    1805                1810                1815

Gln Leu Ala Ala Pro Gly Ala Ala Thr Ala Phe Val Gly Ala Gly
    1820                1825                1830

Leu Ala Gly Ala Ala Ile Gly Ser Val Gly Leu Gly Lys Val Leu
    1835                1840                1845

Ile Asp Ile Leu Ala Gly Tyr Gly Ala Gly Val Ala Gly Ala Leu
    1850                1855                1860

Val Ala Phe Lys Ile Met Ser Gly Glu Val Pro Ser Thr Glu Asp
    1865                1870                1875

Leu Val Asn Leu Leu Pro Ala Ile Leu Ser Pro Gly Ala Leu Val
    1880                1885                1890

Val Gly Val Val Cys Ala Ala Ile Leu Arg Arg His Val Gly Pro
    1895                1900                1905

Gly Glu Gly Ala Val Gln Trp Met Asn Arg Leu Ile Ala Phe Ala
    1910                1915                1920

Ser Arg Gly Asn His Val Ser Pro Thr His Tyr Val Pro Glu Ser
    1925                1930                1935

Asp Ala Ala Ala Arg Val Thr Ala Ile Leu Ser Ser Leu Thr Val
    1940                1945                1950

Thr Gln Leu Leu Arg Arg Leu His Gln Trp Ile Ser Ser Glu Cys
    1955                1960                1965

Thr Thr Pro Cys Ser Gly Ser Trp Leu Arg Asp Ile Trp Asp Trp
    1970                1975                1980

Ile Cys Glu Val Leu Ser Asp Phe Lys Thr Trp Leu Lys Ala Lys
    1985                1990                1995

Leu Met Pro Gln Leu Pro Gly Ile Pro Phe Val Ser Cys Gln Arg
    2000                2005                2010

Gly Tyr Lys Gly Val Trp Arg Val Asp Gly Ile Met His Thr Arg
    2015                2020                2025

Cys His Cys Gly Ala Glu Ile Thr Gly His Val Lys Asn Gly Thr
    2030                2035                2040

Met Arg Ile Val Gly Pro Arg Thr Cys Arg Asn Met Trp Ser Gly
    2045                2050                2055

Thr Phe Pro Ile Asn Ala Tyr Thr Thr Gly Pro Cys Thr Pro Leu
    2060                2065                2070

Pro Ala Pro Asn Tyr Thr Phe Ala Leu Trp Arg Val Ser Ala Glu
    2075                2080                2085

Glu Tyr Val Glu Ile Arg Gln Val Gly Asp Phe His Tyr Val Thr
    2090                2095                2100
```

```
Gly Met Thr Thr Asp Asn Leu Lys Cys Pro Cys Gln Val Pro Ser
    2105            2110            2115

Pro Glu Phe Phe Thr Glu Leu Asp Gly Val Arg Leu His Arg Phe
    2120            2125            2130

Ala Pro Pro Cys Lys Pro Leu Leu Arg Glu Val Ser Phe Arg
    2135            2140            2145

Val Gly Leu His Glu Tyr Pro Val Gly Ser Gln Leu Pro Cys Glu
    2150            2155            2160

Pro Glu Pro Asp Val Ala Val Leu Thr Ser Met Leu Thr Asp Pro
    2165            2170            2175

Ser His Ile Thr Ala Glu Ala Ala Gly Arg Arg Leu Ala Arg Gly
    2180            2185            2190

Ser Pro Pro Ser Val Ala Ser Ser Ser Ala Ser Gln Leu Ser Ala
    2195            2200            2205

Pro Ser Leu Lys Ala Thr Cys Thr Ala Asn His Asp Ser Pro Asp
    2210            2215            2220

Ala Glu Leu Ile Glu Ala Asn Leu Leu Trp Arg Gln Glu Met Gly
    2225            2230            2235

Gly Asn Ile Thr Arg Val Glu Ser Glu Asn Lys Val Val Ile Leu
    2240            2245            2250

Asp Ser Phe Asp Pro Leu Val Ala Glu Glu Asp Glu Arg Glu Ile
    2255            2260            2265

Ser Val Pro Ala Glu Ile Leu Arg Lys Ser Arg Arg Phe Ala Gln
    2270            2275            2280

Ala Leu Pro Val Trp Ala Arg Pro Asp Tyr Asn Pro Pro Leu Val
    2285            2290            2295

Glu Thr Trp Lys Lys Pro Asp Tyr Glu Pro Pro Val Val His Gly
    2300            2305            2310

Cys Pro Leu Pro Pro Pro Lys Ser Pro Pro Val Pro Pro Pro Arg
    2315            2320            2325

Lys Lys Arg Thr Val Val Leu Thr Glu Ser Thr Leu Ser Thr Ala
    2330            2335            2340

Leu Ala Glu Leu Ala Thr Arg Ser Phe Gly Ser Ser Ser Thr Ser
    2345            2350            2355

Gly Ile Thr Gly Asp Asn Thr Thr Thr Ser Ser Glu Pro Ala Pro
    2360            2365            2370

Ser Gly Cys Pro Pro Asp Ser Asp Ala Glu Ser Tyr Ser Ser Met
    2375            2380            2385

Pro Pro Leu Glu Gly Glu Pro Gly Asp Pro Asp Leu Ser Asp Gly
    2390            2395            2400

Ser Trp Ser Thr Val Ser Ser Glu Ala Asn Ala Glu Asp Val Val
    2405            2410            2415

Cys Cys Ser Met Ser Tyr Ser Trp Thr Gly Ala Leu Val Thr Pro
    2420            2425            2430

Cys Ala Ala Glu Glu Gln Lys Leu Pro Ile Asn Ala Leu Ser Asn
    2435            2440            2445

Ser Leu Leu Arg His His Asn Leu Val Tyr Ser Thr Thr Ser Arg
    2450            2455            2460

Ser Ala Cys Gln Arg Gln Lys Lys Val Thr Phe Asp Arg Leu Gln
    2465            2470            2475

Val Leu Asp Ser His Tyr Gln Asp Val Leu Lys Glu Val Lys Ala
    2480            2485            2490
```

-continued

```
Ala Ala Ser Lys Val Lys Ala Asn Leu Leu Ser Val Glu Glu Ala
    2495               2500               2505

Cys Ser Leu Thr Pro Pro His Ser Ala Lys Ser Lys Phe Gly Tyr
    2510               2515               2520

Gly Ala Lys Asp Val Arg Cys His Ala Arg Lys Ala Val Thr His
    2525               2530               2535

Ile Asn Ser Val Trp Lys Asp Leu Leu Glu Asp Asn Val Thr Pro
    2540               2545               2550

Ile Asp Thr Thr Ile Met Ala Lys Asn Glu Val Phe Cys Val Gln
    2555               2560               2565

Pro Glu Lys Gly Gly Arg Lys Pro Ala Arg Leu Ile Val Phe Pro
    2570               2575               2580

Asp Leu Gly Val Arg Val Cys Glu Lys Met Ala Leu Tyr Asp Val
    2585               2590               2595

Val Thr Lys Leu Pro Leu Ala Val Met Gly Ser Ser Tyr Gly Phe
    2600               2605               2610

Gln Tyr Ser Pro Gly Gln Arg Val Glu Phe Leu Val Gln Ala Trp
    2615               2620               2625

Lys Ser Lys Lys Thr Pro Met Gly Phe Ser Tyr Asp Thr Arg Cys
    2630               2635               2640

Phe Asp Ser Thr Val Thr Glu Ser Asp Ile Arg Thr Glu Glu Ala
    2645               2650               2655

Ile Tyr Gln Cys Cys Asp Leu Asp Pro Gln Ala Arg Val Ala Ile
    2660               2665               2670

Lys Ser Leu Thr Glu Arg Leu Tyr Val Gly Gly Pro Leu Thr Asn
    2675               2680               2685

Ser Arg Gly Glu Asn Cys Gly Tyr Arg Arg Cys Arg Ala Ser Gly
    2690               2695               2700

Val Leu Thr Thr Ser Cys Gly Asn Thr Leu Thr Cys Tyr Ile Lys
    2705               2710               2715

Ala Arg Ala Ala Cys Arg Ala Ala Gly Leu Gln Asp Cys Thr Met
    2720               2725               2730

Leu Val Cys Gly Asp Asp Leu Val Val Ile Cys Glu Ser Ala Gly
    2735               2740               2745

Val Gln Glu Asp Ala Ala Ser Leu Arg Ala Phe Thr Glu Ala Met
    2750               2755               2760

Thr Arg Tyr Ser Ala Pro Pro Gly Asp Pro Pro Gln Pro Glu Tyr
    2765               2770               2775

Asp Leu Glu Leu Ile Thr Ser Cys Ser Ser Asn Val Ser Val Ala
    2780               2785               2790

His Asp Gly Ala Gly Lys Arg Val Tyr Tyr Leu Thr Arg Asp Pro
    2795               2800               2805

Thr Thr Pro Leu Ala Arg Ala Ala Trp Glu Thr Ala Arg His Thr
    2810               2815               2820

Pro Val Asn Ser Trp Leu Gly Asn Ile Ile Met Phe Ala Pro Thr
    2825               2830               2835

Leu Trp Ala Arg Met Ile Leu Met Thr His Phe Phe Ser Val Leu
    2840               2845               2850

Ile Ala Arg Asp Gln Leu Glu Gln Ala Leu Asp Cys Glu Ile Tyr
    2855               2860               2865

Gly Ala Cys Tyr Ser Ile Glu Pro Leu Asp Leu Pro Pro Ile Ile
    2870               2875               2880

Gln Arg Leu His Gly Leu Ser Ala Phe Ser Leu His Ser Tyr Ser
```

```
                2885                2890                2895

Pro Gly Glu Ile Asn Arg Val Ala Ala Cys Leu Arg Lys Leu Gly
            2900                2905                2910

Val Pro Pro Leu Arg Ala Trp Arg His Arg Ala Arg Ser Val Arg
        2915                2920                2925

Ala Arg Leu Leu Ala Arg Gly Gly Arg Ala Ala Ile Cys Gly Lys
    2930                2935                2940

Tyr Leu Phe Asn Trp Ala Val Arg Thr Lys Leu Lys Leu Thr Pro
2945                2950                2955

Ile Ala Ala Ala Gly Gln Leu Asp Leu Ser Gly Trp Phe Thr Ala
    2960                2965                2970

Gly Tyr Ser Gly Gly Asp Ile Tyr His Ser Val Ser His Ala Arg
2975                2980                2985

Pro Arg Trp Ile Trp Phe Cys Leu Leu Leu Leu Ala Ala Gly Val
    2990                2995                3000

Gly Ile Tyr Leu Leu Pro Asn Arg
    3005                3010
```

<210> SEQ ID NO 89
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

```
Met Gly Tyr Ile Pro Leu Val Gly Ala Pro Leu Gly Gly Ala Ala Arg
1               5                   10                  15

Ala Leu Ala His Gly Val Arg Val Leu Glu Asp Gly Val Asn Tyr Ala
            20                  25                  30

Thr Gly Asn Leu Pro Gly
        35
```

<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 90

```
His His His His His His
1               5
```

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

```
Met Ser Gly Leu Asn Asp Ile Phe Glu Ala Gln Lys Ile Glu Trp His
1               5                   10                  15

Glu
```

<210> SEQ ID NO 92
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Ser Gly Ser Asn Ser Met
1               5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Ser Gly Ser Gly
1               5

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Leu Asn Asp Ile Phe Glu Ala Gln Lys Ile Glu Trp His Glu
1               5                   10                  15

<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Ser Gly Ser Gly His His His His His His
1               5                   10

<210> SEQ ID NO 96
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Ser Gly Ser Gly His His His His His His Gly Gly
1               5                   10

<210> SEQ ID NO 97
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Thr Asn Arg Arg Pro Gln Asp Val Lys Phe Pro Gly Gly Gly Gln Ile
```

-continued

```
1               5                   10                  15
Val Gly Gly Val Tyr Leu Leu Pro Arg Arg Gly Pro Arg Leu Gly Val
                20                  25                  30

Arg Ala Thr Arg Lys Thr Ser Glu Arg Ser Gln Pro Arg Gly Arg Arg
        35                  40                  45

Gln Pro Ile Pro Lys Ala
    50

<210> SEQ ID NO 98
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Thr Asn Arg Arg Pro Gln Asp Val Lys Phe Pro Gly Gly Gly Gln Ile
1               5                   10                  15

Val Tyr Leu Leu Pro Arg Arg Gly Pro Arg Leu Gly Val Thr Arg Lys
                20                  25                  30

Thr Ser Glu Arg Ser Gln Pro Arg Gly Arg Arg Gln Pro Ile Pro Lys
        35                  40                  45

Ala

<210> SEQ ID NO 99
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Thr Asn Arg Arg Pro Gln Asp Val Lys Phe Pro Gly Gly Gly Gln Ile
1               5                   10                  15

Val Gly Gly Tyr Leu Leu Pro Arg Arg Gly Pro Arg Leu Gly Val Thr
                20                  25                  30

Arg Lys Thr Ser Glu Arg Ser Gln Pro Arg Gly Arg Arg Gln Pro Ile
        35                  40                  45

Pro Lys Ala
    50

<210> SEQ ID NO 100
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Thr Asn Arg Arg Pro Gln Asp Val Lys Phe Pro Gly Gly Gly Gln Ile
1               5                   10                  15

Val Gly Gly Tyr Leu Leu Pro Arg Arg Gly Pro Arg Leu Gly Val Ala
                20                  25                  30

Thr Arg Lys Thr Ser Glu Arg Ser Gln Pro Arg Gly Arg Arg Gln Pro
        35                  40                  45

Ile Pro Lys Ala
    50
```

<210> SEQ ID NO 101
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Thr Asn Arg Arg Pro Gln Asp Val Lys Phe Pro Gly Gly Gly Gln Ile
1               5                   10                  15

Val Gly Gly Tyr Leu Leu Pro Arg Arg Gly Pro Arg Leu Gly Val Arg
            20                  25                  30

Thr Arg Lys Thr Ser Glu Arg Ser Gln Pro Arg Gly Arg Arg Gln Pro
        35                  40                  45

Ile Pro Lys Ala
    50

<210> SEQ ID NO 102
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Thr Asn Arg Arg Pro Gln Asp Val Lys Phe Pro Gly Gly Gly Gln Ile
1               5                   10                  15

Val Gly Gly Tyr Leu Leu Pro Arg Arg Gly Pro Arg Leu Gly Val Ile
            20                  25                  30

Ala Thr Arg Lys Thr Ser Glu Arg Ser Gln Pro Arg Gly Arg Arg Gln
        35                  40                  45

Pro Ile Pro Lys Ala
    50

<210> SEQ ID NO 103
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Thr Asn Arg Arg Pro Gln Asp Val Lys Phe Pro Gly Gly Gly Gln Ile
1               5                   10                  15

Val Gly Gly Gly Tyr Leu Leu Pro Arg Arg Gly Pro Arg Leu Gly Val
            20                  25                  30

Thr Arg Lys Thr Ser Glu Arg Ser Gln Pro Arg Gly Arg Arg Gln Pro
        35                  40                  45

Ile Pro Lys Ala
    50

<210> SEQ ID NO 104
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Thr Asn Arg Arg Pro Gln Asp Val Lys Phe Pro Gly Gly Gly Gln Ile
1               5                   10                  15

Val Gly Gly Gly Tyr Leu Leu Pro Arg Arg Gly Pro Arg Leu Gly Val
                20                  25                  30

Ala Thr Arg Lys Thr Ser Glu Arg Ser Gln Pro Arg Gly Arg Arg Gln
            35                  40                  45

Pro Ile Pro Lys Ala
    50

<210> SEQ ID NO 105
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Thr Asn Arg Arg Pro Gln Asp Val Lys Phe Pro Gly Gly Gly Gln Ile
1               5                   10                  15

Val Gly Gly Gly Tyr Leu Leu Pro Arg Arg Gly Pro Arg Leu Gly Val
                20                  25                  30

Arg Thr Arg Lys Thr Ser Glu Arg Ser Gln Pro Arg Gly Arg Arg Gln
            35                  40                  45

Pro Ile Pro Lys Ala
    50

<210> SEQ ID NO 106
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Thr Asn Arg Arg Pro Gln Asp Val Lys Phe Pro Gly Gly Gly Gln Ile
1               5                   10                  15

Val Gly Gly Gly Tyr Leu Leu Pro Arg Arg Gly Pro Arg Leu Gly Val
                20                  25                  30

Ile Ala Thr Arg Lys Thr Ser Glu Arg Ser Gln Pro Arg Gly Arg Arg
            35                  40                  45

Gln Pro Ile Pro Lys Ala
    50

<210> SEQ ID NO 107
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Ile Ile Pro Asp Arg Glu Val Leu Tyr Arg Glu Phe Asp Glu Met Glu
1               5                   10                  15

Glu Cys Ser Gln His Leu Pro Tyr Ile Glu Gln Gly Met Met Leu Ala
                20                  25                  30

Glu Gln Phe Lys Gln Lys Ala Leu Gly Leu
            35                  40
```

```
<210> SEQ ID NO 108
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Ile Ile Pro Asp Arg Glu Val Leu Tyr Arg Glu Phe Asp Glu Met Glu
1               5                   10                  15

Glu Cys Ser Gln His Leu Pro Tyr Ile Glu Gln Gly Met Met Leu Ala
            20                  25                  30

Glu Gln Phe Lys Gln Lys Ala Leu Gly Leu Cys
        35                  40

<210> SEQ ID NO 109
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Asn Ser Thr Lys
            35                  40                  45

Val Pro Ala Ala Tyr Ala Ala Gln Gly Tyr Lys Val Leu Val Leu Asn
50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Cys Asp Glu Cys His
        115                 120                 125

Ser Thr Asp Ala Thr Ser Ile Leu Gly Ile Gly Thr Val Leu Asp Gln
        130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
        210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255
```

```
Phe Asp Ser Val Ile Asp Cys Asn Thr Cys Val Gln Thr Val Asp
                260                 265                 270

Phe Ser Leu Asp Pro Thr Phe Thr Ile Glu Thr Ile Thr Leu Pro Gln
            275                 280                 285

Asp Ala Val Ser Arg Thr Gln Arg Arg Gly Arg Thr Arg Gly Lys
        290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
                340                 345                 350

Asn Thr Pro Gly Leu Pro Val Cys Gln Asp His Leu Glu Phe Trp Glu
                355                 360                 365

Gly Val Phe Thr Gly Leu Thr His Ile Asp Ala His Phe Leu Ser Gln
            370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
                435                 440                 445

Pro Val Thr Lys Tyr Ile Met Thr Cys Met Ser Ala Asp Leu Glu Val
            450                 455                 460

Val Thr
465

<210> SEQ ID NO 110
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Ala Val Asp Phe Ile Pro Val Glu Asn Leu Glu Thr Thr Met Arg Ser
1               5                   10                  15

Pro Val Phe Thr Asp Asn Ser Ser Pro Pro Val Val Pro Gln Ser Phe
            20                  25                  30

Gln Val Ala His Leu His Ala Pro Thr Gly Ser Gly Lys Ala Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Cys Asp Glu Cys His
        115                 120                 125

Ser Thr Asp Ala Thr Ser Ile Leu Gly Ile Gly Thr Val Leu Asp Gln
130                 135                 140
```

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Val Ala Leu
            165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
            195                 200                 205

Cys Asp Glu Leu Ala Ala Lys Leu Val Ala Leu Gly Ile Asn Ala Val
            210                 215                 220

Ala Tyr Tyr Arg Gly Leu Asp Val Ser Val Ile Pro Thr Ser Gly Asp
225                 230                 235                 240

Val Val Val Ala Thr Asp Ala Leu Met Thr Gly Tyr Thr Gly Asp
            245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
            275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
            325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
            405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
            450                 455                 460

Val Thr
465

<210> SEQ ID NO 111
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Ala Val Asp Phe Ile Pro Val Glu Asn Leu Glu Thr Thr Met Arg Ser
1               5                   10                  15

Pro Val Phe Thr Asp Asn Ser Ser Pro Pro Val Val Pro Gln Ser Phe

```
                20                  25                  30
Gln Val Ala His Leu His Ala Pro Thr Gly Ser Gly Lys Ser Glu Lys
             35                  40                  45
Val Pro Ala Ala Tyr Ala Ala Gln Gly Tyr Lys Val Leu Val Leu Asn
 50                  55                  60
Pro Ser Val Ala Ala Thr Leu Gly Phe Gly Ala Tyr Met Ser Lys Ala
 65                  70                  75                  80
His Gly Ile Asp Pro Asn Ile Arg Thr Gly Val Arg Thr Ile Thr Thr
                 85                  90                  95
Gly Ser Pro Ile Thr Tyr Ser Thr Tyr Gly Lys Phe Leu Ala Asp Gly
            100                 105                 110
Gly Cys Ser Gly Gly Ala Tyr Asp Ile Ile Cys Asp Glu Cys His
            115                 120                 125
Ser Thr Asp Ala Thr Ser Ile Leu Gly Ile Gly Thr Val Leu Asp Gln
        130                 135                 140
Ala Glu Thr Ala Gly Ala Arg Leu Val Val Leu Ala Thr Ala Thr Pro
145                 150                 155                 160
Pro Gly Ser Val Thr Val Pro His Pro Asn Ile Glu Glu Val Ala Leu
                165                 170                 175
Ser Thr Thr Gly Glu Ile Pro Phe Tyr Gly Lys Ala Ile Pro Leu Glu
            180                 185                 190
Val Ile Lys Gly Gly Arg His Leu Ile Phe Cys His Ser Lys Lys Lys
            195                 200                 205
Cys Asp Glu Leu Ala Ala Lys Leu Val Ala Leu Gly Ile Asn Ala Val
        210                 215                 220
Ala Tyr Tyr Arg Gly Leu Asp Val Ser Val Ile Pro Thr Ser Gly Asp
225                 230                 235                 240
Val Val Val Val Ala Thr Asp Ala Leu Met Thr Gly Tyr Thr Gly Asp
                245                 250                 255
Phe Asp Ser Val Ile Asp Cys Asn Thr Cys Val Thr Gln Thr Val Asp
            260                 265                 270
Phe Ser Leu Asp Pro Thr Phe Thr Ile Glu Thr Ile Thr Leu Pro Gln
        275                 280                 285
Asp Ala Val Ser Arg Thr Gln Arg Arg Gly Arg Thr Gly Arg Gly Lys
    290                 295                 300
Pro Gly Ile Tyr Arg Phe Val Ala Pro Gly Glu Arg Pro Ser Gly Met
305                 310                 315                 320
Phe Asp Ser Ser Val Leu Cys Glu Cys Tyr Asp Ala Gly Cys Ala Trp
                325                 330                 335
Tyr Glu Leu Thr Pro Ala Glu Thr Thr Val Arg Leu Arg Ala Tyr Met
            340                 345                 350
Asn Thr Pro Gly Leu Pro Val Cys Gln Asp His Leu Glu Phe Trp Glu
        355                 360                 365
Gly Val Phe Thr Gly Leu Thr His Ile Asp Ala His Phe Leu Ser Gln
    370                 375                 380
Thr Lys Gln Ser Gly Glu Asn Leu Pro Tyr Leu Val Ala Tyr Gln Ala
385                 390                 395                 400
Thr Val Cys Ala Arg Ala Gln Ala Pro Pro Ser Trp Asp Gln Met
                405                 410                 415
Trp Lys Cys Leu Ile Arg Leu Lys Pro Thr Leu His Gly Pro Thr Pro
            420                 425                 430
Leu Leu Tyr Arg Leu Gly Ala Val Gln Asn Glu Ile Thr Leu Thr His
        435                 440                 445
```

-continued

```
Pro Val Thr Lys Tyr Ile Met Thr Cys Met Ser Ala Asp Leu Glu Val
    450                 455                 460

Val Thr
465

<210> SEQ ID NO 112
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
50                  55                  60

Pro Ser Val Ala Ala Thr Leu Gly Phe Gly Ala Ser Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Tyr Gly Lys Phe Leu Ala Asp Gly
            100                 105                 110

Gly Cys Ser Gly Gly Ala Tyr Asp Ile Ile Cys Asp Glu Cys His
        115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
```

```
                    325                 330                 335
Tyr Glu Leu Thr Pro Ala Glu Thr Thr Val Arg Leu Arg Ala Tyr Met
                340                 345                 350

Asn Thr Pro Gly Leu Pro Val Cys Gln Asp His Leu Glu Phe Trp Glu
                355                 360                 365

Gly Val Phe Thr Gly Leu Thr His Ile Asp Ala His Phe Leu Ser Gln
    370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
                435                 440                 445

Pro Val Thr Lys Tyr Ile Met Thr Cys Met Ser Ala Asp Leu Glu Val
    450                 455                 460

Val Thr
465

<210> SEQ ID NO 113
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Ala Val Asp Phe Ile Pro Val Glu Asn Leu Glu Thr Thr Met Arg Ser
1               5                   10                  15

Pro Val Phe Thr Asp Asn Ser Ser Pro Pro Val Val Pro Gln Ser Phe
                20                  25                  30

Gln Val Ala His Leu His Ala Pro Thr Gly Ser Gly Lys Ser Thr Lys
                35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
                100                 105                 110

Gly Cys Ser Gly Gly Ala Tyr Asp Ile Ile Cys Asn Glu Cys His
                115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
                180                 185                 190

Val Ile Lys Gly Gly Arg His Leu Ile Phe Cys His Ser Lys Lys Lys
    195                 200                 205
```

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
    370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
    450                 455                 460

Val Thr
465

<210> SEQ ID NO 114
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Ala Val Asp Phe Ile Pro Val Glu Asn Leu Glu Thr Thr Met Arg Ser
1               5                   10                  15

Pro Val Phe Thr Asp Asn Ser Ser Pro Pro Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

```
Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Cys Asp Gln Gln Cys
        115                 120                 125

His Ser Thr Asp Ala Thr Ser Ile Leu Gly Ile Gly Thr Val Leu Asp
130                 135                 140

Gln Ala Glu Thr Ala Gly Ala Arg Leu Val Val Leu Ala Thr Ala Thr
145                 150                 155                 160

Pro Pro Gly Ser Val Thr Val Pro His Pro Asn Ile Glu Glu Val Ala
                165                 170                 175

Leu Ser Thr Thr Gly Glu Ile Pro Phe Tyr Gly Lys Ala Ile Pro Leu
            180                 185                 190

Glu Val Ile Lys Gly Gly Arg His Leu Ile Phe Cys His Ser Lys Lys
        195                 200                 205

Lys Cys Asp Glu Leu Ala Ala Lys Leu Val Ala Leu Gly Ile Asn Ala
    210                 215                 220

Val Ala Tyr Tyr Arg Gly Leu Asp Val Ser Val Ile Pro Thr Ser Gly
225                 230                 235                 240

Asp Val Val Val Ala Thr Asp Ala Leu Met Thr Gly Tyr Thr Gly
                245                 250                 255

Asp Phe Asp Ser Val Ile Asp Cys Asn Thr Cys Val Thr Gln Thr Val
            260                 265                 270

Asp Phe Ser Leu Asp Pro Thr Phe Thr Ile Glu Thr Ile Thr Leu Pro
        275                 280                 285

Gln Asp Ala Val Ser Arg Thr Gln Arg Arg Gly Arg Thr Gly Arg Gly
    290                 295                 300

Lys Pro Gly Ile Tyr Arg Phe Val Ala Pro Gly Glu Arg Pro Ser Gly
305                 310                 315                 320

Met Phe Asp Ser Ser Val Leu Cys Glu Cys Tyr Asp Ala Gly Cys Ala
                325                 330                 335

Trp Tyr Glu Leu Thr Pro Ala Glu Thr Thr Val Arg Leu Arg Ala Tyr
            340                 345                 350

Met Asn Thr Pro Gly Leu Pro Val Cys Gln Asp His Leu Glu Phe Trp
        355                 360                 365

Glu Gly Val Phe Thr Gly Leu Thr His Ile Asp Ala His Phe Leu Ser
    370                 375                 380

Gln Thr Lys Gln Ser Gly Glu Asn Leu Pro Tyr Leu Val Ala Tyr Gln
385                 390                 395                 400

Ala Thr Val Cys Ala Arg Ala Gln Ala Pro Pro Ser Trp Asp Gln
                405                 410                 415

Met Trp Lys Cys Leu Ile Arg Leu Lys Pro Thr Leu His Gly Pro Thr
            420                 425                 430

Pro Leu Leu Tyr Arg Leu Gly Ala Val Gln Asn Glu Ile Thr Leu Thr
        435                 440                 445

His Pro Val Thr Lys Tyr Ile Met Thr Cys Met Ser Ala Asp Leu Glu
    450                 455                 460

Val Val Thr
465

<210> SEQ ID NO 115
<211> LENGTH: 466
<212> TYPE: PRT
<213> ORGANISM: Artificial Sequence
<220> FEATURE:
```

-continued

<223> OTHER INFORMATION: Description of Artificial Sequence: Synthetic
polypeptide

<400> SEQUENCE: 115

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys Ala
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
    370                 375                 380

Thr Lys Gln Ser Gly Glu Asn Leu Pro Tyr Leu Val Ala Tyr Gln Ala
385                 390                 395                 400
```

```
Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
    450                 455                 460

Val Thr
465

<210> SEQ ID NO 116
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Ala Val Asp Phe Ile Pro Val Glu Asn Leu Glu Thr Thr Met Arg Ser
1               5                   10                  15

Pro Val Phe Thr Asp Asn Ser Ser Pro Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Gly Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
```

```
            275                 280                 285
Asp Ala Val Ser Arg Thr Gln Arg Arg Gly Arg Thr Gly Arg Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
    370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
    450                 455                 460

Val Thr
465

<210> SEQ ID NO 117
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Ala Val Asp Phe Ile Pro Val Glu Asn Leu Glu Thr Thr Met Arg Ser
1               5                   10                  15

Pro Val Phe Thr Asp Asn Ser Ser Pro Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160
```

Pro Gly Ser Val Thr Val Pro His Pro Asn Ile Glu Glu Val Ala Leu
            165                 170                 175

Ser Thr Thr Gly Glu Ile Pro Phe Tyr Gly Lys Ala Ile Pro Leu Glu
        180                 185                 190

Val Ile Lys Gly Gly Arg His Leu Ile Phe Cys His Ser Lys Lys Lys
    195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr His Arg Arg Gly Arg Thr Gly Arg Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
    370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
    450                 455                 460

Val Thr
465

<210> SEQ ID NO 118
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Ala Val Asp Phe Ile Pro Val Glu Asn Leu Glu Thr Thr Met Arg Ser
1               5                   10                  15

Pro Val Phe Thr Asp Asn Ser Ser Pro Pro Val Val Pro Gln Ser Phe
            20                  25                  30

Gln Val Ala His Leu His Ala Pro Thr Gly Ser Gly Lys Ser Thr Lys
        35                  40                  45

```
Val Pro Ala Ala Tyr Ala Ala Gln Gly Tyr Lys Val Leu Val Leu Asn
 50                  55                  60

Pro Ser Val Ala Ala Thr Leu Gly Phe Gly Ala Tyr Met Ser Lys Ala
 65                  70                  75                  80

His Gly Ile Asp Pro Asn Ile Arg Thr Gly Val Arg Thr Ile Thr Thr
                 85                  90                  95

Gly Ser Pro Ile Thr Tyr Ser Thr Tyr Gly Lys Phe Leu Ala Asp Gly
                100                 105                 110

Gly Cys Ser Gly Gly Ala Tyr Asp Ile Ile Cys Asp Glu Cys His
            115                 120                 125

Ser Thr Asp Ala Thr Ser Ile Leu Gly Ile Gly Thr Val Leu Asp Gln
            130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
            195                 200                 205

Cys Asp Glu Leu Ala Ala Lys Leu Val Ala Leu Gly Ile Asn Ala Val
            210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
                260                 265                 270

Phe Ser Leu Asp Pro Thr Phe Thr Ile Glu Thr Ile Thr Leu Pro Gln
            275                 280                 285

Asp Ala Val Ser Arg Thr Gln Arg Arg Gly Ala Thr Gly Arg Gly Lys
            290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
            370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
450                 455                 460
```

```
Val Thr
465
```

<210> SEQ ID NO 119
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Cys Asp Glu Cys His
        115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Lys Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350
```

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
    370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
    450                 455                 460

Val Thr
465

<210> SEQ ID NO 120
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Ala Val Asp Phe Ile Pro Val Glu Asn Leu Glu Thr Thr Met Arg Ser
1               5                   10                  15

Pro Val Phe Thr Asp Asn Ser Ser Pro Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp

```
                225                 230                 235                 240
Val Val Val Val Ala Thr Asp Ala Leu Met Thr Gly Tyr Thr Gly Asp
            245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
            275                 280                 285

Asp Ala Val Ser Arg Thr Gln Arg Arg Gly Arg Thr Gly Arg Gly Lys
            290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Ala
            325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
            370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
            405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
            450                 455                 460

Val Thr
465

<210> SEQ ID NO 121
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Ala Val Asp Phe Ile Pro Val Glu Asn Leu Glu Thr Thr Met Arg Ser
1               5                   10                  15

Pro Val Phe Thr Asp Asn Ser Ser Pro Pro Val Pro Gln Ser Phe
            20                  25                  30

Gln Val Ala His Leu His Ala Pro Thr Gly Ser Gly Lys Ser Thr Lys
            35                  40                  45

Val Pro Ala Ala Tyr Ala Ala Gln Gly Tyr Lys Val Leu Val Leu Asn
            50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
            85                  90                  95

Gly Ser Pro Ile Thr Tyr Ser Thr Tyr Gly Lys Phe Leu Ala Asp Gly
            100                 105                 110
```

Gly Cys Ser Gly Gly Ala Tyr Asp Ile Ile Cys Asp Glu Cys His
115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
                180                 185                 190

Val Ile Lys Gly Gly Arg His Leu Ile Phe Cys His Ser Lys Lys Lys
                195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
                260                 265                 270

Phe Ser Leu Asp Pro Thr Phe Thr Ile Glu Thr Ile Thr Leu Pro Gln
                275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Ser Ala Trp
                325                 330                 335

Tyr Glu Leu Thr Pro Ala Glu Thr Thr Val Arg Leu Arg Ala Tyr Met
                340                 345                 350

Asn Thr Pro Gly Leu Pro Val Cys Gln Asp His Leu Glu Phe Trp Glu
                355                 360                 365

Gly Val Phe Thr Gly Leu Thr His Ile Asp Ala His Phe Leu Ser Gln
370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Pro Ser Trp Asp Gln Met
                405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
                435                 440                 445

Pro Val Thr Lys Tyr Ile Met Thr Cys Met Ser Ala Asp Leu Glu Val
450                 455                 460

Val Thr
465

<210> SEQ ID NO 122
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

```
Ala Val Asp Phe Ile Pro Val Glu Asn Leu Glu Thr Met Arg Ser
1               5                   10                  15

Pro Val Phe Thr Asp Asn Ser Ser Pro Val Val Pro Gln Ser Phe
                20                  25                  30

Gln Val Ala His Leu His Ala Pro Thr Gly Ser Gly Lys Ser Thr Lys
            35                  40                  45

Val Pro Ala Ala Tyr Ala Ala Gln Gly Tyr Lys Val Leu Val Leu Asn
50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
                100                 105                 110

Gly Cys Ser Gly Gly Ala Tyr Asp Ile Ile Cys Asp Glu Cys His
            115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
                180                 185                 190

Val Ile Lys Gly Gly Arg His Leu Ile Phe Cys His Ser Lys Lys Lys
            195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
                260                 265                 270

Phe Ser Leu Asp Pro Thr Phe Thr Ile Glu Thr Ile Thr Leu Pro Gln
    275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
                340                 345                 350

Asn Thr Pro Gly Leu Pro Val Ser Gln Asp His Leu Glu Phe Trp Glu
            355                 360                 365

Gly Val Phe Thr Gly Leu Thr His Ile Asp Ala His Phe Leu Ser Gln
        370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415
```

```
Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
    450                 455                 460

Val Thr
465

<210> SEQ ID NO 123
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
                100                 105                 110

Gly Cys Ser Gly Gly Ala Tyr Asp Ile Ile Ile Cys Asp Glu Ser His
            115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
290                 295                 300
```

-continued

```
Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
            325                 330                 335

Tyr Glu Leu Thr Pro Ala Glu Thr Thr Val Arg Leu Arg Ala Tyr Met
        340                 345                 350

Asn Thr Pro Gly Leu Pro Val Cys Gln Asp His Leu Glu Phe Trp Glu
    355                 360                 365

Gly Val Phe Thr Gly Leu Thr His Ile Asp Ala His Phe Leu Ser Gln
370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
    450                 455                 460

Val Thr
465

<210> SEQ ID NO 124
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Ala Val Asp Phe Ile Pro Val Glu Asn Leu Thr Thr Met Arg Ser
1               5                   10                  15

Pro Val Phe Thr Asp Asn Ser Ser Pro Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
```

```
                    180                 185                 190
Val Ile Lys Gly Gly Arg His Leu Ile Phe Ser His Ser Lys Lys Lys
            195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
    290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
    370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
    450                 455                 460

Val Thr
465

<210> SEQ ID NO 125
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Ala Val Asp Phe Ile Pro Val Glu Asn Leu Glu Thr Thr Met Arg Ser
1               5                   10                  15

Pro Val Phe Thr Asp Asn Ser Ser Pro Pro Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60
```

```
Pro Ser Val Ala Ala Thr Leu Gly Phe Gly Ala Tyr Met Ser Lys Ala
 65                  70                  75                  80

His Gly Ile Asp Pro Asn Ile Arg Thr Gly Val Arg Thr Ile Thr Thr
                 85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Cys Asp Glu Cys His
            115                 120                 125

Ser Thr Asp Ala Thr Ser Ile Leu Gly Ile Gly Thr Val Leu Asp Gln
        130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Ser Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
290                 295                 300

Pro Gly Ile Tyr Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
            340                 345                 350

Asn Thr Pro Gly Leu Pro Val Cys Gln Asp His Leu Glu Phe Trp Glu
        355                 360                 365

Gly Val Phe Thr Gly Leu Thr His Ile Asp Ala His Phe Leu Ser Gln
370                 375                 380

Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
                405                 410                 415

Trp Lys Cys Leu Ile Arg Leu Lys Pro Thr Leu His Gly Pro Thr Pro
            420                 425                 430

Leu Leu Tyr Arg Leu Gly Ala Val Gln Asn Glu Ile Thr Leu Thr His
        435                 440                 445

Pro Val Thr Lys Tyr Ile Met Thr Cys Met Ser Ala Asp Leu Glu Val
    450                 455                 460

Val Thr
465
```

HCV ANTIGEN-ANTIBODY COMBINATION ASSAY AND METHODS AND COMPOSITIONS FOR USE THEREIN

RELATED APPLICATIONS

This application is a Continuation of U.S. Non-Provisional patent application Ser. No. 14/139,108 filed on Dec. 23, 2013; which claims benefit of priority of U.S. Provisional Patent Application No. 61/785,124, which was filed Mar. 14, 2013, and U.S. Provisional Patent Application No. 61/788,136, which was filed Mar. 15, 2013. The entire text of the aforementioned applications is incorporated herein by reference in its entirety.

FIELD OF THE INVENTION

The present invention generally relates to immunoassays for detection and diagnosis of HCV infection. More particularly, the present invention relates to combination immunoassays, reagents and kits for simultaneous detection of HCV antigens and anti-HCV antibodies in a test sample.

BACKGROUND OF THE INVENTION

According to WHO statistics, as many as 170 million people worldwide are infected by hepatitis C virus (HCV), a viral infection of the liver. 75 to 85% of persons infected with HCV progress to chronic infection, approximately 20% of these cases develop complications of chronic hepatitis C, including cirrhosis of the liver or hepatocellular carcinoma after 20 years of infection. The current recommended treatment for HCV infections is a combination of interferon and ribavirin drugs, however the treatment is not effective in all cases and the liver transplantation is indicated in hepatitis C-related end-stage liver disease. At present, there is no vaccine available to prevent HCV infection, therefore all precautions to avoid infection must be taken.

Thus, patient care, as well as the prevention of transmission of Hepatitis C Virus (HCV) by blood and blood products or by close personal contact requires extreme vigilance using sensitive detection assays. This creates a need for specific methods for screening and identifying carriers of HCV and HCV-contaminated blood or blood products. Serological determination of HCV exposure relies on the detection of HCV present in human blood plasma or sera. This can be accomplished by detection of distinct structural and non-structural proteins encoded by the virus or alternatively by detection of antibodies to HCV.

After exposure to the HCV pathogen, there is initially no evidence of viral presence, i.e. no detectable viral RNA or serology markers. This is referred to as the "window period" (WP). Generally, after 10 days following exposure to HCV, viral RNA can be detected while anti-HCV antibodies become detectable approximately 70 days later (Busch M P and Dodd R Y, Transfusion 40(10): 1157-1160, 2000). Prevention of HCV infection spread it is ever more important to have reliable blood-screening tests that are designed to narrow the detection window.

There are numerous methods for the detection of HCV infection based on serological screening of the blood for detecting the presence of HCV core antigen or antibodies against HCV polypeptides in patient serum or plasma. It has been noted that the assays directed at detection of HCV core antigen assay detects HCV infection between 40 to 50 days earlier than the HCV screening based on antibody screening assays. HCV core protein is a structural protein of HCV comprising the first 191 amino acids of the polyprotein and that forms the internal viral coat encapsidating the genomic RNA. Two different types of serologic assays have been developed which permit detection of HCV core antigens in serum. One assay format detects HCV core antigens in subjects prior to seroconversion and is utilized in screening blood donors, while the other assay format detects core antigens only in hepatitis C patients, regardless of their HCV antibody status, and is utilized in clinical laboratories to diagnose exposure to HCV or to monitor antiviral therapy.

Typically however, the HCV core antigen blood screening assays only detect core antigen at pre-seroconversion or early post-seroconversion phase. Furthermore, HCV core antigen assays are unable to detect core antigen when the antigen forms immune-complexes with anti-core antibodies in the late seroconversion phase. This creates a need for a serological assay that can detect HCV core antigen in the pre-seroconversion phase as well as anti-HCV antibodies in the seroconversion phase, thus narrowing the WP significantly.

The utility of such combination HCV screening assays is significant as such assays will be a significant improvement over the current serology blood screening method with respect to narrowing the WP. However, one of the challenges to the successful antigen antibody combined assay is to select appropriate antigens and antibodies for performing such assays. The present invention addresses this need.

BRIEF SUMMARY OF THE INVENTION

The present invention generally relates to combination immunoassays, reagents and kits for simultaneous detection of HCV antigens and anti-HCV antibodies in a test sample More particularly, the present invention describes an immunoassay for the combined detection of HCV antigen and HCV antibody in a test sample comprising:
  a) simultaneously providing the following reagents:
  i. a solid phase capable of binding to biotin
  ii. biotinylated anti-HCV antibody for the capture of an HCV antigen present the test sample;
  iii. a biotinylated HCV antigen for the capture of anti-HCV antibody in the test sample; and
  iv. a detectably labeled HCV antigen for binding to anti-HCV antibody captured by the biotinylated HCV antigen of (iii); and
  b) incubating the reagents of step (a) under conditions to produce a reaction mixture that
    (i) the biotinylated anti-HCV antibody of (a)(ii) binds to the solid phase through the biotin and specifically binds to HCV antigen present in the test sample to produce an anti-HCV antibody-HCV antigen complex captured on the solid phase;
    (ii) the biotinylated antigen of (a)(iii) binds to the solid phase through the biotin and specifically binds to anti-HCV antibodies present in the test sample to produce an HCV antigen-anti-HCV antibody complex captured on the solid phase and the detectably labeled HCV antigen of (a)(iv) specifically binds to the anti-HCV antibody in the an HCV antigen-anti-HCV antibody complex captured on the solid phase;
  c) isolating solid phase that comprises attached captured antibody, and captured HCV antigen from unreacted test sample and reagents
  d. contacting the isolated solid phase with a detectably labeled conjugate antibody that binds to the HCV antigen captured in the an anti-HCV antibody-HCV antigen complex of (b)(ii); and e. detecting the signal generated from the detectable label moieties upon triggering of the signal, wherein presence of the signal indicates presence of HCV in the test sample.

In an exemplary embodiment, the immunoassay may further comprise:

(a) providing (v) a second biotinylated HCV antigen for the capture of anti-HCV antibody in the test sample wherein the second HCV antigen is distinct from the HCV antigen in step (aiii); and (vi). a detectably labeled HCV antigen for binding to anti-HCV antibody captured by the biotinylated HCV antigen of (v); and (b) (iii) the biotinylated antigen of (a)(v) binds to the solid phase through the biotin and specifically binds to anti-HCV antibodies present in the test sample to produce an HCV antigen-anti-HCV antibody complex captured on the solid phase and the detectably labeled HCV antigen of (a)(vi) specifically binds to the anti-HCV antibody in the an HCV antigen-anti-HCV antibody complex captured on the solid phase.

Such an immunoassay may also detect a third or a plurality of additional HCV antigens by:

(a) providing (vii) a third (or plurality of additional) biotinylated HCV antigen for the capture of anti-HCV antibody in the test sample wherein the third HCV antigen is distinct from the HCV antigen in step 1 (a)(iii) or step 2 (a)(v); and (viii) a detectably labeled HCV antigen for binding to anti-HCV antibody captured by the biotinylated HCV antigen of (vii); and (b) (iv) the biotinylated antigen of (a)(vii) binds to the solid phase through the biotin and specifically binds to anti-HCV antibodies present in the test sample to produce an HCV antigen-anti-HCV antibody complex captured on the solid phase and the detectably labeled HCV antigen of (a)(viii) specifically binds to the anti-HCV antibody in the an HCV antigen-anti-HCV antibody complex captured on the solid phase.

Another aspect of the invention describes an immunoassay for the simultaneous detection of both HCV antigens and HCV antibodies in a test sample, wherein the combination assay comprises:

a. a first capture antigen comprising a peptide sequence of a first HCV protein;

b a first detection antigen comprising a peptide sequence of a first HCV protein and further comprising a detectable label c. a second capture antigen comprising an antigenic sequence from a second HCV protein d. a second detection antigen comprising an antigenic sequence from a second HCV protein and further comprising a detectable label e. a third capture antigen comprising an antigenic sequence from a third HCV protein f. a third detection antigen comprising an antigenic sequence from a third HCV protein and further comprising a detectable label g. a first capture antibody h. a conjugate antibody comprising a detectable label wherein the capture antibody and the conjugate antibody specifically bind a fourth HCV protein from the test sample, and the combination assay is performed by:

(i) contacting the test sample with the capture antigen, the detection antigen, the capture antibody and the conjugate antibody under conditions to allow:

a) formation of a sandwich complex between the first capture antigen and the detection antigen and first anti-HCV antibody present in the test sample;

b) formation of a sandwich complex between the second capture antigen and the second detection antigen and an anti-HCV antibody against the second HCV protein present in the test sample;

c) formation of a sandwich complex between the third capture antigen and the third detection antigen and an anti-HCV antibody against the third HCV protein present in the test sample; and d) formation of a complex between the capture antibody, the conjugate antibody and an HCV antigen present in the sample; and (ii) measuring a signal generated from the detectable labels as a result of formation of the complexes, thereby simultaneously detecting HCV antigens and HCV antibodies present in the sample.

In any of the immunoassay summarized above, the first, second, third and fourth HCV proteins are independently selected from the group consisting of core antigen, E1, E2, NS2, NS3, NS4 and NS5 or distinct and independent portions of any one of core antigen, E1, E2, NS2, NS3, NS4 and NS5.

In certain embodiments, two or more of the first, second, third and fourth HCV proteins are independently selected from different portions of the same protein selected from the group consisting of core antigen, E1, E2, NS2, NS3, NS4 and NS5.

In specific preferred embodiments, in the immunoassays of the invention the first HCV protein is core antigen designed for the detection of anti-Core antibodies present in a test sample. More specifically, the capture antigen for capturing anti-Core antibodies is a core peptide that comprises a deletion of amino acids 34 and 48 and amino acids 115-121. In some embodiments, the detection antigen for detection anti-Core antibodies also is a core peptide that comprises a deletion of amino acids 34 and 48 and amino acids 115-121. In particular embodiments, the combination immunoassay is designed for the detection of both core antigens and anti-core antibodies in the test sample. Such a detection is facilitated by use of the core deletion antigens summarized above as capture and detection antigens. Hence, in the immunoassays outlines above, both the first antigen and the fourth protein each are Core related proteins, namely, the first antigen is supplied in the test assay and the fourth protein is present in the test sample as a result of presence of HCV in the sample.

In particular embodiments that employ capture of antigens from the test sample, the immunoassays may employ a plurality of antibodies wherein each of the plurality of antibodies is directed to distinct epitope of the same HCV antigen (e.g., an antibody directed to the lipid binding region of Core and an antibody directed to the DNA binding region of Core as two separate capture antibodies for capturing Core antigen).

The immunoassays of the invention further comprise providing a second pair of capture antibody and conjugate antibody, wherein the second capture/conjugate antibody pair specifically bind to the same HCV protein as the first capture/conjugate antibody pair of the immunoassay summarized above or specifically bind a different HCV protein.

In particular embodiments, the capture antigens and the capture antibody are attached to a solid support.

In other embodiments, the first capture antigen is a biotinylated core peptide, and the first detection antigen is an acridinylated core peptide wherein each the biotinylated and detection antigen is a core peptide comprising a deletion of amino acids 34 and 48 and amino acids 115-121.

Additional specific embodiment comprise the second capture antigen is a biotinylated NS3 recombinant antigen and the second detection antigen is an acridinylated NS3 recombinant antigen. In other specific embodiments the third capture antigen is biotinylated NS4 peptide and the third detection antigen is an acridinylated NS4 peptide.

In particular embodiments, the capture antibody is biotinylated C11-7 monoclonal antibody.

In other embodiments, the detection antibody conjugate comprises antibodies selected from the group consisting of C11-9 and C11-14 or combinations thereof.

Also described herein is an immunoassay for detection of multiple HCV components from a test sample comprising:
  a. providing a biotin-binding solid phase
  b. contacting the solid phase with a mixture that comprises:
    i. biotinylated first capture antigen, biotinylated second capture antigen, biotinylated third capture antigen and biotinylated antibody specific for a fourth HCV antigen; and
    ii detectably labeled first, second, and third detection antigens
  under conditions and time sufficient for
    (1) immune complexes to form between antibodies in the test sample that are independently immunoreactive with and captured by the first, second and third biotinylated antigens, respectively and HCV proteins in the sample that are immunoreactive with the biotinylated antibody, and
    (2) immune complexes to form between the capture antibodies and the respective first, second and third detectably labeled antigens;
  c. isolating solid phase that comprises attached detectably labeled captured antibodies, and captured fourth HCV antigen from unreacted test sample and reagents
  d. contacting the isolated solid phase with a detectably labeled conjugate antibody that binds to the captured fourth HCV antigen; and
  e. detecting the signal generated from the detectably labeled moieties upon triggering of the signal, wherein presence of the signal indicates presence of HCV in the test sample.

Again in such an assay, the first, second, third, and fourth HCV protein is independently selected from the group consisting of group consisting of core antigen, E1, E2, NS2, NS3, NS4 and NS5. More specifically, in one particular embodiment, the HCV core antigen comprising a deletion of amino acids 34 and 48 and amino acids 115-121; the second antigen is NS3 antigen; the third antigen is NS4 antigen; and the biotinylated antibody is directed against HCV core antigen. In specific embodiments, the anti-Core monoclonal antibody is an antibody specific for the lipid binding domain of HCV core. Alternatively, or additionally, the NS3 antigen is a recombinant HCV NS3 antigen comprising a NS3 helicase sequence that comprises each of domains I, II and III of the helicase, wherein the antigen has increased immunoreactivity against HCV antibodies from serum as compared to C33 antigen.

Also contemplated herein is an immunoassay for detection of multiple HCV antibodies from a test sample comprising:
  a. providing a biotin-binding solid phase
  b. contacting the solid phase with a mixture that comprises:
    i. biotinylated first capture antigen, biotinylated second capture antigen, biotinylated third capture antigen; and
    ii detectably labeled first, second, and third detection antigens under conditions and time sufficient for
    (1) immune complexes to form between antibodies in the test sample that are independently immunoreactive with and captured by the first, second and third biotinylated antigens, respectively, and
    (2) immune complexes to form between the capture antibodies and the respective first, second and third detectably labeled antigens;
  c. isolating solid phase that comprises attached detectably labeled captured antibodies, from unreacted test sample and reagents; and
  d. detecting the signal generated from the detectably labeled moieties upon triggering of the signal, wherein presence of the signal indicates presence of HCV in the test sample. Again, in such an immunoassay the first, second, and third HCV protein is independently selected from the group consisting of group consisting of core antigen, E1, E2, NS2, NS3, NS4 and NS5. In one particular exemplary assay, the first antigen is HCV core antigen; the second antigen is NS3 antigen; and the third antigen is NS4 antigen. More particularly, the capture core antigen may be, but need not be an antigen comprises a deletion of amino acids 34 and 48 and amino acids 115-121. The NS3 antigen also may be any NS3 antigen derived from NS3. In certain embodiments, the NS3 antigen is a recombinant HCV NS3 antigen comprising a NS3 helicase sequence that comprises each of domains I, II and III of the helicase, wherein the antigen has increased immunoreactivity against HCV antibodies from serum as compared to C33 antigen.

The invention further comprises kits for the simultaneous detection of HCV antigens and antibodies in a sample comprising:
  a first pair of capture antigen and detection antigen for detecting a first anti-HCV antibody against a first HCV protein, wherein the detection antigen is detectably labeled
  a second pair of capture antigen and detection antigen for detecting a second anti-HCV antibody against a second HCV protein; wherein the detection antigen is detectably labeled
  a third pair of capture antigen and detection antigen for detecting a third anti-HCV antibody against a third HCV protein, wherein the detection antigen is detectably labeled
  a first pair of capture antibody and conjugate antibody for detecting a fourth HCV protein, wherein the conjugate antibody is detectably labeled.

In the kits, the first, second, third and fourth HCV proteins are independently selected from the group consisting of core antigen, E1, E2, NS2, NS3, NS4 and NS5 or distinct and independent portions of any one of core antigen, E1, E2, NS2, NS3, NS4 and NS5. Specifically, the kits are designed to detect two or more of the first, second, third and fourth HCV proteins which are independently selected from different portions of the same protein selected from the group consisting of core antigen, E1, E2, NS2, NS3, NS4 and NS5. In preferred kits, the first HCV protein is core antigen, preferably, it is core peptide that comprises a deletion of amino acids 34 and 48 and amino acids 115-121. The kit comprising an anti-Core antibody detection antigen wherein the core peptide in the detection antigen comprises a deletion of amino acids 34 and 48 and amino acids 115-121. The kits also may detect core antigens in the sample and hence may advantageously comprise an anti-Core capture and detection antibody. Such a capture antibody may comprise two or more antibodies.

The kit may also comprise a second pair of capture antibody and conjugate antibodies, wherein the second capture/conjugate antibody pair specifically bind to the same HCV protein as the first capture/conjugate antibody pair or specifically bind a different HCV protein. In particular embodiments, the capture antigens and the capture antibody are attached to a solid support.

Any of the immunoassays employing the antigens of the invention may readily be adapted for use in an automated system or a semi-automated system.

BRIEF DESCRIPTION OF SEVERAL VIEWS OF THE DRAWINGS

FIG. 1 shows the position of HCV NS3 recombinant antigens of the present invention.

DETAILED DESCRIPTION OF THE INVENTION

The present invention provides HCV combination immunoassays that provide enhanced detection of exposure to HCV, by detecting both antibodies to HCV as is performed in conventional immunoassays, and by detecting HCV core antigen that may be present in the blood of individuals in the early stage of infection, prior to the development of antibodies to HCV. This invention meets the need in the art for a combination immunoassay for the simultaneous detection of both HCV antigens and anti-HCV antibodies in a sample in a single assay. The antigen/antibody combination assay methods rely on the identification and use of antigenic and immunogenic HCV antibodies and antigens that are present during the early stages of HCV seroconversion, thereby increasing detection accuracy and reducing the incidence of false results during the window period.

Biological samples that can be tested for HCV using the combination assays of the present invention include any sample suspected to contain HCV virions, antigens or antibodies. The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, (e.g., whole blood or components thereof), plasma, serum, urine, saliva, amniotic fluid, synovial fluid, endothelial cells, leukocytes, monocytes, other cells, organs, tissues, bone marrow, lymph nodes and spleen.

In the anti-HCV antibody detection aspect of the combination assay at least one (i.e., one or more) capture antigen is employed to bind and therefore captures anti-HCV antibodies present in the test sample. The capture antigens are generally antigenic peptides (containing one or more epitopes) derived from an HCV protein encoded by the HCV genome. The sequence of the entire HCV genome and the encoded HCV polyprotein sequence are documented in GenBank (accession #M62321 and #AAA45676, respectively) and available to those skilled in the art. Some exemplary core antigens that could be used include antigens derived from the DNA binding domain (amino acids 1-125) of core protein. Still other preferred core antigens are derived from the lipid binding domain of core located at amino acid residues 134-171 of core protein (MGYIPLVGAPLG-GAARALAHGVRVLEDGVNYATGNLPG) (SEQ ID NO: 89). However, in the present invention particularly preferred core antigens include antigens derived from core protein that comprise certain deletions or substitution in the known epitope binding regions for specific monoclonal antibodies such that monoclonal antibodies used for HCV core antigen detection would fail to detect these modified core antigens but would nonetheless detect complete core antigen from the test sample. Thus, these novel modified core antigens can be coated onto a solid phase support and/or used in solution phase to capture antibodies present in human serum or plasma that are directed toward the Core region of HCV but at the same time evade detection by the conjugate antibody used for the detection of Core Ag in an HCV Combo assay, but at the same time, allow detection of anti-Core antibodies that would also be expected to be in the test sample and identified in the same HCV Combo assay format. Preferred core antigens for use in the assays of the present invention comprise mutant core proteins that comprise a deletion of amino acids 34 and 48 and amino acids 115-121.

By using the novel core capture antigens described herein, the present invention overcomes a significant problem that is seen with the currently available *Ac-DBA-c11-9/c11-14 conjugate that is used for the detection of core antigen in an HCV combination assay because the currently available core antigens used for capture of anti-core antibodies also react with detection antibodies designed to conduct serological detection of core antigen. Previously, constructs were made to obviate this problem by deletion of 5 amino acids (amino acids 32 33 and 34 for the C11-9 binding region and amino acids and residues 47 and 48 from the c11-14 binding region of core), however, these constructs yielded poorer anti-core antibody detection as these residues are highly immunogenic in anti-Core positive patients. The use of the core antigens that are described herein as capture antigens overcomes this problems due to their design which encompasses more minimal deletions that can successfully avoid detection by the *Ac-DBA c11-9/c11-14 conjugate but preserve or enhance detection of anti-core reactive specimens. In the combination assays of the present invention core antigens for the capture and detection of anti-HCV core antibodies advantageously comprise deletions of core amino acids sufficient for elimination of the binding of the capture antibody to the detection core antigen, for example, amino acids 115-121 are deleted.

Definitions

The present invention provides reagents for the detection of HCV in a test sample. Preferably, this detection is achieved by the simultaneous detection of both HCV antigens and anti-HCV antibodies in the test sample. Throughout the specification certain terms are frequently used and as such the following section provides additional definitions of those terms. The term "antibody" (Ab) and "antibodies" (Abs) refer to monoclonal antibodies (mAb (singular) or mAbs (plural)), polyclonal antibodies (pAbs (plural)), multispecific antibodies, human antibodies, humanized antibodies (fully or partially humanized; a polypeptide comprising a modified variable region of a human antibody wherein a portion of the variable region has been substituted by the corresponding sequence from a non-human sequence and wherein the modified variable region is linked to at least part of the constant region of a human antibody), animal antibodies (such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies (cAb; a polypeptide comprising all or a part of the heavy and light chain variable regions of an antibody from one host species linked to at least part of the antibody constant regions from another host species), single chain antibodies, single domain antibodies, Fab fragments, F(ab') fragments, Fab'-SH fragments, F(ab')2 fragments, Fd fragments, Fv fragments, single-chain Fv fragments ("scFv"), disulfide-linked Fv fragments ("sdFv"), dAb fragments, diabodies, an isolated complementarity determining region (CDR), and anti-idiotypic ("anti-Id") antibodies, bifunctional or dual-domain antibodies (e.g., dual variable domain antibodies, or DVD-IgGs), and functionally active, epitope-binding fragments (or antigenically reactive fragments) of any of the above. In particular, antibodies include immunoglobulin molecules and immunologically active (or antigenically reactive) fragments of immunoglobulin molecules, namely, molecules that contain an analyte-binding site as further described in (n) herein, and variants as further described in (ac) herein Immunoglobulin molecules can be of any type (for example, IgG, IgE, IgM, IgD, IgA and IgY), class (for example, IgG1, IgG2, IgG3, IgG4, IgA1 and IgA2), or subclass. An antibody, whose affinity (namely, KD, kd or ka) has been increased or improved via the screening of a combinatory antibody library that has been prepared using bio-display, is referred to as an "affinity maturated antibody." For simplicity sake, an antibody against an analyte is frequently referred to herein as being either an "anti-analyte antibody" or merely an "analyte antibody" (e.g., an anti-HCV antibody or an HCV antibody).

In the present invention the assay "component," "components," and "at least one component," refer generally to a capture antibody, a detection or conjugate antibody, a control, a calibrator, a series of calibrators, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, serum or plasma sample, in accordance with the methods described herein and other methods known in the art. Thus, in the context of the present disclosure, "at least one component," "component," and "components" can include a polypeptide as described herein, which is optionally immobilized on a solid support. Some components can be in solution or lyophilized for reconstitution for use in an assay.

In conducting the assays of the present invention, it may be useful to use a control. "Control" refers to a composition known to not contain anti-HCV antibody ("negative control") or to contain anti-HCV antibody ("positive control"). A positive control can comprise a known concentration of anti-HCV antibody. "Control," "positive control," and "calibrator" may be used interchangeably herein to refer to a composition comprising a known concentration of anti-HCV antibody. A "positive control" can be used to establish assay performance characteristics and is a useful indicator of the integrity of reagents (e.g., analytes).

The NS3 antigens of the present invention are useful in serological assays for the detection of anti-HCV antibodies in a test sample because such antibodies recognize epitopes contained within the NS3 antigens of the present invention. "Epitope," "epitopes" and "epitopes of interest" refer to a site(s) on any molecule (in this case the NS3 antigens described herein) that is recognized and can bind to a complementary site on a specific binding partner, such as an antibody or antigenically reactive fragment thereof. An epitope consists of the precise amino acid residues of a region of an antigen (or fragment thereof) known to bind to the complementary site on the specific binding partner. An antigenic fragment can contain more than one epitope.

In the assays that are described herein, one or other component of the assay may comprise a detectable label. The terms "label" and "detectable label" mean a moiety attached to a specific binding partner, such as an antibody or an analyte, to render the reaction between members of a specific binding pair, such as an antibody and an analyte, detectable, and the specific binding partner, e.g., antibody or analyte, so labeled is referred to as "detectably labeled." A label can produce a signal that is detectable by visual or instrumental means. Various labels include signal-producing substances, such as chromogens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety itself may not be detectably labeled but may become detectable upon reaction with yet another moiety. Use of "detectably labeled" is intended to encompass the latter type of detectable labeling.

"Linking sequence" refers to a natural or artificial polypeptide sequence that is connected to one or more polypeptide sequences of interest (e.g., full-length, fragments, etc.). The term "connected" refers to the joining of the linking sequence to the polypeptide sequence of interest. Such polypeptide sequences are preferably joined by one or more peptide bonds. Linking sequences can have a length of from about 4 to about 50 amino acids. Preferably, the length of the linking sequence is from about 6 to about 30 amino acids. Natural linking sequences can be modified by amino acid substitutions, additions, or deletions to create artificial linking sequences. Exemplary linking sequences include, but are not limited to: (i) Histidine residues (His tags), such as a 6×His tag (SEQ ID NO: 90), which contains six histidine residues, are useful as linking sequences to facilitate the isolation and purification of polypeptides and antibodies of interest. (ii) Enterokinase cleavage sites, like His tags, are used in the isolation and purification of proteins and antibodies of interest. Often, enterokinase cleavage sites are used together with His tags in the isolation and purification of proteins and antibodies of interest. Various enterokinase cleavage sites are known in the art. (iii) Miscellaneous sequences can be used to link or connect the light and/or heavy chain variable regions of single chain variable region fragments. Examples of other linking sequences can be found in Bird et al., Science 242: 423-426 (1988); Huston et al., PNAS USA 85: 5879-5883 (1988); and McCafferty et al., Nature 348: 552-554 (1990). Linking sequences also can be modified for additional functions, such as attachment of drugs or attachment to solid supports. In the context of the present disclosure, an mAb, for example, can contain a linking sequence, such as a His tag, an enterokinase cleavage site, or both.

"Patient" and "subject" may be used interchangeably herein to refer to an animal, such as a bird (e.g., a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, and a mouse) and a primate (for example, a monkey, a chimpanzee, and a human). Preferably, the patient or subject is a human, such as a human at risk for HCV infection or a human infected with HCV.

In analysis of the results of the immunoassays described herein it may be useful to include certain levels of detection as cutoff levels. "Predetermined cutoff" and "predetermined level" refer generally to an assay cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.). While the present disclosure may provide exemplary predetermined levels, it is well-known that cutoff values may vary depending on the nature of the immunoassay (e.g., antibodies employed, etc.). It further is well within the ordinary skill of one in the art to adapt the disclosure herein for other immunoassays to obtain immunoassay-specific cutoff values for those other immunoassays based on this disclosure. Whereas the precise value of the predetermined cutoff/level may vary between assays, the correlations as described herein should be generally applicable.

As described below, it may be desirable in some embodiments of the invention to provide a pretreatment of the test sample. "Pretreatment reagent," e.g., lysis, precipitation and/or solubilization reagent, as used in a diagnostic assay as described herein is one that lyses any cells and/or solubilizes any analyte that is/are present in a test sample. Pretreatment is not necessary for all samples, as described further herein. Among other things, solubilizing the analyte (i.e., anti-HCV antibody) entails release of the analyte from any endogenous binding proteins present in the sample. A pretreatment reagent may be homogeneous (not requiring a separation step) or heterogeneous (requiring a separation step). With use of a heterogeneous pretreatment reagent there is removal of any precipitated analyte binding proteins from the test sample prior to proceeding to the next step of the assay. The pretreatment reagent optionally can comprise: (a) one or more solvents and salt, (b) one or more solvents, salt and detergent, (c) detergent, (d) detergent and salt, or (e) any reagent or combination of reagents appropriate for cell lysis and/or solubilization of analyte.

The assays also may be subject to rigorous quality control. "Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction so as to comprise a "sensitivity panel."

The terms "sample," "test sample," and "patient sample" may be used interchangeably herein. The sample, such as a sample of urine, serum, plasma, amniotic fluid, cerebrospinal fluid, placental cells or tissue, endothelial cells, leukocytes, or monocytes, can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art. Preferably, the sample is urine, serum or plasma.

In some assays, it may be desirable to provide calibration of the assay. "Series of calibrating compositions" refers to a plurality of compositions comprising a known concentration of anti-HCV antibody, wherein each of the compositions differs from the other compositions in the series by the concentration of anti-HCV antibody.

Throughout the present specification, it is noted that the NS3 antigens and/or other reagents may be bound to a solid support or solid phase, both of which terms are used interchangeably. The term "solid phase" refers to any material that is insoluble, or can be made insoluble by a subsequent reaction. The solid phase can be chosen for its intrinsic ability to attract and immobilize a capture agent. Alternatively, the solid phase can have affixed thereto a linking agent that has the ability to attract and immobilize the capture agent. The linking agent can, for example, include a charged substance that is oppositely charged with respect to the capture agent itself or to a charged substance conjugated to the capture agent. In general, the linking agent can be any binding partner (preferably specific) that is immobilized on (attached to) the solid phase and that has the ability to immobilize the capture agent through a binding reaction. The linking agent enables the indirect binding of the capture agent to a solid phase material before the performance of the assay or during the performance of the assay. The solid phase can, for example, be plastic, derivatized plastic, magnetic or non-magnetic metal, glass or silicon, including, for example, a test tube, microtiter well, sheet, bead, microparticle, chip, and other configurations known to those of ordinary skill in the art.

In certain descriptions of the assays described herein it may be useful to refer to either the NS3, NS4 or core antigen or the HCV antibody as a specific binding partner. "Specific binding partner" is a member of a specific binding pair. A specific binding pair comprises two different molecules, which specifically bind to each other through chemical or physical means. Therefore, in addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes, fragments, and variants (including fragments of variants) thereof, whether isolated or recombinantly produced. The term "specific" and "specificity" in the context of an interaction between members of a specific binding pair (e.g., an antigen (or fragment thereof) and an antibody (or antigenically reactive fragment thereof)) refer to the selective reactivity of the interaction. The phrase "specifically binds to" and analogous phrases refer to the ability of antibodies (or antigenically reactive fragments thereof) to bind specifically to a given antigen (or a fragment thereof) and not bind specifically to other entities.

Antigens For Use in the Present Invention

As described herein the present invention describes the detection of a combination of HCV antigens in one assay to advantageously provide a sensitive and selective detection of HCV in the test sample being assayed. In certain preferred embodiments, the combination assay further detects the presence of anti-HCV antibodies. More particularly, the HCV antigens may be any antigen that is typically monitored in an HCV assay. Such antigens include but are not limited to core antigen, E1, E2, NS2, NS3, NS4 and NS5 or distinct and independent portions of any one of core antigen, E1, E2, NS2, NS3, NS4 and NS5. Immunoassays for the detection of such antigens individually are commercially available to those of skill in the art and any of the antigens used in such commercially available assays may readily be used as capture or detection antigens in the immunoassays of the present invention. For example, HCV NS3 protein and mutants thereof principally have to two main protein parts, the first corresponds to amino acids 1192-1457 per the HCV polyprotein numbering of P26664 (Genbank, reproduced herein as SEQ ID NO:2; Choo et al., PNAS 1991;) also known as C33 (as described originally by Chiron) or as "9NB49H". The second portion of the NS3 protein corresponds to amino acids 1192-1657 also known as NS3 helicase or "NS3h." Antigens comprising all or portions of these two proteins can readily be used in the detection of anti-HCV antibodies in a test sample. For example, C33 is a well-known antigen derived from the NS3 protein of HCV and may readily be used herein as either the capture or detection antigen for the detection NS3 antibodies in the combination immunoassays of the present invention.

Other NS3 derived antigens include those described in concurrently filed U.S. Provisional Application No. 61/784,822 entitled "HCV NS3 Recombinant Antigens and Mutants Thereof for Improved Antibody Detection". Such antigens are variant of the C33 and the NS3 helicase proteins in which the N-termini or C-termini sequences were modified. In some embodiments, antigens were created that included cysteine to serine mutations. These mutations allowed for increased resistance of the antigen to oxidation thereby preserving epitope presentation and hence immunoreactivity. The cysteine to serine mutations also allowed for site-specific modification of the protein (via chemical conjugation using maleimide reagents) by mutating only selected cysteine residues, e.g. those deemed to be unimportant for maintenance of immunoreactivity. Furthermore, at least some of the cysteine to serine substituted mutants disrupt the ability of full length helicase enzyme (HCV aa1192-1657) to bind nucleotide triphosphates (e.g. ATP). This maintains the protein in an open or extended conformation (see Gu & Rice, PNAS, 2010, 107:521-528 and references therein) and is shown in the present invention to produce enhanced immunoreactivity.

Exemplary NS3 antigens that may be used in of the present invention are shown in Table 1 herein below. In general, these NS3 antigens may be described as recombinant HCV NS3 antigen comprising a NS3 helicase sequence that comprises each of domains I, II and III of said helicase, wherein said antigen has increased immunoreactivity against HCV antibodies from serum as compared to C33 antigen, wherein said recombinant HCV NS3 antigen comprises one or more of the characteristics selected from the group consisting of: diminished ATP-binding activity as compared to the ATP-binding activity of wild-type NS3 helicase; diminished ATPase activity as compared to wild-type NS3 as compared to the ATP-binding activity of wild-type NS3 helicase, and increased redox stability as compared to the redox stability of wild-type NS3 helicase. More particularly, in the context of the present invention, the wild-type HCV NS3 comprises a sequence of SEQ ID NO: 87 and wherein the recombinant antigen of the invention comprises at least one mutation as compared to the sequence of SEQ ID NO: 87. Detailed description of production and testing of these antigens is provided in concurrently filed U.S. Provisional Application No. 61/784,822, entitled "HCV NS3 Recombinant Antigens and Mutants Thereof for Improved Antibody Detection".

TABLE 1

| Antigen designation | Antigen | Sequence |
|---|---|---|
| A | K210N | avdfipven lettmrspvf tdnssppvvp qsfqvahlha ptgsgNstkv paayaaqgyk vlvlnpsvaa tlgfgaymsk ahgidpnirt gvrtittgsp itystygkfl adggcsggay diiicdechs tdatsilgig tvldqaetag arlvvlatat ppgsvtvphp nieevalstt geipfygkai plevikggrh lifchskkkc delaaklval ginavayyrg ldvsviptsg dvvvvatdal mtgytgdfds vidcntcvtq tvdfsldptf tietitlpqd avsrtqrrgr tgrgkpgiyr fvapgerpsg mfdssvlcec ydagcawyel tpaettvrlr aymntpglpv cqdhlefweg vftglthida hflsqtkqsg enlpylvayq atvcaraqap ppswdqmwkc lirlkptlhg ptpllyrlga vqneitlthp vtkyimtcms adlevvt (SEQ ID NO: 109) |
| B | S211A | avdfipven lettmrspvf tdnssppvvp qsfqvahlha ptgsgkAtkv paayaaqgyk vlvlnpsvaa tlgfgaymsk ahgidpnirt gvrtittgsp itystygkfl adggcsggay diiicdechs tdatsilgig tvldqaetag arlvvlatat ppgsvtvphp nieevalstt geipfygkai plevikggrh lifchskkkc delaaklval ginavayyrg ldvsviptsg dvvvvatdal mtgytgdfds vidcntcvtq tvdfsldptf tietitlpqd avsrtqrrgr tgrgkpgiyr fvapgerpsg mfdssvlcec ydagcawyel tpaettvrlr aymntpglpv cqdhlefweg vftglthida hflsqtkqsg enlpylvayq atvcaraqap ppswdqmwkc lirlkptlhg ptpllyrlga vqneitlthp vtkyimtcms adlevvt (SEQ ID NO: 110) |
| C | T212E | avdfipven lettmrspvf tdnssppvvp gsfqvahlha ptgsgksEkv paayaaqgyk vlvlnpsvaa tlgfgaymsk ahgidpnirt gvrtittgsp itystygkfl adggcsggay diiicdechs tdatsilgig tvldqaetag arlvvlatat ppgsvtvphp nieevalstt geipfygkai plevikggrh lifchskkkc delaaklval ginavayyrg ldvsviptsg dvvvvatdal mtgytgdfds vidcntcvtq tvdfsldptf tietitlpqd avsrtqrrgr tgrgkpgiyr fvapgerpsg mfdssvlcec ydagcawyel tpaettvrlr aymntpglpv cqdhlefweg yftglthida hflsqtkqsg enlpylvayq atvcaraqap ppswdqmwkc lirlkptlhg ptpllvrlga vqneitlthp vtkyimtcms adlevvt (SEQ ID NO: 111) |

TABLE 1-continued

| Antigen designation | Antigen | Sequence |
|---|---|---|
| D | Y241S, | avdfipven lettmrspvf tdnssppvvp qsfqvahlha ptgsgkstkv paayaaqgyk vlvlnpsvaa tlgfgaSmsk ahgidpnirt gvrtittgsp itystygkfl adggcsggay diiicdechs tdatsilgig tvldqaetag arlvvlatat ppgsvtvphp nieevalstt geipfygkai plevikggrh lifchskkkc delaaklval TABLE 1-continued

| Antigen designation | Antigen | Sequence |
|---|---|---|
| | | ppswdqmwkc lirlkptlhg ptpllyrlga vqneitlthp vtkyimtcms adlevvt (SEQ ID NO: 117) |
| J | R464A | avdfipven lettmrspvf tdnssppvvp qsfqvahlha ptgsgkstkv paayaaqgyk vlvlnpsvaa tlgfgaymsk ahgidpnirt gvrtittgsp itystygkfl adggcsggay diiicdechs tdatsilgig tvldqaetag arlvvlatat ppgsvtvphp nieevalstt geipfygkai plevikggrh lifchskkkc delaaklval ginavayyrg ldvsviptsg dvvvvatdal mtgytgdfds vidcntcvtq tvdfsldptf tietitlpqd avsrtqrrgA tgrgkpgiyr fvapgerpsg mfdssvlcec ydagcawyel tpaettvrlr aymntpglpv cqdhlefweg vftglthida hflsqtkqsg enlpylvayq atvcaraqap ppswdqmwkc lirlkptlhg ptpllyrlga vqneitlthp vtkyimtcms adlevvt (SEQ ID NO: 118) |
| K | R467K | avdfipven lettmrspvf tdnssppvvp qsfqvahlha ptgsgkstkv paayaaqgyk vlvlnpsvaa tlgfgaymsk ahgidpnirt gvrtittgsp itystygkfl adggcsggay diiicdechs tdatsilgig tvldqaetag arlvvlatat ppgsvtvphp nieevalstt geipfygkai plevikggrh lifchskkkc delaaklval ginavayyrg ldvsviptsg dvvvvatdal mtgytgdfds vidcntcvtq tvdfsldptf tietitlpqd avsrtqrrgr tgKgkpgiyr fvapgerpsg mfdssvlcec ydagcawyel tpaettvrlr aymntpglpv cqdhlefweg vftglthida hflsqtkqsg enlpylvayq atvcaraqap ppswdqmwkc lirlkptlhg ptpllyrlga vqneitlthp vtkyimtcms adlevvt (SEQ ID NO: 119) |
| L | W501A | avdfipven lettmrspvf tdnssppvvp qsfqvahlha ptgsgkstkv paayaaqgyk vlvlnpsvaa tlgfgaymsk ahgidpnirt gvrtittgsp itystygkfl adggcsggay diiicdechs tdatsilgig tvldqaetag arlvvlatat ppgsvtvphp nieevalstt geipfygkai plevikggrh lifchskkkc delaaklval ginavayyrg ldvsviptsg dvvvvatdal mtgytgdfds vidcntcvtq tvdfsldptf tietitlpqd avsrtqrrgr tgrgkpgiyr fvapgerpsg mfdssvlcec ydagcaAyel tpaettvrlr aymntpglpv cqdhlefweg vftglthida hflsqtkqsg enlpylvayq atvcaraqap ppswdqmwkc lirlkptlhg ptpllyrlga vqneitlthp vtkyimtcms adlevvt (SEQ ID NO: 120) |
| M | Any combination of two mutations selected from the group consisting of K210N, S211A, T212E, Y241S, D290N, E291Q, H293A, T419G, Q460H, R464A, R467K and W501A | |
| N | Any combination of three mutations selected from the group consisting of K210N, S211A, T212E, Y241S, D290N, E291Q, H293A, T419G, Q460H, R464A, R467K and W501A | |
| O | Any combination of four mutations selected from the group consisting of K210N, S211A, T212E, Y241S, D290N, E291Q, H293A, T419G, Q460H, R464A, R467K and W501A | |
| P | combination of five mutations selected from the group consisting of K210N, S211A, T212E, Y241S, D290N, E291Q, H293A, T419G, Q460H, R464A, R467K and W501A | |
| Q | Any combination of six mutations selected from the group consisting of K210N, S211A, T212E, Y241S, D290N, E291Q, H293A, T419G, Q460H, R464A, R467K and W501A | |
| R | combination of seven mutations selected from the group consisting of K210N, S211A, T212E, Y241S, D290N, E291Q, H293A, T419G, Q460H, R464A, R467K and W501A | |
| S | Any combination of eight, mutations selected from the group consisting of K210N, S211A, T212E, Y241S, D290N, E291Q, H293A, T419G, Q460H, R464A, R467K and W501A | |
| T | Any combination of nine mutations selected from the group consisting of K210N, S211A, T212E, Y241S, D290N, E291Q, H293A, T419G, Q460H, R464A, R467K and W501A | |
| U | Any combination of ten mutations selected from the group consisting of K210N, S211A, T212E, Y241S, D290N, E291Q, H293A, T419G, Q460H, R464A, R467K and W501A | |

TABLE 1-continued

| Antigen designation | Antigen Sequence |
|---|---|
| V | Any combination of eleven mutations selected from the group consisting of K210N, S211A, T212E, Y241S, D290N, E291Q, H293A, T419G, Q460H, R464A, R467K and W501A |
| W | Any combination of twelve mutations selected from the group consisting of K210N, S211A, T212E, Y241S, D290N, E291Q, H293A, T419G, Q460H, R464A, R467K and W501A |
| X | avdfipven lettmrspvf tdnssppvvp qsfqvahlha ptgsgkstkv paayaaqgyk vlvlnpsvaa tlgfgaymsk ahgidpnirt gvrtittgsp itystygkfl adg*c*sggay diii*cde*c*hs t*datsilgig tvldqaetag arlvvlatat ppgsvtvphp nieevalstt geipfygkai plevikggrh lif*chskkk*c *delaaklval ginavayyrg ldvsviptsg dvvvvatdal mtgytgdfds vid*cnt*c*vtq tvdfsldptf tietitlpqd avsrtqrrgr tgrgkpgiyr fvapgerpsg mfdssvl*cec ydag*S*awyel tpaettvrlr aymntpglpv cqdhlefweg vftglthida hflsqtkqsg enlpylvayq atv*caraqap ppswdqmwkc lirlkptlhg ptpllyrlga vqneitlthp vtkyimtcms adlevvt (SEQ ID NO: 121) |
| Y | avdfipven lettmrspvf tdnssppvvp qsfqvahlha ptgsgkstkv paayaaqgyk vlvlnpsvaa tlgfgaymsk ahgidpnirt gvrtittgsp itystygkfl adg*c*sggay diii*cde*c*hs t*datsilgig tvldqaetag arlvvlatat ppgsvtvphp nieevalstt geipfygkai plevikggrh lif*chskkk*c *delaaklval ginavayyrg ldvsviptsg dvvvvatdal mtgytgdfds vid*cnt*c*vtq tvdfsldptf tietitlpqd avsrtqrrgr tgrgkpgiyr fvapgerpsg mfdssvl*cec ydagcawyel tpaettvrlr aymntpglpv *S*qdhlefweg vftglthida hflsqtkqsg enlpylvayq atv*caraqap ppswdqmwkc lirlkptlhg ptpllyrlga vqneitlthp vtkyimtcms adlevvt (SEQ ID NO: 122) |
| Z | avdfipven lettmrspvf tdnssppvvp qsfqvahlha ptgsgkstkv paayaaqgyk vlvlnpsvaa tlgfgaymsk ahgidpnirt gvrtittgsp itystygkfl adg*c*sggay diii*cde*S*hs t*datsilgig tvldqaetag arlvvlatat ppgsvtvphp nieevalstt geipfygkai plevikggrh lif*chskkk*c *delaaklval ginavayyrg ldvsviptsg dvvvvatdal mtgytgdfds vid*cnt*c*vtq tvdfsldptf tietitlpqd avsrtqrrgr tgrgkpgiyr fvapgerpsg mfdssvl*cec ydagcawyel tpaettvrlr aymntpglpv cqdhlefweg vftglthida hflsqtkqsg enlpylvayq atv*caraqap ppswdqmwkc lirlkptlhg ptpllyrlga vqneitlthp vtkyimtcms adlevvt (SEQ ID NO: 123) |
| A1 | avdfipven lettmrspvf tdnssppvvp qsfqvahlha ptgsgkstkv paayaaqgyk vlvlnpsvaa tlgfgaymsk ahgidpnirt gvrtittgsp itystygkfl adg*c*sggay diii*cde*c*hs t*datsilgig tvldqaetag arlvvlatat ppgsvtvphp nieevalstt geipfygkai plevikggrh lif*S*hskkk*c *delaaklval ginavayyrg ldvsviptsg dvvvvatdal mtgytgdfds vid*cnt*c*vtq tvdfsldptf tietitlpqd avsrtqrrgr tgrgkpgiyr fvapgerpsg mfdssvl*cec ydagcawyel tpaettvrlr aymntpglpv cqdhlefweg vftglthida hflsqtkqsg enlpylvayq atv*caraqap ppswdqmwkc lirlkptlhg ptpllyrlga vqneitlthp vtkyimtcms adlevvt (SEQ ID NO: 124) |
| A2 | avdfipven lettmrspvf tdnssppvvp qsfqvahlha ptgsgkstkv paayaaqgyk vlvlnpsvaa tlgfgaymsk ahgidpnirt gvrtittgsp itystygkfl adg*c*sggay diii*cde*c*hs t*datsilgig tvldqaetag arlvvlatat ppgsvtvphp nieevalstt geipfygkai plevikggrh lif*chskkk*S *delaaklval ginavayyrg ldvsviptsg dvvvvatdal mtgytgdfds vid*cnt*c*vtq tvdfsldptf tietitlpqd avsrtqrrgr tgrgkpgiyr fvapgerpsg mfdssvl*cec ydagcawyel tpaettvrlr aymntpglpv cqdhlefweg vftglthida hflsqtkqsg enlpylvayq atv*caraqap ppswdqmwkc lirlkptlhg ptpllyrlga vqneitlthp vtkyimtcms adlevvt (SEQ ID NO: 125) |
| A3 | Any combination of mutations of any of A-W in combination with one two or three, four or five of the mutations shown in X, Y, Z, A1, and A2. |

In other embodiments, another aspect of the combination immunoassay detects the presence of antibodies to Core antigen. Some exemplary core antigens that could be used include antigens derived from the DNA binding domain (amino acids 1-125) of core protein. Still other preferred core antigens are derived from the lipid binding domain of core located at amino acid residues 134-171 of core protein (MGYIPLVGAPLGGAAPRALAHGVRVLEDGVNYATGNLPG) (SEQ ID NO: 89). However, in the present invention particularly preferred core antigens include antigens derived from core protein that comprise certain deletions or substitution in the known epitope binding regions for specific monoclonal antibodies such that monoclonal antibodies used for HCV core antigen detection would fail to detect these modified core antigens but would nonetheless detect complete core antigen from the test sample. Thus, these novel modified core antigens can be coated onto a solid phase support and/or used in solution phase to capture antibodies present in human serum or plasma that are directed toward the Core region of HCV but at the same time evade detection by the conjugate antibody used for the detection of Core antigen present in a test sample in an HCV combination immunoassay. Thus a combination immunoassay can be performed that detects both Core antigen present in the test sample at the same time as detecting anti-Core antibodies that would also be expected to be in the test sample and identified in the same HCV Combo assay format. The Core antigens that can be used for the purpose of detecting anti-Core antibodies from the test sample preferably comprise deletions of amino acids 34 and 48 and amino acids 115-121 of Core antigen.

As noted herein throughout the methods of the invention typically are immunoassay methods. In exemplary embodiments, such methods include methods for isolating a molecule of interest (such as for example a specific antibody that is present in a test sample, or a specific antigen that may be present in the test sample). In order to facilitate such isolation, the molecule of interest comprises or is attracted to a purification tag that contacts a tag binding partner. The association of the purification tag and the tag binding partner thus may be used to separate the molecule of interest from a mixture of molecules. Purification tags can comprise moieties with the same or similar structures. In certain embodiments, the tagging moiety of an affinity tag can be associated with a functional tag directly by a single bond or via a linkage of stable chemical bonds, in linear, branched or cyclic arrangements, optionally including single, double, triple bond, aromatic carbon-carbon bonds, as well as carbon-nitrogen bonds, nitrogen-nitrogen bonds, carbon-oxygen bonds, carbon-sulfur bonds, phosphorus-oxygen bonds, phosphorus-nitrogen bonds, and any combination thereof. In certain embodiments, the association between the tagging moiety and functional tag comprises ether, thioether, carboxamide, sulfonamide, urea or urethane moieties. In preferred embodiments, the linkage comprises a polyalkylene chain, i.e., a linear or branched arrangement of carbon-carbon bonds. In other embodiments, the linkage comprises a polyalkylene oxide chain, including a polyethylene glycol moiety. Examples, of affinity tags include, but are not limited to, biotin, digoxigenin (Dig), dinitrophenol (DNP), zinc fingers, fluorinated polymers, and polypeptide sequences such as polyhistidine motifs.

The affinity tags are in some embodiments advantageously used to isolate the molecule of interest by relying on the binding or attraction of the affinity tag and a functional group that is attracted to or binds the affinity tag. In some embodiments, solid substrates having an affinity for the tag in that the solid substrate is derivatized with the tag binding partner. In some embodiments, the binding partner may be immobilized on an affinity substrate. The term "affinity substrate" can refer to an immobile matrix or support bound to a binding partner that is capable of forming a strong and preferably reversible interaction with the purification tag of a molecule. An affinity substrate can include a resin, a bead, a particle, a membrane, a gel. The binding partner recognizes or binds to the purification tag specifically. Specific binding partners will depend on the affinity tag, but include charged moieties and one member of a binding pair such as receptor-ligand, antibody-antigen, carbohydrate-lectin, and biotin-streptavidin (or avidin, neutravidin or an anti-biotin antibody).

In specific and preferred embodiments, either the C or the N terminus of any or all of the antigens used in the combination immunoassay may be biotinylated or may comprise a biotin binding moiety (e.g., avidin or streptavidin or neutravidin or an anti-biotin) as the affinity tag. These peptides are biotinylated or avidin/streptavidin-conjugated peptides and will serve as capture antigens. Likewise, the antigens may alternatively be labeled with a detection label in which case they will serve as detection antigens. The detection and capture antigens may have the same underlying amino acid sequence or alternatively, may have different sequences. In exemplary embodiments, the capture antigens are biotinylated at either the C or the N terminus to facilitate binding thereof to solid supports that have the biotin binding partner (i.e., avidin or streptavidin). For exemplary production purposes, the biotinylated peptides are recombinantly expressed in $E.$ $coli$ BL2L(DE3) cells via an IPTG induction system at 25° C. In situ biotinylation at the C-terminal or N-terminal biotinylation is accomplished by co-transformation of the BL21(DE3) cells with the HCV expression plasmid expressing the desired peptide and a second plasmid containing the BirA gene from $E.$ $coli$ (Weiss et al. (1994) Protein Expression & Purif, 14:751-755; Schatz et al. (1993) Biotechnology, 11:1138-1143). Purification of the recombinant proteins is performed using divalent cation chelators that are shown to prevent metal-catalyzed oxidation and aggregation of the protein. Protein stability is significantly improved when EDTA or related divalent cation chelator is added to the buffers used during purification and to the final storage buffer or buffers used in the immunoassay.

Antibodies for Use in the Combinations Assays

As discussed herein throughout the combination immunoassays advantageously also determine the presence of one or more HCV antigens present in the test sample. In such embodiments, it will be desirable to use monoclonal anti-HCV antibodies to capture the antigen from the test sample and then use further conjugate antibodies to detect the presence of antigen that has been captured. There are numerous commercially available antibodies that may be used in this endeavor. Specifically, such antibodies preferably determine the presence of Core antigen in the test sample. Antibodies directed to Core antigen are known to those of skill in the art include, for example, those described in US Patent Publication No. 20120009196. In addition, the present invention further contemplates that use of monoclonal antibodies described in concurrently filed U.S. Patent Application No. 61/783,529, entitled "HCV Core Lipid Binding Domain Monoclonal Antibodies"that is specifically immunoreactive with the lipid binding domain of HCV core antigen. More particularly, the HCV core antigen is amino acid residues 134-171 of HCV. In more particular embodiments, the antibody specifically binds at least one epitope formed by amino acid sequence MGYIPLVGAPLG-GAARALAHGVRVLEDGVNYATGNLPG (SEQ ID NO: 89). In more specific embodiments, the antibody is immunoreactive with an epitope formed by amino acids 141-161, 134-154 and 151 to 171 of HCV core antigen.

In specific exemplary embodiments the antibodies used in the combination immunoassay are antibodies designed to detect HCV core protein or fragments thereof in a test sample. Such antibodies may detect the DNA binding domain, the lipid binding domain or indeed the complete Core protein. In some embodiments, the detection antibody used in the immunoassay is directed to the lipid binding domain of core peptide and exemplary such antibodies are described in concurrently filed U.S. Provisional Application No. 61/783,529 entitled "HCV Core Lipid Binding Domain Monoclonal Antibodies". In still other embodiments, the anti-HCV Core antibodies used in the combination assays may be for example, C11-3, C11-7, C11-9, and C11-14 (as described in U.S. Pat. No. 6,727,092; Morota, et al, J. Virol. Meth., 2009, 157:8-14).

In a specific assay of the present invention, the combination immunoassay at least detects core antigen as well detecting core antibodies in the test sample. In such embodiments, it becomes desirable, although not essential to ensure that the capture antigen that is designed to capture anti-Core one that preferably comprise certain deletions or substitution in the known epitope binding regions for specific monoclonal antibodies such that monoclonal antibodies used for HCV core antigen detection would fail to detect these modified core antigens but would nonetheless detect complete core antigen from the test sample. Exemplary anti-core antibodies to be used as capture antibodies include antibodies AOT3, C11-3, C11-7, C11-9, and C11-14 as described in U.S. Pat. No. 6,727,092 as well as Morota, et al, J. Virol. Meth., 2009, 157:8-14.

Immunodiagnostic Assays and Reagents

In particular embodiments, the antigens and antibodies described above are contemplated for use as immunodiagnostic reagents in combination immunoassays designed for the detection of multiple HCV components found in a test sample suspected of having been infected with HCV. Immunodiagnostic reagents (be they antibodies or antigens) will be comprised of the above-described antigen polypeptides and antibodies (typically in combination) such that they can be used in a combination immunoassay designed for the detection of HCV antigens including but not limited to the NS3 region of HCV, the core antigen of HCV, the NS4 region of HCV or combinations thereof as well as anti-HCV antibodies directed against one or more of these regions. For purposes of capture, the antigens and/or antibodies of which the immunodiagnostic reagent is comprised can be coated on a solid support such as for example, a microparticle, (e.g., magnetic particle), bead, test tube, microtiter plate, cuvette, membrane, scaffolding molecule, film, filter paper, disc or chip. In this regard, where the immunodiagnostic reagent comprises a combination of antigens (e.g., directed at different HCV proteins or different fragments of the same HCV protein), the antigens can be co-coated on the same solid support or can be on separate solid supports. Likewise, where the immunodiagnostic reagent comprises one or more antibodies that will be used to capture one or more antigens from the test sample, such antibodies can be co-coated on the same solid support or can be on separate solid supports.

Notably, the immunodiagnostic reagent will include the antigens and antibodies may be labeled with a detectable label or labeled with a specific partner that allows capture or detection. For example, the labels may be a detectable label, such as a fluorophore, radioactive moiety, enzyme, biotin/avidin label, chromophore, chemiluminescent label, or the like. Such labels are described in further detail infra.

Still further the invention contemplates the preparation of HCV diagnostic kits comprising the immunodiagnostic reagents described herein and instructions for the use of the immunodiagnostic reagents in combination immunoassays for determining the presence of HCV in a test sample by detecting the presence of two or more HCV proteins and/or anti-HCV antibodies in such a sample. For example, the kit can comprise instructions for assaying the test sample for anti-HCV antibody (e.g., an anti-Core antibody in the test sample) by immunoassay. While preferred embodiments employ chemiluminescent microparticle immunoassay for assaying the test sample, it should be understood that the antigens and antibodies used in the combination immunoassays of the present invention may be used in any other immunoassay formats known to those of skill in the art for determining the presence of HCV in a test sample. The instructions can be in paper form or computer-readable form, such as a disk, CD, DVD, or the like. Alternatively or additionally, the kit can comprise a calibrator or control, e.g., purified, and optionally lyophilized, anti-HCV antibody or antigen, and/or at least one container (e.g., tube, microtiter plates or strips, which can be already coated with one or more of the capture components (antigens and/or antibodies) of the combination immunoassay) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. In specific embodiments, it is preferred that all the components are individually presented in the kit such that the immunoassay may be performed as a capture-on-the-fly type combination immunoassay in which the solid support is coated with an agent that allows binding of the capturing moiety (e.g., a biotinylated antigen or a biotinylated antibody) and the kit further comprises each of the individual capture and detection antigen pairs and the biotinylated capture antibodies in one container and a second container provides the detection antibody conjugate. The instructions for conducting the assay also can include instructions for generating a standard curve or a reference standard for purposes of quantifying anti-HCV antibody.

Any antibodies, which are provided in the kit, such as anti-IgG antibodies and anti-IgM antibodies, can also incorporate a detectable label, such as a fluorophore, radioactive moiety, enzyme, biotin/avidin label, chromophore, chemiluminescent label, or the like, or the kit can include reagents for labeling the antibodies or reagents for detecting the antibodies (e.g., detection antibodies) and/or for labeling the analytes or reagents for detecting the analyte. The antibodies, calibrators and/or controls can be provided in separate containers or pre-dispensed into an appropriate assay format, for example, into microtiter plates. In a preferred combination immunoassay there are two containers provided. In the first container is provided at least a first, second and third pair of antigens, wherein the first antigen in each pair is a capture antigen from a given HCV protein that is biotinylated and the second antigen in each pair is a detection antigen from the same protein as the first antigen but is labeled with a detectable label (e.g., it is acridinylated) as well as one or more biotinylated antibodies designed for detecting one or more HCV antigens from a test sample; and in the second container is provided the antibody that forms the conjugation partner for detection of the antigen that is captured by the biotinylated antibodies from the first container. It is contemplated that where there are multiple biotinylated antibodies in the first container, the multiple antibodies that form the conjugation partners may be present in a single container or individual containers for each different antigen detecting conjugate antibody.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

In preferred embodiments, the detectable label is at least one acridinium compound. In such embodiments, the kit can comprise at least one acridinium-9-carboxamide, at least one acridinium-9-carboxylate aryl ester, or any combination thereof. If the detectable label is at least one acridinium compound, the kit also can comprise a source of hydrogen peroxide, such as a buffer, solution, and/or at least one basic solution. It should be understood that in the immunodiagnostic reagent the antigens for antibody detection may be detectably labeled, and any antibodies provided in kit for use along with such reagents also may be detectably labeled.

If desired, the kit can contain a solid support phase, such as a magnetic particle, bead, test tube, microtiter plate, cuvette, membrane, scaffolding molecule, film, filter paper, disc or chip.

Method of Determining the Presence, Amount or Concentration of HCV in a Test Sample The present disclosure provides a combination immunoassay method for determining the presence, amount or concentration of anti-HCV antibodies and HCV antigens in a test sample. Any suitable assay known in the art can be used in such a method as long as such an assay uses one or more of antigens for detecting HCV antibodies and/or one or more anti-HCV antibodies for detecting one or more HCV antigens in the test sample. Examples of such assays include, but are not limited to, immunoassay, such as sandwich immunoassay (e.g., monoclonal-polyclonal sandwich immunoassays, including radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, Minn.)), competitive inhibition immunoassay (e.g., forward and reverse), fluorescence polarization immunoassay (FPIA), enzyme multiplied immunoassay technique (EMIT), bioluminescence resonance energy transfer (BRET), and homogeneous chemiluminescent assay, etc.

In specific embodiments of the combination immunoassays, the recombinant antigens (e.g., core, NS3 and NS4 antigens) may be used as capture reagents (e.g., by using such antigens in which the amino- or carboxy-terminal of the antigen comprises a biotin tag) or as a detection (conjugate) reagents in which the antigens are either directly or indirectly labeled with acridinium. Indirect labeling requires the use of acridinylated BSA covalently coupled to the free thiol of unpaired cysteine residues within a protein via SMCC-type linker. To facilitate such indirect labeling certain of the antigens used in the combination immunoassays of the present invention may readily be further modified to include additional cysteine residues at the C-terminus.

Typically, immunoassays are performed in 1-step or 2-step format. Solid phase reagents for capture of immune complexes formed in solution in the 1-step assay include anti-biotin monoclonal antibody, streptavidin or neutravidin to capture the biotinylated moiety (be it a biotinylated antigen for capture of an HCV antibody or a biotinylated antibody for the capture of an HCV protein/antigen in the test sample).

In a SELDI-based immunoassay, a capture reagent that specifically binds anti-HCV-antibody or an HCV antigen is attached to the surface of a mass spectrometry probe, such as a pre-activated protein chip array. The anti-HCV antibody or the antigen is then specifically captured on the biochip, and the captured moiety is detected by mass spectrometry. Alternatively, the anti-HCV antibody can be eluted from the capture reagent and detected by traditional MALDI (matrix-assisted laser desorption/ionization) or by SELDI. A chemiluminescent microparticle immunoassay, in particular one employing the ARCHITECT® automated analyzer (Abbott Laboratories, Abbott Park, Ill.), is an example of a preferred immunoassay in which a combination of multiple antigens (preferably antigens from two or more HCV proteins) as well as multiple anti-HCV antibodies may readily be employed. An agglutination assay, such as a passive hemagglutination assay, also can be used. In an agglutination assay an antigen-antibody reaction is detected by agglutination or clumping. In a passive hemagglutination assay, erythrocytes are coated with the antigen and the coated erythrocytes are used in the agglutination assay.

Methods well-known in the art for collecting, handling and processing urine, blood, serum and plasma, and other body fluids, are used in the practice of the present disclosure, for instance, when the immunodiagnostic reagents comprise multiple antigens and/or in an anti-HCV antibody immunoassay kit. The test sample can comprise further moieties in addition to the polypeptide of interest, such as antibodies, antigens, haptens, hormones, drugs, enzymes, receptors, proteins, peptides, polypeptides, oligonucleotides or polynucleotides. For example, the sample can be a whole blood sample obtained from a subject. It can be necessary or desired that a test sample, particularly whole blood, be treated prior to immunoassay as described herein, e.g., with a pretreatment reagent. Even in cases where pretreatment is not necessary (e.g., most urine samples), pretreatment optionally can be done for mere convenience (e.g., as part of a regimen on a commercial platform).

The pretreatment reagent can be any reagent appropriate for use with the combination immunoassay and kits of the invention. The pretreatment optionally comprises: (a) one or more solvents (e.g., methanol and ethylene glycol) and salt, (b) one or more solvents, salt and detergent, (c) detergent, or (d) detergent and salt. Pretreatment reagents are known in the art, and such pretreatment can be employed, e.g., as used for assays on Abbott TDx, AxSYM®, and ARCHITECT® analyzers (Abbott Laboratories, Abbott Park, Ill.), as described in the literature (see, e.g., Yatscoff et al., Abbott TDx Monoclonal Antibody Assay Evaluated for Measuring Cyclosporine in Whole Blood, Clin. Chem. 36: 1969-1973 (1990), and Wallemacq et al., Evaluation of the New AxSYM Cyclosporine Assay: Comparison with TDx Monoclonal Whole Blood and EMIT Cyclosporine Assays, Clin. Chem. 45: 432-435 (1999)), and/or as commercially available. Additionally, pretreatment can be done as described in Abbott's U.S. Pat. No. 5,135,875, European Pat. Pub. No. 0 471 293, U.S. Provisional Pat. App. 60/878,017, filed Dec. 29, 2006, and U.S. Pat. App. Pub. No. 2008/0020401 (incorporated by reference in its entirety for its teachings regarding pretreatment). The pretreatment reagent can be a heterogeneous agent or a homogeneous agent.

With use of a heterogeneous pretreatment reagent, the pretreatment reagent precipitates analyte binding protein (e.g., protein that can bind to anti-HCV antibody or an antigen that can bind to an anti-HCV antibody form the present in the sample. Such a pretreatment step comprises removing any analyte binding protein by separating from the precipitated analyte binding protein the supernatant of the mixture formed by addition of the pretreatment agent to sample. In such an assay, the supernatant of the mixture absent any binding protein is used in the assay, proceeding directly to the antibody capture step.

With use of a homogeneous pretreatment reagent there is no such separation step. The entire mixture of test sample and pretreatment reagent are contacted with a labeled specific binding partner for anti-HCV antibody (i.e., an antigen) or the labeled specific binding partner for the HCV antigen (i.e., an antibody). The pretreatment reagent employed for such an assay typically is diluted in the pretreated test sample mixture, either before or during capture by the first specific binding partner. Despite such dilution, a certain amount of the pretreatment reagent (for example, 5 M methanol and/or 0.6 methylene glycol) is still present (or remains) in the test sample mixture during capture.

In a heterogeneous format, after the test sample is obtained from a subject, a first mixture is prepared. The mixture contains the test sample being assessed for anti-HCV antibodies and a first specific capture binding partner, wherein the first specific capture binding partner and any anti-HCV antibodies contained in the test sample form a first specific capture binding partner-anti-HCV antibody complex. The first specific capture binding partner may be any of a core antigen, an NS3 antigen or an NS3. Exemplary NS3 antigens used in the invention may be any one or more of the antigens shown in Table 1 herein above. Likewise, in the combination assays of the invention the mixture also contains a second and third specific capture binding partner and these second and third specific capture binding partners form second and third specific capture binding partner-anti-HCV antibody complexes with anti-HCV antibodies that are present in the test sample. Such second, third and fourth antigens may be one or more of at least one HCV antigen selected from the group consisting of core antigen, NS3, NS4, NS5, and portions thereof.

In addition the combination immunoassay may, and preferably does, include at least one anti-HCV capture antibody that will form a specific complex with a fourth specific binding partner that is found in the test sample (i.e., an antigen or HCV protein that is found in the test sample) so as to form an anti-HCV antibody-fourth specific binding partner complex with the fourth antigen that is present in the test sample. Preferably, the fourth specific binding pair is one that detects Core antigen in a test sample, and hence the binding pair is an anti-Core antibody for detection of the fourth antigen (Core) in the test sample.

The order in which the test sample and the various specific binding partners are added to form the mixture is not critical. In some embodiments, the first, second, and third specific capture binding partners (i.e., antigens) and the anti-HCV capture antibody are immobilized on a solid phase. In still other embodiments, none of these four components are immobilized but are instead all added at the same time to the test sample to effect capture onto the solid phase. The solid phase used in the combination immunoassay can be any solid phase known in the art, such as, but not limited to, a magnetic particle, a bead, a test tube, a microtiter plate, a cuvette, a membrane, a scaffolding molecule, a film, a filter paper, a disc and a chip.

After the immunocomplexes are formed between the first, second and third specific capture binding partners and their respective anti-HCV antibodies found in the test sample, and the first anti-HCV capture antibodies (e.g., anti-Core) and their respective HCV antigens or HCV proteins found in the test sample, any unbound anti-HCV antibody or HCV antigen/protein is removed from the complex using any technique known in the art. For example, the unbound anti-HCV antibody or antigen can be removed by washing. Desirably, however, the first, second and third specific binding partners and the anti-HCV antibodies are present in excess of any anti-HCV antibody and antigens, respectively present in the test sample, such that all anti-HCV antibody and antigens that are present in the test sample become bound by the first, second, and third specific binding partner and anti-HCV capture antibodies respectively.

After any unbound anti-HCV antibody and antigen is removed, detection is achieved by addition of a first specific detection binding partner to the mixture to form a first specific capture binding partner-anti-HCV antibody-first specific detection binding partner complex. The first specific detection binding partner is preferably a combination of an anti-IgG antibody and an anti-IgM antibody. Moreover, also preferably, the first specific detection binding partner is labeled with or contains a detectable label as described above. In specific embodiments, the first specific detection partner may instead or in addition be an antigen that binds the captured antibody. Likewise, in the combination assays of the invention the mixture also contains a second and third specific detection binding partner and these second and third specific detection binding partners form second or third specific capture binding partner-anti-HCV antibody-second or third specific detection binding partner complexes with the captured anti-HCV antibodies that are present in the test sample. Again, the second and third specific detection binding partners may be a combination of an anti-IgG antibody and an anti-IgM antibody. In specific embodiments, the second and third specific detection partners may instead or in addition be an antigen that binds the captured antibody. Moreover, also preferably, the second and third specific detection binding partners, be they anti-IgM or IgG antibodies or antigens, are labeled with or contains a detectable label as described above. In addition the combination immunoassay may, and preferably does, include at least one anti-HCV conjugate antibody that will form a specific complex with the captured antigen or HCV protein that is found in the test sample so as to form a anti-HCV antibody—fourth specific binding partner-anti-HCV conjugate antibody complex with the fourth antigen that captured from the test sample.

Any suitable detectable label as is known in the art can be used as any one or more of the detectable labels. For example, the detectable label can be a radioactive label (such as $^{3}H$, $^{125}I$, $^{35}S$, $^{14}C$, $^{32}P$, and $^{33}P$), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, Introduction to Immunocytochemistry, 2nd ed., Springer Verlag, N.Y. (1997), and in Haugland, Handbook of Fluorescent Probes and Research Chemicals (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)).

A preferred acridinium compound is an acridinium-9-carboxamide. Methods for preparing acridinium 9-carboxamides are described in Mattingly, J. Biolumin. Chemilumin. 6: 107-114 (1991); Adamczyk et al., J. Org. Chem. 63: 5636-5639 (1998); Adamczyk et al., Tetrahedron 55: 10899-10914 (1999); Adamczyk et al., Org. Lett. 1: 779-781 (1999); Adamczyk et al., Bioconjugate Chem. 11: 714-724 (2000); Mattingly et al., In Luminescence Biotechnology: Instruments and Applications; Dyke, K. V. Ed.; CRC Press: Boca Raton, pp. 77-105 (2002); Adamczyk et al., Org. Lett. 5: 3779-3782 (2003); and U.S. Pat. Nos. 5,468,646, 5,543,524 and 5,783,699 (each of which is incorporated herein by reference in its entirety for its teachings regarding same).

Another preferred acridinium compound is an acridinium-9-carboxylate aryl ester. An example of an acridinium-9-carboxylate aryl ester of formula II is 10-methyl-9-(phenoxycarbonyl)acridinium fluorosulfonate (available from Cayman Chemical, Ann Arbor, Mich.). Methods for preparing acridinium 9-carboxylate aryl esters are described in McCapra et al., Photochem. Photobiol. 4: 1111-21 (1965); Razavi et al., Luminescence 15: 245-249 (2000); Razavi et al., Luminescence 15: 239-244 (2000); and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, High Throughput Bioanalytical Sample Preparation. Methods and Automation Strategies, Elsevier (2003)). The amount of protein removed or separated from the test sample can be about 40%, about 45%, about 50%, about 55%, about 60%, about 65%, about 70%, about 75%, about 80%, about 85%, about 90%, or about 95%. Further details regarding acridinium-9-carboxylate aryl ester and its use are set forth in U.S. patent application Ser. No. 11/697,835, filed Apr. 9, 2007, and published on Oct. 9, 2008, as U.S. Pat. App. Pub. No. 2008/0248493. Acridinium-9-carboxylate aryl esters can be dissolved in any suitable solvent, such as degassed anhydrous N,N-dimethylformamide (DMF) or aqueous sodium cholate.

Chemiluminescent assays can be performed in accordance with the methods described in Adamczyk et al., Anal. Chim. Acta 579(1): 61-67 (2006). While any suitable assay format can be used, a microplate chemiluminometer (Mithras LB-940, Berthold Technologies U.S.A., LLC, Oak Ridge, Tenn.) enables the assay of multiple samples of small volumes rapidly. The chemiluminometer can be equipped with multiple reagent injectors using 96-well black polystyrene microplates (Costar #3792). Each sample can be added into a separate well, followed by the simultaneous/sequential addition of other reagents as determined by the type of assay employed. Desirably, the formation of pseudobases in neutral or basic solutions employing an acridinium aryl ester is avoided, such as by acidification. The chemiluminescent response is then recorded well-by-well. In this regard, the time for recording the chemiluminescent response will depend, in part, on the delay between the addition of the reagents and the particular acridinium employed.

The order in which the test sample and the specific binding partner(s) are added to form the mixture for chemiluminescent assay is not critical. If the first specific capture binding partner is detectably labeled with an acridinium compound, detectably labeled first specific capture binding partner-anti-HCV antibody complexes form. Alternatively, if a first specific detection binding partner is used and the first specific detection binding partner is detectably labeled with an acridinium compound, detectably labeled first specific capture binding partner-anti-HCV antibody-first specific detection binding partner complexes form (similarly, for second and third complexes in the combination assays described above). Any unbound specific binding partner, whether labeled or unlabeled, can be removed from the mixture using any technique known in the art, such as washing.

Hydrogen peroxide can be generated in situ in the mixture or provided or supplied to the mixture before, simultaneously with, or after the addition of an above-described acridinium compound. Hydrogen peroxide can be generated in situ in a number of ways such as would be apparent to one skilled in the art.

Alternatively, a source of hydrogen peroxide can be simply added to the mixture. For example, the source of the hydrogen peroxide can be one or more buffers or other solutions that are known to contain hydrogen peroxide. In this regard, a solution of hydrogen peroxide can simply be added.

Upon the simultaneous or subsequent addition of at least one basic solution to the sample, a detectable signal, namely, a chemiluminescent signal, indicative of the presence of anti-HCV antibody (where capture is with an antigen) or antigen (where capture is with an antibody) is generated. The basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample.

The chemiluminescent signal that is generated can be detected using routine techniques known to those skilled in the art. Based on the intensity of the signal generated, the amount of anti-HCV antibody and/or antigen in the sample can be quantified. Specifically, the amount of anti-HCV antibody and/or in the sample is proportional to the intensity of the signal generated. The amount of anti-HCV antibody and/or antigen present can be quantified by comparing the amount of light generated to a standard curve for anti-HCV antibody and/or antigen or by comparison to a reference standard. The standard curve can be generated using serial dilutions or solutions of known concentrations of anti-HCV antibody by mass spectroscopy, gravimetric methods, and other techniques known in the art.

Anti-HCV antibody and/or antigen immunoassays can be conducted using any suitable format known in the art. Generally speaking, a sample being tested for (for example, suspected of containing) anti-HCV antibodies can be contacted with a capture antigen and at least one detection antibody (which can be a second detection antibody or a third detection antibody), such as labeled anti-IgG and anti-IgM antibodies, either simultaneously or sequentially and in any order. Similarly, the test for presence of an antigen can be contacted with a captured antibody which binds the antigen in the test sample and the bound antigen may then be detected by a detection antibody.

For example, the test sample can be first contacted with at least one capture antigen and then (sequentially) with at least one detection antibody. Alternatively, the test sample can be first contacted with at least one detection antibody and then (sequentially) with at least one capture antibody. In yet another alternative, the test sample can be contacted simultaneously with a capture antigen and a detection antibody.

In the sandwich assay format, a sample suspected of containing anti-HCV antibodies (or a fragment thereof) is first brought into contact with an at least one first capture antigen under conditions that allow the formation of a first capture antigen/anti-HCV antibody complex. In the combination assay, the same is repeated or simultaneously conducted with a second, third or more capture antigens. If more than one capture antigen is used, multiple first capture antigen/anti-HCV antibody complexes are formed. In a sandwich assay, the antigen(s), preferably, the at least one capture antigen, is/are used in molar excess amounts of the maximum amount of anti-HCV antibodies expected in the test sample. For example, from about 5 μg to about 1 mg of antigen per mL of buffer (e.g., microparticle coating buffer) can be used.

Competitive inhibition immunoassays, which are often used to measure small analytes, comprise sequential and classic formats. In a sequential competitive inhibition immunoassay the one or more capture antigen(s) (i.e., a polypeptide, and preferably a pair of polypeptides, as described herein) to an antibody of interest (i.e., an anti-HCV antibody) is/are coated onto a well of a microtiter plate. When the sample containing the antibody/antibodies of interest is added to the well, the antibody of interest binds to the capture antigen(s). After washing, a known amount of labeled (e.g., biotin or horseradish peroxidase (HRP)) antibody is added to the well. A substrate for an enzymatic label is necessary to generate a signal. An example of a suitable substrate for HRP is 3,3',5,5'-tetramethylbenzidine (TMB). After washing, the signal generated by the labeled antibody is measured and is inversely proportional to the amount of antibody in the sample. In a classic competitive inhibition immunoassay antigen for an antibody of interest is coated onto a well of a microtiter plate. However, unlike the sequential competitive inhibition immunoassay, the sample containing the antibody of interest (i.e., an anti-HCV antibody) and the labeled antibody are added to the well at the same. Any antibody in the sample competes with labeled antibody for binding to the capture antigen. After washing, the signal generated by the labeled analyte is measured and is inversely proportional to the amount of analyte in the sample.

Optionally, prior to contacting the test sample with the at least one capture antigen (for example, the first capture antigen), the at least one capture antigen can be bound to a solid support, which facilitates the separation of the first antigen/anti-HCV antibody complex from the test sample. The substrate to which the capture antigen is bound can be any suitable solid support or solid phase that facilitates separation of the capture antigen-anti-HCV antibody complex from the sample. Examples include a well of a plate, such as a microtiter plate, a test tube, a porous gel (e.g., silica gel, agarose, dextran, or gelatin), a polymeric film (e.g., polyacrylamide), beads (e.g., polystyrene beads or magnetic beads), a strip of a filter/membrane (e.g., nitrocellulose or nylon), microparticles (e.g., latex particles, magnetizable microparticles (e.g., microparticles having ferric oxide or chromium oxide cores and homo- or hetero-polymeric coats and radii of about 1-10 microns). The substrate can comprise a suitable porous material with a suitable surface affinity to bind antigens and sufficient porosity to allow access by detection antibodies. A microporous material is generally preferred, although a gelatinous material in a hydrated state can be used. Such porous substrates are preferably in the form of sheets having a thickness of about 0.01 to about 0.5 mm, preferably about 0.1 mm. While the pore size may vary quite a bit, preferably the pore size is from about 0.025 to about 15 microns, more preferably from about 0.15 to about 15 microns. The surface of such substrates can be activated by chemical processes that cause covalent linkage of an antibody to the substrate. Irreversible binding, generally by adsorption through hydrophobic forces, of the antigen to the substrate results; alternatively, a chemical coupling agent or other means can be used to bind covalently the antigen to the substrate, provided that such binding does not interfere with the ability of the antigen to bind to anti-HCV antibodies.

Alternatively, the anti-HCV antibody from the test sample can be bound with microparticles, which have been previously coated with antigen. If desired, one or more capture reagents, such as a pair of polypeptides as described herein, each of which can be bound by an anti-HCV antibody, can be attached to solid phases in different physical or addressable locations (e.g., such as in a biochip configuration (see, e.g., U.S. Pat. No. 6,225,047, Int'l Pat. App. Pub. No. WO 99/51773; U.S. Pat. No. 6,329,209; Int'l Pat. App. Pub. No. WO 00/56934, and U.S. Pat. No. 5,242,828). If the capture reagent is attached to a mass spectrometry probe as the solid support, the amount of anti-HCV antibodies bound to the probe can be detected by laser desorption ionization mass spectrometry. Alternatively, a single column can be packed with different beads, which are derivatized with the one or more capture reagents, thereby capturing the anti-HCV antibody in a single place (see, antibody derivatized, bead-based technologies, e.g., the xMAP technology of Luminex (Austin, Tex.)).

After the test sample being assayed for anti-HCV antibodies is brought into contact with at least one capture antigen (for example, the first capture antigen), the mixture is incubated in order to allow for the formation of a first antigen (or multiple antigen)-anti-HCV antibody (or a fragment thereof) complex. The incubation can be carried out at a pH of from about 4.5 to about 10.0, at a temperature of from about 2° C. to about 45° C., and for a period from at least about one (1) minute to about eighteen (18) hours, preferably from about 1 to about 24 minutes, most preferably for about 4 to about 18 minutes. The immunoassay described herein can be conducted in one step (meaning the test sample, at least one capture antibody and at least one detection antibody are all added sequentially or simultaneously to a reaction vessel) or in more than one step, such as two steps, three steps, etc.

After or simultaneously with formation of the (first or multiple) capture antigen/anti-HCV antibody complex, the complex is then contacted with at least one detection antibody (under conditions which allow for the formation of a (first or multiple) capture antigen/anti-HCV antibody/first antibody detection complex). The at least one detection antibody can be the second, third, fourth, etc. antibodies used in the immunoassay. If the capture antigen/anti-HCV antibody complex is contacted with more than one detection antibody, then a (first or multiple) capture antigen/anti-HCV antibody/(multiple) detection antibody complex is formed. As with the capture antigen (e.g., the first capture antigen), when the at least second (and subsequent) detection antibody is brought into contact with the capture antigen/anti-HCV antibody complex, a period of incubation under conditions similar to those described above is required for the formation of the (first or multiple) capture antigen/anti-HCV antibody/(second or multiple) detection antibody complex. Preferably, at least one detection antibody contains a detectable label. The detectable label can be bound to the at least one detection antibody (e.g., the second detection antibody) prior to, simultaneously with, or after the formation of the (first or multiple) capture antigen/anti-HCV antibody/(second or multiple) detection antibody complex. Any detectable label known in the art can be used (see discussion above, including Polak and Van Noorden (1997) and Haugland (1996)).

The detectable label can be bound to the antibodies (or antigens which may comprise detectable labels) either directly or through a coupling agent. An example of a coupling agent that can be used is EDAC (1-ethyl-3-(3-dimethylaminopropyl)carbodiimide, hydrochloride), which is commercially available from Sigma-Aldrich, St. Louis, Mo. Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as CPSP-Acridinium Ester (i.e., 9-[N-tosyl-N-(3-carboxypropyl)]-10-(3-sulfopropyl)acridinium carboxamide) or SPSP-Acridinium Ester (i.e., N10-(3-sulfopropyl)-N-(3-sulfopropyl)-acridinium-9-carboxamide).

The (first or multiple) capture antigen/anti-HCV antibody/(second or multiple) detection antibody complex can be, but does not have to be, separated from the remainder of the test sample prior to quantification of the label. For example, if the at least one capture antigen (e.g., the first capture antigen) is bound to a solid support, such as a well or a bead, separation can be accomplished by removing the fluid (of the test sample) from contact with the solid support. Alternatively, if the at least first capture antigen is bound to a solid support, it can be simultaneously contacted with the anti-HCV antibody-containing sample and the at least one second detection antibody (or the labeled detection antigen) to form a first (multiple) antigen/anti-HCV antibody/second (multiple) antibody (and/or labeled detection antigen) complex, followed by removal of the fluid (test sample) from contact with the solid support. If the at least one first capture antigen is not bound to a solid support, then the (first or multiple) capture antigen/anti-HCV antibody/(second or multiple) detection antibody (and/or detection antigen for the captured antibody) complex does not have to be removed from the test sample for quantification of the amount of the label.

After formation of the labeled capture antigen/anti-HCV antibody/detection antigen (and/or detection antibody) complex (e.g., the first capture antigen/anti-HCV antibody/first detection antigen complex optionally also with a second detection antibody), the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified by detecting the light emitted either visually or by using luminometers, x-ray film, high speed photographic film, a CCD camera, etc. Once the amount of the label in the complex has been quantified, the concentration of anti-HCV antibody or antigen in the test sample is determined by use of a standard curve that has been generated using serial dilutions of anti-HCV antibody or antigens of known concentration. Other than using serial dilutions of anti-HCV antibodies or HCV antigens, the standard curve can be generated gravimetrically, by mass spectroscopy and by other techniques known in the art.

In a chemiluminescent microparticle assay employing the ARCHITECT® analyzer, the conjugate diluent pH should be about 6.0+/−0.2, the microparticle coating buffer should be maintained at room temperature (i.e., at about 17 to about 27° C.), the microparticle coating buffer pH should be about 6.5+/−0.2, and the microparticle diluent pH should be about 6.5+/−0.2. Solids preferably are less than about 0.2%, such as less than about 0.15%, less than about 0.14%, less than about 0.13%, less than about 0.12%, or less than about 0.11%, such as about 0.10%.

FPIAs are based on competitive binding immunoassay principles. A fluorescently labeled compound, when excited by a linearly polarized light, will emit fluorescence having a degree of polarization inversely proportional to its rate of rotation. When a fluorescently labeled tracer-antibody complex is excited by a linearly polarized light, the emitted light remains highly polarized because the fluorophore is constrained from rotating between the time light is absorbed and the time light is emitted. When a "free" tracer compound (i.e., a compound that is not bound to an antibody) is excited by linearly polarized light, its rotation is much faster than the corresponding tracer-antibody conjugate produced in a competitive binding immunoassay. FPIAs are advantageous over RIAs inasmuch as there are no radioactive substances requiring special handling and disposal. In addition, FPIAs are homogeneous assays that can be easily and rapidly performed.

Commercially available anti-HCV antibodies as well as anti-IgG and anti-IgM antibodies can be used in the methods of assay and kits thereof. Commercially available antibodies include those available from Abnova (Walnut, Calif., and Taiwan) and GenWay Biotech, Inc. (San Diego, Calif.). See, also, European Pat. App. EP2099825 A2 regarding the preparation of anti-HCV antibodies.

Any suitable control composition can be used in the anti-HCV antibody and HCV antigen combination immunoassays. The control composition generally comprises anti-HCV antibodies and known antigens and any desirable additives.

Thus, in view of the above, a method of determining the presence, amount, or concentration of anti-HCV antibodies or antigens in a test sample is provided. The method comprises assaying the test sample for anti-HCV antibodies or antigens by an assay:

(i) employing an immunodiagnostic reagent comprising at least an isolated or purified polypeptide comprising HCV antigens, and at least one detectable label, and comparing a signal generated by the detectable label as a direct or indirect indication of the presence, amount or concentration of anti-HCV antibodies in the test sample to a signal generated as a direct or indirect indication of the presence, amount or concentration of anti-HCV antibodies in a control or calibrator, which is optionally part of a series of calibrators in which each of the calibrators differs from the other calibrators in the series by the concentration of anti-HCV antibodies. The method can comprise the following steps:

(i) contacting the test sample with the immunodiagnostic reagent comprising one of more recombinant HCV antigens so as to form first, second and third specific capture binding partner/anti-HCV antibody complexes with HCV antibodies that may be present in the test sample, (ii) contacting the first, second and third specific capture binding partner/first, second and third anti-HCV antibody complexes with at least one detectably labeled second specific binding partner for anti-HCV antibody (e.g., anti-IgG antibody and anti-IgM antibody or polypeptides as described herein) so as to form first specific binding partner/first, second and third anti-HCV antibody, respectively/second specific binding partner complexes, and (iii) determining the presence, amount or concentration of anti-HCV antibodies in the test sample by detecting or measuring the signal generated by the detectable label in the first specific binding partner/anti-HCV antibody/second specific binding partner complexes formed in (ii).

Optionally or preferably, in addition to, or instead of, use of the anti-IgG and IgM antibodies, the second step comprises addition of first, second and third detection antigens that will specifically bind the anti-HCV antibodies that have been specifically captured by the first, second and third capture antigens, respectively so as to form first specific binding partner/anti-HCV antibody/second specific binding partner complexes, and the third step comprises:

(iii) determining the presence, amount or concentration of anti-HCV antibodies in the test sample by detecting or measuring the signal generated by the detectable label in the first, second and third specific capture binding partner/first, second and third anti-HCV antibodies/first, second and third specific detection binding partner complexes formed in (ii).

Alternatively, the method can comprise the following steps:

(i) contacting the test sample with the immunodiagnostic reagent comprising one of more recombinant antigens and simultaneously or sequentially, in either order, contacting the test sample with at least one detectably labeled second specific binding partner, which can compete with anti-HCV antibody for binding to the at least one pair of first specific binding partners and which comprises detectably labeled anti-HCV antibodies, wherein any anti-HCV antibody present in the test sample and the at least one detectably labeled second specific binding partner compete with each other to form first specific binding partner/anti-HCV antibody complexes and first specific binding partner/second specific binding partner complexes, respectively, and (ii) determining the presence, amount or concentration of anti-HCV antibodies in the test sample by detecting or measuring the signal generated by the detectable label in the first specific binding partner/second specific binding partner complex formed in (ii), wherein the signal generated by the detectable label in the first specific binding partner/second specific binding partner complex is inversely proportional to the amount or concentration of anti-HCV antibodies in the test sample. The recombinant antigens of which the immunodiagnostic reagent is comprised can be coated on microparticles. In this regard, the antigens of which the immunodiagnostic reagent is comprised can be co-coated on the same microparticles as additional HCV antigens. When the polypeptides of which the immunodiagnostic reagent is comprised are co-coated on the same microparticles (e.g., a microparticle suspension containing 4% solids (4% weight/volume microparticles or 4 gr microparticles/100 mL microparticle suspension)), preferably the polypeptides are co-coated on the same microparticles in a ratio of about 1:2 to about 1:6, wherein, when the polypeptides are co-coated on the same microparticles in a ratio of about 1:2, the concentration of an isolated or purified antigen of the present invention (e.g., those described in Table 1) is at least about 40 µg/mL and the concentration of the other isolated or purified polypeptide is at least about 80 µg/mL. If the test sample was obtained from a patient, the method may further comprise diagnosing, prognosticating, or assessing the efficacy of a therapeutic/prophylactic treatment of the patient. If the method further comprises assessing the efficacy of a therapeutic/prophylactic treatment of the patient, the method optionally can further comprise modifying the therapeutic/prophylactic treatment of the patient as needed to improve efficacy. The method can be adapted for use in an automated system or a semi-automated system.

Also, in view of the above, a method of determining the presence, amount, or concentration of anti-HCV antibodies or HCV antigens or proteins in a test sample is provided. The method comprises assaying the test sample by an assay:

(i) employing: an immunodiagnostic reagent comprising at least one HCV antigen (and preferably two, three or more antigens) at least one detectable label (preferably each antigen being detectably labeled), and (ii) comparing a signal generated by the detectable label as a direct or indirect indication of the presence, amount or concentration of anti-HCV antibodies in the test sample to a signal generated as a direct or indirect indication of the presence, amount or concentration of anti-HCV antibodies in a control or calibrator, which is optionally part of a series of calibrators in which each of the calibrators differs from the other calibrators in the series by the concentration of anti-HCV antibodies. The method can comprise the following steps:

(i) contacting the test sample with the immunodiagnostic reagent comprising at least one, two, three or more recombinant HCV antigens invention so as to form first specific capture binding partner/anti-HCV antibody complexes, (ii) contacting the first specific capture binding partner/anti-HCV antibody complexes with at least one detectably labeled second specific binding partner for anti-HCV antibody (e.g., anti-IgG antibody and anti-IgM antibody or labeled antigens that bind the anti-HCV antibodies) so as to form first specific binding partner/anti-HCV antibody/second specific binding partner complexes, and (iii) determining the presence, amount or concentration of anti-HCV antibodies in the test sample by detecting or measuring the signal generated by the detectable label in the first specific binding partner/anti-HCV antibody/second specific binding partner complexes formed in (ii). Alternatively, the method can comprise the following steps:

(i) contacting the test sample with the immunodiagnostic reagent comprising at least one, two, three or more different HCV antigens and simultaneously or sequentially, in either order, contacting the test sample with at least one detectably labeled second specific binding partner, which can compete with anti-HCV antibody for binding to the at least one pair of first specific binding partners and which comprises detectably labeled anti-HCV antibodies, wherein any anti-HCV antibody present in the test sample and the at least one second specific binding partner compete with each other to form first specific binding partner/anti-HCV antibody complexes and a first specific binding partner/second specific binding partner complexes, respectively, and (ii) determining the presence, amount or concentration of anti-HCV antibodies in the test sample by detecting or measuring the signal generated by the detectable label in the first specific binding partner/second specific binding partner complex formed in (ii), wherein the signal generated by the detectable label in the first specific binding partner/second specific binding partner complex is inversely proportional to the amount or concentration of anti-HCV antibodies in the test sample. The polypeptides of which the immunodiagnostic reagent is comprised can be coated on microparticles. In this regard, the polypeptides of which the immunodiagnostic reagent is comprised can be co-coated on the same microparticles. When the polypeptides of which the immunodiagnostic reagent is comprised are co-coated on the same microparticles (e.g., a microparticle suspension containing 4% solids (4% weight/volume microparticles or 4 gr microparticles/100 mL microparticle suspension)), preferably the polypeptides are co-coated on the same microparticles in a ratio of about 1:2 to about 1:6, wherein, when the polypeptides are co-coated on the same microparticles in a ratio of about 1:2, the concentration of an isolated or purified polypeptide comprising the recombinant HCV antigen is at least about 40 µg/mL and the concentration of the other isolated or purified polypeptide is at least about 80 µg/mL. If the test sample was obtained from a patient, the method can further comprise diagnosing, prognosticating, or assessing the efficacy of a therapeutic/prophylactic treatment of the patient. If the method further comprises assessing the efficacy of a therapeutic/prophylactic treatment of the patient, the method optionally can further comprise modifying the therapeutic/prophylactic treatment of the patient as needed to improve efficacy. The method can be adapted for use in an automated system or a semi-automated system.

Generally, a predetermined level can be employed as a benchmark against which to assess results obtained upon assaying a test sample for anti-HCV antibodies. Generally, in making such a comparison, the predetermined level is obtained by running a particular assay a sufficient number of times and under appropriate conditions such that a linkage or association of analyte presence, amount or concentration with a particular stage or endpoint of a disease, disorder or condition (e.g., preeclampsia or cardiovascular disease) or with particular indicia can be made. Typically, the predetermined level is obtained with assays of reference subjects (or populations of subjects).

In particular, with respect to a predetermined level as employed for monitoring disease progression and/or treatment, the amount or concentration of anti-HCV antibodies may be "unchanged," "favorable" (or "favorably altered"), or "unfavorable" (or "unfavorably altered"). "Elevated" or "increased" refers to an amount or a concentration in a test sample that is higher than a typical or normal level or range (e.g., predetermined level), or is higher than another reference level or range (e.g., earlier or baseline sample). The term "lowered" or "reduced" refers to an amount or a concentration in a test sample that is lower than a typical or normal level or range (e.g., predetermined level), or is lower than another reference level or range (e.g., earlier or baseline sample). The term "altered" refers to an amount or a concentration in a sample that is altered (increased or decreased) over a typical or normal level or range (e.g., predetermined level), or over another reference level or range (e.g., earlier or baseline sample).

The typical or normal level or range for anti-HCV antibodies or HCV antigens is defined in accordance with standard practice. Because the levels of anti-HCV antibodies and/or HCV antigens in some instances will be very low, a so-called altered level or alteration can be considered to have occurred when there is any net change as compared to the typical or normal level or range, or reference level or range, that cannot be explained by experimental error or sample variation. Thus, the level measured in a particular sample will be compared with the level or range of levels determined in similar samples from a so-called normal subject. In this context, a "normal subject" is an individual with no detectable hepatitis, for example, and a "normal" (sometimes termed "control") patient or population is/are one(s) that exhibit(s) no detectable hepatitis, for example. Furthermore, given that anti-HCV antibodies and HCV antigens are not routinely found at a high level in the majority of the human population, a "normal subject" can be considered an individual with no substantial detectable increased or elevated amount or concentration of anti-HCV antibodies or HCV antigens, and a "normal" (sometimes termed "control") patient or population is/are one(s) that exhibit(s) no substantial detectable increased or elevated amount or concentration of anti-HCV antibodies. An "apparently normal subject" is one in which anti-HCV antibodies or HCV antigen has not been or is being assessed. The level of an analyte is said to be "elevated" when the analyte is normally undetectable (e.g., the normal level is zero, or within a range of from about 25 to about 75 percentiles of normal populations), but is detected in a test sample, as well as when the analyte is present in the test sample at a higher than normal level. Thus, inter alia, the disclosure provides a method of screening for a subject having, or at risk of having, hepatitis, for example, as defined herein.

Accordingly, the methods described herein also can be used to determine whether or not a subject has or is at risk of developing hepatitis. Specifically, such a method can comprise the steps of:

(a) determining the concentration or amount in a test sample from a subject of anti-HCV antibodies and/or HCV antigens (e.g., using the methods described herein, or methods known in the art); and (b) comparing the concentration or amount of anti-HCV antibodies and HCV antigens determined in step (a) with a predetermined level, wherein, if the concentration or amount of anti-HCV antibodies and/or HCV antigens determined in step (a) is favorable with respect to a predetermined level, then the subject is determined not to have or be at risk for hepatitis. However, if the concentration or amount of anti-HCV antibodies and/or HCV antigens determined in step (a) is unfavorable with respect to the predetermined level, then the subject is determined to have or be at risk for hepatitis.

Additionally, provided herein is method of monitoring the progression of disease in a subject. Optimally the method comprising the steps of:

(a) determining the concentration or amount in a test sample from a subject of anti-HCV antibodies and/or HCV antigens;

(b) determining the concentration or amount in a later test sample from the subject of anti-HCV antibodies and/or HCV antigens; and (c) comparing the concentration or amount of anti-HCV antibodies and/or HCV antigens as determined in step (b) with the concentration or amount of anti-HCV antibodies and/or HCV antigens determined in step (a), wherein if the concentration or amount determined in step (b) is unchanged or is unfavorable when compared to the concentration or amount of anti-HCV antibodies and/or antigens determined in step (a), then the disease in the subject is determined to have continued, progressed or worsened. By comparison, if the concentration or amount of anti-HCV antibodies and/or antigens as determined in step (b) is favorable when compared to the concentration or amount of anti-HCV antibodies and/or antigens as determined in step (a), then the disease in the subject is determined to have discontinued, regressed or improved Optionally, the method further comprises comparing the concentration or amount of anti-HCV antibodies and/or HCV antigens as determined in step (b), for example, with a predetermined level. Further, optionally the method comprises treating the subject with one or more pharmaceutical compositions for a period of time if the comparison shows that the concentration or amount of anti-HCV antibodies and/or anti-HCV antigens as determined in step (b), for example, is unfavorably altered with respect to the predetermined level.

Still further, the methods can be used to monitor treatment in a subject receiving treatment with one or more pharmaceutical compositions. Specifically, such methods involve providing a first test sample from a subject before the subject has been administered one or more pharmaceutical compositions. Next, the concentration or amount in a first test sample from a subject of anti-HCV antibodies and/or HCV antigens is determined (e.g., using the methods described herein or as known in the art). After the concentration or amount of anti-HCV antibodies and/or HCV antigens is determined, optionally the concentration or amount of anti-HCV antibodies is then compared with a predetermined level. If the concentration or amount of anti-HCV antibodies and/or HCV antigens as determined in the first test sample is lower than the predetermined level, then the subject is not treated with one or more pharmaceutical compositions. However, if the concentration or amount of anti-HCV antibodies and/or HCV antigens as determined in the first test sample is higher than the predetermined level, then the subject is treated with one or more pharmaceutical compositions for a period of time. The period of time that the subject is treated with the one or more pharmaceutical compositions can be determined by one skilled in the art (for example, the period of time can be from about seven (7) days to about two years, preferably from about fourteen (14) days to about one (1) year).

During the course of treatment with the one or more pharmaceutical compositions, second and subsequent test samples are then obtained from the subject. The number of test samples and the time in which said test samples are obtained from the subject are not critical. For example, a second test sample could be obtained seven (7) days after the subject is first administered the one or more pharmaceutical compositions, a third test sample could be obtained two (2) weeks after the subject is first administered the one or more pharmaceutical compositions, a fourth test sample could be obtained three (3) weeks after the subject is first administered the one or more pharmaceutical compositions, a fifth test sample could be obtained four (4) weeks after the subject is first administered the one or more pharmaceutical compositions, etc.

After each second or subsequent test sample is obtained from the subject, the concentration or amount of anti-HCV antibodies and/or HCV antigens is determined in the second or subsequent test sample is determined (e.g., using the methods described herein or as known in the art). The concentration or amount of anti-HCV antibodies and/or HCV antigens as determined in each of the second and subsequent test samples is then compared with the concentration or amount of anti-HCV antibodies and/or HCV antigens as determined in the first test sample (e.g., the test sample that was originally optionally compared to the predetermined level). If the concentration or amount of anti-HCV antibodies and/or HCV antigens as determined in step (c) is favorable when compared to the concentration or amount of anti-HCV antibodies and/or HCV antigens as determined in step (a), then the disease in the subject is determined to have discontinued, regressed or improved, and the subject should continue to be administered the one or pharmaceutical compositions of step (b). However, if the concentration or amount determined in step (c) is unchanged or is unfavorable when compared to the concentration or amount of anti-HCV antibodies and/or HCV antigens as determined in step (a), then the disease in the subject is determined to have continued, progressed or worsened, and the subject should be treated with a higher concentration of the one or more pharmaceutical compositions administered to the subject in step (b) or the subject should be treated with one or more pharmaceutical compositions that are different from the one or more pharmaceutical compositions administered to the subject in step (b). Specifically, the subject can be treated with one or more pharmaceutical compositions that are different from the one or more pharmaceutical compositions that the subject had previously received to decrease or lower said subject's anti-HCV antibodies and/or HCV antigens level.

Generally, for assays in which repeat testing may be done (e.g., monitoring disease progression and/or response to treatment), a second or subsequent test sample is obtained at a period in time after the first test sample has been obtained from the subject. Specifically, a second test sample from the subject can be obtained minutes, hours, days, weeks or years after the first test sample has been obtained from the subject. For example, the second test sample can be obtained from the subject at a time period of about 1 minute, about 5 minutes, about 10 minutes, about 15 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years after the first test sample from the subject is obtained. When used to monitor disease progression, the above assay can be used to monitor the progression of disease in subjects suffering from acute conditions. Acute conditions, also known as critical care conditions, refer to acute, life-threatening diseases or other critical medical conditions involving, for example, the cardiovascular system or excretory system. Typically, critical care conditions refer to those conditions requiring acute medical intervention in a hospital-based setting (including, but not limited to, the emergency room, intensive care unit, trauma center, or other emergent care setting) or administration by a paramedic or other field-based medical personnel. For critical care conditions, repeat monitoring is generally done within a shorter time frame, namely, minutes, hours or days (e.g., about 1 minute, about 5 minutes, about 10 minutes, about 15 minutes, about 30 minutes, about 45 minutes, about 60 minutes, about 2 hours, about 3 hours, about 4 hours, 4 about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days or about 7 days), and the initial assay likewise is generally done within a shorter timeframe, e.g., about minutes, hours or days of the onset of the disease or condition.

The assays also can be used to monitor the progression of disease in subjects suffering from chronic or non-acute conditions. Non-critical care or, non-acute conditions, refers to conditions other than acute, life-threatening disease or other critical medical conditions involving, for example, the cardiovascular system and/or excretory system. Typically, non-acute conditions include those of longer-term or chronic duration. For non-acute conditions, repeat monitoring generally is done with a longer timeframe, e.g., hours, days, weeks, months or years (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years), and the initial assay likewise generally is done within a longer time frame, e.g., about hours, days, months or years of the onset of the disease or condition.

Furthermore, the above assays can be performed using a first test sample obtained from a subject where the first test sample is obtained from one source, such as urine, serum or plasma. Optionally the above assays can then be repeated using a second test sample obtained from the subject where the second test sample is obtained from another source. For example, if the first test sample was obtained from urine, the second test sample can be obtained from serum or plasma. The results obtained from the assays using the first test sample and the second test sample can be compared. The comparison can be used to assess the status of a disease or condition in the subject.

Moreover, the present disclosure also relates to methods of determining whether a subject predisposed to or suffering from hepatitis will benefit from treatment. In particular, the disclosure relates to HCV companion diagnostic methods and products. Thus, the method of "monitoring the treatment of disease in a subject" as described herein further optimally also can encompass selecting or identifying candidates for therapy.

Thus, in particular embodiments, the disclosure also provides a method of determining whether a subject having, or at risk for, hepatitis is a candidate for therapy. Generally, the subject is one who has experienced some symptom of hepatitis or who has actually been diagnosed as having, or being at risk for, hepatitis and/or who demonstrates an unfavorable concentration or amount of anti-HCV antibodies or a fragment thereof and/or HCV antigens, as described herein.

The method optionally comprises an assay as described herein, where analyte is assessed before and following treatment of a subject with one or more pharmaceutical compositions (e.g., particularly with a pharmaceutical related to a mechanism of action involving HCV), with immunosuppressive therapy, or by immunoabsorption therapy, with anti-angiogenic therapy, or where analyte is assessed following such treatment and the concentration or the amount of analyte is compared against a predetermined level. An unfavorable concentration of amount of analyte observed following treatment confirms that the subject will not benefit from receiving further or continued treatment, whereas a favorable concentration or amount of analyte observed following treatment confirms that the subject will benefit from receiving further or continued treatment. This confirmation assists with management of clinical studies, and provision of improved patient care.

Adaptation of Kit and Method

The kit (or components thereof), as well as the method of determining the concentration of anti-HCV antibodies and/or HCV antigens in a test sample by an immunoassay as described herein, can be adapted for use in a variety of automated and semi-automated systems (including those wherein the solid phase comprises a microparticle), as described, e.g., in U.S. Pat. Nos. 5,089,424 and 5,006,309, and as commercially marketed, e.g., by Abbott Laboratories (Abbott Park, Ill.) as ARCHITECT®.

Some of the differences between an automated or semi-automated system as compared to a non-automated system (e.g., ELISA) include the substrate to which the first specific binding partner (e.g., antigen) is attached (which can impact sandwich formation and analyte reactivity), and the length and timing of the capture, detection and/or any optional wash steps. Whereas a non-automated format such as an ELISA may require a relatively longer incubation time with sample and capture reagent (e.g., about 2 hours), an automated or semi-automated format (e.g., ARCHITECT®, Abbott Laboratories) may have a relatively shorter incubation time (e.g., approximately 18 minutes for ARCHITECT®). Similarly, whereas a non-automated format such as an ELISA may incubate a detection antibody such as the conjugate reagent for a relatively longer incubation time (e.g., about 2 hours), an automated or semi-automated format (e.g., ARCHITECT®) may have a relatively shorter incubation time (e.g., approximately 4 minutes for the ARCHITECT®).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays Immunosensors and their methods of manufacture and operation in single-use test devices are described, for example in, U.S. Pat. No. 5,063,081, U.S. Pat. App. Pub. No. 2003/0170881, U.S. Pat. App. Pub. No. 2004/0018577, U.S. Pat. App. Pub. No. 2005/0054078, and U.S. Pat. App. Pub. No. 2006/0160164, which are incorporated in their entireties by reference for their teachings regarding same.

In particular, with regard to the adaptation of an assay to the I-STAT® system, the following configuration is exemplary. A microfabricated silicon chip is manufactured with a pair of gold amperometric working electrodes and a silver-silver chloride reference electrode. On one of the working electrodes, polystyrene beads (0.2 mm diameter) with immobilized capture antibody are adhered to a polymer coating of patterned polyvinyl alcohol over the electrode. This chip is assembled into an I-STAT® cartridge with a fluidics format suitable for immunoassay. On a portion of the wall of the sample-holding chamber of the cartridge there is a layer comprising the detection antibody labeled with alkaline phosphatase (or other label). Within the fluid pouch of the cartridge is an aqueous reagent that includes p-aminophenol phosphate.

In operation, a sample suspected of containing anti-HCV antibody and/or HCV antigens is added to the holding chamber of the test cartridge and the cartridge is inserted into the I-STAT® reader. After the detection antibody or detectably labeled detection antigen has dissolved into the sample, a pump element within the cartridge forces the sample into a conduit containing the chip. Here it is oscillated to promote formation of the sandwich between the capture antigen (or capture antibody), anti-HCV antibody (or HCV antigen), and the labeled detection antibody (and/or detection antigen). In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of anti-HCV antibody or HCV antigen in the sample by means of an embedded algorithm and factory-determined calibration curve.

The methods and kits as described herein encompass other reagents and methods for carrying out the immunoassay. For instance, encompassed are various buffers such as are known in the art and/or which can be readily prepared or optimized to be employed, e.g., for washing, as a conjugate diluent, and/or as a calibrator diluent. An exemplary conjugate diluent is ARCHITECT® conjugate diluent employed in certain kits (Abbott Laboratories, Abbott Park, Ill.) and containing 2-(N-morpholino)ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent. Additionally, as described in U.S. Patent Application No. 61/142,048 filed Dec. 31, 2008, and U.S. patent application Ser. No. 12/650,241, improved signal generation may be obtained, e.g., in an I-STAT® cartridge format, using a nucleic acid sequence linked to the signal antibody as a signal amplifier.

EXAMPLES

Example 1

Cloning and Expression of HCV NS3 9NB49H

The nucleotide sequence (Seq ID #1) encoding amino acids 1192-1457 of HCV-1 (Seq ID #) 2) was codon optimized for *E. coli* expression and cloned into a modified pET32a vector wherein the sequence encoding a thioredoxin fusion protein was eliminated, and replaced with Methionine (M). In addition, a carboxy-terminal hexahistidine tag (SEQ ID NO: 90) was included to facilitate purification via immobilized metal affinity chromatography (IMAC). *E. coli* BL21(DE3) cells were transformed with purified plasmid DNA and transformants screened. The resulting plasmid was designated p9NB49H and the protein expressed therefrom was designated as 9NB49H.

Protein expression was achieved by culturing the p9NB49H-transformed *E. coli* BL21(DE3) cells in terrific broth (TB) medium. Cells were grown in shake flasks to an OD600 nm of 0.50 and then induced with 1 mM IPTG and grown at 25-37° C. for approximately three hours until an OD600 nm of approximately 3.5 was obtained. Cells were harvested by centrifugation, and suspended in lysis buffer (50 mM KPO4, 300 mM KCl, 5 mM Imidazole, pH 8.0) supplemented with protease inhibitors. The cell suspension was frozen and thawed, benzonase was added, and the cells were lysed by sonication on ice. The lysate was divided into soluble and insoluble fractions by centrifugation. SDS-PAGE revealed that the NS3 9NB49H protein was present in the soluble fraction. IMAC purification was performed on the lysate soluble fraction using the Native IMAC Buffer Kit and Profinity IMAC cartridge (BioRad) according to the manufacture's protocol. Buffer exchange of the purified protein into PBS was accomplished by a desalting column or by dialysis. All buffers used throughout the purification procedure contained 20 mM beta-mercaptoethanol (βME).

Example 2

Cloning and Expression of HCV NS3 Nbt-9NB49H

The nucleotide sequence encoding the NS3 9NB49H protein described in Example 1 was subcloned into a modified pET32a plasmid wherein the open reading frame encodes an amino-terminal biotinylation tag (MSGLNDIFEAQKIEWHE) (SEQ ID NO: 91) with a GSGSNSM-linker (SEQ ID NO: 92) sequence upstream of the NS3-encoding sequence followed by a carboxyl-terminal hexahistidine tag (SEQ ID NO: 90) followed by a stop codon. The resulting plasmid was designated pNbt-9NB49H. The biotinylation tag, described by Beckett et al. (Protein Science, 8(4):921-929, 1999) permits site-specific biotin incorporation via a biotin ligase enzyme encoded by the E. coli BirA gene. E. coli BL21(DE3) cells were co-transformed with the pNbt-9NB49H expression plasmid and a second plasmid (pBirAcm) expressing the biotin ligase under control of an IPTG inducible promoter. Cells were grown in shake flasks at 37° C. in Terrific Broth with biotin added to 0.050 mM final concentration to an OD600 nm of 0.50 and then induced with 1 mM IPTG and grown at 25° C. overnight. Cells were then collected via centrifugation and resuspended in lysis buffer and sonicated to disrupt the cells. In some instances, to further ensure a high level of site-specific biotinylation, ATP and biotin were added to the lysed cells (3 mM and 0.25 mM final concentrations, respectively) and incubated at room temperature for 2 hours. Recombinant protein was then purified via IMAC as described in Example 1.

Example 3

Cloning and Expression of HCV NS3 9NB49H-Cbt

The nucleotide sequence encoding the NS3 9NB49H protein described in Example 1, was subcloned into a modified pET32a vector wherein the open reading frame encodes N-terminal methionine followed by NS3 followed by a GSGSG-linker (SEQ ID NO: 93) and a hexahistidine tag (SEQ ID NO: 90) followed by a GG-linker and the biotinylation tag (GLNDIFEAQKIEWHE) (SEQ ID NO: 94) and finally the stop codon. The resulting plasmid was designated p9NB49H-Cbt. Protein expression and biotinylation was performed as described in Examples 1 and 2.

Example 4

Cloning and Expression of HCV NS3h and Variants Thereof

Recombinant HCV NS3 helicase variants were constructed by using the same amino terminus expressed by p9NB49H (i.e. amino acids 1192-1215 of the HCV polyprotein) fused to various regions of the HCV NS3 helicase as described in the table 2 below and as shown in FIG. 1. Nucleotide sequences encoding the helicase constructs were cloned into a modified pET32a vector (minus thioredoxin fusion) with either a carboxyl-terminal GSGSG-hexahistidine tag (SEQ ID NO: 95) as described in Example 1 or a carboxyl-terminal GSGSG-hexahistidine-GG-biotinylation tag (SEQ ID NO: 96) as described in Example 2. Protein expression with or without biotinylation and purification were performed as described in Examples 1 and 2.

TABLE 2

| Region of HCV Polyprotein | Region of HCV NS3 | Plasmid Designation | Expressed Protein Designation | Seq ID# (nucleotide, amino acid) |
|---|---|---|---|---|
| 1216-1658 | 190-632 | pNS3h(±Cbt) | NS3h (helicase) (- ±Cbt) | 19, 20 |

Example 5

Fermentation, Protein Expression and Purification

The NS3 recombinant proteins (e.g. 9NB49H or NS3h or variants thereof) were expressed in E. coli BL21(DE3) cells cultured in 10 L fermenters. An 120 mL seed culture grown in a shake flask containing Superbroth (SB) Media (rich media with glycerol as a carbon source) was used to inoculate a 10 L fermenter containing SB media. Cells were grown at 37° C. until an optical density at 600 nm of 8-12 was reached. Protein expression was induced by adding isopropyl β-D-1-thiogalactopyranoside (IPTG) to a final concentration of 1 mM. The culture was then grown an additional 4 hours at 25-37° C. Cells were then harvested from the fermenter and then passed through a hollow fiber membrane filter to concentrate the harvest from the starting volume of 10 L to 1-2 liters. The concentrated cells were then pelleted via centrifugation, the supernatant removed, and the resulting pellets were stored at −80° C. until used for protein purification.

In vivo biotinylation of recombinant HCV NS3 proteins containing either an amino-terminal or carboxyl-terminal biotinylation tag sequence (see Examples 2 and 3) was achieved by conducting fermentation as described above except that biotin was added to a final concentration of 0.05 mM at the time of induction. The culture was then grown an additional 4 hours at 25-37° C. and processed as described in the above paragraph.

Frozen E. coli cell pellets containing expressed soluble HCV NS3 recombinant antigens were thawed then resuspended in chilled lysis buffer (40 mM NaPO$_4$, 300 mM NaCl, 1.5 mM MgCl$_2$, 5% Glycerol, 5 mM beta-mercaptoethanol, pH 7.2) followed by lysis via continuous flow sonication at 0° C. for 45 minutes. After centrifugation to remove insoluble material, GE nickel sepharose Fast Flow resin was added to the supernatant and incubated overnight at 2-8° C. (shaking at 125 rpm). The resin containing bound antigen was then washed under mild vacuum with wash buffer (40 mM NaPO$_4$., pH 7.2, 500 mM NaCl, 1 mM EDTA, 20 mM imidizole, 5 mM beta-mercaptoethanol) and bound antigen was eluted using buffer containing 40 mM NaPO$_4$, 150 mM NaCl, 1 mM EDTA, 500 mM imidizole, 10 mM DTT, pH 7.2. The antigen was further purified via anion exchange chromatography as follows: antigen was bound to a GE Q HP anion exchange resin in 20 mM Tris pH 8.4, followed by gradient elution with 20 mM Tris, pH 8.4, 1 M NaCl, 5 mM EDTA. The eluted protein was then desalted using a GE Sephadex G25 column into final buffer containing 10 mM Phosphate, 150 mM NaCl, 5 mM EDTA, pH 7.2. The purified NS3 protein was stored at −70° C.

Example 6

Preparation of Acridinium-Bovine Serum Albumin (Acr-BSA)

A 30% solution (300 mg/mL) of bovine serum albumin (BSA) containing 0.1% sodium azide as preservative was purchased from a commercial source (Proliant Biologicals, Ankeny, Iowa). One milliliter (300 mg) of the 30% BSA solution was diluted with 2.0 mL of 0.1M PBS pH 8.0, transferred to a 0.5-3.0 mL Slide-A-Lyzer dialysis cassette (ThermoFisher, Waltham, Mass.) and dialyzed against 0.1M PBS pH 8.0 (2 exchanges, 600 mL/exchange) overnight at 2-8° C. The concentration of the dialyzed BSA solution was 97.1 mg/mL based on UV absorbance at 280 nm. Two hundred milligrams (2.060 mL, 3.0 umol, 1.0 mol equivalent) of the 97.1 mg/mL BSA solution was added to an amber glass vial containing 10.181 mL of 0.1M PBS pH 8.0. To this mixture was added 39 mg (1.092 mL, 45 umol, 15.0 mol equivalent) of SPSP-acridinium active ester in DMF [N,N-dimethylformamide. The reaction vial was capped; the solution was mixed by stirring at 350 rpm for 30 min, and then placed at room temperature overnight (20-26 h). After incubation, free acridinium and aggregates were removed chromatographically (Sephacryl HR S-200 column, GE Healthsciences, PA) using 0.01M PBS/0.1% CHAPS pH 6.3 running buffer. Fractions corresponding to monomeric Acr-BSA conjugate were pooled and characterized by UV spectrophotometry (240-600 nm scan). Absorbance values at 280 nm and 370 nm were used to determine protein concentration and to calculate incorporation of acridinium per BSA molecule. The calculated protein concentration was 6.779 mg/mL with an average number of 6.2 acridiniums per BSA molecule.

Example 7

Preparation of Maleimide-Activated Acr-BSA

Preparation of Maleimide-Activated Acr-BSA. Acr-BSA (Example 8; 13.5 milligrams, 202 nmoles, 1.0 mol equivalent) 1.99 mL in PBS/0.1% CHAPS pH 6.3 was added to an amber glass vial and treated with 0.254 mL of 0.4M phosphate/8 mM EDTA/1.6% CHAPS pH 7.4 to adjust reaction pH to 7.4. To the homogeneous solution was added 0.040 mL (0.35 mg, 4.0 mole equivalents) of a fresh 0.02M aqueous solution of Succinimidyl 4-(N maleimidomethyl)-cyclohexane-1-carboxylate (Sulfo-SMCC, Pierce Chemical Co., Rockford, Ill.). The reaction vial was capped; the solution was stirred for 20 min without foaming and then allowed to incubate statically at room temperature for 60-90 minutes in the dark. The reaction mixture was desalted to remove unincorporated sulfo-SMCC by applying to a Zeba spin column (Pierce, Rockford, III) pre-equilibrated with 0.1M PBS/0.1% CHAPS/5 mM EDTA pH 6.7. The absorbance of the eluted Acr-BSA-Mal reagent was measured at 280 and 370 nm to estimate protein concentration. The calculated protein concentration was 6.28 mg/mL. The Acr-BSA-Mal was used immediately in the conjugation of HCV NS3 antigen.

Conjugation of Recombinant 9NB49H to Acr-BSA-Mal. Acr-BSA-Mal (5.6 milligrams, 84 nmoles, 2.0 mole equivalents) in 0.789 mL of 0.1M PBS/0.1% CHAPS/5 mM EDTA pH 6.7 was added to a polypropylene tube. To this was added 1.2 mg (1.3 mL, 42 nmoles, 1.0 mol equivalent) of recombinant 9NB49H antigen in 0.01M PBS/5 mM EDTA pH 7.2. The solution was stirred for 30 min without foaming, and then allowed to incubate statically at room temperature overnight in dark. The conjugate was purified either at this stage or after carboxymethylation of 9NB49H free cysteines. In the case of carboxymethylation, the crude conjugate solution was treated with 0.270 mL of 0.5M phosphate buffer pH 11.0 to adjust pH to 8.0. The mixture was stirred for 5 min, then 0.94 mg (0.020 mL, 120 mole equivalents) of a fresh 0.25M iodoacetic (IAA) solution in 1N NaOH or 0.25M aqueous iodoacetaminde (IAM) was added under mixing to effect 9NB49H free Cys-carboxymethylation. The mixture was reacted statically at room temperature and dark for 60 min, and then passed thru a PD10 column equilibrated in 0.01M PBS/0.1% CHAPS/5 mM EDTA pH 6.3 (3.0 mL elution volume).

The Acr-BSA-9NB49H conjugate protein concentration was determined from the 280 nm absorbance of the conjugate after subtracting the 280 nm absorbance contributed by the Acr-BSA. The absorbance of a 1% (w/v) solution of 9NB49H of 0.52 was used to calculate the protein concentration. The 9NB49H concentration calculated as described was 0.406 mg/mL.

Example 8

Preparation of Acridinium-BSA-NS3h Conjugate

Preparation of (LC)Maleimide-Activated Acr-BSA. Acr-BSA (Example 8; 3.0 mg, 0.443 mL, 45 nmol, or 1.0 mol equivalent) in PBS/0.1% CHAPS pH 6.3 was added to an amber glass vial and treated with 0.058 ml of 0.4M phosphate/8 mM EDTA/1.6% CHAPS pH 7.4 buffer to adjust the reaction pH to 7.4. To the homogeneous solution was added 0.018 mL (0.080 mg, 180 nmoles, 4.0 mol equivalent) of a fresh 0.01M solution of Succinimidyl 4-(N-maleimidomethyl)cyclohexane-1-carboxy-(6-amidocaproate) (Lon Chain or LC-SMCC, Pierce Chemical Co., Rockford, Ill.) in dimethylsulfoxide (DMSO, Sigma Aldrich, St Louis, Mo.). The reaction vial was capped; the solution was stirred for 20 min without foaming and then allowed to incubate statically at room temperature for 60 minutes in dark. The reaction mixture was desalted to remove unincorporated LC-SMCC by applying to a Zeba spin column (Pierce, Rockford, Ill.) pre-equilibrated with 0.1M PBS/0.1% CHAPS/5 mM EDTA pH 6.7. The absorbance of the eluted Acr-BSA-Mal reagent was measured at 280 and 370 nm to estimate protein concentration. The calculated protein concentration was 5.25 mg/mL. The Acr-BSA-(LC)Mal was used immediately in the next conjugation step.

Conjugation of Recombinant NS3h to Acr-BSA-(LC)Mal. 1.20 mL (3.12 mg) of a 2.6 mg/mL solution of NS3h in 0.025M phosphate/0.25M NaCl/5 mM beta-mercaptoethanol/5 mM EDTA pH 8.0 was passed through a PD10 desalting column to remove the beta-mercaptoethanol. The NS3h protein was eluted with 2.5 mL of 0.01M PBS/5 mM EDTA pH 7.2 and the concentration of the eluent was calculated to be 2.9 mg/mL by absorbance at 280 nm. To a polypropylene tube were added 1.56 mg (0.297 mL, 23.4 nmoles, 2.0 mol equivalent) of Acr-BSA-(LC)Mal in 0.1M PBS/0.1% CHAPS/5 mM EDTA pH 6.7 followed by 0.60 mg (0.518 mL, 11.7 nmoles, 1.0 mol equivalent) of recombinant NS3h antigen in 0.01M PBS/5 mM EDTA pH 7.2. The solution was stirred for 30 min without foaming, and then allowed to incubate statically at room temperature overnight in dark. To the conjugate solution was added 0.093 mL of 0.5M phosphate buffer pH 11.0 to adjust mixture pH to 8.0. The mixture was stirred for 5 min, then 0.56 mg (0.012 mL, 120 mole equivalent) of a fresh 0.25M iodoacetic (IAA, Thermofisher Scientific, Waltham, Mass.) solution in 1N NaOH was added under mixing to effect NS3 free Cys-carboxymethylation. The mixture was reacted statically at room temperature and dark for 60 min, the final volume adjusted to 1.0 ml with 0.080 mL of 0.01M PBS/0.1% CHAPS/5 mM EDTA pH 6.3 and passed thru a PD10 column equilibrated in 0.01M PBS/0.1% CHAPS/5 mM EDTA pH 6.3 (2.5 mL elution volume). The desalted conjugate was next purified by SEC chromatography (TosoHaas G3000SWxl column, Toso Bioscience LLC, King of Prussia, Pa.) to remove undesired aggregates. The Acr-BSA-NS3h conjugate protein concentration was determined from the 280 nm absorbance of the conjugate after subtracting the 280 nm absorbance contributed by the Acr-BSA. The absorbance of a 1% (w/v) solution of NS3h of 0.95 was used to calculate the protein concentration.

Example 9

Automated Magnetic Microparticle-Based Immunoassays

The HCV NS3-derived proteins were tested for their ability to detect anti-HCV NS3 antibodies using an automated immunoanalyzer that utilizes paramagnetic microparticles and chemiluminescent conjugates (ARCHITECT® system; Abbott Laboratories; see "Bulk Reagent Random-Access Analyzer: ARCHITECT i2000" Frank A. Quinn, pages 363-367. In The Immunoassay Handbook, Third Edition, edited by David Ward, Nature Publishing Group, London, UK; U.S. Pat. No. 5,795,784 and U.S. Pat. No. 5,856,194). Assay formats examined included a 2-step format or a 1-step format. Assays can generally be described as comprising two formats: 2-step and 1-step (also described as 'pseudo' 1-step). In the 2-step format, human samples, assay specific diluent buffer and recombinant antigen coated paramagnetic microparticles are mixed into a reaction vessel, vortexed, and incubated for 18 min, wherein antibodies directed against the recombinant antigen are captured by the microparticles. Following this incubation, the microparticle/immune complexes are sequestered at the side of the reaction vessel using a magnet and the reaction supernatant is removed. The microparticles are then washed with water/detergent solution. In the second step, antibodies from the sample bound to the microparticles are detected by suspension and incubation (4 min) of the particles in buffer containing acridinium-labeled conjugate. The conjugate may be an acridinium-labeled antibody directed against human immunoglobulin(s) or an acridinium-labeled recombinant antigen. Incubation with conjugate is followed by a second wash step and finally an activation of the acridinium and simultaneous measurement of light output, which is proportional to the amount of conjugate bound onto the microparticles.

In the 1-step format, human samples, recombinant antigen coated paramagnetic microparticles and an assay specific diluent buffer containing a conjugate comprised of acridinium-labeled recombinant antigen were mixed into a reaction vessel. Following an 18-minute incubation, wherein antibodies directed against the recombinant antigen were simultaneously captured by the magnetic microparticles and bound to the acridinium-labeled recombinant antigen. Subsequently, the microparticle/immune complexes were sequestered at the side of the reaction vessel using a magnet and washed with a water/detergent mixture. Particles were then released from the vessel wall and suspended in diluent and incubated for 4 minutes. Incubation was followed by a second wash step and finally an activation of the acridinium and simultaneous measurement of light output, which was proportional to the amount of conjugate bound onto the microparticles.

Biotin-capture immunoassays. Biotin capture mediated immunoassays on the Architect analyzer used biotinylated NS3 protein (e.g, Nbt or Cbt as described in Example 2-6, or NS3 protein to which biotin has been coupled by chemical means in a non-site-specific manner) and a biotin capture protein (e.g. avidin, Streptavidin, Neutravidin, or anti-biotin antibody) coated paramagnetic particles. In this format, immune complexes formed between NS3 antibodies present in the sample and biotinyl-NS3 were captured onto the microparticle surface via the biotin capture protein immobilized onto the microparticle surface. A conjugate consisting of an acridinylated NS3 recombinant antigen can be added to the first step or the second step (i.e. following the capture step) to detect captured anti-NS3. Alternatively, an anti-human antibody acridinium conjugate can be added to the second step to detect captured anti-NS3.

Example 10

Immunoassay Formats

The following human specimens were used:

Negative control sample is recalcified nonreactive human plasma (nonreactive for HBsAg, and negative for anti-HCV, HIV-1 RNA or HIV-1 Ag, anti-HIV-1/HIV-2 and anti-HTLV-I/HTLV-II).

Positive control sample known as 'Panel B' is a human recalcifed human plasma sample reactive for a single anti-HCV marker as determined by Chiron RIBA HCV 3.0 SIA (2+ or greater c33 band intensity and nonreactive for other bands). This panel is diluted in recalcified nonreactive human plasma (nonreactive for HBsAg, and negative for anti-HCV, HIV-1 RNA or HIV-1 Ag, anti-HIV-1/HIV-2 and anti-HTLV-I/HTLV-II) containing disodium-EDTA and sodium azide.

Blood samples: A panel of commercially available human blood samples, referred to as seroconversion panels was obtained from SeraCare (Gaithersburg, Md.) and Zeptometrix (Franklin, Mass.). The seroconversion panels consist of serial blood samples obtained from an individual who is negative for antibodies to HCV in early bleed dates, but reactive for antibodies in the later bleed dates. Seroconversion panels are utilized to determine the sensitivity of various antibody tests, and antigen/antibody tests. More sensitive tests detect exposure to HCV at an earlier time than less sensitive tests Core Antigen specimen ST5 1:10 is human plasma that is HCV RNA positive and HCV antibody negative and has been diluted 1:10 in recalcified nonreactive human plasma (nonreactive for HBsAg, and negative for anti HCV, HIV-1 RNA or HIV-1 Ag, anti HIV 1/HIV-2 and anti-HTLV-I/HTLV-II) containing disodium-EDTA and sodium azide.

CAL is a recalcified human plasma reactive for antibody to HCV core, NS3 and NS4 and diluted into recalcified nonreactive human plasma (nonreactive for HBsAg, and negative for anti HCV, HIV-1 RNA or HIV-1 Ag, anti HIV 1/HIV-2 and anti-HTLV-I/HTLV-II) containing disodium-EDTA and sodium azide.

Example 11

HCV Antigen/Antibody (Combo) Assay Format

Described herein is a method for detection of Hepatitis C (HCV) core antigen and antibody in a single reaction on the ARCHITECT immunoassay platform developed at Abbott Laboratories. A prototype chemiluminescent immunoassay was developed for simultaneous detection of HCV core antigen and antibody to HCV (anti-HCV) in sera and plasma. The prototype combination assay is a 2-step (18'/4'), 3 bottle assay on the ARCHITECT instrument platform. The HCV combo test provides detection of human antibodies to the core, NS3 and NS4 proteins of HCV in addition to detection of HCV core antigen that may be present in the blood of HCV infected individuals.

In the first step, the instrument dispenses 110 ul of specimen plus 50 ul of the reaction mixture from bottle 1 plus 50 ul of streptavidin/neutravidin or anti-biotin paramagnetic microparticles from bottle 2 diluted in a detergent containing microparticle diluent (20 mM MES, pH 6.6, 0.15 M NaCl, 5 mM EDTA, 13.6% Sucrose, 0.1% Nipasept, 0.0005% Quinolone, and 5 mM DTT & 5 mM glutathione and containing 24.3 mM SB3-14 (N-Tetradecyl-N,N-dimethyl-3-ammonio-1-propanesulfonate). Bottle 1 contains a mixture of both biotin and acridinium labeled HCV specific reagents (peptides, proteins, and antibodies as well as various detergents and buffers) that enable immune complex formation with HCV antibody or antigen present in the serum or plasma. Specifically, bottle 1 contains: Acridinylated-Core peptide 5 (aa 15-68^34^48), Biotinylated-Core peptide 5 (aa 15-68^34^48), Acridinylated-NS3 recombinant antigen (9NB49H or NS3h), Biotinylated-NS3 recombinant antigen (9NB49H-Cbt or NS3h-Cbt), Acridinylated-NS4 peptide aa 1694-1735, Biotinylated-NS4 peptide aa 1694-1735, and Biotinylated-c11-7 monoclonal antibody in 80 mM Bis-Tris, pH 6.3, 0.92 M NaCl, 8% Sucrose, 1.7% Dextran 2000, 3% BSA, 0.3% Triton X100, 0.04% Methylcellulose, 7 mM EDTA, 0.04% sodium azide). The first step of the reaction therefore includes 110 ul specimen plus 50 ul of the reaction mixture from bottle 1 plus 50 ul of streptavidin/neutravidinlanti-biotin microparticles from bottle 2 and extends for 18 minutes—allowing various immune complexes to form.

The first step of the antibody detection assays are described as follows. Specifically, for anti-Core detection, one biotin labeled Core peptide and one acridinium labeled Core peptide need be present in the reaction mixture that can be bound by anti-Core antibody present in the specimen. This immune complex then binds to the solid phase coated with a biotin binding protein, in this case neutravidin, but could alternatively be streptavidin or anti-biotin. The process for the anti-NS3 reaction follows that one biotin labeled NS3 protein plus one acridinium labeled NS3 protein need be present in the reaction mixture that can be bound by anti-NS3 antibody present in the specimen. Likewise for anti-NS4, one biotin labeled NS4 peptide and one acridinium NS4 labeled peptide need be present in the reaction mixture that can be bound by anti-NS4 antibody present in the specimen.

The first step of the antigen detection assay is described as follows. For the Core antigen detection reaction, a biotin labeled monoclonal antibody (Mab c11-7) capable of binding to HCV Core antigen in serum or plasma is present in the 1st reaction (bottle 1). This immune complex then binds to the solid phase, also via the biotin moiety.

The second step of the antibody and antigen reactions are as follows. After an 18 minute incubation step, the microparticles are washed to remove unbound reactants from the mixture. The microparticles are then incubated with the conjugate *Ac-DBA c11-9/c11-14 conjugate from bottle 3 diluted in buffered solution containing various detergents and proteins (80 mM Bis Tris, pH 6.3, 0.924 M NaCl, 3.0% Sucrose, 5.0% Sorbitol, 7 mM EDTA, 1.7% Dextran 2000, 0.8% PVSA (25% solution), 3.0% BSA, 0.02% Benzethonium Chloride, 55,000 units/L Heparin Sodium, 0.2% Sodium Flouride, 0.3% Triton X-100, 0.3% Glycine, 0.2% SB3-12, 0.4% SB3-16, 0.2% SB3-18, 0.15% CHAPS, 0.2% Saponin, 0.35% CTAB, 0.02% TTAB, 0.1% Sodium Azide, 0.1% Nipasept, 1% A56620, 0.04% Methylcellulos). In this step, any immune-complexed Core antigen on the solid phase will be conjugated. After the 4 minute incubation of the 2nd step, the microparticles complete with labeled immune complexes intact are again washed and separated from unreacted components by a magnet. The reaction is then triggered and chemiluminescent signal generated from the acridinium-labeled conjugates bound to the solid phase via immune complexes is read proportional to the amount of analyte that was present in the sample being tested.

Example 12

Core Peptide Design

Detection of HCV infection requires the use of multiple HCV proteins for antibody detection (including HCV core, NS3 and in some cases, NS4 and NS5 peptides or proteins). Detection of HCV core antigen requires the use of antibodies that bind to the HCV core antigen, and such antibodies may bind to the HCV core protein utilized in the antibody side of the HCV combo test. Research scientists have identified the amino acid sequences on the HCV core antigen that are targeted by the antibodies used in the core antigen test—both for those utilized to capture the HCV core antigen (in this assay C-11-7), and those utilized to generate a signal (C11-9/C11-14). For each of the sites recognized by the antibodies, the amino acids comprising that recognition site must be modified by amino acid substitution or amino acid deletion.

A modified Core peptide was generated by removing 5 amino acids (amino acid residues 32-34, and 47-48) from the core protein, thus, avoiding recognition by the two monoclonal (C11-14 and C11-9) used in the ARCHITECT HCV Core Antigen test. An unwanted result of removing these 5 amino acids is that human antibody response to the core protein was compromised by the loss of these amino acids.

Thus, a series of Core peptides were generated to determine if minimal modifications can be made to the core protein—so that the minimally-modified peptides are not recognized by the antibodies utilized in the core antigen test—but allow adequate detection of antibodies to the core protein. These modified peptides were designed to restore some of the lost reactivity observed with the Core peptide that had five amino acids deleted. It was postulated that certain deletions/substitutions in the known epitope binding regions for the monoclonal antibody c11-9 (aa 29-37) and cl1-14 (aa 45-49) could be designed that would evade detection by this conjugate.

The design of the Core peptides involves targeted amino acid deletions and/or substitutions in distinct regions of the Core sequence of HCV whereby these deletion/substitutions successfully avoid detection by the *Ac-DBA c11-9/c11-14 conjugate used for detection of Core Ag in an HCV Combo assay.

TABLE 3

| New HCV Core Peptides Synthesized aa 15-68 | |
|---|---|
| Peptide 1: | TNRRPQDVKFPGGGQIVGGVYLLPRRGPRLGVRATRKTSE RSQPRGRRQPIPKA (SEQ ID NO: 97) |
| Peptide 2: | TNRRPQDVKFPGGGQIV---YLLPRRGPRLGV- TRKTSERSQPRGRRQPIPKA (SEQ ID NO: 98) |
| Peptide 3: | TNRRPQDVKFPGGGQIVGG-YLLPRRGPRLGV- TRKTSERSQPRGRRQPIPKA (SEQ ID NO: 99) |

TABLE 3-continued New HCV Core Peptides Synthesized aa 15-68

| Peptide 4: | TNRRPQDVKFPGGGQIVGG-YLLPRRGPRLGV-ATRKTSERSQPRGRRQPIPKA (SEQ ID NO: 100) |
| Peptide 5: | TNRRPQDVKFPGGGQIVGG-YLLPRRGPRLGVR-TRKTSERSQPRGRRQPIPKA (SEQ ID NO: 101) |
| Peptide 6: | TNRRPQDVKFPGGGQIVGG-YLLPRRGPRLGVIATRK TSERSQPRGRRQPIPKA (SEQ ID NO: 102) |
| Peptide 7: | TNRRPQDVKFPGGGQIVGGGYLLPRRGPRLGV-TRKTSERSQPRGRRQPIPKA (SEQ ID NO: 103) |
| Peptide 8: | TNRRPQDVKFPGGGQIVGGGYLLPRRGPRLGV-ATRKTSERSQPRGRRQPIPKA (SEQ ID NO: 104) |
| Peptide 9: | TNRRPQDVKFPGGGQIVGGGYLLPRRGPRLGVR-TRKTSERSQPRGRRQPIPKA (SEQ ID NO: 105) |
| Peptide 10: | TNRRPQDVKFPGGGQIVGGGYLLPRRGPRLGVIATRKTSE RSQPRGRRQPIPKA (SEQ ID NO: 106) |

Each of the newly synthesized Core peptides was coated onto neutravidin paramagnetic microparticles and probed with the *Ac-DBA c11-9/c11-14 conjugate. As shown below (table 4), peptide 1 (intact sequence between amino acids 15-68) provides high signal to noise (S/N) values when reacted with the *Ac-DBA c11-9/c11-14 conjugate. NOTE: the negative controls include microparticles that do NOT contain either on the solid phase or in liquid phase any HCV core epitope recognition molecules. These negative controls produce low S/N (signal to noise) values. The positive control (6C37 coated microparticles) contains HCV recombinant protein (compromising amino acids 1-150 of the HCV core protein) produces high S/N values due to its recognition by the *Ac-DBA c11-9/c11-14 conjugate.

TABLE 4

Detection by *Ac-c11-9/c11-14 Conjugate

| S/N Summary | Negative Controls | | Positive Control | HCV Core Peptides | | | | | | | | | |
|---|---|---|---|---|---|---|---|---|---|---|---|---|---|
| | Neut uparts | BSA uparts | 6C37 uparts | 1 | 2 | 3 | 4 | 5 | 6 | 7 | 8 | 9 | 10 |
| Sample Architect wash buffer | S/N 1.0 | S/N 1.1 | S/N 18465.9 | S/N 15176.8 | S/N 1.6 | S/N 0.5 | S/N 10.0 | S/N 1.1 | S/N 2456.3 | S/N 1695.2 | S/N 2697.6 | S/N 2666.0 | S/N 10030.5 |

Peptide 1 above represents the intact amino acid sequence between amino acids 15-68 that has been previously used to detect antibodies to the HCV core protein. Peptide 2 above has a total of 5 amino acids deleted, 3 of these amino acids (32, 33, and 34) representing part of the epitope recognition site for the C 11-9 monoclonal antibody, and 2 of these amino acids (47 and 48) representing the epitope recognition site for the C 11-14 monoclonal antibody. The signal for Peptide 1 is high since it is recognized by the HCV core conjugate, *Ac-DBA c11-9/c11-14. The S/N values for peptides 4 and 6-10 have S/N values >3.0 and are not candidates for use in the HCV combination assay since they are also recognized by the core conjugate. The S/N values for Peptides 2, 3 and 5 are very low, similar to the S/N values noted for the negative control, and thus, are not recognized by the HCV core antigen conjugate thereby making their design useful for the HCV combo test.

TABLE 5

Immunoreactivity of core peptides 2, 3 and 5 with Human Specimens
Indirect Anti-Human Assay - S/N Summary

| | Negative Controls | | Positive Control | HCV Core Peptides | | | | |
|---|---|---|---|---|---|---|---|---|
| | Neutravidin uparts | BSA uparts | 6C37 uparts | 1 | 2 | 3 | 4 | 5 |
| Sample CAL | S/N 2.5 | S/N 2.9 | S/N 205.3 | S/N 24.4 | S/N 9.5 | S/N 21.4 | S/N 15.2 | S/N 13.1 |

Shown above in Table 5, peptides 2, 3 & 5 all show immunoreactivity with human specimens reactive for anti-HCV in an Indirect Assay format. The S/N values for the human samples containing antibodies to HCV were slightly higher with both peptides 3 and 5 over that seen with peptide 2, but since peptide 5 contains the most minimal deletion of these two peptides (only aa's 34 and 48 are deleted), peptide 5 was chosen as the peptide of choice for HCV Combo development. Thus, peptide 5, which successfully avoids detection by the *Ac-DBA c11-9/c11-14 conjugate and is immunoreactive for human specimens infected with HCV was considered as the candidate peptide for HCV Combo.

Example 13

Monoclonal Antibodies

The HCV combo test utilizes three monoclonal antibodies (C11-7, C11-14, and C11-9). Two of the monoclonal antibodies (C11-7, C11-14) have been previously described in the Abbott US patent "Methods for the simultaneous detection of HCV Antigens and HCV antibodies". U.S. Pat. No. 6,727,092 by Shah et al., issued Apr. 27, 2004. However, the original disclosure of these two monoclonal antibodies was cited in U.S. Pat. No. 6,623,921 by Aoyagi et al., issued Sep. 23, 2003. The third monoclonal antibody was disclosed in publications (Morota et al., J. Virol. Meth 157:8 (2009) and is discussed in Patent Application number 20120009196 by Muerhoff, et al. (publication date 2012 Jan. 12).

Example 14

Preparation of Microparticles

The HCV Combo assay uses one type of paramagnetic microparticle capable of capturing biotin-labeled proteins (streptavidin, neutravidin, and anti-biotin). Briefly, Dynal M270 Carboxylic Acid raw particles are washed with 2 exchanges into MES-Chaps Buffer, pH 5.5 (25 mM 2-(N-Morpholino)ethanesulfonic acid (MES), 0.1% 3-[(3-Cholamidopropyl)dimethylammonio]-1-propanesulfonate (Chaps)). Particles are pre-activated with EDAC (N-Ethyl-N'-(3-dimethylaminopropyl)carbodiimide hydrochloride) at 0.25 mg/mL for 30 minutes at 1% solids. Particles are washed with 1 exchange into MES-Chaps Buffer, pH 5.5. Neutravidin/Streptavidin/anti-Biotin Ab stock solution is added to the particles at 0.40 mg/mL for 60 minutes at 1% solids. Particles are washed with 3 exchanges into PBS-Chaps Buffer, pH 7.2 (phosphate buffered saline (PBS), 0.1% Chaps). Final particle concentration is 1% solids in PBS-Chaps Buffer, pH 7.2. These microparticles are subsequently diluted to 0.075% solids in microparticle diluent (20 mM MES, pH 6.6, 0.15 M NaCl, 5 mM EDTA, 13.6% Sucrose, 0.1% Nipasept, 0.0005% Quinolone, and 5 mM DTT & 1.54 g/L glutathione and containing 24 mM SB3-14 (N-Tetradecyl-N,N-dimethyl-3-ammonio-1-propanesulfonate).

Example 15

HCV Core Peptide

The synthetic peptides were manufactured by AnaSpec (Fremont, Calif.). Purity level >95%.

```
Biotin -
                                              (SEQ ID NO: 101)
TNRRPQDVKFPGGGQIVGGYLLPRRGPRLGVRTRKTSERSQPRGRRQP

IPKA
```

2. Acridinylated labeled HCV core peptide 5 was used as a conjugate for the assay and is represented as follows:

```
                                              (SEQ ID NO: 101)
TNRRPQDVKFPGGGQIVGGYLLPRRGPRLGVRTRKTSERSQPRGRRQP

IPKA
```

The acridinylation process for Core peptide 5 is described in Example 18.

Example 16

NS4 Peptides (Amino Acids 1694-1735)

These synthetic peptides were manufactured by Ana Spec (Fremont Calif.). Purity level >95%.

The HCV combo test utilized the HCV NS4 peptide in two forms:

1. Biotinylated NS4 peptide was captured on streptavidin coated microparticles as follows:

```
Biotin -
                                    (SEQ ID NO: 107)
IIPDREVLYREFDEMEECSQHLPYIEQGMMLAEQFKQKALGL
```

2. Acridinylated labeled NS4 peptide was used as a conjugate for the assay and is represented as follows:

```
Acridinium -
                                    (SEQ ID NO: 108)
IIPDREVLYREFDEMEECSQHLPYIEQGMMLAEQFKQKALGLC
```

The acridinylation process for the NS4 is described in Example 17.

Example 17

Preparation of Acr-BSA-NS4 Peptide Conjugate

Thirteen milligrams (2.0 mL, 0.196 umol, 1.0 mol equivalent) of Acr-BSA-Mal in 0.1M PBS/0.1% CHAPS/5 mM EDTA pH 6.7 (from Example 2) was added to a polypropylene tube. To this solution was added 0.100 mL (4.02 mg, 0.784 umol, 4.0 mol equivalent) of a fresh 41 mg/mL solution of C-terminal cysteine NS4 peptide (AnaSpec, Fremont, Calif.) in dimethylsulfoxide (DMSO, Sigma Aldrich, St Louis, Mo.). The reaction vial was capped, the solution vortexed briefly without foaming and allowed to incubate at room temperature in dark overnight. The crude conjugate was next treated for about 30 min with a 0.25M mercaptoethylamine HCl (MEA) aqueous solution to a final 1.14 mM MEA reaction concentration to quench unreacted maleimide groups. The conjugate was immediately purified by SEC chromatography on a TosoHaas G3000SW column (Tosoh Bioscience LLC., King of Prussia, Pa.) using 0.01M PBS/0.1% CHAPS pH 6.3. The fractions corresponding to the main conjugate peak were pooled. The absorbance of the conjugate pool was measured at 280 and 370 nm and used to determine a corrected 280 nm absorbance value. The conjugate was stored at −20° C. between uses.

Example 18

Preparation of Acr-BSA-Core Peptide Conjugate

Six milligrams (1.01 mL, 90 nmoles, 1.0 mol equivalent) of Acr-BSA in 0.1M PBS/0.1% CHAPS pH 6.3 (from Example 1) was added to a polypropylene tube. To this solution was added 0.431 mL (4.31 mg, 22.5 umol, 250 mol equivalents) of a fresh 10 mg/mL 1-Ethyl-3-[3-dimethylaminopropyl]carbodiimide hydrochloride (EDAC) solution in water and 0.259 mL (2.58 mg, 22.5 umol, 250 mol equivalent) of a fresh 10 mg/mL N-hydroxysuccinimide (NHS) solution in water. The mixture was vortexed gently and then allowed to react statically at room temperature and dark for 10 min. To the activated Acr-BSA conjugate solution was added 4.4 mg (0.881 mL, 0.72 umol, 8 mol equivalent) of a fresh 5.0 mg/mL Core peptide (AnaSpec, Fremont, Calif.) solution in 0.01M PBS pH 7.2. The solution was vortexed gently and allowed to react at room temperature in dark overnight. The conjugate was purified by SEC chromatography on a TosoHaas G3000SWxl column (Tosoh Bioscience LLC., King of Prussia, Pa.) using 0.01M PBS/0.1% CHAPS pH 6.3 to remove aggregates. The fractions corresponding to the major conjugate peak were pooled. The absorbance of the Acr-BSa-NS4 peptide conjugate pool was measured at 280 and 370 nm and used to determine a corrected 280 nm absorbance value. The conjugate was stored at −20° C. between uses.

Example 19

Preparation of Biotinylated C11-7 Monoclonal Antibody

Thirteen milligrams (1.0 mL, 86.6 nmoles, 1.0 mol equivalent) of a 13.1 mg/mL solution of C11-7 monoclonal antibody (mAb) in 0.01M PBS pH 7.2 was added to an amber glass vial containing 0.916 mL of 0.01M PBS pH 7.2 buffer. To this solution was added 0.144 mL of 0.133M phosphate/0.376M NaCl/7.5% CHAPS pH 8.0 to adjust the reaction pH to 7.4-7.5 and the mixture was stirred for 5 min without foaming. To the stirring C11-7 mAb solution was added 0.350 mg (0.100 mL, 433 nmoles, 5.0 mol equivalent) of a 5.71 mg/mL solution of Chromalink Biotin (CLB, SoluLink, San Diego, Calif.) in anhydrous dimethylformamide (DMF, Sigma Aldrich, St Louis, Mo.). The mixture was stirred for 30 min, then reacted statically at room temperature overnight in dark. The crude conjugate mixture was passes. The reaction mixture was desalted to remove unincorporated CLB biotin by passing thru a Zeba spin column (Pierce, Rockford, Ill.) equilibrated with 0.01M PBS/0.1% CHAPS pH 7.2. The absorbance of the eluted C11-7 mAb-CLB conjugate was measured at 280 and 354 nm to estimate protein concentration and calculate incorporation of biotin per antibody molecule. The calculated protein concentration was 4.03 mg/mL with an average number of 4.12 biotins per C11-7 mAb molecule.

Example 20

Preparation of the Dextran-BSA 1.068 mL of a 100 mg/mL solution of sodium periodate (Sigma Chemical Co., St. Louis, Mo.) prepared in distilled water was added to a solution of dextran that was prepared by dissolving 117.48 mg of dextran (150,000 MW GPC Grade, Pharmacosmos, Holbaek, Denmark) in 2.1 mL of distilled water and incubated in a 23° C. waterbath in the dark, with stirring for 120 minutes. At the end of the 120 minutes, 6.408 mL of a 55 mg/mL solution of BSA (Proliant Biologicals, Boone, Iowa) equilibrated in 150 mM HEPBS (Sigma Chemical, St. Louis, Mo.) buffer, pH 8.9 was added to the oxidized dextran solution and the reaction continued for an additional 120 minutes at 23° C. in the dark. At the end of the incubation 1.06 g of borane-dimethylamine complex (97%, Sigma-Aldrich, St. Louis, Mo.) was added to the dextran-BSA solution for 60 minutes at 23° C. in the dark followed by addition of 1.34 mL of a 0.65 M Tris-HCl (Sigma Chemical Co., St. Louis, Mo.)), pH 7.5 buffer for 16-20 hours at 23° C. The resulting solution was purified using a HiPrep Sephacryl S300 26/60 column (GE Healthcare, Uppsala, Sweden) that was equilibrated in PBS at 2.6 mL/min. The crude dextran-BSA was loaded onto the column and run at 2.6 mL/min. while monitoring the absorbance at 280 nm. 2.6 mL fractions were collected and the voided fractions were pooled. The pooled fractions were then concentrated to less than 10 mL using Amicon Ultra-15 centrifugal concentrators (50,000 MWCO, EMD Millipore Corporation, Billerica, Mass.). The concentrated dextran-BSA was spiked with a solution of sodium azide and CHAPS (Sigma Chemical Co., St. Louis, Mo.) to a final concentration of 0.1% sodium azide and 0.5% CHAPS. This solution was heat stressed in a 45° C. oven for 7 days and stored at 2-8° C. prior to additional HiPrep Sephacryl S400 column purification. A HiPrep Sephacryl S400 26/60 column (GE Healthcare, Uppsala, Sweden) was equilibrated with PBS at a flow rate of 2.6 mL/min. and the heat stressed dextran-BSA was loaded onto the column. Fractions were pooled in order to eliminate high molecular weight aggregate and low molecular weight degradation products.

The pooled fractions were concentrated to greater than 5 mg/mL using Amicon Ultra-15 centrifugal concentrators (as above) and the solution stored at 2-8° C. until used to prepare the conjugate.

Example 21

Preparation of the C11-9/C11-14 Dextran-BSA Conjugate 6 mg of the purified, heat stressed dextran-BSA solution (from above) was reacted with 1.62 mg of acridinium SPSP (9-[[[[4-[4-oxo-4-(2,3,4,5,6-pentafluorophenoxy)butyl]phenyl]sulfonyl](3-sulfopropyl)amino]carbonyl]-10-(3-sulfopropyl) in a conjugation buffer containing sodium phosphate, 150 mM NaCl, 1 mM EDTA (Sigma Chemical Co., St. Louis, Mo.), 0.2% CHAPS (Sigma Chemical Co., St. Louis, Mo.), pH 7.4. The reaction was allowed to proceed overnight at room temperature in the dark. At the end of the overnight reaction, 2.7 mg of Sulfosuccinimidyl-4-(N-maleimidomethyl)cyclohexane-1-carboxylate (sSMCC, Thermo-Fisher Scientific, Rockford, Ill.) was added to the SPSP-dextran-BSA solution and incubation continued for 60 minutes at room temperature in the dark. The unreacted SPSP and sSMCC were removed by gel filtration using a column equilibrated with a buffer containing sodium phosphate, NaCl, 1 mM EDTA, 0.5% CHAPS, pH 6.0. The final solution was concentrated to greater than 10 mg/mL using Amicon Ultra-4 centrifugal concentrators (30,000 MWCO) and the absorbance at 280 nm and 370 nm was determined.

8.76 mg of a 2.5:1 (mg:mg) mixture of C11-9:C11-14 F(ab')2 fragments in a conjugation buffer containing sodium phosphate, NaCl, 1 mM EDTA, pH 6.0 was equilibrated at 37° C. in a waterbath. 0.39 mL of a 120 mM solution of cysteamine HCl (Sigma-Aldrich, St. Louis, Mo.) prepared in sodium phosphate buffer containing EDTA at pH 6.0 was added to the temperature equilibrated antibody fragments and incubated at 37° C. for 90 minutes. After reduction of the fragments, excess cysteamine HCl was removed by gel filtration using a column equilibrated with a buffer containing sodium phosphate, NaCl, 1 mM EDTA, 0.5% CHAPS, pH 6.0 and the solution was concentrated to greater than 8 mg/mL using Amicon Ultra-4 centrifugal concentrators (10,000 MWCO). A final conjugation reaction containing 5 mg/mL of the SPSP and sSMCC labeled dextran-BSA and 4 mg/mL of the reduced fragments was incubated in the sodium phosphate, NaCl, 1 mM EDTA, 0.5% CHAPS, pH 6.0 buffer at 2-8° C. 16-24 in the dark.

After blocking any unreacted maleimide groups with excess cysteamine HCl, the crude conjugation reaction was purified using a HiPrep Sephacryl S400 column (GE Healthcare, Uppsala, Sweden) equilibrated in PBS with 0.1% CHAPS, pH 6.3. Fractions were pooled from the main conjugate peak in order to eliminate high molecular weight material and any unbound antibody fragments. The concentration of the conjugate was expressed as the amount of antibody fragments and was determined using the absorbance at 280 nm and 370 nm of the conjugate compared to the absorbances of the SPSP and sSMCC labeled dextran-BSA.

Example 22

Assay Diluent Formulations

In order to enable detection of Core antigen in the HCV Combo format, exposure of the Core capsid proteins is required. This exposure requires the use of a detergent present in either the outer ring bottle (bottle 1) or the middle ring bottle (bottle 2), and this detergent can be of non-ionic classification and/or contain alkyl chain groups with amines. (Aoyagi et al: G01N 33/576, WO 00/07023, Feb. 10, 2000).

The detergents required to detect HCV core antigen have a negative impact on the ability of antibodies to bind to the NS3 protein utilized in the HCV combo assay. This loss of anti-NS3 signal is reproducible, and has been monitored during the assay development process using an anti-NS3 "only" sample that contains antibodies to NS3, but not to other HCV proteins. The sample utilized in our studies is referred to as Panel B, and is prepared by diluting a highly reactive sample in normal human plasma that is negative for antibodies to NS3. Panel B is diluted to contain a moderate reactivity, and serves as a surrogate marker for the capacity of the immunoassay to detect antibodies to NS3 in patient samples. In monitoring the anti-NS3 reactivity, the signal to noise (S/N) ratio is utilized to denote relative reactivity, with high S/N's being desirable. Previous experience with anti-HCV assays has shown that a viable antibody assay should provide an S/N value of >20.

Example 23

Effect of Detergents on HCV Combo Assay

Using the Combo format described in Example 11 (and all the capture reagents of the combo assay described herein), the data in Table 6 shows the effect of varying hydrocarbon chain length of zwitterionic detergent sulfobetaine (SB3) in the detection of anti-NS3 (Panel B) and core antigen in the HCV combo assay format. When no detergent is present in the reaction, Panel B detection is high (S/N=39.6) but detection of Core antigen is low (S/N=3.8). When a hydrocarbon chain length of 8 (SB3-8) is used in the reaction, both Panel B and Core antigen detection are low. As the hydrocarbon chain length is increased, particularly to 12 or 14, Core antigen reactivity improves. However, when the chain length is 16, both Core antigen detection and Panel B reactivity decline suggesting that the optimal hydrocarbon chain length to strike a suitable balance between Panel B detection and Core antigen detection appears to be 12 to 14.

TABLE 6

Table 6: Effect of different zwitterionic detergents in the detection of anti-NS3 and core antigen in the HCV combo assay format (S/N: Ratio of sample rlu/negative plasma rlu).

| samples | control diluent - no detergents | control diluent + SB3-8 | control diluent + SB3-10 | control diluent + SB3-12 | control diluent + SB3-14 | control diluent + SB3-16 |
|---|---|---|---|---|---|---|
| | S/N | S/N | S/N | S/N | S/N | S/N |
| Panel B | 39.6 | 9.8 | 36.9 | 26.9 | 26.4 | 15.2 |
| core antigen ST5 1:10 | 3.8 | 1.5 | 4.2 | 72.1 | 94.9 | 62.0 |

Table 7 shows the use of various detergents and their effect on both Panel B detection and Core antigen detection. The control diluent with no detergent shows good detection of Panel B (S/N=63.9) but virtually no detection of Core antigen (S/N=2.2). Other detergents show moderate detection of both Panel B and Core antigen (C7BzO). The best detection is seen with detergent SB3-14 where detection of both Panel B and Core antigen is the highest at an S/N of 71.7 and 81.9, respectively.

TABLE 7

|  | control diluent - no detergent | control diluent + SB3-14 | control diluent + CHAPS | control diluent + C7BzO | control diluent + Empigen BB | control diluent + TSP16 | control diluent + ASB-16 | control diluent + NDSB256 sulfobetaine | control diluent + NDSB201 sulfobetaine |
|---|---|---|---|---|---|---|---|---|---|
| samples | S/N | S/N | S/N | S/N | S/N | S/N | S/N | S/N | S/N |
| Panel B: anti-NS3 | 63.9 | 71.7 | 46.8 | 56.4 | 32.5 | 58.3 | 35.2 | 46.2 | 26.8 |
| core antigen ST5 1:10 | 2.2 | 81.9 | 5.1 | 56.2 | 40.4 | 10.3 | 43.6 | 1.9 | 1.8 |

Summary of detergents used in study: The detergents SB3-14, CHAPS, C7BzO (3-(4-Heptyl)phenyl-3-hydroxypropyl)dimethylammoniopropanesulfonate), Empigen BB (EMPIGEN® BB, Sigma-Aldrich), and ASB-16 (Amidosulfobetaine-16) are classified as zwitterionic surfactants; they possess a neutral charge resulting from the presence of equal numbers of positive and negative charged chemical groups within the molecule. This group of detergents possesses the ability to solubilize membrane proteins (Sigmaaldrich.com). TSP-16 is classified as a non-ionic surfactant, which contains an uncharged hydrophilic headgroup. The sulfobetaines, NDSB256 (Dimethylbenzylammonium propane sulfonate; N-phenyl-methyl-N,N-dimethylammonium-propane-sulfonate), and NDSB201 (3-(1-Pyridino)-1-propane Sulfonate), are classified as non-detergent sulfobetaines which are zwitterionic compounds that can reduce aggregation and aid in refolding of proteins. They are not considered detergents because they cannot aggregate to form micelles.

Shown in Table 8 is a titration of detergent SB3-14 from 0 to 100 mM in the microparticle diluent (bottle 2, middle ring). The concentration of SB3-14 detergent for optimal detection of both Panel B and Core antigen appears to be between 25-75 mM, with acceptable Panel B (S/N>20) and core Ag (S/N>20) sensitivity.

TABLE 8

|  | control diluent - no detergent | control diluent + 0.1 mM SB3-14 | control diluent + 1 mM SB3-14 | control diluent + 10 mM SB3-14 | control diluent + 25 mM SB3-14 | control diluent + 50 mM SB3-14 | control diluent + 75 mM SB3-14 | control diluent + 100 mM SB3-14 |
|---|---|---|---|---|---|---|---|---|
| samples | S/N | S/N | S/N | S/N | S/N | S/N | S/N | S/N |
| Panel B: anti-NS3 | 28.5 | 32.4 | 33.9 | 33.2 | 27.2 | 25.1 | 22.2 | 8.8 |
| core antigen ST5 1:10 | 4.1 | 4.5 | 4.4 | 8.1 | 35.8 | 38.3 | 43.7 | 56.8 |

Example 24

Assay Performance—Placement of Detergent

Table 9 shows the HCV Combo assay performance on select seroconversion panels where the detergent used for Core antigen detection is placed in the outer ring (bottle 1) or, alternatively, placed in the middle ring (bottle 2). Performance remains roughly the same with the total number of bleeds detected being 19/23.

TABLE 9

Table 9: HCV Combo Assay Stability when SB3-14 is in the outer ring bottle (bottle 1) or the middle ring bottle (bottle 2)

| Panel | Sample | Bleed Date | Days from 0 | PCR | RNA Copies/ml (Vendor) | RIBA 3.0 | Anti-HCV Antibody Data by 6C37 Assay S/CO | HCV Antibody/Antigen Combination Assay (HCV Combo)-Detergent in Outer Ring (bottle 1) S/CO | HCV combo blend CoF-Detergent in Middle ring (bottle 2) S/CO |
|---|---|---|---|---|---|---|---|---|---|
| PHV-912 | 1 | 6 Jan. 1996 | 0 | + | 40,000 | — | 0.23 | 0.6 | 0.8 |
| Genotype 2b/3 | 2 | 10 Jan. 1996 | 4 | + | >500,000 | — | 0.16 | 3.4 | 17.6 |
|  | 3 | 13 Jan. 1996 | 7 | + | 40,000 | core | 7.91 | 15.7 | 18.7 |
| PHV-919 | 1 | 31 Dec. 1999 | 0 | − | BLD | — | 0.32 | 0.8 | 0.6 |

TABLE 9-continued

Table 9: HCV Combo Assay Stability when SB3-14 is in the outer ring bottle (bottle 1) or the middle ring bottle (bottle 2)

| Panel | Sample | Bleed Date | Days from 0 | PCR | RNA Copies/ml (Vendor) | RIBA 3.0 | Anti-HCV Antibody Data by 6C37 Assay S/CO | HCV Antibody/Antigen Combination Assay (HCV Combo)-Detergent in Outer Ring (bottle 1) S/CO | HCV combo blend CoF-Detergent in Middle ring (bottle 2) S/CO |
|---|---|---|---|---|---|---|---|---|---|
| Genotype 1a | 2 | 7 Jan. 2000 | 7 | − | BLD | — | 0.48 | 0.7 | 0.8 |
| | 3 | 12 Jan. 2000 | 12 | − | BLD | — | 0.26 | 0.7 | 0.5 |
| | 4 | 25 Jan. 2000 | 25 | + | 200,000 | — | 0.46 | 2.5 | 3.3 |
| | 5 | 28 Jan. 2000 | 28 | + | 20,000 | core/NS3 | 2.76 | 12.2 | 13.9 |
| | 6 | 1 Feb. 2000 | 32 | + | 100,000 | core/NS3 | 13.99 | 8.8 | 9.7 |
| | 7 | 4 Feb. 2000 | 35 | + | 100,000 | core/NS3 | 13.90 | 5.7 | 6.0 |
| BCP 6214 | 1 | 13 Jan. 1996 | 0 | + | 246,000 | — | 0.12 | 1.6 | 2.3 |
| | 2 | 15 Jan. 1996 | 2 | + | 181,000 | — | 0.12 | 3.2 | 7.1 |
| Genotype 1a | 3 | 21 Jan. 1996 | 8 | + | 241,000 | — | 0.09 | 3.9 | 4.7 |
| | 4 | 23 Jan. 1996 | 10 | + | 186,000 | — | 0.11 | 3.1 | 2.3 |
| | 5 | 20 Jan. 1996 | 16 | + | 290,000 | — | 0.10 | 2.1 | 4.0 |
| | 6 | 31 Jan. 1996 | 18 | + | 177,000 | — | 0.08 | 2.2 | 1.8 |
| | 7 | 5 Feb. 1996 | 23 | + | 312,000 | — | 0.27 | 3.0 | 3.5 |
| | 8 | 7 Feb. 1996 | 25 | + | 408,000 | — | 0.56 | 6.5 | 7.6 |
| | 9 | 12 Feb. 1996 | 30 | + | 290,000 | NS3 | 3.51 | 3.1 | 4.6 |
| | 10 | 14 Feb. 1996 | 32 | + | 632,000 | NS3 | 4.44 | 3.5 | 4.6 |
| | 11 | 2 Mar. 1996 | 49 | + | 228,000 | NS3/NS4 | 13.07 | 1.8 | 2.7 |
| | 12 | 6 Mar. 1996 | 53 | + | 228,000 | NS3/NS4 | 13.21 | 2.5 | 3.9 |
| | 13 | 9 Mar. 1996 | 56 | + | 193,000 | NS3/NS4 | 13.00 | 4.1 | 4.7 |

S/CO: 10 NC used for cutoff calculation
S/CO >/=1.0 is considered reactive

Example 25

Assay Stability of SB3-14 in Different Reagent Bottle

As mentioned above, the detergent(s) necessary for Core antigen detection can be located either in the outer ring bottle (bottle 1) or in the middle ring bottle (bottle 2) with equivalent performance. However, stability testing over a 62 day period showed an approximate 67% drop in retention of rlu's for an NS3 specimen (Panel B) when the detergent was kept in the outer ring bottle vs. no apparent loss in rlu retention when the detergent was moved into the middle ring bottle (Table 10).

TABLE 10

Table 10: The Assay Stability of SB3-14 in different reagent bottle. RLU of NS3 panel over time when reagent stored at 2 to 8 degree C.

| | SB3-14 in Outer Ring bottle | | SB3-14 in Middle Ring bottle | |
|---|---|---|---|---|
| | RLU | % retention | RLU | % retention |
| Day 1 | 157668 | | 157894 | |
| Day 3 | 144312 | 91.5% | 158378 | 100.3% |
| Day 8 | 132705 | 84.2% | 157401 | 99.7% |
| Day 15 | 103128 | 65.4% | 162609 | 102.9% |
| Day 35 | 84415 | 53.5% | 163996 | 103.8% |
| Day 62 | 51064 | 32.4% | 161422 | 102.2% |

Example 26

Performance of the HCV Combination Assay on Seroconversion Panels

A total of 9 seroconversion panels, PHV-907, PHV-909, PHV-912, PHV-913, PHV-914, PHV-919 (commercially available from SeraCare) and BCP 6214, BCP 6229 and BCP 9044 (commercially available from ZeptoMetrix) were tested by an anti-HCV only assay (Abbott ARCHITECT LN6C37) and the HCV Combo Assay (described above). The results are expressed in terms of S/CO (sample/cutoff) where an S/CO of 1.0 or greater is considered reactive. As shown in Table 11, the HCV Combo assay detects evidence of infection in these panels earlier than that detected by the Antibody only assay (6C37). Shown below (Table 12) is the average window period reduction in days for seroconversion panels that were RNA positive on the $1^{st}$ bleed of the series. The HCV Combo assay showed detection, on average, approximately 18.4 days earlier than the antibody only assay and roughly equivalent to that detected by RNA. The single seroconversion panel shown above that became RNA positive during the course of collection (PHV-919) shows detection by the HCV Combo assay at the same time as RNA and 3 days ahead of detection by the antibody only assay.

These data demonstrate the value of the HCV antigen/antibody Combo test in detection of exposure to HCV earlier than antibody only tests.

TABLE 11

| Panel | Sample | Bleed Date | Days from 0 | PCR | RNA Copies/ml (Vendor) | RIBA 3.0 | Anti-HCV Antibody Data by 6C37 Assay S/CO | HCV Antibody/Antigen Combination Assay (HCV Combo) S/CO |
|---|---|---|---|---|---|---|---|---|
| PHV-907 Genotype 1b | 1 | 6 Apr. 1996 | 0 | + | >500,000 | — | 0.07 | 14.0 |
| | 2 | 10 Apr. 1996 | 4 | + | >500,000 | — | 0.06 | 24.8 |
| | 3 | 13 Apr. 1996 | 7 | + | >500,000 | — | 0.06 | 14.3 |
| | 4 | 19 Apr. 1996 | 13 | + | >500,000 | core | 0.46 | 7.4 |
| | 5 | 24 Apr. 1996 | 18 | + | >500,000 | core | 2.37 | 3.1 |
| | 6 | 27 Apr. 1996 | 21 | + | >500,000 | core/NS3 | 2.55 | 4.1 |
| | 7 | 17 Sep. 1996 | 164 | + | 40,000 | core, NS3, NS4 | 12.56 | 23.3 |
| PHV-909 Genotype 3 | 1 | 18 Jan. 1996 | 0 | + | 10,000 | — | 0.12 | 8.6 |
| | 2 | 15 Feb. 1996 | 28 | + | 40,000 | core | 1.37 | 3.3 |
| | 3 | 17 Feb. 1996 | 30 | + | 20,000 | core | 1.13 | 2.7 |
| PHV-912 Genotype 2b/3 | 1 | 6 Jan. 1996 | 0 | + | 40,000 | — | 0.23 | 0.6 |
| | 2 | 10 Jan. 1996 | 4 | + | >500,000 | — | 0.16 | 3.4 |
| | 3 | 13 Jan. 1996 | 7 | + | 40,000 | core | 7.91 | 15.7 |
| PHV-913 Genotype 2b | 1 | 27 Feb. 1997 | 0 | + | >500,000 | — | 0.07 | 13.7 |
| | 2 | 1 Mar. 1997 | 2 | + | >500,000 | — | 0.23 | 15.0 |
| | 3 | 6 Mar. 1997 | 7 | + | >500,000 | core | 2.50 | 10.9 |
| | 4 | 8 Mar. 1997 | 9 | + | >500,000 | core | 1.12 | 6.1 |
| PHV-914 Genotype 2b | 1 | 9 Apr. 1997 | 0 | + | >500,000 | — | 0.05 | 7.6 |
| | 2 | 14 Apr. 1997 | 5 | + | >500,000 | — | 0.05 | 11.3 |
| | 3 | 18 Apr. 1997 | 9 | + | >500,000 | — | 0.06 | 7.8 |
| | 4 | 21 Apr. 1997 | 12 | + | >500,000 | — | 0.10 | 7.7 |
| | 5 | 25 Apr. 1997 | 16 | + | >500,000 | core | 0.75 | 4.6 |
| | 6 | 28 Apr. 1997 | 19 | + | >500,000 | core | 2.24 | 6.3 |
| | 7 | 3 May 1997 | 24 | + | >500,000 | core | 3.82 | 3.4 |
| | 8 | 9 May 1997 | 30 | + | >500,000 | core/NS3 | 5.02 | 7.5 |
| | 9 | 12 May 1997 | 33 | + | >500,000 | core/NS3 | 7.84 | 13.7 |
| PHV-919 Genotype 1a | 1 | 31 Dec. 1999 | 0 | − | BLD | — | 0.32 | 0.8 |
| | 2 | 7 Jan. 2000 | 7 | − | BLD | — | 0.48 | 0.7 |
| | 3 | 12 Jan. 2000 | 12 | − | BLD | — | 0.26 | 0.7 |
| | 4 | 25 Jan. 2000 | 25 | + | 200,000 | — | 0.46 | 2.5 |
| | 5 | 28 Jan. 2000 | 28 | + | 20,000 | core/NS3 | 2.76 | 12.2 |
| | 6 | 1 Feb. 2000 | 32 | + | 100,000 | core/NS3 | 13.99 | 8.8 |
| | 7 | 4 Feb. 2000 | 35 | + | 100,000 | core/NS3 | 13.90 | 5.7 |
| BCP 6214 Genotype 1a | 1 | 13 Jan. 1996 | 0 | + | 246,000 | — | 0.12 | 1.6 |
| | 2 | 15 Jan. 1996 | 2 | + | 181,000 | — | 0.12 | 3.2 |
| | 3 | 21 Jan. 1996 | 8 | + | 241,000 | — | 0.09 | 3.9 |
| | 4 | 23 Jan. 1996 | 10 | + | 186,000 | — | 0.11 | 3.1 |
| | 5 | 29 Jan. 1996 | 16 | + | 290,000 | — | 0.10 | 2.1 |
| | 6 | 31 Jan. 1996 | 18 | + | 177,000 | — | 0.08 | 2.2 |
| | 7 | 5 Feb. 1996 | 23 | + | 312,000 | — | 0.27 | 3.0 |
| | 8 | 7 Feb. 1996 | 25 | + | 408,000 | — | 0.56 | 6.5 |
| | 9 | 12 Feb. 1996 | 30 | + | 290,000 | NS3 | 3.51 | 3.1 |
| | 10 | 14 Feb. 1996 | 32 | + | 632,000 | NS3 | 4.44 | 3.5 |
| | 11 | 2 Mar. 1996 | 49 | + | 228,000 | NS3/NS4 | 13.07 | 1.8 |
| | 12 | 6 Mar. 1996 | 53 | + | 228,000 | NS3/NS4 | 13.21 | 2.5 |
| | 13 | 9 Mar. 1996 | 56 | + | 193,000 | NS3/NS4 | 13.00 | 4.1 |

TABLE 11-continued

| Panel | Sample | Bleed Date | Days from 0 | PCR | RNA Copies/ml (Vendor) | RIBA 3.0 | Anti-HCV Antibody Data by 6C37 Assay S/CO | HCV Antibody/Antigen Combination Assay (HCV Combo) S/CO |
|---|---|---|---|---|---|---|---|---|
| BCP | 1 | 14 Nov. 1996 | 0 | + | >5,000,000 | — | 0.35 | 31.8 |
| 6229 | 2 | 17 Nov. 1996 | 3 | + | >5,000,000 | — | 0.36 | 30.2 |
| Genotype | 3 | 21 Nov. 1996 | 7 | + | >5,000,000 | — | 0.18 | 23.8 |
| 1a | 4 | 24 Nov. 1996 | 10 | + | >5,000,000 | — | 0.42 | 38.3 |
|  | 5 | 1 Dec. 1996 | 17 | + | >5,000,000 | — | 1.22 | 20.9 |
|  | 6 | 4 Dec. 1996 | 20 | + | >5,000,000 | — | 1.56 | 27.5 |
|  | 7 | 8 Dec. 1996 | 24 | + | >5,000,000 | NS3 | 2.65 | 17.3 |
|  | 8 | 12 Dec. 1996 | 28 | + | >5,000,000 | NS3 | 7.02 | 15.7 |
| BCP | 1 | 14 Apr. 1997 | 0 | + |  | — | 0.07 | 26.0 |
| 9044 | 2 | 18 Apr. 1997 | 4 | + |  |  | 0.03 | 21.9 |
| Genotype | 3 | 1 May 1997 | 17 | + |  | — | 0.07 | 30.9 |
| 1a | 4 | 5 May 1997 | 21 | + |  | — | 0.62 | 33.4 |
|  | 5 | 9 May 1997 | 25 | + |  | NS3 | 3.00 | 29.9 |
|  | 6 | 13 May 1997 | 29 | + |  | NS3 | 5.58 | 24.9 |

BLD: Below limit of Detection
S/CO: 10 NC used for cutoff calculation
S/CO >/= 1.0 is considered reactive Example 27

TABLE 12

Table 12: Window Period Reduction by HCV Combo Assay.
Time (days) to detection of HCV Ag or Ab in HCV seroconversion
panels with HCV RNA detected in the 1$^{st}$ bleed.

| Panel | Genotype | RNA | First Day to Detection of: Anti-HCV Assay | First Day to Detection of: HCV Combo Assay | RNA-Combo Differential (Days) | HCV Combo-Ab Differential (Days) |
|---|---|---|---|---|---|---|
| PHV-907 | 1b | 0 | 18 | 0 | 0 | 18 |
| PHV-909 | 3 | 0 | 28 | 0 | 0 | 28 |
| PHV-912 | 2b/3 | 0 | 7 | 4 | 4 | 3 |
| PHV-913 | 2b | 0 | 7 | 0 | 0 | 7 |
| PHV-914 | 2b | 0 | 19 | 0 | 0 | 19 |
| BCP 6214 | 1a | 0 | 30 | 0 | 0 | 30 |
| BCP 6229 | 1a | 0 | 17 | 0 | 0 | 17 |
| BCP 9044 | 1a | 0 | 25 | 0 | 0 | 25 |
|  |  |  | Mean window period reduction |  | 0.5 | 18.4 |

Average window period reduction by HCV Combo: 18.4 days

Example 28

Table 13 shows that the highest number of seroconversion bleeds detected by any format is by the Capture-on-the-Fly HCV Combo Assay format with a total number of 17 bleeds detected (out of a potential 21 bleeds). The 6C37 antibody only assay detected 11 bleeds while the Murex HCV Combo (MiDAS Report, Health Protection Agency-Centre for Infections, Report PER06007, February, 2007.) detected 9 bleeds. Table 14 shows the S/CO information on both seroconversion panels shown in table 13. Further, in Table 14, the S/CO values are shown for Panel B (anti-NS3 only sample). The Capture-on-the-fly format is more robust, S/CO of 6.19 vs. that of 6C37 at S/CO of 3-4 indicating that the Capture-on-the Fly format for HCV Combo is the most

TABLE 13

Table 13: Sensitivity comparison of different assay formats for 2 key seroconversion panels

|  | 6C37 Anti-HCV Only Assay | Murex HCV Combo Assay | HCV Combo in Capture-on-the-Fly Format |
|---|---|---|---|
| BCP6212 | 8 | 2 | 9 |
| BCP6213 | 3 | 7 | 8 |
| Total Bleeds Detected | 11 | 9 | 17 |

Number of Reactive Bleeds from Each Seroconversion Panel (10 NC Used as Cutoff)

TABLE 14

| | | Anti-HCV 6C37 | HCV combo Murex | HCV combo CotF format |
|---|---|---|---|---|
| | RIBA Data | S/CO | S/CO | S/CO* |
| Panel B (anti-NS3) | NS3 | 3~4 | | 6.19 |
| BCP6212-1 | — | 0.07 | 0.795 | 1.18 |
| BCP6212-2 | — | 1.49 | 0.407 | 2.36 |
| BCP6212-3 | — | 2.12 | 0.417 | 2.24 |
| BCP6212-4 | NS3 | 6.48 | 0.499 | 2.69 |
| BCP6212-5 | NS3 | 7.97 | 0.489 | 6.96 |
| BCP6212-6 | NS3 | 8.13 | 0.529 | 5.18 |
| BCP6212-7 | NS3 | 8.17 | 0.509 | 4.95 |
| BCP6212-8 | NS3 | 11.80 | 1.071 | 18.5 |
| BCP6212-9 | NS3 | 12.23 | 1.245 | 19.5 |
| BCP6213-1 | — | 0.09 | 0.348 | 0.22 |
| BCP6213-2 | — | 0.09 | 0.371 | 0.22 |
| BCP6213-3 | — | 0.11 | 0.470 | 0.20 |
| BCP6213-4 | — | 0.09 | 0.532 | 0.30 |
| BCP6213-5 | — | 0.08 | 0.969 | 1.27 |
| BCP6213-6 | — | 0.09 | 1.110 | 2.11 |
| BCP6213-7 | — | 0.09 | 2.233 | 3.52 |
| BCP6213-8 | — | 0.08 | 5.609 | 4.69 |
| BCP6213-9 | — | 0.14 | 2.608 | 5.05 |
| BCP6213-10 | — | 1.47 | 4.489 | 10.30 |
| BCP6213-11 | Core/NS3 | 10.48 | 9.192 | 12.27 |
| BCP6213-12 | Core/NS3 | 10.30 | 6.860 | 6.13 |

S/CO*: 10 NC used for cutoff calculation

Example 29

Seroconversion Sensitivity of 9NB49H and NS3h

The NS3 recombinant antigens 9NB49H (Acr-BSA-9NB49H and 9NB49H-Cbt) and NS3h (NS3h-Cbt and Acr-BSA-NS3h) were examined in the HCV Ag/Ab Combo format for their ability to detect antibodies among individual serum samples from a seroconversion panel from an HCV infected individual. The results are expressed in terms of S/CO (sample/cutoff) where samples with S/CO ≥1.0 are considered to be reactive and samples with S/CO <1.0 are considered to be non-reactive. The assay using NS3h resulted in greater seroconversion sensitivity, i.e. most reactive bleeds detected with the highest S/CO values, as compared to the assay using 9NB49H and the Murex HCV Ag/Ab Combo.

TABLE 15

| Panel Member | Bleed Date | ARCHITECT Anti-HCV S/CO | Murex HCV Ag/Ab Combo S/CO | HCV Ag/Ab Combo (9NB49H) S/CO | HCV Ag/Ab Combo (NS3h) S/CO |
|---|---|---|---|---|---|
| 6228-1 | 20 Nov. 1996 | 0.03 | 0.58 | nd | 0.49 |
| 6228-2 | 22 Nov. 1996 | 0.03 | 0.42 | 0.19 | 0.23 |
| 6228-3 | 27 Nov. 1996 | 0.04 | 1.03 | 0.82 | 1.06 |
| 6228-4 | 29 Nov. 1996 | 0.03 | 0.58 | 0.31 | 0.35 |
| 6228-5 | 4 Dec. 1996 | 0.04 | 0.35 | 0.13 | 0.18 |
| 6228-6 | 6 Dec. 1996 | 0.03 | 0.30 | 0.08 | 0.11 |
| 6228-7 | 11 Dec. 1996 | 0.09 | 0.49 | 0.34 | 0.41 |
| 6228-8 | 14 Dec. 1996 | 0.10 | 0.61 | 0.42 | 0.67 |
| 6228-9 | 18 Dec. 1996 | 1.37 | 0.56 | nd | 3.04 |
| 6228-10 | 21 Dec. 1996 | 4.52 | 1.09 | 0.29 | 15.39 |
| 6228-11 | 26 Dec. 1996 | 6.62 | 1.67 | 0.39 | 17.01 |
| 6228-12 | 28 Dec. 1996 | 7.12 | 1.53 | 0.30 | 17.12 | nd: not determined

The invention claimed is:

1. A method for the combined detection of an HCV antigen and an HCV antibody in a test sample, the method comprising:
   a) providing the following components:
      i. a solid phase comprising a tagged anti-HCV core monoclonal antibody and a first tagged HCV capture antigen bound thereto, wherein the anti-HCV core monoclonal antibody binds an HCV core antigen in the test sample and the first HCV capture antigen binds a first anti-HCV antibody in the test sample, and wherein the first HCV capture antigen consisting of the amino acid sequence of SEQ ID NO: 97, 98, 99, 100, 102, 103, 104, 105, or 106; and
      ii. a first detectably labeled HCV detection antigen for binding to the first anti-HCV antibody captured by the first HCV capture antigen;
   b) incubating the components of step (a) under conditions whereby:
      i. the tagged anti-HCV core monoclonal antibody specifically binds to the HCV core antigen present in the test sample to produce an anti-HCV core monoclonal antibody-HCV core antigen complex captured on the solid phase;
      ii. the first tagged HCV capture antigen specifically binds to the first anti-HCV antibody present in the test sample to produce a first HCV capture antigen-first anti-HCV antibody complex captured on the solid phase; and
      iii. the first detectably labeled HCV detection antigen specifically binds to the anti-HCV antibody of the first HCV capture antigen-first anti-HCV antibody complex captured on the solid phase;
   c) isolating the solid phase comprising the captured HCV antigen and the first captured anti-HCV antibody from unreacted test sample and reagents;
   d) contacting the isolated solid phase with a detectably labeled conjugate antibody that binds to the HCV core antigen of the anti-HCV core monoclonal antibody-HCV core antigen complex; and
   e) detecting;
      i. a first signal generated from the detectably labeled conjugate antibody, wherein presence of the first signal indicates presence of the HCV core antigen in the test sample; and
      ii. a second signal generated from the first detectably labeled HCV detection antigen, wherein presence of the second signal indicates presence of the first anti-HCV antibody in the test sample.

2. The method of claim 1, wherein:
   step (a) further comprises:
      iii. a second tagged HCV capture antigen bound to the solid phase that is distinct from the first tagged HCV capture antigen, and binds to a second anti-HCV antibody in the test sample, wherein the second HCV capture antigen comprises domains I, II, and III of HCV NS3 helicase;
      iv. a second detectably labeled HCV detection antigen for binding to the second anti-HCV antibody, wherein the second HCV detection antigen comprises domains I, II, and III of HCV NS3 helicase;
   step (b) further comprises incubating the components of step (a) under conditions whereby:
      iv. the second tagged HCV capture antigen specifically binds to the second anti-HCV antibody present in the test sample to produce a second HCV capture antigen-second anti-HCV antibody complex captured on the solid phase;
      v. the second detectably labeled HCV detection antigen specifically binds to the second anti-HCV antibody in the second HCV capture antigen-second anti-HCV antibody complex captured on the solid phase; and
   step (e) further comprises:
      iii. detecting a third signal generated from the second detectably labeled HCV detection antigen, wherein presence of the third signal indicates presence of the second anti-HCV antibody in the test sample.

3. The method of claim 2, wherein:
   step (a) further comprises:
      v. a third tagged HCV capture antigen bound to the solid phase that is distinct from the first and the second tagged HCV capture antigens and binds to a third anti-HCV antibody present in the test sample, wherein the third HCV capture antigen comprises at least a portion of domain I of HCV NS3 helicase;
      vi. a third detectably labeled HCV detection antigen for binding to the third anti-HCV antibody wherein the third HCV detection antigen comprises at least a portion of domain I of HCV NS3 helicase;
   step (b) further comprises incubating the components of step (a) under conditions whereby:
      vi. the third tagged HCV capture antigen specifically binds to the third anti-HCV antibody present in the test sample to produce a third HCV capture antigen-third anti-HCV antibody complex captured on the solid phase; and
      vii. the third detectably labeled HCV detection antigen specifically binds to the third anti- HCV antibody in the third HCV capture antigen-third anti-HCV antibody complex captured on the solid phase; and
   step (e) further comprises:
      iv. detecting a fourth signal generated from the third detectably labeled HCV detection antigen, wherein presence of the fourth signal indicates presence of the third anti-HCV antibody in the test sample.

4. The method of claim 1, wherein the solid phase comprises avidin or streptavidin, and the first, second, and third HCV capture antigens are tagged with biotin.

* * * * *